US007504396B2

(12) United States Patent
Nunes et al.

(10) Patent No.: US 7,504,396 B2
(45) Date of Patent: Mar. 17, 2009

(54) SUBSTITUTED HETEROCYCLIC COMPOUNDS AND METHODS OF USE

(75) Inventors: Joseph J. Nunes, Andover, MA (US); Xiaotian Zhu, Newton, MA (US); Patricia Amouzegh, Didcot (GB); Chiara Ghiron, Isola d'Arbia -Asciano (IT); David N. Johnson, Abingdon (GB); Eoin Christopher Power, Abingdon (GB)

(73) Assignee: Amgen Inc., Thousand Oaks, CA (US)

( * ) Notice: Subject to any disclaimer, the term of this patent is extended or adjusted under 35 U.S.C. 154(b) by 343 days.

(21) Appl. No.: 10/875,896

(22) Filed: Jun. 23, 2004

(65) Prior Publication Data

US 2005/0209221 A1 Sep. 22, 2005

Related U.S. Application Data

(60) Provisional application No. 60/482,375, filed on Jun. 24, 2003.

(51) Int. Cl.
*C07D 239/48* (2006.01)
*C07D 403/12* (2006.01)
*A61K 31/505* (2006.01)

(52) U.S. Cl. .............................. 514/235.8; 514/252.11; 514/252.14; 514/252.19; 514/272; 544/122; 544/295; 544/321

(58) Field of Classification Search ................. 544/122, 544/295, 321; 514/235.8, 252.11, 252.14, 514/252.19, 272
See application file for complete search history.

(56) References Cited

U.S. PATENT DOCUMENTS

| 3,845,055 A | 10/1974 | Hoegerle et al. |
| 4,250,178 A | 2/1981 | Bucher et al. |

FOREIGN PATENT DOCUMENTS

| EP | 0039051 | 7/1985 |
| EP | 1054004 | 11/2000 |
| EP | 1184376 | 3/2002 |
| EP | 1277741 | 1/2003 |
| JP | 03127790 | 5/1991 |
| WO | WO 00/39101 | 7/2000 |
| WO | WO 02/04429 | 1/2002 |
| WO | WO 03/002544 | 1/2003 |
| WO | WO 03004492 A1 | 1/2003 |
| WO | WO 03/032997 | 4/2003 |
| WO | WO 03/048133 | 6/2003 |
| WO | WO 03/063794 | 8/2003 |
| WO | WO 2004/002964 | 1/2004 |

OTHER PUBLICATIONS

Casanova et al., PubMed Abstract (Rev Neurol. 28(9):909-15) May 1999.*
Kosegi et al., CAPLUS Abstract 115:183346, 1991.*
Kane, LP et al. "Signal Transduction by the TCR for Antigen," Current Opinion in Immunol. 12: 242 (2000).
Bolen, JB, and Brugge, "Leukocyte protein Tyrosine Kinases:Potential Targets for Drug Discovery" JS Annu. Rev. Immunol. 15: 371 (1997).
Soriano, P. et al., Cell, "Targeted disruption of the c-src proto-oncogene leads to osteopetrosis in mice" 64: 693 (1991).
Anderson, SJ et al. "Involvement of the Protein Tyrosine Kinase p56$^{lck}$ in T Cell Signaling and Thymocyte Development" Adv. Immunol. 56: 151 (1994).
Goldman, FD et al. "Defective Expression of p65lck in an Infant with Severe Combined Immunodeficiency" J. Clin. Invest. 102: 421 (1998).
Manser et.al., "A non-receptor tyrosine kinase that inhibits the GTPase activity of p21cdc42" Nature 363(6427): 364-367, (1993).
Appleby, MW et al. "Defective T Cell Receptor Signaling in Mice Lacking the Thymic Isoform of p59$^{fyn}$" Cell 70: 751 (1992).
Vicentini, L. et al. "Fgr Deficiency Results in Defective Eosinophil Recruitment to the Lung During Allergic Airway Inflammation" J. Immunol. 168: 6446 (2002).
Turner, H. and Kinet, J-P "Signalling through the high-affinity IgE receptor Fc epsilon RI" Nature 402: B24 (1999).
Abram, CL and Courtneidge, SA "Src Family Tyrosine Kinases and Growth Factor Signaling" Exp. Cell Res. 254: 1 (2000).
Paul, R. et al. "Src deficiency or blockade of Src activity in mice provides cerebral protection following stroke" Nature Medicine 7: 222 (2001).
Snow, RJ et al. "Discovery of 2-Phenylamino-imidazo[4,5-*h*]isoquinolin-9-ones: A New Class of Inhibitors of Lck Kinase" J. Med. Chem. 45: 3394 (2002).

(Continued)

*Primary Examiner*—Deepak Rao
(74) *Attorney, Agent, or Firm*—G. Prabhakar Reddy

(57) ABSTRACT

The present invention relates to pyrimidine or pyridine carboxamides or pharmaceutically-acceptable salts thereof. Also included is a method of treatment of inflammation, inhibition of T cell activation and proliferation, arthritis, rheumatoid arthritis, psoriatic arthritis, osteoarthritis, organ transplant, acute transplant or heterograft or homograft rejection, transplantation tolerance induction, ischemic or reperfusion injury, myocardial infarction, stroke, multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea, atopic dermatitis, colon carcinoma or thymoma in a mammal comprising administering a therapeutically-effective amount a compound as described above.

12 Claims, No Drawings

OTHER PUBLICATIONS

Burchat, AF et al. "Design, synthesis and brief SAR of pyrazolo(3,4-d) and pyrrolo(2,3-d)pyrimidines as potent inhibitors of lck" et al. Bioorganic and Med. Chem. Letters 12: 1687 (2002).

Hanke, JH et al. "Discovery of a Novel, Potent, and Src Family-selective Tyrosine Kinase Inhibitor" J. Biol. Chem. 271: 695 (1996).

Altmann, E et al. "7-Pyrrolidinyl- and 7-piperidinyl-5-aryl-pyrrolo(2,3-d)-pyrimidines: Potent inhibitors of the tyrosine kinase c-Src" Bioorganic and Med. Chem. Letters 11: 853 (2001).

Wang, YD et al. "Inhibitors of Src Tyrosine Kinase: The Preparation and Structure-Activity Relationship of 4-Anilino-3-cyanoquinolines and 4-Anilinoquinazoles" Bioorganic and Med. Chem. Letters 10: 2477 (2000).

Chen, P. et al. "Synthesis and SAR of novel imidazoquinoxaline-based Lck inhibitors: Improvement of cell potency" Bioorganic and Med. Chem. Letters 12: 3153 (2002).

Berge et al., "Pharmaceutical Salts" J. Pharm. Sci. 66:1 (1977).

Bundgaard, H. et al. "A Novel Solution-Stable Water-Soluble Prodrug Type For Drugs Containing A Hydroxyl Or An Amino-Acidic Group" J. Med. Chem. 32(12): 2503 (1989).

Terashima, K. et al. "Studies on Antiulcer Agents.II. 1) Antiulcer Properties of N-(1H-Tetrazol-5-yl)-2-anilino-5-pyrimidinecarboxamides Inhibiting Release of Histamine from Passively Sensitized Rat Peritoneal Mast Cells" Chem. Pharm. Bull. 43(6): 1042-1044 (1995).

Hirokawa, Yoshimi et al. "Synthesis and Structure-Affinity Relationships of Novel N-(1-Ethyl-4-methylhexahydro-1,4-diazepin-6-yl)pyridine-3-carboxamides with Potent Serotonin $5\text{-}HT_3$ and Dopamine $D_2$ Receptor Antagonist Activity," J. Med. Chem. 46: 702 (2003).

Terashima, Kohji et al. "Studies on antiulcer agents II. Antiulcer properties of N-1(1H-tetrazol-5-yl)-2-anilino-5-pyrimidinecarboxamides inhibiting release of histamine from passively sensitized rat peritoneal mast cells," Chem. & Pharm. Bulletin 43(6): 1042 (1995).

Kim, Dong Han "Reactions of ethyl 4-chloro-5-pyrimidinecarboxylates with 2-aminopyridine. Synthesis of 5H-pyrido[1,2-a]pyrimido[5,4l-e]pyrimidin-5-ones and 5H-pyrido[1,2-a]pyrimido[4,5-d]pyrimidin-5-ones and rearrangement of the former to the latter," J. of Heterocyclic Chem. 22(1): 173, 1985.

Dostert, P. et al. "Studies on the neuroleptic benzamides. I. Synthesis and antidopaminergic properties of new pyrimidine derivatives," EP J. of Med. Chem. 17(5); 437 (1982).

* cited by examiner

SUBSTITUTED HETEROCYCLIC COMPOUNDS AND METHODS OF USE

This application claims the benefit of U.S. Provisional Application No. 60/482,375 filed Jun. 24, 2003, which is hereby incorporated by reference.

BACKGROUND OF THE INVENTION

T cells play a pivotal role in the regulation of immune responses and are important for establishing immunity to pathogens. In addition, T cells are often activated during inflammatory autoimmune diseases, such as rheumatoid arthritis, inflammatory bowel disease, type I diabetes, multiple sclerosis, Sjogren's disease, myasthenia gravis, psoriasis, and lupus. T cell activation is also an important component of transplant rejection, allergic reactions, and asthma.

T cells are activated by specific antigens through the T cell receptor (TCR) which is expressed on the cell surface. This activation triggers a series of intracellular signaling cascades mediated by enzymes expressed within the cell (Kane, L P et al. Current Opinion in Immunol. 200, 12, 242). These cascades lead to gene regulation events that result in the production of cytokines, like interleukin-2 (IL-2). IL-2 is a critical cytokine in T cell activation, leading to proliferation and amplification of specific immune responses.

One class of enzymes shown to be important in signal transduction are the kinases. Members of the Src-family of tyrosine kinases include, for example: Lck, Fyn(B), Fyn(T), Lyn, Src, Yes, Hck, Fgr and Blk (for review see: Bolen, J B, and Brugge, J S Annu. Rev. Immunol 1997, 15, 371). Gene disruption studies suggest that inhibition of some members of the src family of kinases would potentially lead to therapeutic benefit. Src(-/-) mice have abnormalities in bone remodeling or osteopetrosis (Soriano, P. Cell 1991, 64, 693), suggesting that inhibition of this kinase might be useful in diseases of bone resorption, such as osteoporosis. Lck(-/-) mice have defects in T cell maturation and activation (Anderson, S J et al. Adv. Immunol. 1994, 56, 151), suggesting that inhibition of this kinase might be useful in diseases of T cell mediated inflammation. In addition, human patients have been identified with mutations effecting Lck kinase activity (Goldman, F D et al. J. Clin. Invest. 1998, 102, 421). These patients suffer from a severe combined immunodeficiency disorder (SCID).

Ack, a gene containing a tyrosine kinase domain, is also reported to possess tyrosine kinase activity, lending to the belief that it is involved in the regulatory mechanism that sustains the GTP-bound active form of cdc42Hs, which is directly linked to a tyrosine phosphorylation signal transduction pathway (Manser et. Al., Nature 363(6427), 364-367, 1994). More specifically, the activated p21cdc42Hs kinase gene encodes an intracellular, non-receptor tyrosine kinase that binds cdc42Hs in its GTP-bound form and inhibits the GTPase activity of p21cdc42, a Ras-like protein involved in cell growth. Accordingly, Ack is a target believed to be useful in the regulation of cancer.

Without wishing to imply that the compounds disclosed in the present invention possess pharmacological activity only by virtue of an effect on a single biological process, it is believed that the compounds modulate T cell activation by way of inhibition of one or more of the multiple protein tyrosine kinases involved in early signal transduction steps leading to T cell activation, for example by way of inhibition of Lck kinase.

Src-family kinases are also important for signaling downstream of other immune cell receptors. Fyn, like Lck, is involved in TCR signaling in T cells (Appleby, M W et al. Cell 1992, 70, 751). Hck and Fgr are involved in Fcγ receptor signaling leading to neutrophil activation (Vicentini, L. et al. J. Immunol. 2002, 168, 6446). Lyn and Src also participate in Fcγ receptor signaling leading to release of histamine and other allergic mediators (Turner, H. and Kinet, J-P Nature 1999, 402, B24). These findings suggest that Src family kinase inhibitors may be useful in treating allergic diseases and asthma.

Src kinases have also been found to be activated in tumors including sarcoma, melanoma, breast, and colon cancers suggesting that Src kinase inhibitors may be useful anti-cancer agents (Abram, C L and Courtneidge, S A Exp. Cell Res. 2000, 254, 1).

Src kinase inhibitors have also been reported to be effective in an animal model of cerebral ischemia (R. Paul et al. Nature Medicine 2001, 7, 222), suggesting that Src kinase inhibitors may be effective at limiting brain damage following stroke.

Several groups have published on inhibitors of Src family kinase and the activities of these inhibitors in various in vitro and in vivo biological systems. These include the 2-phenylamino-imidazo [4,5-h]isoquinolin-9-ones (Snow, R J et al. J. Med. Chem. 2002, 45, 3394), the pyrazolo [3,4-d]pyrimidines (Burchat, A F et al. Bioorganic and Med. Chem. Letters 2002, 12, 1687. Hanke, J H et al. J. Biol. Chem. 1996, 271, 695), the pyrrolo [2,3-d]pyrimidines (Altmann, E et al. Bioorganic and Med. Chem. Letters 2001, 11, 853), the anilinoquinazolines (Wang, Y D et al. Bioorganic and Med. Chem. Letters 2000, 10, 2477), and the imidazoquinoxalines (Chen, P. et al. Bioorganic and Med. Chem. Letters 2002, 12, 3153).

BRIEF DESCRIPTION OF THE INVENTION

The compounds of the present invention inhibit the Src-family of protein tyrosine kinases, such as Lck, Fyn(B), Fyn(T), Lyn, Src, Yes, Hck, Fgr and Blk, as well as other protein tyrosine kinases including Ack, and are thus useful in the treatment, including prevention and therapy, of protein tyrosine kinase-associated disorders such as immunologic disorders. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a preferred embodiment of the present invention. Compounds of the present invention, which selectively block T cell activation and proliferation are preferred. Also, compounds of the present invention which may block the activation of endothelial cell protein tyrosine kinase by oxidative stress, thereby limiting surface expression of adhesion molecules that induce neutrophil binding, and which can inhibit protein tyrosine kinase necessary for neutrophil activation would be useful, for example, in the treatment of ischemia and reperfusion injury.

The present invention also provides methods for the treatment of protein tyrosine kinase-associated disorders, comprising the step of administering to a subject in need thereof at least one compound of the formula I in an amount effective therefore. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compound(s) of the present invention in treating protein tyrosine kinase-associated disorders is exemplified by, but is not limited to, treating a range of disorders such as: arthritis (such as rheumatoid arthritis, psoriatic arthritis or osteoarthritis); transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; multiple sclerosis; inflammatory bowel disease, including ulcerative colitis and Crohn's disease; lupus (systemic lupus erythematosis); graft vs. host diseases; T-cell mediated hypersensitivity diseases, including contact hypersensitivity, delayed-type hypersensitivity, and gluten-sensitive enteropathy (Celiac disease); Type 1 diabetes; psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers where Ack and Lck or other Src-family kinases such as Src are activated or overexpressed, such as colon carcinoma and thymoma, or cancers where Src-family kinase activity facilitates tumor growth or survival; glomerulonephritis, serum sickness; uticaria; allergic diseases such as respiratory allergies (asthma, hayfever, allergic rhinitis) or skin allergies; scleracielma; mycosis fungoides; acute inflammatory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The present invention also provides for a method for treating the aforementioned disorders such as atopic dermatitis by administration of a therapeutically effective amount of a compound of the present invention, which is an inhibitor of protein tyrosine kinase, to a patient in need of such treatment.

Src-family kinases other than Lck, such as Hck and Fgr, are important in the Fcγ receptor induced respiratory burst of neutrophils as well as the Fcγ receptor responses of monocytes and macrophages. The compounds of the present invention may inhibit the Fcγ induced respiratory burst response in neutrophils, and may also inhibit the Fcγ dependent production of TNFα. The ability to inhibit Fcγ receptor dependent neutrophil, monocyte and macrophage responses would result in additionalanti-inflammatory activity for the present compounds in additton to their effects on T cells. This activity would be especially of value, for example, in the treatment of inflammatory diseases, such as arthritis or inflammatory bowel disease. The present compounds may also be of value for the treatment of autoimmune glomerulonephritis and other instances of glomerulonephritis induced by deposition of immune complexes in the kidney that trigger Fcγ receptor responses and which can lead to kidney damage.

In addition, certain Src family kinases, such as Lyn and Fyn(B), may be important in the Fcε receptor induced degranulation of mast cells and basophils that plays an important role in asthma, allergic rhinitis, and other allergic disease. Fcε receptors are stimulated by IgE-antigen complexes. The compounds of the present invention may inhibit the Fcε induced degranulation responses. The ability to inhibit Fcε receptor dependent mast cell and basophil responses may result in additional anti-inflammatory activity for the present compounds beyond their effect on T cells.

The combined activity of the present compounds towards monocytes, macrophages, T cells, etc. may prove to be a valuable tool in the treatment of any of the aforementioned disorders.

In a particular embodiment, the compounds of the present invention are useful for the treatment of the aforementioned exemplary disorders irrespective of their etiology, for example, for the treatment of rheumatoid arthritis, transplant rejection, multiple sclerosis, inflammatory bowel disease, lupus, graft v. host disease, T cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, or atopic dermatitis whether or not associated with PTK.

The compounds of the invention are represented by the following general structure:

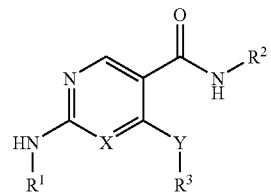

wherein X, Y, $R^1$, $R^2$ and $R^3$ are defined herein below.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In accordance with the present invention, one aspect of the invention relates to a compound of Formula I

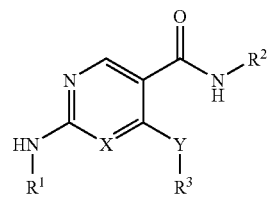

or a pharmaceutically-acceptable salt thereof, wherein
X is N or CH;
Y is NH, O or S;
$R^1$ is selected from $—R^{11}$, $—R^{11}—R^{12}$, $—R^{11}—R^{14}$, $—R^{12}—R^{14}$, $—R^{11}—R^{12}—R^{14}$, $—R^{11}—R^{13}—R^{14}$, $—R^{12}—R^{13}—R^{14}$, $—R^{11}—R^{13}—R^{12}—R^{14}$ and $—R^{11}—R^{12}—R^{13}—R^{14}$, any of which is substituted by 0, 1, 2, 3 or 4 substituents independently selected from $R^c$;
$R^2$ is selected from $—R^{21}$, $—R^{21}—R^{22}$, $—R^{21}—R^{24}$, $—R^{22}—R^{24}$, $—R^{21}—R^{22}—R^{24}$, $—R^{21}—R^{23}—R^{24}$, $—R^{22}—R^{23}—R^{24}$, $—R^{21}—R^{23}—R^{22}—R^{24}$ and $—R^{21}—R^{22}—R^{23}—R^{24}$, any of which is substituted by 0, 1, 2, 3 or 4 substituents independently selected from $R^c$;

$R^3$ is selected from —$R^{31}$, —$R^{31}$—$R^{32}$, —$R^{31}$—$R^{34}$, —$R^{32}$—$R^{34}$, —$R^{31}$—$R^{32}$—$R^{34}$, —$R^{31}$—$R^{33}$—$R^{34}$, —$R^{32}$—$R^{33}$—$R^{34}$, —$R^{31}$—$R^{33}$—$R^{32}$—$R^{34}$ and —$R^{31}$—$R^{32}$—$R^{33}$—$R^{34}$, any of which is substituted by 0, 1, 2, 3 or 4 substituents independently selected from $R^c$;

$R^{11}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{12}$ is independently at each instance $C_{1-8}$alkyl;

$R^{13}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

$R^{14}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{21}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{22}$ is independently at each instance $C_{1-8}$alkyl;

$R^{23}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

$R^{24}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{31}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{32}$ is independently at each instance $C_{1-8}$alkyl;

$R^{33}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

$R^{34}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^a$ is independently at each instance H or $R^b$;

$R^b$ is independently at each instance $C_{1-8}$alkyl, phenyl or benzyl; and $R^c$ is independently at each instance $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$.

In one embodiment of the present invention, X is N or CH.

In another embodiment, in conjunction with any of the above or below embodiments, X is N.

In another embodiment, in conjunction with any of the above or below embodiments, X is CH.

In another embodiment, in conjunction with any of the above or below embodiments, Y is NH, O or S.

In another embodiment, in conjunction with any of the above or below embodiments, Y is NH.

In another embodiment, in conjunction with any of the above or below embodiments, Y is O.

In another embodiment, in conjunction with any of the above or below embodiments, Y is S.

Embodiment A: In another embodiment, in conjunction with any of the above or below embodiments, $R^1$ is selected from —$R^{11}$, —$R^{11}$—$R^{14}$, —$R^{11}$—$R^{12}$, —$R^{12}$—$R^{14}$, —$R^{11}$—$R^{12}$—$R^{14}$, —$R^{11}$—$R^{13}$—$R^{14}$, —$R^{12}$—$R^{13}$—$R^{14}$, —$R^{11}$—$R^{13}$—$R^{12}$—$R^{14}$ and —$R^{11}$—$R^{12}$—$R^{13}$—$R^{14}$, any of which is substituted by 0, 1, 2, 3 or 4 substituents independently selected from $R^c$.

In another embodiment, in conjunction with any of the above or below embodiments, $R^1$ is selected from —$R^{11}$, —$R^{11}$—$R^{14}$, —$R^{11}$—$R^{12}$, —$R^{11}$—$R^{12}$—$R^{14}$, —$R^{11}$—$R^{13}$—$R^{14}$, —$R^{11}$—$R^{13}$—$R^{12}$—$R^{14}$ and —$R^{11}$—$R^{12}$—$R^{13}$—$R^{14}$, any of which is substituted by 0, 1, 2, 3 or 4 substituents independently selected from $R^c$.

In another embodiment, in conjunction with any of the above or below embodiments, $R^1$ is $R^{11}$, which is substituted by 0, 1, 2, 3 or 4 substituents independently selected from $R^c$.

Embodiment B: In another embodiment, in conjunction with any of the above or below embodiments, $R^1$ is —$R^{11}$—$R^{14}$, which is substituted by 0, 1, 2, 3 or 4 substituents independently selected from $R^c$.

Embodiment C: In another embodiment, in conjunction with any of the above or below embodiments, $R^1$ is —$R^{11}$—$R^{12}$, which is substituted by 0, 1, 2, 3 or 4 substituents independently selected from $R^c$.

In another embodiment, in conjunction with any of the above or below embodiments, $R^1$ is —$R^{11}$—$R^{12}$—$R^{14}$, which is substituted by 0, 1, 2, 3 or 4 substituents independently selected from $R^c$.

In another embodiment, in conjunction with any of the above or below embodiments, $R^1$ is —$R^{11}$—$R^{13}$—$R^{14}$, which is substituted by 0, 1, 2, 3 or 4 substituents independently selected from $R^c$.

Embodiment D: In another embodiment, in conjunction with any of the above or below embodiments, $R^1$ is —$R^{11}$—$R^{13}$—$R^{12}$—$R^{14}$, which is substituted by 0, 1, 2, 3 or 4 substituents independently selected from $R^c$.

In another embodiment, in conjunction with any of the above or below embodiments, $R^1$ is —$R^{11}$—$R^{12}$—$R^{13}$—$R^{14}$, which is substituted by 0, 1, 2, 3 or 4 substituents independently selected from $R^c$.

In another embodiment, in conjunction with any of the above or below embodiments, $R^2$ is selected from —$R^{21}$, —$R^{21}$—$R^{24}$, —$R^{21}$—$R^{22}$, —$R^{22}$—$R^{24}$, —$R^{21}$—$R^{22}$—$R^{24}$, —$R^{21}$—$R^{23}$—$R^{24}$, —$R^{22}$—$R^{23}$—$R^{24}$, —$R^{21}$—$R^{23}$—$R^{22}$—$R^{24}$, and —$R^{21}$—$R^{22}$—$R^{23}$—$R^{24}$, any of which is substituted by 0, 1, 2, 3 or 4 substituents independently selected from $R^c$.

Embodiment E: In another embodiment, in conjunction with any of the above or below embodiments, $R^2$ is selected from —$R^{21}$, —$R^{21}$—$R^{24}$, —$R^{21}$—$R^{22}$, —$R^{21}$—$R^{22}$—$R^{24}$, —$R^{21}$—$R^{23}$—$R^{24}$, —$R^{21}$—$R^{23}$—$R^{22}$—$R^{24}$, and —$R^{21}$—$R^{22}$—$R^{23}$—$R^{24}$, any of which is substituted by 0, 1, 2, 3 or 4 substituents independently selected from $R^c$.

Embodiment F: In another embodiment, in conjunction with any of the above or below embodiments, $R^2$ is $R^{21}$, which is substituted by 0, 1, 2, 3 or 4 substituents independently selected from $R^c$.

In another embodiment, in conjunction with any of the above or below embodiments, $R^2$ is —$R^{21}$—$R^{24}$, which is substituted by 0, 1, 2, 3 or 4 substituents independently selected from $R^c$.

In another embodiment, in conjunction with any of the above or below embodiments, $R^2$ is —$R^{21}$—$R^{22}$, which is substituted by 0, 1, 2, 3 or 4 substituents independently selected from $R^c$.

In another embodiment, in conjunction with any of the above or below embodiments, $R^2$ is —$R^{21}$—$R^{22}$—$R^{24}$, which is substituted by 0, 1, 2, 3 or 4 substituents independently selected from $R^c$.

In another embodiment, in conjunction with any of the above or below embodiments, $R^2$ is —$R^{21}$—$R^{23}$—$R^{24}$, which is substituted by 0, 1, 2, 3 or 4 substituents independently selected from $R^c$.

Embodiment G: In another embodiment, in conjunction with any of the above or below embodiments, $R^2$ is —$R^{21}$—$R^{23}$—$R^{22}$—$R^{24}$, which is substituted by 0, 1, 2, 3 or 4 substituents independently selected from $R^c$.

In another embodiment, in conjunction with any of the above or below embodiments, $R^2$ is —$R^{21}$—$R^{22}$—$R^{23}$—$R^{24}$, which is substituted by 0, 1, 2, 3 or 4 substituents independently selected from $R^c$.

In another embodiment, in conjunction with any of the above or below embodiments, $R^2$ is phenyl substituted by 1, 2, 3 or 4 substituents independently selected from $R^c$.

In another embodiment, in conjunction with any of the above or below embodiments, $R^2$ is a 2,5-disubstituted phenyl, wherein the two substituents are independently selected from $R^c$.

In another embodiment, in conjunction with any of the above or below embodiments, $R^2$ is a 2,5-disubstituted phenyl, wherein the two substituents are independently selected from $C_{1-2}$alkyl, halo and $C_{1-2}$haloalkyl.

In another embodiment, in conjunction with any of the above or below embodiments, $R^2$ is a 2,5-disubstituted phenyl, wherein the two substituents are independently selected from $CH_3$ and Cl.

In another embodiment, in conjunction with any of the above or below embodiments, $R^2$ is 2,5-dichlorophenyl.

In another embodiment, in conjunction with any of the above or below embodiments, $R^2$ is 2,5-dimethylphenyl.

In another embodiment, in conjunction with any of the above or below embodiments, $R^3$ is selected from —$R^{31}$, —$R^{31}$—$R^{34}$, —$R^{31}$—$R^{32}$, —$R^{32}$—$R^{34}$, —$R^{31}$—$R^{32}$—$R^{34}$, —$R^{31}$—$R^{33}$—$R^{34}$, —$R^{32}$—$R^{33}$—$R^{34}$, —$R^{31}$—$R^{33}$—$R^{32}$—$R^{34}$, and —$R^{31}$—$R^{32}$—$R^{33}$—$R^{34}$, any of which is substituted by 0, 1, 2, 3 or 4 substituents independently selected from $R^c$.

Embodiment H: In another embodiment, in conjunction with any of the above or below embodiments, $R^3$ is selected from —$R^{31}$, —$R^{31}$—$R^{34}$, —$R^{31}$—$R^{32}$, —$R^{31}$—$R^{32}$—$R^{34}$, —$R^{31}$—$R^{33}$—$R^{34}$—, —$R^{31}$—$R^{33}$—$R^{32}$—$R^{34}$ and —$R^{31}$—$R^{32}$—$R^{33}$—$R^{34}$, any of which is substituted by 0, 1, 2, 3 or 4 substituents independently selected from $R^c$.

Embodiment I: In another embodiment, in conjunction with any of the above or below embodiments, $R^3$ is —$R^{31}$, which is substituted by 0, 1, 2, 3 or 4 substituents independently selected from $R^c$.

Embodiment J: In another embodiment, in conjunction with any of the above or below embodiments, $R^3$ is —$R^{31}$—$R^{34}$, which is substituted by 0, 1, 2, 3 or 4 substituents independently selected from $R^c$.

Embodiment K: In another embodiment, in conjunction with any of the above or below embodiments, $R^3$ is —$R^{31}$—$R^{32}$, which is substituted by 0, 1, 2, 3 or 4 substituents independently selected from $R^c$.

In another embodiment, in conjunction with any of the above or below embodiments, $R^3$ is —$R^{31}$—$R^{32}$—$R^{34}$, which is substituted by 0, 1, 2, 3 or 4 substituents independently selected from $R^c$.

In another embodiment, in conjunction with any of the above or below embodiments, $R^3$ is —$R^{31}$—$R^{33}$—$R^{34}$, which is substituted by 0, 1, 2, 3 or 4 substituents independently selected from $R^c$.

Embodiment L: In another embodiment, in conjunction with any of the above or below embodiments, $R^3$ is —$R^{31}$—$R^{33}$—$R^{32}$—$R^{34}$, which is substituted by 0, 1, 2, 3 or 4 substituents independently selected from $R^c$.

In another embodiment, in conjunction with any of the above or below embodiments, $R^3$ is —$R^{31}$—$R^{32}$—$R^{33}$—$R^{34}$, which is substituted by 0, 1, 2, 3 or 4 substituents independently selected from $R^c$.

In another embodiment, in conjunction with any of the above or below embodiments, —$R^{11}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{11}$ is independently at each instance an unsaturated 5- or 6-membered monocyclic or 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{11}$ is independently at each instance an unsaturated 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{11}$ is independently at each instance an unsaturated 5- or 6-membered monocyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{11}$ is independently at each instance an unsaturated 5-membered monocyclic ring containing 1 atom selected from N, O and S.

In another embodiment, in conjunction with any of the above or below embodiments, $R^{11}$ is independently at each instance an unsaturated 6-membered monocyclic ring containing 0, 1 or 2 N atoms.

Embodiment M: In another embodiment, in conjunction with any of the above or below embodiments, $R^{11}$ is phenyl.

Embodiment N: In another embodiment, in conjunction with any of the above or below embodiments, $R^{11}$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{11}$ is independently at each instance an unsaturated 6-membered monocyclic ring containing 1 or 2 N atoms.

In another embodiment, in conjunction with any of the above or below embodiments, $R^{11}$ is pyridinyl, pyrimidinyl or pyridazinyl.

In another embodiment, in conjunction with any of the above or below embodiments, $R^{12}$ is independently at each instance $C_{1-8}$-alkyl.

In another embodiment, in conjunction with any of the above or below embodiments, $R^{12}$ is independently at each instance $C_{1-4}$alkyl.

In another embodiment, in conjunction with any of the above or below embodiments, $R^{12}$ is independently at each instance $C_{2-4}$alkyl.

Embodiment O: In another embodiment, in conjunction with any of the above or below embodiments, $R^{13}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{13}$ is independently at each instance —C(=O)—, —C(=O)O—, —C(=O)NR$^a$—, —C(=NR$^a$)NR$^a$—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{13}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{13}$ is —O—.

In another embodiment, in conjunction with any of the above or below embodiments, $R^{13}$ is —N(R$^a$)—.

In another embodiment, in conjunction with any of the above or below embodiments, $R^{13}$ is —N(R$^a$)C(=O)—, —C(=O)NR$^a$—, —C(=O)O— or —OC(=O)—.

In another embodiment, in conjunction with any of the above or below embodiments, $R^{13}$ is —O—, —N(R$^a$)—, —N(R$^a$)C(=O)—, —C(=O)NR$^a$—, —C(=O)O— or —OC(=O)—.

Embodiment P: In another embodiment, in conjunction with any of the above or below embodiments, $R^{14}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{14}$ is phenyl.

In another embodiment, in conjunction with any of the above or below embodiments, $R^{14}$ is naphthyl.

In another embodiment, in conjunction with any of the above or below embodiments, $R^{14}$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{14}$ is independently at each instance a saturated or unsaturated 5-, 6- or 7-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{14}$ is independently at each instance a saturated 5- or 6-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{14}$ is independently at each instance a saturated 5- or 6-membered monocyclic ring containing 1 or 2 N atoms, wherein the carbon atoms of the ring are substituted by 0 or 1 oxo groups.

In another embodiment, in conjunction with any of the above or below embodiments, $R^{14}$ is piperidinyl, piperazinyl or pyrrolidinyl.

In another embodiment, in conjunction with any of the above or below embodiments, $R^{21}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{21}$ is independently at each instance an unsaturated 5- or 6-membered monocyclic or 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{21}$ is independently at each instance an unsaturated 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{21}$ is independently at each instance an unsaturated 5- or 6-membered monocyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{21}$ is independently at each instance an unsaturated 5-membered monocyclic ring containing 1 atom selected from N, O and S.

In another embodiment, in conjunction with any of the above or below embodiments, $R^{21}$ is independently at each instance an unsaturated 6-membered monocyclic ring containing 0, 1 or 2 N atoms.

Embodiment Q: In another embodiment, in conjunction with any of the above or below embodiments, $R^{21}$ is phenyl.

Embodiment R: In another embodiment, in conjunction with any of the above or below embodiments, $R^{21}$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{21}$ is independently at each instance an unsaturated 6-membered monocyclic ring containing 1 or 2 N atoms.

In another embodiment, in conjunction with any of the above or below embodiments, $R^{21}$ is pyridinyl, pyrimidinyl or pyridazinyl.

In another embodiment, in conjunction with any of the above or below embodiments, $R^{12}$ is independently at each instance $C_{1-8}$alkyl.

In another embodiment, in conjunction with any of the above or below embodiments, $R^{22}$ is independently at each instance $C_{1-4}$alkyl.

In another embodiment, in conjunction with any of the above or below embodiments, $R^{22}$ is independently at each instance $C_{2-4}$alkyl.

Embodiment S: In another embodiment, in conjunction with any of the above or below embodiments, $R^{23}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$_a$)—, —NR$^a$C$_{2-6}$alkylN(R$^a$)— or —NR$^a$C$_{2-6}$alkalkyO—.

In another embodiment, in conjunction with any of the above or below embodiments, $R^{23}$ is independently at each instance —C(=O)—, —C(=O)O—, —C(=O)NR$^a$—, —C(=NR$^a$)NR$^a$—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{23}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{23}$ is —O—.

In another embodiment, in conjunction with any of the above or below embodiments, $R^{23}$ is —N(R$^a$)—.

In another embodiment, in conjunction with any of the above or below embodiments, $R^{23}$ is —N(R$^a$)C(=O)—, —C(=O)NR$^a$—, —C(=O)O— or —OC(=O)—.

In another embodiment, in conjunction with any of the above or below embodiments, $R^{23}$ is —O—, —N(R$^a$)—, —N(R$^a$)C(=O)—, —C(=O)NR$^a$—, —C(=O)O— or —OC(=O)—.

Embodiment T: In another embodiment, in conjunction with any of the above or below embodiments, $R^{24}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{24}$ is phenyl.

In another embodiment, in conjunction with any of the above or below embodiments, $R^{24}$ is naphthyl.

In another embodiment, in conjunction with any of the above or below embodiments, $R^{24}$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{24}$ is independently at each instance a saturated or unsaturated 5-, 6- or 7-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{24}$ is independently at each instance a saturated 5- or 6-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{24}$ is independently at each instance a saturated 5- or 6-membered monocyclic ring containing 1 or 2 N atoms, wherein the carbon atoms of the ring are substituted by 0 or 1 oxo groups.

In another embodiment, in conjunction with any of the above or below embodiments, $R^{24}$ is piperidinyl, piperazinyl or pyrrolidinyl.

In another embodiment, in conjunction with any of the above or below embodiments, $R^{31}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{31}$ is independently at each instance an unsaturated 5- or 6-membered monocyclic or 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{31}$ is independently at each instance an unsaturated 9- or 10-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{31}$ is independently at each instance an unsaturated 5- or 6-membered monocyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{31}$ is independently at each instance an unsaturated 5-membered monocyclic ring containing 1 atom selected from N, O and S.

In another embodiment, in conjunction with any of the above or below embodiments, $R^{31}$ is independently at each instance an unsaturated 6-membered monocyclic ring containing 0, 1 or 2 N atoms.

Embodiment U: In another embodiment, in conjunction with any of the above or below embodiments, $R^{31}$ is phenyl.

Embodiment V: In another embodiment, in conjunction with any of the above or below embodiments, $R^{31}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{31}$ is independently at each instance an unsaturated 6-membered monocyclic ring containing 1 or 2 N atoms.

In another embodiment, in conjunction with any of the above or below embodiments, $R^{31}$ is pyridinyl, pyrimidinyl or pyridazinyl.

In another embodiment, in conjunction with any of the above or below embodiments, $R^{32}$ is independently at each instance $C_{1-8}$alkyl.

In another embodiment, in conjunction with any of the above or below embodiments, $R^{32}$ is independently at each instance $C_{1-4}$alkyl.

In another embodiment, in conjunction with any of the above or below embodiments, $R^{32}$ is independently at each instance $C_{2-4}$alkyl.

Embodiment W: In another embodiment, in conjunction with any of the above or below embodiments, $R^{33}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkalkyNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{33}$ is independently at each instance —C(=O)—, —C(=O)O—, —C(=O)NR$^a$—, —C(=NR$^a$)NR$^a$—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{33}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)C(=O)—, —N(R$^a$)C(=O)O—, —N(R$^a$)C(=O)N(R$^a$)—, —N(R$^a$)C(=NR$_a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—.

In another embodiment, in conjunction with any of the above or below embodiments, $R^{33}$ is —O—.

In another embodiment, in conjunction with any of the above or below embodiments, $R^{33}$ is —N(R$^a$)—.

In another embodiment, in conjunction with any of the above or below embodiments, $R^{33}$ is —N(R$^a$)C(=O)—, —C(=O)NR$^a$—, —C(=O)O— or —OC(=O)—.

In another embodiment, in conjunction with any of the above or below embodiments, $R^{33}$ is —O—, —N(R$^a$)—, —N(R$^a$)C(=O)—, —C(=O)NR$^a$—, —C(=O)O— or —OC(=O)—.

Embodiment X: In another embodiment, in conjunction with any of the above or below embodiments, $R^{34}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{34}$ is phenyl.

In another embodiment, in conjunction with any of the above or below embodiments, $R^{34}$ is naphthyl.

In another embodiment, in conjunction with any of the above or below embodiments, $R^{34}$ is independently at each instance a saturated or unsaturated 5-, 6- or 7-membered monocyclic or 6-, 7-, 8-, 9-, 10- or 11-membered bicyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{34}$ is independently at each instance a saturated or unsaturated 5-, 6- or 7-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{34}$ is independently at each instance a saturated 5- or 6-membered monocyclic ring containing 1, 2, 3 or 4 atoms selected from N, O and S, so long as the combination of O and S atoms is not greater than 2, wherein the carbon atoms of the ring are substituted by 0, 1 or 2 oxo groups.

In another embodiment, in conjunction with any of the above or below embodiments, $R^{34}$ is independently at each instance a saturated 5- or 6-membered monocyclic ring containing 1 or 2 N atoms, wherein the carbon atoms of the ring are substituted by 0 or 1 oxo groups.

In another embodiment, in conjunction with any of the above or below embodiments, $R^{34}$ is piperidinyl, piperazinyl or pyrrolidinyl.

In yet another embodiment, the invention relates to a compound of Formula I

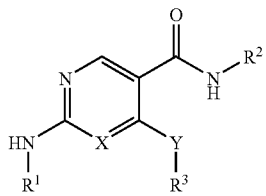

I or a pharmaceutically-acceptable salt thereof, wherein

X is N;

Y is O;

$R^1$ is selected from $-R^{11}$, $-R^{11}-R^{12}$, $-R^{11}-R^{14}$, $-R^{12}-R^{14}$, $-R^{11}-R^{12}-R^{14}$, $-R^{11}-R^{13}-R^{14}$, $-R^{12}-R^{13}-R^{14}$, $-R^{11}-R^{13}-R^{12}-R^{14}$ and $-R^{11}-R^{12}-R^{13}-R^{14}$, any of which is substituted by 0, 1, 2, 3 or 4 substituents independently selected from $R^c$;

$R^2$ is selected from $-R^{21}$ substituted by 0, 1, 2, 3 or 4 substituents independently selected from $R^c$;

$R^3$ is selected from $-R^{31}$, $-R^{31}-R^{32}$, $-R^{31}-R^{34}$, $-R^{32}-R^{34}$, $-R^{31}-R^{32}-R^{34}$, $-R^{31}-R^{33}-R^{34}$, $-R^{32}-R^{33}-R^{34}$, $-R^{31}-R^{33}-R^{32}-R^{34}$ and $-R^{31}-R^{32}-R^{33}-R^{34}$, any of which is substituted by 0, 1, 2, 3 or 4 substituents independently selected from $R^c$;

$R^{11}$ is independently at each instance a saturated or unsaturated 5-, 6- or 7-membered monocyclic ring containing 0, 1, 2, 3 or 4 atoms selected from N, O and S;

$R^{12}$ is independently at each instance $C_{1-8}$alkyl;

$R^{13}$ is independently at each instance $-C(=O)-$, $-C(=O)NR^a-$, $-C(=NR^a)NR^a-$, $-O-$, $-OC_{2-6}$alkyl$NR^a-$, $-OC_{2-6}$alkylO$-$, $-S-$, $-S(=O)-$, $-S(=O)_2-$, $-S(=O)_2NR^a-$, $-N(R^a)-$, $-N(R^a)C(=O)-$, $-N(R^a)C(=O)N(R^a)-$, $-N(R^a)C(=NR^a)N(R^a)-$, $-N(R^a)S(=O)_2-$, $-N(R^a)S(=O)_2N(R^a)-$, $-NR^aC_{2-6}$alkyl$N(R^a)-$ or $-NR^aC_{2-6}$alkylO$-$;

$R^{14}$ is independently at each instance a saturated or unsaturated 5-, 6- or 7-membered monocyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{21}$ is phenyl;

$R^{31}$ is independently at each instance a saturated or unsaturated 5-, 6- or 7-membered monocyclic ring containing 0, 1, 2, 3 or 4 atoms selected from N, O and S;

$R^{32}$ is independently at each instance $C_{1-8}$alkyl;

$R^{33}$ is independently at each instance $-C(=O)-$, $-C(=O)NR^a-$, $-C(=NR^a)NR^a-$, $-O-$, $-OC_{2-6}$alkyl$NR^a-$, $-OC_{2-6}$alkylO$-$, $-S-$, $-S(=O)-$, $-S(=O)_2-$, $-S(=O)_2NR^a-$, $-S(=O)_2N(R^a)C(=O)O-$, $-S(=O)_2N(R^a)C(=O)NR^a-$, $-N(R^a)-$, $-N(R^a)C(=O)-$, $-N(R^a)C(=O)N(R^a)-$, $-N(R^a)C(=NR^a)N(R^a)-$, $-N(R^a)S(=O)_2-$, $-N(R^a)S(=O)_2N(R^a)-$, $-NR^aC_{2-6}$alkyl$N(R^a)-$ or $-NR^aC_{2-6}$alkylO$-$;

$R^{34}$ is independently at each instance a saturated or unsaturated 5-, 6- or 7-membered monocyclic ring containing 0, 1, 2, 3 or 4 atoms selected from N, O and S;

$R^a$ is independently at each instance H or $R^b$;

$R^b$ is independently at each instance $C_{1-8}$alkyl, phenyl or benzyl; and $R^c$ is independently at each instance $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}$alkyl$NR^aR^a$, $-OC_{2-6}$alkyl$OR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkyl$NR^aR^a$ or $-NR^aC_{2-6}$alkyl$OR^a$.

As stated above, the above embodiments may be used in conjuction with other embodiments listed. The following table is a non-exclusive, non-limiting list of the combinations of embodiments. For the structure

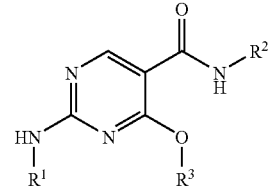

wherein $R^{12}$, $R^{22}$ and $R^{32}$ are independently selected from $C_{1-4}$alkyl; $R^{13}$, $R^{23}$ and $R^{33}$ are independently selected from Embodiments O, S and W, respectively; and $R^{14}$, $R^{24}$ and $R^{34}$ are independently selected from Embodiments P, T and X, respectively.

| No. | $R^1$ | $R^{11}$ | $R^2$ | $R^{21}$ | $R^3$ | $R^{31}$ | No. | $R^1$ | $R^{11}$ | $R^2$ | $R^{21}$ | $R^3$ | $R^{31}$ |
|---|---|---|---|---|---|---|---|---|---|---|---|---|---|
| 1001 | A | M | E | Q | H | U | 1078 | A | N | E | R | K | V |
| 1002 | A | M | E | Q | H | V | 1079 | A | N | E | R | L | U |
| 1003 | A | M | E | Q | I | U | 1080 | A | N | E | R | L | V |
| 1004 | A | M | E | Q | I | V | 1081 | A | N | F | Q | H | U |
| 1005 | A | M | E | Q | J | U | 1082 | A | N | F | Q | H | V |
| 1006 | A | M | E | Q | J | V | 1083 | A | N | F | Q | I | U |
| 1007 | A | M | E | Q | K | U | 1084 | A | N | F | Q | I | V |
| 1008 | A | M | E | Q | K | V | 1085 | A | N | F | Q | J | U |
| 1009 | A | M | E | Q | L | U | 1086 | A | N | F | Q | J | V |
| 1010 | A | M | E | Q | L | V | 1087 | A | N | F | Q | K | U |
| 1011 | A | M | E | R | H | U | 1088 | A | N | F | Q | K | V |
| 1012 | A | M | E | R | H | V | 1089 | A | N | F | Q | L | U |
| 1013 | A | M | E | R | I | U | 1090 | A | N | F | Q | L | V |
| 1014 | A | M | E | R | I | V | 1091 | A | N | F | R | H | U |
| 1015 | A | M | E | R | J | U | 1092 | A | N | F | R | H | V |
| 1016 | A | M | E | R | J | V | 1093 | A | N | F | R | I | U |
| 1017 | A | M | E | R | K | U | 1094 | A | N | F | R | I | V |
| 1018 | A | M | E | R | K | V | 1095 | A | N | F | R | J | U |
| 1019 | A | M | E | R | L | U | 1096 | A | N | F | R | J | V |
| 1020 | A | M | E | R | L | V | 1097 | A | N | F | R | K | U |
| 1021 | A | M | F | Q | H | U | 1098 | A | N | F | R | K | V |
| 1022 | A | M | F | Q | H | V | 1099 | A | N | F | R | L | U |
| 1023 | A | M | F | Q | I | U | 1100 | A | N | F | R | L | V |
| 1024 | A | M | F | Q | I | V | 1101 | A | N | G | Q | H | U |
| 1025 | A | M | F | Q | J | U | 1102 | A | N | G | Q | H | V |
| 1026 | A | M | F | Q | J | V | 1103 | A | N | G | Q | I | U |
| 1027 | A | M | F | Q | K | U | 1104 | A | N | G | Q | I | V |
| 1028 | A | M | F | Q | K | V | 1105 | A | N | G | Q | J | U |
| 1029 | A | M | F | Q | L | U | 1106 | A | N | G | Q | J | V |
| 1030 | A | M | F | Q | L | V | 1107 | A | N | G | Q | K | U |
| 1031 | A | M | F | R | H | U | 1108 | A | N | G | Q | K | V |
| 1032 | A | M | F | R | H | V | 1109 | A | N | G | Q | L | U |
| 1033 | A | M | F | R | I | U | 1110 | A | N | G | Q | L | V |
| 1034 | A | M | F | R | I | V | 1111 | A | N | G | R | H | U |
| 1035 | A | M | F | R | J | U | 1112 | A | N | G | R | H | V |
| 1036 | A | M | F | R | J | V | 1113 | A | N | G | R | I | U |
| 1037 | A | M | F | R | K | U | 1114 | A | N | G | R | I | V |
| 1038 | A | M | F | R | K | V | 1115 | A | N | G | R | J | U |
| 1039 | A | M | F | R | L | U | 1116 | A | N | G | R | J | V |
| 1040 | A | M | F | R | L | V | 1117 | A | N | G | R | K | U |
| 1041 | A | M | G | Q | H | U | 1118 | A | N | G | R | K | V |
| 1042 | A | M | G | Q | H | V | 1119 | A | N | G | R | L | U |
| 1043 | A | M | G | Q | I | U | 1120 | A | N | G | R | L | V |
| 1044 | A | M | G | Q | I | V | 1121 | B | M | E | Q | H | U |
| 1045 | A | M | G | Q | J | U | 1122 | B | M | E | Q | H | V |
| 1046 | A | M | G | Q | J | V | 1123 | B | M | E | Q | I | U |
| 1047 | A | M | G | Q | K | U | 1124 | B | M | E | Q | I | V |
| 1048 | A | M | G | Q | K | V | 1125 | B | M | E | Q | J | U |
| 1049 | A | M | G | Q | L | U | 1126 | B | M | E | Q | J | V |
| 1050 | A | M | G | Q | L | V | 1127 | B | M | E | Q | K | U |
| 1051 | A | M | G | R | H | U | 1128 | B | M | E | Q | K | V |
| 1052 | A | M | G | R | H | V | 1129 | B | M | E | Q | L | U |
| 1053 | A | M | G | R | I | U | 1130 | B | M | E | Q | L | V |
| 1054 | A | M | G | R | I | V | 1131 | B | M | E | R | H | U |
| 1055 | A | M | G | R | J | U | 1132 | B | M | E | R | H | V |
| 1056 | A | M | G | R | J | V | 1133 | B | M | E | R | I | U |
| 1057 | A | M | G | R | K | U | 1134 | B | M | E | R | I | V |
| 1058 | A | M | G | R | K | V | 1135 | B | M | E | R | J | U |
| 1059 | A | M | G | R | L | U | 1136 | B | M | E | R | J | V |
| 1060 | A | M | G | R | L | V | 1137 | B | M | E | R | K | U |
| 1061 | A | N | E | Q | H | U | 1138 | B | M | E | R | K | V |
| 1062 | A | N | E | Q | H | V | 1139 | B | M | E | R | L | U |
| 1063 | A | N | E | Q | I | U | 1140 | B | M | E | R | L | V |
| 1064 | A | N | E | Q | I | V | 1141 | B | M | F | Q | H | U |
| 1065 | A | N | E | Q | J | U | 1142 | B | M | F | Q | H | V |
| 1066 | A | N | E | Q | J | V | 1143 | B | M | F | Q | I | U |
| 1067 | A | N | E | Q | K | U | 1144 | B | M | F | Q | I | V |
| 1068 | A | N | E | Q | K | V | 1145 | B | M | F | Q | J | U |
| 1069 | A | N | E | Q | L | U | 1146 | B | M | F | Q | J | V |
| 1070 | A | N | E | Q | L | V | 1147 | B | M | F | Q | K | U |
| 1071 | A | N | E | R | H | U | 1148 | B | M | F | Q | K | V |
| 1072 | A | N | E | R | H | V | 1149 | B | M | F | Q | L | U |
| 1073 | A | N | E | R | I | U | 1150 | B | M | F | Q | L | V |
| 1074 | A | N | E | R | I | V | 1151 | B | M | F | R | H | U |
| 1075 | A | N | E | R | J | U | 1152 | B | M | F | R | H | V |
| 1076 | A | N | E | R | J | V | 1153 | B | M | F | R | I | U |
| 1077 | A | N | E | R | K | U | 1154 | B | M | F | R | I | V |

| No. | R¹ | R¹¹ | R² | R²¹ | R³ | R³¹ |
|---|---|---|---|---|---|---|
| 1155 | B | M | F | R | J | U |
| 1156 | B | M | F | R | J | V |
| 1157 | B | M | F | R | K | U |
| 1158 | B | M | F | R | K | V |
| 1159 | B | M | F | R | L | U |
| 1160 | B | M | F | R | L | V |
| 1161 | B | M | G | Q | H | U |
| 1162 | B | M | G | Q | H | V |
| 1163 | B | M | G | Q | I | U |
| 1164 | B | M | G | Q | I | V |
| 1165 | B | M | G | Q | J | U |
| 1166 | B | M | G | Q | J | V |
| 1167 | B | M | G | Q | K | U |
| 1168 | B | M | G | Q | K | V |
| 1169 | B | M | G | Q | L | U |
| 1170 | B | M | G | Q | L | V |
| 1171 | B | M | G | R | H | U |
| 1172 | B | M | G | R | H | V |
| 1173 | B | M | G | R | I | U |
| 1174 | B | M | G | R | I | V |
| 1175 | B | M | G | R | J | U |
| 1176 | B | M | G | R | J | V |
| 1177 | B | M | G | R | K | U |
| 1178 | B | M | G | R | K | V |
| 1179 | B | M | G | R | L | U |
| 1180 | B | M | G | R | L | V |
| 1181 | B | N | E | Q | H | U |
| 1182 | B | N | E | Q | H | V |
| 1183 | B | N | E | Q | I | U |
| 1184 | B | N | E | Q | I | V |
| 1185 | B | N | E | Q | J | U |
| 1186 | B | N | E | Q | J | V |
| 1187 | B | N | E | Q | K | U |
| 1188 | B | N | E | Q | K | V |
| 1189 | B | N | E | Q | L | U |
| 1190 | B | N | E | Q | L | V |
| 1191 | B | N | E | R | H | U |
| 1192 | B | N | E | R | H | V |
| 1193 | B | N | E | R | I | U |
| 1194 | B | N | E | R | I | V |
| 1195 | B | N | E | R | J | U |
| 1196 | B | N | E | R | J | V |
| 1197 | B | N | E | R | K | U |
| 1198 | B | N | E | R | K | V |
| 1199 | B | N | E | R | L | U |
| 1200 | B | N | E | R | L | V |
| 1201 | B | N | F | Q | H | U |
| 1202 | B | N | F | Q | H | V |
| 1203 | B | N | F | Q | I | U |
| 1204 | B | N | F | Q | I | V |
| 1205 | B | N | F | Q | J | U |
| 1206 | B | N | F | Q | J | V |
| 1207 | B | N | F | Q | K | U |
| 1208 | B | N | F | Q | K | V |
| 1209 | B | N | F | Q | L | U |
| 1210 | B | N | F | Q | L | V |
| 1211 | B | N | F | R | H | U |
| 1212 | B | N | F | R | H | V |
| 1213 | B | N | F | R | I | U |
| 1214 | B | N | F | R | I | V |
| 1215 | B | N | F | R | J | U |
| 1216 | B | N | F | R | J | V |
| 1217 | B | N | F | R | K | U |
| 1218 | B | N | F | R | K | V |
| 1219 | B | N | F | R | L | U |
| 1220 | B | N | F | R | L | V |
| 1221 | B | N | G | Q | H | U |
| 1222 | B | N | G | Q | H | V |
| 1223 | B | N | G | Q | I | U |
| 1224 | B | N | G | Q | I | V |
| 1225 | B | N | G | Q | J | U |
| 1226 | B | N | G | Q | J | V |
| 1227 | B | N | G | Q | K | U |
| 1228 | B | N | G | Q | K | V |
| 1229 | B | N | G | Q | L | U |
| 1230 | B | N | G | Q | L | V |
| 1231 | B | N | G | R | H | U |
| 1232 | B | N | G | R | H | V |
| 1233 | B | N | G | R | I | U |
| 1234 | B | N | G | R | I | V |
| 1235 | B | N | G | R | J | U |
| 1236 | B | N | G | R | J | V |
| 1237 | B | N | G | R | K | U |
| 1238 | B | N | G | R | K | V |
| 1239 | B | N | G | R | L | U |
| 1240 | B | N | G | R | L | V |
| 1241 | C | M | E | Q | H | U |
| 1242 | C | M | E | Q | H | V |
| 1243 | C | M | E | Q | I | U |
| 1244 | C | M | E | Q | I | V |
| 1245 | C | M | E | Q | J | U |
| 1246 | C | M | E | Q | J | V |
| 1247 | C | M | E | Q | K | U |
| 1248 | C | M | E | Q | K | V |
| 1249 | C | M | E | Q | L | U |
| 1250 | C | M | E | Q | L | V |
| 1251 | C | M | E | R | H | U |
| 1252 | C | M | E | R | H | V |
| 1253 | C | M | E | R | I | U |
| 1254 | C | M | E | R | I | V |
| 1255 | C | M | E | R | J | U |
| 1256 | C | M | E | R | J | V |
| 1257 | C | M | E | R | K | U |
| 1258 | C | M | E | R | K | V |
| 1259 | C | M | E | R | L | U |
| 1260 | C | M | E | R | L | V |
| 1261 | C | M | F | Q | H | U |
| 1262 | C | M | F | Q | H | V |
| 1263 | C | M | F | Q | I | U |
| 1264 | C | M | F | Q | I | V |
| 1265 | C | M | F | Q | J | U |
| 1266 | C | M | F | Q | J | V |
| 1267 | C | M | F | Q | K | U |
| 1268 | C | M | F | Q | K | V |
| 1269 | C | M | F | Q | L | U |
| 1270 | C | M | F | Q | L | V |
| 1271 | C | M | F | R | H | U |
| 1272 | C | M | F | R | H | V |
| 1273 | C | M | F | R | I | U |
| 1274 | C | M | F | R | I | V |
| 1275 | C | M | F | R | J | U |
| 1276 | C | M | F | R | J | V |
| 1277 | C | M | F | R | K | U |
| 1278 | C | M | F | R | K | V |
| 1279 | C | M | F | R | L | U |
| 1280 | C | M | F | R | L | V |
| 1281 | C | M | G | Q | H | U |
| 1282 | C | M | G | Q | H | V |
| 1283 | C | M | G | Q | I | U |
| 1284 | C | M | G | Q | I | V |
| 1285 | C | M | G | Q | J | U |
| 1286 | C | M | G | Q | J | V |
| 1287 | C | M | G | Q | K | U |
| 1288 | C | M | G | Q | K | V |
| 1289 | C | M | G | Q | L | U |
| 1290 | C | M | G | Q | L | V |
| 1291 | C | M | G | R | H | U |
| 1292 | C | M | G | R | H | V |
| 1293 | C | M | G | R | I | U |
| 1294 | C | M | G | R | I | V |
| 1295 | C | M | G | R | J | U |
| 1296 | C | M | G | R | J | V |
| 1297 | C | M | G | R | K | U |
| 1298 | C | M | G | R | K | V |
| 1299 | C | M | G | R | L | U |
| 1300 | C | M | G | R | L | V |
| 1301 | C | N | E | Q | H | U |
| 1302 | C | N | E | Q | H | V |
| 1303 | C | N | E | Q | I | U |
| 1304 | C | N | E | Q | I | V |
| 1305 | C | N | E | Q | J | U |
| 1306 | C | N | E | Q | J | V |
| 1307 | C | N | E | Q | K | U |
| 1308 | C | N | E | Q | K | V |

| No. | R$^1$ | R$^{11}$ | R$^2$ | R$^{21}$ | R$^3$ | R$^{31}$ |
|---|---|---|---|---|---|---|
| 1309 | C | N | E | Q | L | U |
| 1310 | C | N | E | Q | L | V |
| 1311 | C | N | E | R | H | U |
| 1312 | C | N | E | R | H | V |
| 1313 | C | N | E | R | I | U |
| 1314 | C | N | E | R | I | V |
| 1315 | C | N | E | R | J | U |
| 1316 | C | N | E | R | J | V |
| 1317 | C | N | E | R | K | U |
| 1318 | C | N | E | R | K | V |
| 1319 | C | N | E | R | L | U |
| 1320 | C | N | E | R | L | V |
| 1321 | C | N | F | Q | H | U |
| 1322 | C | N | F | Q | H | V |
| 1323 | C | N | F | Q | I | U |
| 1324 | C | N | F | Q | I | V |
| 1325 | C | N | F | Q | J | U |
| 1326 | C | N | F | Q | J | V |
| 1327 | C | N | F | Q | K | U |
| 1328 | C | N | F | Q | K | V |
| 1329 | C | N | F | Q | L | U |
| 1330 | C | N | F | Q | L | V |
| 1331 | C | N | F | R | H | U |
| 1332 | C | N | F | R | H | V |
| 1333 | C | N | F | R | I | U |
| 1334 | C | N | F | R | I | V |
| 1335 | C | N | F | R | J | U |
| 1336 | C | N | F | R | J | V |
| 1337 | C | N | F | R | K | U |
| 1338 | C | N | F | R | K | V |
| 1339 | C | N | F | R | L | U |
| 1340 | C | N | F | R | L | V |
| 1341 | C | N | G | Q | H | U |
| 1342 | C | N | G | Q | H | V |
| 1343 | C | N | G | Q | I | U |
| 1344 | C | N | G | Q | I | V |
| 1345 | C | N | G | Q | J | U |
| 1346 | C | N | G | Q | J | V |
| 1347 | C | N | G | Q | K | U |
| 1348 | C | N | G | Q | K | V |
| 1349 | C | N | G | Q | L | U |
| 1350 | C | N | G | Q | L | V |
| 1351 | C | N | G | R | H | U |
| 1352 | C | N | G | R | H | V |
| 1353 | C | N | G | R | I | U |
| 1354 | C | N | G | R | I | V |
| 1355 | C | N | G | R | J | U |
| 1356 | C | N | G | R | J | V |
| 1357 | C | N | G | R | K | U |
| 1358 | C | N | G | R | K | V |
| 1359 | C | N | G | R | L | U |
| 1360 | C | N | G | R | L | V |
| 1361 | D | M | E | Q | H | U |
| 1362 | D | M | E | Q | H | V |
| 1363 | D | M | E | Q | I | U |
| 1364 | D | M | E | Q | I | V |
| 1365 | D | M | E | Q | J | U |
| 1366 | D | M | E | Q | J | V |
| 1367 | D | M | E | Q | K | U |
| 1368 | D | M | E | Q | K | V |
| 1369 | D | M | E | Q | L | U |
| 1370 | D | M | E | Q | L | V |
| 1371 | D | M | E | R | H | U |
| 1372 | D | M | E | R | H | V |
| 1373 | D | M | E | R | I | U |
| 1374 | D | M | E | R | I | V |
| 1375 | D | M | E | R | J | U |
| 1376 | D | M | E | R | J | V |
| 1377 | D | M | E | R | K | U |
| 1378 | D | M | E | R | K | V |
| 1379 | D | M | E | R | L | U |
| 1380 | D | M | E | R | L | V |
| 1381 | D | M | F | Q | H | U |
| 1382 | D | M | F | Q | H | V |
| 1383 | D | M | F | Q | I | U |
| 1384 | D | M | F | Q | I | V |
| 1385 | D | M | F | Q | J | U |
| 1386 | D | M | F | Q | J | V |
| 1387 | D | M | F | Q | K | U |
| 1388 | D | M | F | Q | K | V |
| 1389 | D | M | F | Q | L | U |
| 1390 | D | M | F | Q | L | V |
| 1391 | D | M | F | R | H | U |
| 1392 | D | M | F | R | H | V |
| 1393 | D | M | F | R | I | U |
| 1394 | D | M | F | R | I | V |
| 1395 | D | M | F | R | J | U |
| 1396 | D | M | F | R | J | V |
| 1397 | D | M | F | R | K | U |
| 1398 | D | M | F | R | K | V |
| 1399 | D | M | F | R | L | U |
| 1400 | D | M | F | R | L | V |
| 1401 | D | M | G | Q | H | U |
| 1402 | D | M | G | Q | H | V |
| 1403 | D | M | G | Q | I | U |
| 1404 | D | M | G | Q | I | V |
| 1405 | D | M | G | Q | J | U |
| 1406 | D | M | G | Q | J | V |
| 1407 | D | M | G | Q | K | U |
| 1408 | D | M | G | Q | K | V |
| 1409 | D | M | G | Q | L | U |
| 1410 | D | M | G | Q | L | V |
| 1411 | D | M | G | R | H | U |
| 1412 | D | M | G | R | H | V |
| 1413 | D | M | G | R | I | U |
| 1414 | D | M | G | R | I | V |
| 1415 | D | M | G | R | J | U |
| 1416 | D | M | G | R | J | V |
| 1417 | D | M | G | R | K | U |
| 1418 | D | M | G | R | K | V |
| 1419 | D | M | G | R | L | U |
| 1420 | D | M | G | R | L | V |
| 1421 | D | N | E | Q | H | U |
| 1422 | D | N | E | Q | H | V |
| 1423 | D | N | E | Q | I | U |
| 1424 | D | N | E | Q | I | V |
| 1425 | D | N | E | Q | J | U |
| 1426 | D | N | E | Q | J | V |
| 1427 | D | N | E | Q | K | U |
| 1428 | D | N | E | Q | K | V |
| 1429 | D | N | E | Q | L | U |
| 1430 | D | N | E | Q | L | V |
| 1431 | D | N | E | R | H | U |
| 1432 | D | N | E | R | H | V |
| 1433 | D | N | E | R | I | U |
| 1434 | D | N | E | R | I | V |
| 1435 | D | N | E | R | J | U |
| 1436 | D | N | E | R | J | V |
| 1437 | D | N | E | R | K | U |
| 1438 | D | N | E | R | K | V |
| 1439 | D | N | E | R | L | U |
| 1440 | D | N | E | R | L | V |
| 1441 | D | N | F | Q | H | U |
| 1442 | D | N | F | Q | H | V |
| 1443 | D | N | F | Q | I | U |
| 1444 | D | N | F | Q | I | V |
| 1445 | D | N | F | Q | J | U |
| 1446 | D | N | F | Q | J | V |
| 1447 | D | N | F | Q | K | U |
| 1448 | D | N | F | Q | K | V |
| 1449 | D | N | F | Q | L | U |
| 1450 | D | N | F | Q | L | V |
| 1451 | D | N | F | R | H | U |
| 1452 | D | N | F | R | H | V |
| 1453 | D | N | F | R | I | U |
| 1454 | D | N | F | R | I | V |
| 1455 | D | N | F | R | J | U |
| 1456 | D | N | F | R | J | V |
| 1457 | D | N | F | R | K | U |
| 1458 | D | N | F | R | K | V |
| 1459 | D | N | F | R | L | U |
| 1460 | D | N | F | R | L | V |
| 1461 | D | N | G | Q | H | U |
| 1462 | D | N | G | Q | H | V |

-continued

| No. | R¹ | R¹¹ | R² | R²¹ | R³ | R³¹ |
|---|---|---|---|---|---|---|
| 1463 | D | N | G | Q | I | U |
| 1464 | D | N | G | Q | I | V |
| 1465 | D | N | G | Q | J | U |
| 1466 | D | N | G | Q | J | V |
| 1467 | D | N | G | Q | K | U |
| 1468 | D | N | G | Q | K | V |
| 1469 | D | N | G | Q | L | U |
| 1470 | D | N | G | Q | L | V |
| 1471 | D | N | G | R | H | U |
| 1472 | D | N | G | R | H | V |
| 1473 | D | N | G | R | I | U |
| 1474 | D | N | G | R | I | V |
| 1475 | D | N | G | R | J | U |
| 1476 | D | N | G | R | J | V |
| 1477 | D | N | G | R | K | U |
| 1478 | D | N | G | R | K | V |
| 1479 | D | N | G | R | L | U |
| 1480 | D | N | G | R | L | V |

Another aspect of the invention relates to a pharmaceutical composition comprising a compound according to any one of the above embodiments and a pharmaceutically acceptable carrier.

Another aspect of the invention relates to a method of treatment of inflammation comprising administering a therapeutically-effective amount of a compound according to any one of the above embodiments.

Another aspect of the invention relates to a method of inhibition of T cell activation and proliferation in a mammal in need thereof, comprising administering a therapeutically-effective amount of a compound according to any one of the above embodiments.

Another aspect of the invention relates to a method of treatment of arthritis, rheumatoid arthritis, psoriatic arthritis, or osteoarthritis in a mammal comprising administering a therapeutically-effective amount of a compound according to any one of the above embodiments.

Another aspect of the invention relates to a method of treatment of organ transplant, acute transplant or heterograft or homograft rejection, or transplantation tolerance induction in a mammal comprising administering a therapeutically-effective amount of a compound according to any one of the above embodiments.

Another aspect of the invention relates to a method of treatment of ischemic or reperfusion injury, myocardial infarction, or stroke in a mammal in need thereof, comprising administering a therapeutically-effective amount of a compound according to any one of the above embodiments.

Another aspect of the invention relates to a method of treatment of multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal comprising administering a therapeutically-effective amount of a compound according to any one of the above embodiments.

Another aspect of the invention relates to a method of treatment of colon carcinoma or thymoma in a mammal comprising administering a therapeutically-effective amount of a compound according to any one of the above embodiments.

Another aspect of the invention relates to the manufacture of a medicament comprising a compound according to any one of the above embodiments.

Another aspect of the invention relates to the manufacture of a medicament for the treatment of inflammation comprising a therapeutically-effective amount of a compound according to any one of the above embodiments.

Another aspect of the invention relates to the manufacture of a medicament for the inhibition of T cell activation and proliferation in a mammal in need thereof, comprising a therapeutically-effective amount of a compound according to any one of the above embodiments.

Another aspect of the invention relates to the manufacture of a medicament for the treatment of arthritis, rheumatoid arthritis, psoriatic arthritis, or osteoarthritis in a mammal comprising a therapeutically-effective amount of a compound according to any one of the above embodiments.

Another aspect of the invention relates to the manufacture of a medicament for the treatment of organ transplant, acute transplant or heterograft or homograft rejection, or transplantation tolerance induction in a mammal comprising a therapeutically-effective amount of a compound according to any one of the above embodiments.

Another aspect of the invention relates to the manufacture of a medicament for the treatment of ischemic or reperfusion injury, myocardial infarction, or stroke in a mammal in need thereof, comprising a therapeutically-effective amount of a compound according to any one of the above embodiments.

Another aspect of the invention relates to the manufacture of a medicament for the treatment of multiple sclerosis, inflammatory bowel disease, including ulcerative colitis, Crohn's disease, lupus, contact hypersensitivity, delayed-type hypersensitivity, and gluten-sensitive enteropathy, type 1 diabetes, psoriasis, contact dermatitis, Hashimoto's thyroiditis, Sjogren's syndrome, autoimmune hyperthyroidism, Addison's disease, autoimmune polyglandular disease, autoimmune alopecia, pernicious anemia, vitiligo, autoimmune hypopituatarism, Guillain-Barre syndrome, glomerulonephritis, serum sickness, uticaria, allergic diseases, asthma, hayfever, allergic rhinitis, scleracielma, mycosis fungoides, dermatomyositis, alopecia areata, chronic actinic dermatitis, eczema, Behcet's disease, Pustulosis palmoplanteris, Pyoderma gangrenum, Sezary's syndrome, atopic dermatitis, systemic schlerosis, morphea or atopic dermatitis in a mammal comprising a therapeutically-effective amount of a compound according to any one of the above embodiments.

Another aspect of the invention relates to the manufacture of a medicament for the treatment of colon carcinoma or thymoma in a mammal comprising a therapeutically-effective amount of a compound according to any one of the above embodiments.

Another aspect of the invention relates to a method of making a compound as described herein, comprising the steps of:

chloronating a compound having the structure

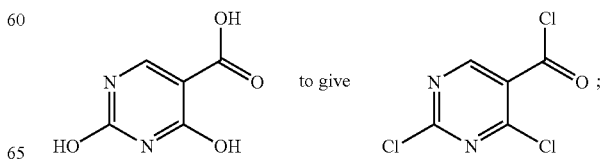

reacting the chloronated compound with R²NH₂ to give

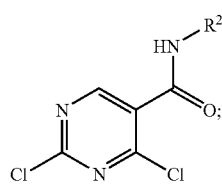

reacting the formed amide with R³OH to give

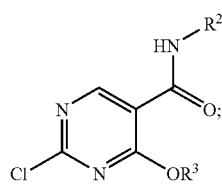

and
reacting the formed ether with R¹NH₂ to give

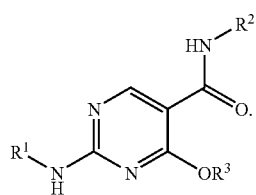

The compounds of this invention may have in general several asymmetric centers and are typically depicted in the form of racemic mixtures. This invention is intended to encompass racemic mixtures, partially racemic mixtures and separate enantiomers and diasteromers.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups from the genus.

Unless otherwise specified, the following definitions apply to terms found in the specification and claims:

"Aryl" means a phenyl or naphthyl radical, wherein the phenyl may be fused with a $C_{3-4}$cycloalkyl bridge.

"Benzo group", alone or in combination, means the divalent radical $C_4H_4$═, one representation of which is —CH═CH—CH═CH—, that when vicinally attached to another ring forms a benzene-like ring—for example tetrahydronaphthylene, indole and the like.

"$C_{\alpha-\beta}$alkyl" means an alkyl group comprising from α to β carbon atoms in a branched, cyclical or linear relationship or any combination of the three. The alkyl groups described in this section may also contain double or triple bonds. Examples of $C_{1-8}$alkyl include, but are not limited to, the following:

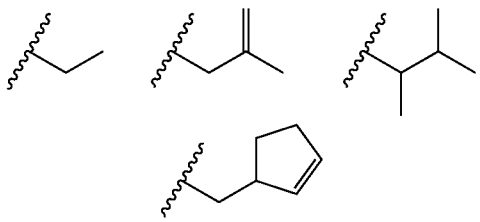

"Halogen" and "halo" mean a halogen atoms selected from F, Cl, Br and I.

"$C_{\alpha-\beta}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

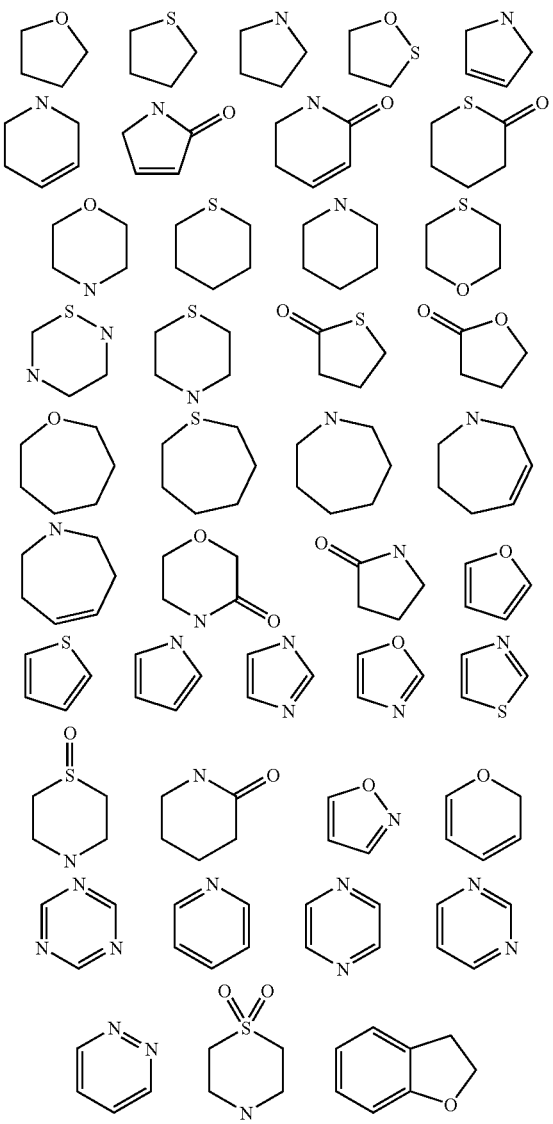

-continued

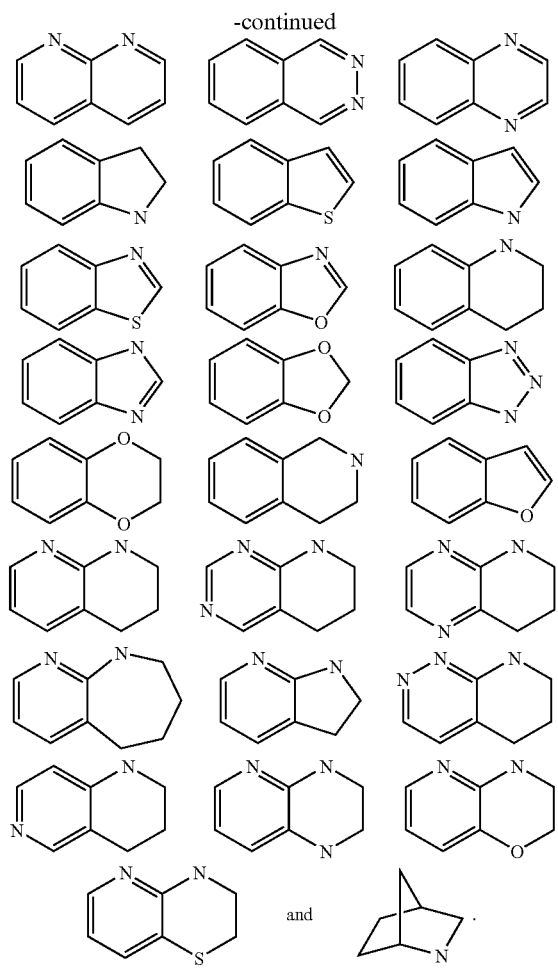

"Saturated or unsaturated" means a substitutent that is completely saturated, completely unsaturated, or has any degree of unsaturation in between. Examples of a saturated or unsaturated 6-membered ring carbocycle would include phenyl, cyclohexyl, cyclohexenyl and cyclohexadienyl.

Substituents, including rings and alkyl groups, may be either monovalent or polyvalent depending on the context of their usage. For example, if description contained the group $R^\alpha$—$R^\beta$—$R^\gamma$ and $R^\beta$ was defined as $C_{1-6}$alkyl, then the $R^\beta$ alkyl would be considered polyvalent because it must be bonded to at least $R^\alpha$ and $R^\gamma$. Alternatively, if $R^\gamma$ was defined as $C_{1-6}$alkyl, then the $R^\gamma$ alkyl would be monovalent (excepting any further substitution language).

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions, which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

ological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

"Cytokine" means a secreted protein that affects the functions of other cells, particularly as it relates to the modulation of interactions between cells of the immune system or cells involved in the inflammatory response. Examples of cytokines include but are not limited to interleukin 1 (IL-1), pref-

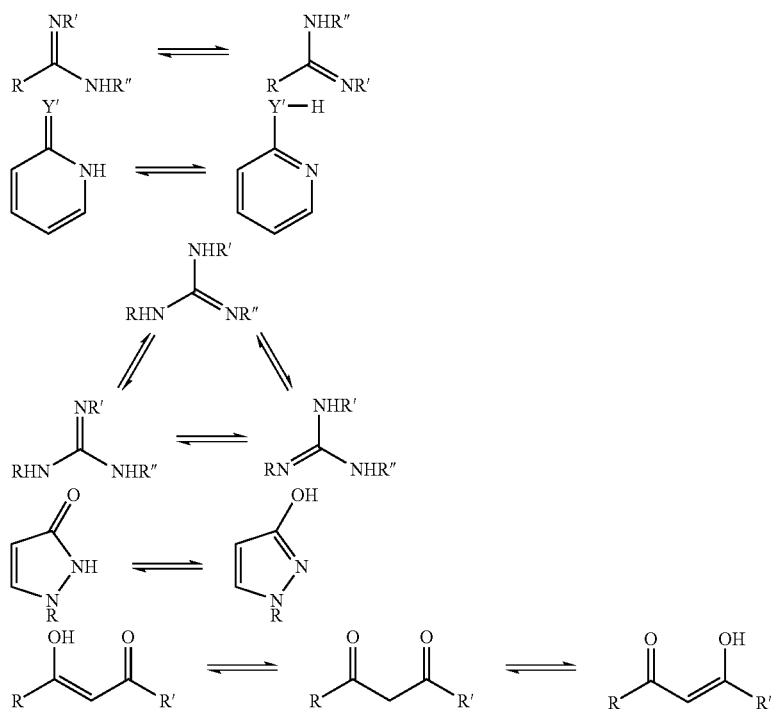

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physierably IL-1β, interleukin 6 (IL-6), interleukin 8 (IL-8) and TNF, preferably TNF-α (tumor necrosis factor-α).

"TNF, IL-1, IL-6, and/or IL-8 mediated disease or disease state" means all disease states wherein TNF, IL-1, IL-6, and/or IL-8 plays a role, either directly as TNF, IL-1, IL-6, and/or IL-8 itself, or by TNF, IL-1, IL-6, and/or IL-8 inducing another cytokine to be released. For example, a disease state in which IL-1 plays a major role, but in which the production of or action of IL-1 is a result of TNF, would be considered mediated by TNF.

Synthesis

Compounds according to the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

The following Examples are presented for illustrative purposes only and are not intended, nor should they be construed, as limiting the invention in any manner. Those skilled in the art will appreciate that modifications and variations of the compounds disclosed herein can be made without violating the spirit or scope of the present invention.

Aniline Synthesis

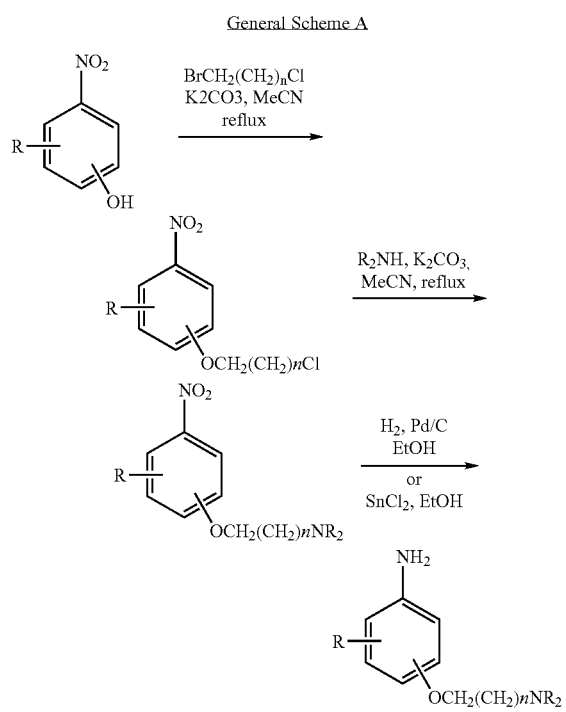

General Scheme A

General Method A 3-(4-Nitrophenoxy)propyl chloride

Nitrophenol (10 g, 72 mmol) was dissolved in acetonitrile (100 mL) and potassium carbonate (24.9 g, 180 mmol) added followed by bromochloropropane (113.2 g, 720 mmol). The mixture was heated and stirred under reflux overnight. The reaction was cooled to room temperature, the solid was then filtered off and the solvent evaporated under reduced pressure, taking care to remove all excess alkylating agent, to give the title compound.

N,N-dimethyl-3-(4-nitrophenoxy)propylamine

A mixture of 3-(4-nitrophenoxy)propyl chloride (2 g, 9.27 mmol), potassium carbonate (7.69 g, 46.4 mmol) and acetonitrile (15 mL) were stirred in a sealed tube and dimethylamine hydrochloride (3.78 g, 46.4 mmol) added quickly. The mixture was stirred and heated overnight at 80° C. The mixture was cooled well before opening the pressure tube, then water and dichloromethane were added and the aqueous layer was extracted with dichloromethane. The combined organics were dried and evaporated giving the title product. $^1$H NMR (400 MHz, CDCl$_3$): 1.95 (2H, t, J 7 Hz); 2.2 (6H, s); 2.35-2.45 (2H, m); 4.05 (2H, t, J 7 Hz); 6.9 (2H, d, J 8 Hz); 8.1 (2H, d, J 8 Hz)

N,N-dimethyl-3-(4-aminophenoxy)propylamine

N,N-dimethyl-3-(4-nitrophenoxy)propylamine (4.4 g, 19.6 mmol) was hydrogenated over Pd (10% on C, 0.4 g) in ethanol (ca 50 mL) for 16 h. The catalysts was filtered off and the solvent removed under reduced pressure to afford the title compound as a brown oil. $^1$H NMR (400 MHz, dmso-d6): 1.95 (2H, t, J 6.5 Hz); 2.25 (6H, s); 2.35-2.45 (2H, m); 3.95 (2H, t, J 6.5 Hz); 4.7 (2H, bs); 6.9 (2H, d,J 8 Hz); 8.1 (2H, d, J 8 Hz); 6.65 (2H, d, J 8 Hz); 6.75 (2H, d, J 8 Hz)

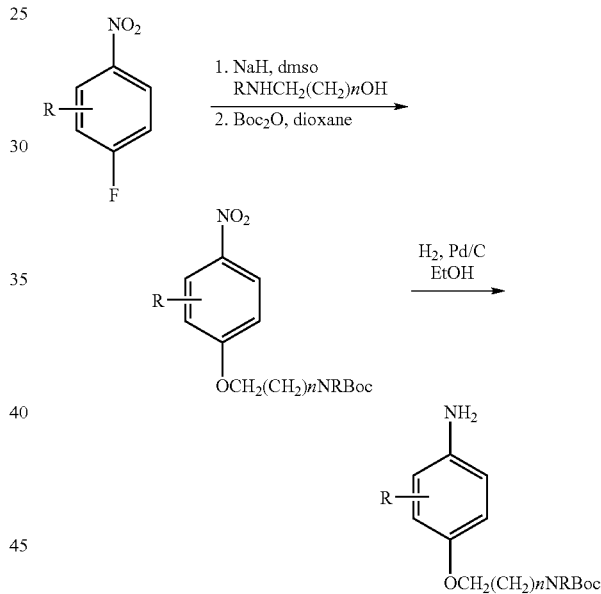

General Scheme B

General Method B

Isopropyl-[2-(4-nitrophenoxy)ethyl]amine

Deprotonation of DMSO (anhydrous, 5 mL) was effected with NaH (0.40 g, 60 wt % in mineral oil, 10 mmol) over 30 min at 40° C. with stirring under a nitrogen atmosphere. When 2-isopropylaminoethanol (1.15 mL, 10 mmol) was added to the solution of the DMSO anion at room temperature, some effervescence occurred. 4-Fluoronitrobenzene (1.06 mL, 10 mmol) was added after 10 min and the dark red solution was then stirred at room temperature for further 20 min. The reaction was diluted with dichloromethane (100 mL), washed with water (50 mL) and then extrected twice with 3M HCl (100 mL). The combined acidic extracts were washed once with dichloromethane (50 mL). Ethyl acetate (125 mL) was then added and the mixture was cooled to 6-8° C. before the aqueous layer was adjusted to pH 11 by gradual addition of 5M aq. NaOH (ca. 150 mL), with vigorous stirring. The organic layer was separated and washed twice with water (50 mL) dried over magnesium sulfate, and concentrated in vacuo at 35° C. to afford the title compound as a yellow oil. $^1$H NMR (400 MHz, CDCl$_3$): 1.10 (6H, d, J 6.25), 2.88 (1H, m, J 6.25), 3.04 (2H, t, J 5.2), 4.16 (2H, t, J 5.2), 6.96 (2H, d, J 9.3), 8.18 (2H, d, J 9.3); MS: 225

Isopropyl-[2-(4-nitrophenoxy)ethyl]carbamic acid tert-butyl ester

Isopropyl-[2-(4-nitrophenoxy)ethyl]amine (1.80 g, 8.05 mmol) was dissolved in 1,4-dioxane (containing 1% water, 20 mL) and cooled to 0-5° C. Di-tert-butyldicarbonate (1.76 g, 8.05 mmol) was added slowly with vigorous stirring. The reaction was stirred at 0° C. for 0.5 h, then at room temperature for 20 h. The solvent was removed in vacuo and the residue taken up into EtOAc. The organic layer was washed twice with water (25 mL), the aqueous washes are extracted back with EtOAc (25 mL). The combined organic extracts were washed twice with 0.3 M HCl (25 mL), then brine and are dried over sodium sulfate. The solvent was removed in vacuo to afford a yellow solid, which was recrystallised from hot n-hexane to give the crystalline title compound as fine, light-yellow needles. $^1$H NMR: (400 MHz, CDCl$_3$): 1.06 (6H, d, J 6.8), 1.37 (9H, s), 3.90 (2H, bm, 2H), 4.06 (2H, bm), 4.26 (1H, bm), 6.86 (2H, d, J 9.0), 8.09 (2H, d, J 9.2).MS: 225 [M+H$^+$-Boc]).

Isopropyl-[2-(4-aminophenoxy)ethyl]carbamic acid tert-butyl ester

A solution of isopropyl-[2-(4-aminophenoxy)ethyl]carbamic acid tert-butyl ester (2.09 g, 6.45 mmol) in ethanol/tetrahydrofuran (30 mL, 2:1) was reduced over palladium on carbon (10 wt %, 50% wet, 0.4 g) with hydrogen under atmospheric pressure at room temperature for 20 h. The catalyst was separated by filtration through celite. The solvent was removed in vacuo to afford the title compound as a red oil. $^1$H NMR: (400 MHz, CDCl$_3$): 1.08 (6H, d, J 6.7),1.39 (9H, s), 3.34 (2H, bm), 3.90 (2H, bm), 4.26 (1H, bm), 6.56 (2H, d, J 8.9), 6.67 (2H, d, J 8.9); MS: 195 [M+H$^+$-Boc], 295 [M+H$^+$]

General Scheme C

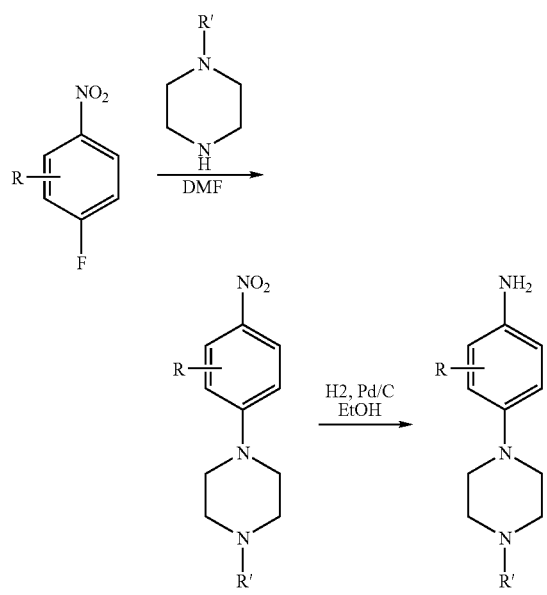

General Method C 1-(2-Fluoro-4-nitrophenyl)-4-methylpiperazine

N-Methylpiperazine (30 mL, 27.1 g, 0.268 mol) was cooled in ice/water while adding 3,4-difluoronitrobenzene (2.0 g, 0.0126 mol) with stirring. The mixture was then heated at 100° C. overnight, evaporated to remove all excess N-methylpiperazine and the residue dissolved in 1M hydrochloric acid (30 mL). After washing twice with 20 mL portions of dichloromethane the solution was basified with 5M sodium hydroxide (10 mL). The product was extracted into dichloromethane (twice with 20 mL), dried over sodium sulphate and evaporated giving a yellow oil which solidified on standing. $^1$H NMR (CDCl$_3$) 8.00 (m, 1H) 7.91 (m, 1H) 6.92 (m, 1H) 3.33 (m, 4H) 2.63 (m, 4H) 2.39 (s, 3H).

1-(2-Fluoro-4-aminophenyl)-4-methylpiperazine

Obtained by hydrogenation over Pd-10% C of the corresponding nitro compound in ethanol. $^1$H NMR (CDCl$_3$) 6.75 (m, 1H) 6.33 (m, 2H) 3.48 (m, 2H) 2.94 (m, 4H) 2.53 (m, 4H) 2.29 (s, 3H).

Specific Syntheses:

tert-Butyl 4-(2-difluoromethoxy-4-nitrophenyl)piperazine-1-carboxylate 1-(2-Difluoromethoxy-4-nitrophenyl)piperazine A stirred mixture of 1-bromo-2-difluoromethoxy-4-nitrobenzene (prepared from the corresponding phenol following the procedure outlined in WO9749710A1; 2.68 g, 10 mmol), piperazine (1.12 g, 13 mmol), potassium carbonate (2.07 g, 15 mmol), tetrabutylammonium bromide (0.03 g, 0.1 mmol) and dry dimethyl sulphoxide (20 mL) was heated under nitrogen at 120° C. for 3 h. The product was added to water (100 mL) and 6M hydrochloric acid (10 mL, 60 mmol), washed with ethyl acetate until washings colourless and the aqueous layer basified with 5M sodium hydroxide solution (20 mL, 100 mmol). Extraction with ethyl acetate (3× with 50 mL), drying (sodium sulphate) and evaporating gave product as viscous orange oil. $^1$H NMR (CDCl$_3$) 8.00 (m, 1H) 7.92 (m, 1H) 6.93 (m,1H) 6.47 (t, J=73.6, 1H) 3.18 (m, 2H) 2.98 (m, 2H) 2.54 (s, 1H)

tert-Butyl 4-(2-difluoromethoxy-4-nitrophenyl)piperazine-1-carboxylate

The above product (1.64 g, 6 mmol) was dissolved in dry tetrahydrofuran (25 mL) and di-tert-butyl dicarbonate (1.2 g, 6 mmol) added. After stirring overnight the mixture was evaporated and the resulting orange solid recrystallised from ethyl acetate giving the final product. $^1$H NMR (CDCl$_3$) 8.03 (m, 1H) 7.93 (m, 1H) 6.48 (t, 1H) 3.53 (m, 2H) 3.15 (m, 2H) 1.42 (s, 9H).

tert-Butyl 4-(2-difluoromethoxy-4-aminophenyl)piperazine-1-carboxylate

Obtained by hydrogenation over Pd-10% C of the corresponding nitro compound in ethanol. $^1$H NMR (CDCl$_3$) 7.73 (m, 1H) 6.56 (t, 1H) 6.42 (m, 2H) 3.46 (m, 2H) 2.80 (m, 2H) 1.40 (s, 9H).

General Scheme D

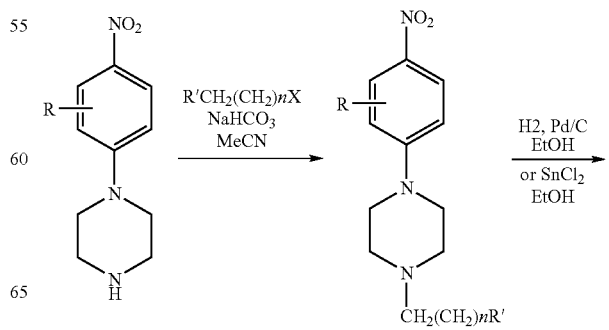

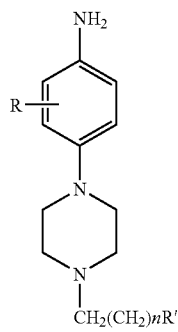

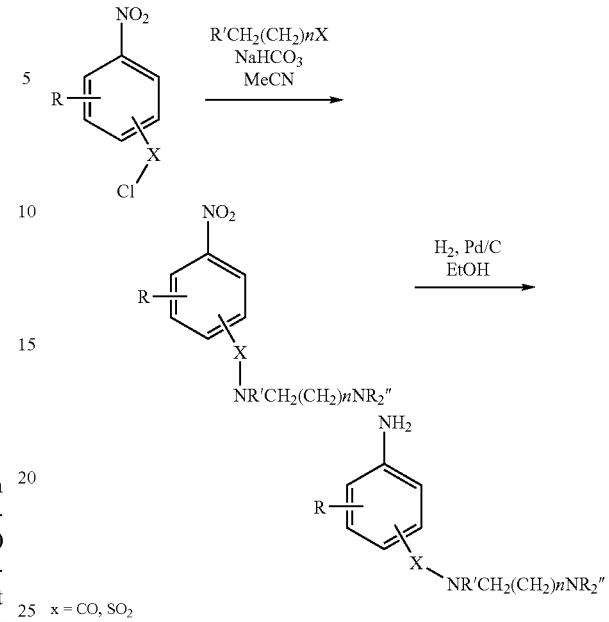

General Scheme E x = CO, SO₂

General Method D

4-(4-(3-dimethylaminopropyl)piperazino)nitrobenzene

Prepared according to a slightly modified procedure from U.S. Pat. No. 3,331,845. A mixture of 4-nitrophenylpiperazine (2.1 g, 10 mmol), sodium hydrogen carbonate (2.5 g, 30 mmol), N,N-dimethyl-N-(3-chloropropyl)amine hydrochloride (1.9 g, 12 mmol) in isopropanol (80 mL) was heated at 80° C. for 18 h. The mixture was then allowed to cool, the solid filtered off and the solvent removed under reduced pressure. Ethyl acetate (ca. 200 mL) was added and the residue was washed with saturated brine twice (50 mL each time). The organic layer was dried over sodium sulphate and the solvent evaporated under reduced pressure. The crude compound was purified by column, eluting with dichloromethane/methanol 9/1 (containing 1% N,N-dimethylethylamine) to give the title compound as a yellow solid. $^1$H NMR (CDCl$_3$, 400 MHz): 1.6 (2H, m); 2.15 (6H, s); 2.25 (2H, m); 2.35 (2H, m); 2.5-2.55 (4H, m); 3.35-3.4 (4H, m); 6.75 (2H, d, J 8 Hz); 8.05 (2H, d, J 8 Hz) MS: 293, 248

4-(4-(3-Dimethylaminopropyl)piperazino)aniline

A solution of 4-(4-(3-dimethylaminopropyl)piperazino)nitrobenzene (1.5 g) in methanol (50 mL) was hydrogenated at atmospheric pressure over Pd (5% on carbon) (0.3 g; 50% water content) for 4 h. The catalyst was filtered off and the solvent removed under reduced pressure to give the title compound as a brown solid $^1$H NMR (CDCl$_3$, 400 MHz): 1.65 (2H, m); 2.15 (6H, s); 2.25 (2H, m); 2.35 (2H, m); 2.5-2.55 (4H, m); 2.95-3.05 (4H, m); 6.55 (2H, d, J 7 Hz); 6.75 (2H, d, J 7 Hz) MS: 263, 218

4-(4-(3-chlorobenzyl)piperazino)aniline 4-(4-(3-chlorobenzyl)piperazino)nitrobenzene (3 g, 9 mmol, prepared as in the general method) was dissolved in ethanol (100 mL). Tin (II) chloride dihydrate (10.1 g, 45 mmol) was added and the reaction heated to 80° C. for 66 h. The reaction mixture was concentrated under reduced pressure. A saturated solution (200 mL) of Rochelle's salt (sodium potassium tartrate) was prepared, and solid NaHCO$_3$ was added to this until no more would dissolve. Ethyl acetate (200 mL) was added to the vessel, followed by the reaction mixture. The solution was then stirred until clear. The phases were separated, and the aqueous layer washed with ethyl acetate (50 mL). The organic layers were combined, washed with saturated brine, dried over magnesium sulphate, and evaporated to give the title compound. $^1$H NMR (CDCl$_3$, 400 MHz): 2.5-2.55 (4H, m); 2.95-3.05 (4H, m); 3.47 (2H, s); 6.5-6.6 (2H, m);6.7-6.8 (4H, m); 7.15-7.25 (4H,m); MS: 302, 304

General Method E

N-(2-dimethylaminoethyl)-3-nitrobenzamide

3-Nitrobenzoyl chloride (2 g, 10.77 mmol) was loaded into a round bottomed flask, placed under a N$_2$ atmosphere and dissolved in anhydrous dichloromethane (10 mL). The mixture was cooled to 0° C. and N,N-dimethylethylenediamine (0.98 mL, 8.98 mmol) was added to the reaction. The reaction was allowed to warm to room temperature and left to stir for 18 h. After 18 h the reaction had given a precipitate which was isolated by filtration and washed with dichloromethane to give 2.28 g of a white solid, which was partitioned between dichloromethane and a saturated aqueous NaHCO$_3$ solution. The organic layer was removed under educed pressure and the aqueous layer was then re-extracted dichloromethane. The organic layers were combined, dried over Na$_2$SO$_4$ and the solvent was removed under reduced pressure to afford the title compound as a yellow solid. MS: 193, 238; $^1$H NMR (400 MHz, dmso-d6): 2.19 (6H, s), 2.42 (2H, t, J 6.8 Hz), 3.39 (2H, q, J 12.4 Hz, 6.7 Hz), 7.78 (1H, t, J 7.9 Hz), 8.29 (1H, ddd, J 7.9 1.8, 1.1 Hz), 8.38 (1H, ddd, J 8.1 Hz, 2.3, 1.0 Hz), 8.68 (1H, t, J 1.8 Hz), 8.81 (1H, t, J 5.7 Hz).

3-(N-(2-dimethylaminoethylcarbamoyl))aniline

Palladium on carbon (200 mg, 10% w/w) was loaded to a three-necked flask and ethanol (1 mL) was added. This was then fitted with a three-way tap with balloon. The flask was then placed under vacuum then purged with nitrogen, this was repeated twice more. The amide (2.0 g, 8.4 mmol) was dissolved in ethanol (20 mL), this was then added to the reaction. The reaction was then placed under vacuum and purged with nitrogen three more times. It was then placed under vacuum again then purged with hydrogen, this was repeated once more leaving the balloon filled with hydrogen. The reaction was left at room temperature overnight under a hydrogen atmosphere. The reaction solution was then filtered through a celite plug washing with ethanol. The filtrates were combined and solvent removed to give a clear colourless oil. MS: 208; $^1$H NMR (400 MHz, CDCl$_3$): 2.22 (6H, s), 2.27 (2H, t, J 5.9 Hz), 3.45 (2H, q, J 11.6, 5.3 Hz), 6.71 (1H, ddd, J 7.9, 2.4, 1.0 Hz), 6.85 (1H, bs), 7.0-7.15 (3H, m)

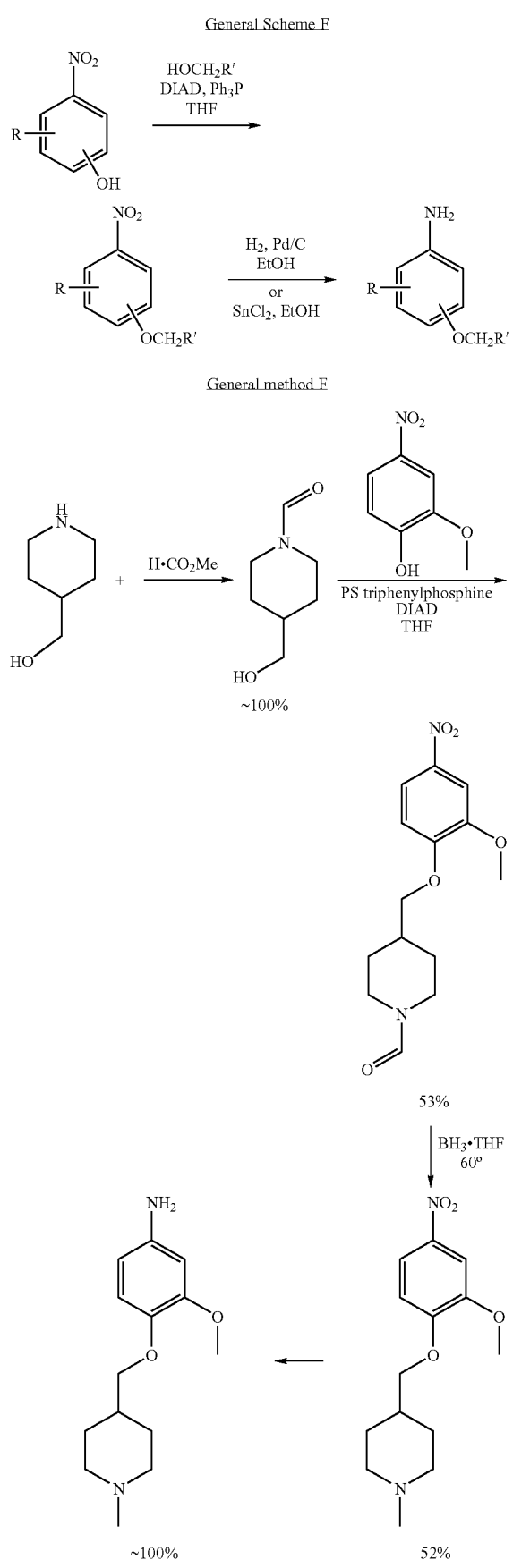

N-Formyl-4-piperidinemethanol

4-Piperidinemethanol (10 g, 87 mmol) was dissolved in methyl formate (7 mL, 113 mmol) 0° C., and maintained at that temperature for 30 min, then allowed to reach 20° C. and stirred 90 min. Solid sodium hydroxide was added (0.87 g, pellets) and the mixture was left overnight. Dichloromethane was added, the NaOH removed by filtration and the solution treated with 1M HCl in ether (10 mL). The mixture was filtered through Celite and the solvent was removed under reduced pressure to afford the crude title compound. $^1$H NMR (400 MHz, CDCl$_3$): 0.85-1.1 (2H, m); 1.55-1.85 (3H, m); 2.5-2.7 (1H, m); 2.95-3.1 (1H, m); 3.3 (2H, d, J 7 Hz); 3.6-3.7 (1H, m); 4.1-4.3 (1H, m); 8 (1H, s)

N-Formyl-4-(2-methoxy-4-nitrophenoxymethyl)piperidine

4-Nitroguaiacol (2 g, 11.8 mmol), N-formyl 4-piperidinemethanol (1.13 g, 7.89 mmol) and polymer-supported triphenylphosphine (3 mmol/g, 3.94 g, 11.8 mmol) were dissolved in tetrahydrofuran (30 mL). The mixture was cooled to 0° C. and diisopropyl azodicarboxylate (2.33 mL, 11.8 mmol) was added dropwise. The mixure was stirred at 0° C. for 30 min then at 20° C. overnight. The resin was filtered off, washed with dichloromethane then methanol and the filtrate evaporated to give a deep orange oil. The oil was taken up in dichloromethane, washed with 2M NaOH, 2M HCl then brine, dried and evaporated giving a pale brown oil. This was taken up in 50:50 ethyl acetate : hexane, filtered through celite, filtrate evaporated, taken up in ethyl acetate and washed further with 1M NaOH. The organic layer was separated, dried over Na$_2$SO$_4$, the solvent removed under reduced pressure and the residue columned in 50:50 ethyl acetate: hexane to remove impurities. The product was then eluted with 9:1 dichloromethane : methanol to give a yellow oil, which crystallised on cooling. $^1$H NMR (400 MHz, CDCl$_3$): 1.15-1.3 (2H, m); 1.85-1.9 (1H, m); 2.6-2.7 (1H, m); 3-3.1 (1H, m); 3.7-3.8 (1H, m); 4.0 (2H, d, J 7 Hz); 4.15-.25 (1H, m); 7.2 (1H, d, J 8 Hz); 7.75 (1H, d, J 2 Hz); 7.9 (1H, dd, J 2 and 8 Hz); 8 (1H, s)

N-Methyl-4-(2-methoxy-4-nitrophenoxymethyl)piperidine

A suspension of N-formyl-4-(2-methoxy-4-nitrophenoxymethyl)piperidine (1.24 g, 4.2 mmol) in tetrahydrofuran (5 mL) under nitrogen was stirred while adding the borane solution (8.4 mL of a 1M soln in THF) then heated to 60° C. for 2 h. Further borane solution (to a total of 5 equivalents) and 20 mL tetrahydrofuran (20 mL) were added and the mixture was heated overnight. The mixture was cooled, methanol (25 mL) was added carefully followed by dichloromethane. The mixture was then washed with brine, 2M NaOH, dried over Na$_2$SO$_4$ and solvent evaporated. The residue was dissolved in methanol, a few drops of acetic acid added and the mixture was heated under reflux for 3 days. Evaporation of the solvent and chromatography in 9:1 dichloromethane:methanol containing 1% triethylamine afforded the product as a brown solid. $^1$H NMR (400 MHz, dmso-d$_6$): 1.4-1.5 (2H, m); 1.85-2 (3H, m); 2-2.1 (2H, m); 2.8-3 (2H, m); 4.05 (3H, s); 4.15 (2H, d, J 7 Hz); 7.35 (1H, d, J 8 Hz); 7.9 (1H, d, J 2 Hz); 8.05 (1H, dd, J 2 and 8 Hz)

N-Methyl-4-(2-methoxy-4-nitrophenoxymethyl)piperidine

Catalytic reduction over Pd (10% C) in EtOH gave the aniline as a red-brown solid. $^1$H NMR (400 MHz, CDCl$_3$): 1.3-1.5 (2H, m); 1.7-1.9 (3H, m); 2-2.1 (2H, m); 2.9-3 (2H, m); 3.4 (2H, broad s); 3.7 (2H, d, J 7 Hz); 3.75 (3H, s); 6.15 (1H, dd, J 1 and 7 Hz); 6.25 (1H, d, J 1 Hz); 6.65 (1H, d, J 7 Hz)

Further examples of anilines include the following (NMR spectra at 400 MHz, in CDCl$_3$ unless otherwise stated):

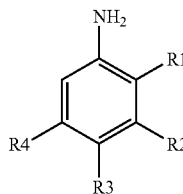

| Ex. | Method | R1 | R2 | R3 | R4 | MS | NMR |
|---|---|---|---|---|---|---|---|
| 1 | A (chloroalkyl phenol displacement) | H | H | 3-(dimethylamino)-ethoxy | H | 181 | 2.25 (6H, s); 2.65 (2H, t, J7 Hz); 3.9 (2H, t, J7 Hz); 6.5-7 (2H, m); 6.65-6.75 (2H, m) |
| 2 | A (chloroalkyl phenol displacement) | H | H | 3-(dimethylamino)-propoxy | | | See specific example |
| 3 | A (chloroalkyl phenol displacement) | H | OCH₃ | 2-((4-CH₃)piperazin-1-yl)ethoxy | OCH₃ | 296 | 2.25 (3H, s); 2.4-2.7 (8H, m); 2.75 (2H, t, J7 Hz); 3.7 (6H, s); 3.9 (2H, t, J7 Hz); 5.9 (2H, s) |
| 4 | A (chloroalkyl phenol displacement) | H | OCH₃ | 3-((4-CH₃)piperazin-1-yl)propoxy | OCH₃ | 310 | 1.8-1.9 (2H, m); 2.2 (3H, s); 2.3-2.6 (10H, m); 3.7 (6H, s); 3.85 (2H, t, J7 Hz); 5.9 (2H, s) |
| 5 | A (chloroalkyl phenol displacement) | H | OCH₃ | 2-((4-CH₃)piperazin-1-yl)ethoxy | H | 266 | 2.35 (3H, s); 2.55-2.8 (10H, m); 3.7 (3H, s); 4 (2H, t, J7 Hz); 6.1 (1H, dd, J2 and 8 Hz); 6.2 (1H, d, J2 Hz); 7.7 (1H, d, J8 Hz) |
| 6 | A (chloroalkyl phenol displacement) | H | OCH₃ | 3-((4-CH₃)piperazin-1-yl)propoxy | H | 280 | 1.9-2.1 (2H, m); 2.35 (3H, s); 2.4-2.6 (10H, m); 3.8 (3H, s); 4 (2H, t, J7 Hz); 6.2 (1H, dd, J2 and 8 Hz); 6.3 (1H, d, J2 Hz); 6.8 (1H, d, J8 Hz) |
| 7 | A (chloroalkyl phenol displacement) | H | OCH₃ | OCH₃ | 2-((4-CH₃)piperazin-1-yl)ethoxy | 296 | 2.2 (3H, s); 2.3-2.5 (4H, m); 2.5-2.7 (4H, m); 2.8 (2H, t, J7 Hz); 3.65 (3H, s); 3.75 (3H, s); 4 (2H, t, J7 Hz); 5.8-5.85 (2H, m) |
| 8 | A (chloroalkyl phenol displacement) | H | OCH₃ | OCH₃ | 3-((4-CH₃)piperazin-1-yl)propoxy | 310 | 1.85-1.95 (2H, m); 2.2 (3H, s); 2.3-2.5 (10H, m); 3.65 (3H, s); 3.75 (3H, s); 3.95 (2H, t, J7 Hz); 6.85-6.9 (2H, m) |
| 9 | A (chloroalkyl phenol displacement) | H | OCH₃ | 2-(piperidino)-ethoxy | OCH₃ | 281 | 1.3-1.4 (2H, m); 1.5-1.6 (4H, m); 2.45-2.6 (4H, m); 2.75 (2H, t, J7 |

-continued

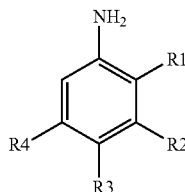

| Ex. | Method | R1 | R2 | R3 | R4 | MS | NMR |
|---|---|---|---|---|---|---|---|
| | ment) | | | | | | Hz); 3.65 (6H, s); 3.95 (2H, t, J7 Hz); 5.85 (2H, s) |
| 10 | A (phenol alkylation) | H | H | 2-(morpholino)ethoxy | H | 223 | 2.45-2.55 (4H, m); 2.7 (2H, t, J7 Hz); 3.65-3.7 (4H, m); 3.95 (2H, t, J7 Hz); 6.5-6.6 (2H, m); 6.65-6.7 (2H, m) |
| 11 | A (chloroalkyl phenol displacement) | H | OCH$_3$ | 2-(morpholino)ethoxy | OCH$_3$ | 283 | 2.5-2.55 (4H, m); 2.7 (2H, t, J7 Hz); 3.6-3.7 (4H, m); 3.7 (6H, s); 4.95 (2H, t, J7 Hz); 5.8 (2H, s) |
| 12 | A (chloroalkyl phenol displacement) | H | H | (S)-((1-CH$_3$)pyrrolidin-2-yl)methoxy | H | 207 | (dmso-d$_6$) 1.5-1.6 (1H, m); 1.6-1.65 (2H, m); 1.9-2 (1H, m); 2.15-2.25 (1H, m); 2.35 (3H, s); 2.5-2.6 (1H, m); 2.9-3 (1H, m); 4.65-4.7 (1H, m); 4.7-4.75 (1H, m); 6.45-6.5 (2H, m); 6.6-6.65 (2H, m) |
| 13 | A (chloroalkyl phenol displacement) | H | F | 3-((4-CH$_3$)piperazin-1-yl)propoxy | H | 268 | 1.8-1.9 (2H, m); 2.2 (3H, s); 2.3-2.55 (10H, m); 3.9 (2H, t, J7 Hz); 6.3 (1H, m); 6.4 (1H, m); 6.7 (1H, m) |
| 14 | A (chloroalkyl phenol displacement) | H | F | 3-(piperidino)propoxy | H | 253 | 1.3-1.4 (2H, m); 1.4-1.5 (4H, m); 1.7-1.8 (2H, m); 2.25-2.4 (6H, m); 3.9 (2H, t, J7 Hz); 6.25-6.3 (1H, m); 6.35-6.4 (1H, m); 6.75-6.85 (1H, m) |
| 15 | A (chloroalkyl phenol displacement) | H | F | 3-(diethylamino)propoxy | H | 241 | 1.05 (6H, t, J7 Hz); 1.9-2 (2H, m); 2.5-2.7 (6H, m); 4 (2H, t, J7 Hz); 6.35-6.4 (1H, m); 6.4-6.45 (1H, m); 6.8-6.9 (1H, m) |
| 16 | A (chloroalkyl phenol displacement) | H | F | 2-((4-CH$_3$)-piperazin-1-yl)ethoxy | H | 254 | 2.2 (3H, s); 2.3-2.4 (4H, m); 2.4-2.65 (4H, m); 2.75 (2H, t, J7 Hz); 4 (2H, t, J7 Hz); 6.25-6.3 (1H, m); 6.3-6.35 (1H, m); 6.75-6.85 (1H, m) |
| 17 | A (chloroalkyl phenol displacement) | H | 3-(piperidino)propoxy | H | H | 235 | 1.3-1.4 (2H, m); 1.45-1.55 (4H, m); 2.3-2.5 (6H, m); 3.9 (2H, t, J7 Hz); 6.1-6.3 (3H, m); 6.9-7 (1H, m) |

-continued

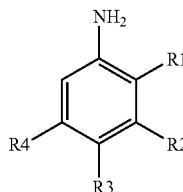

| Ex. | Method | R1 | R2 | R3 | R4 | MS | NMR |
|---|---|---|---|---|---|---|---|
| 18 | A (chloroalkyl phenol displacement) | H | 3-((4-CH₃)-piperazin-1-yl)propoxy | H | H | 250 | 1.9-2 (2H, m); 2.3 (3H, s); 2.4-2.7 (10H, m); 4 (2H, m); 6.2-6.4 (3H, m); 7-7.1 (1H, m) |
| 19 | F (Mitsunobu) | H | OCH₃ | (R)-(pyrrolidin-2-yl)-methoxy | 323, 223 (as N-Boc protected) | | (as N-Boc protected); (dmso-d₆): 1.4 (9H, broad s); 1.7-1.8 (2H, m); 1.8-2 (3H, m); 3.2-3.25 (2H, m); 3.65 (3H, s); 3.75-3.85 (2H, m); 4.7-4.8 (2H, broad s); 6 (1H, dd, J2 and 8 Hz); 6.25 (1H, d, J2 Hz); 6.65 (1H, d, J8 Hz) |
| 20 | A (chloroalkyl phenol displacement) | H | Cl | 2-(piperidino)-ethoxy | H | 255 257 | 1.3-1.4 (2H, m); 1.5-1.6 (4H, m); 2.4-2.6 (4H, m); 2.8 (2H, t, J7 Hz); 4.1 (2H, t, J7 Hz); 6.55 (1H, dd, J2 and 8 Hz); 7.7 (1H, d, J2 Hz); 7.8 (1H, d, J8 Hz) |
| 21 | A (chloroalkyl phenol displacement) | H | F | 2-((4-isopropyl)-piperazin-1-yl)-ethoxy | H | 282 | 1.05 (6H, d, J7 Hz); 2.5-2.7 (9H, m); 2.8 (2H, t, J7 Hz); 4.1 (2H, t, J7 Hz); 6.35-6.4 (1H, m); 6.45 (1H, m); 6.8-6.9 (1H, m) |
| 22 | A (chloroalkyl phenol displacement) | H | OCH₃ | 2-((4-isopropyl)-piperazin-1-yl)-ethoxy | H | 294 | 1.05 (6H, d, J7 Hz); 2.5-2.7 (9H, m); 2.8 (2H, t, J7 Hz); 3.8 (3H, s); 4.1 (2H, t, J7 Hz); 6.2 (1H, d, J2 and 8 Hz); 6.3 (1H, d, J2 Hz); 6.75 (1H, d, J8 Hz) |
| 23 | A (chloroalkyl phenol displacement) | H | OCH₃ | 3-((4-isopropyl)-piperazin-1-yl)propoxy | H | 308 | 1.05 (6H, d, J7 Hz); 1.9-2 (2H, m); 2.5-2.7 (11H, m); 3.4 (2H, broad s); 3.8 (3H, s); 4 (2H, t, J7 Hz); 6.2 (1H, d, J2 and 8 Hz); 6.3 (1H, d, J2 Hz); 6.75 (1H, d, J8 Hz) |
| 24 | A (chloroalkyl phenol displacement) | CH₃ | H | 3-((4-CH₃)piperazin-1-yl)propoxy | H | 264 | 1.9-2 (2H, m); 2.1 (3H, s); 2.35 (3H, s); 2.4-2.7 (10H, m); 4 (2H, t, J7 Hz); 6.25-6.4 (2H, m); 6.9-7 (1H, m) |
| 25 | A (chloroalkyl phenol displacement) | CH₃ | H | 3-(piperidino)propoxy | H | 249 | 1.4-1.55 (2H, m); 1.6-1.7 (4H, m); 1.95-2.05 (2H, m); 2.1 (3H, s); 2.4-2.6 (6H, m); 4 (2H, t, J7 Hz); 6.3-6.4 (2H, m); 6.9-7 (1H, m) |
| 26 | F (Mitsunobu) | H | OCH₃ | ((1-CH₃)-piperidin-4-yl)-methoxy | H | 251 | See specific example |

-continued

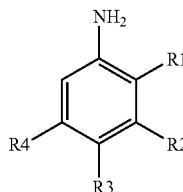

| Ex. | Method | R1 | R2 | R3 | R4 | MS | NMR |
|---|---|---|---|---|---|---|---|
| 27 | F (Mitsunobu) | H | OCH₃ | 2-((1-CH₃)piperidin-4-yl)ethoxy | H | 265 | 1.2-1.35 (2H, m); 1.4-1.55 (1H, m); 1.65-1.75 (4H, m); 1.85-1.95 (2H, m); 2.2 (3H, s); 2.8-2.9 (2H, m); 3.7 (3H, s); 3.9 (2H, t, J7 Hz); 6.15 (1H, dd, J2 and 8 Hz); 6.2 (1H, d, J2 Hz); 6.65 (1H, d, J8 Hz) |
| 28 | F (Mitsunobu) | H | H | 2-((1-CH₃)piperidin-4-yl)ethoxy | H | 235 | 1.2-1.35 (2H, m); 1.4-1.55 (1H, m); 1.6-1.7 (4H, m); 1.85-1.95 (2H, m); 2.2 (3H, s); 2.8-2.9 (2H, m); 3.8-3.9 (2H, m); 6.5-6.6 (2H, m); 6.7-6.8 (2H, m) |
| 29 | F (Mitsunobu) | H | H | (S)-(pyrrolidin-2-yl)methoxy | H | 293 193 | (as N-Boc protected); (dmso-d₆): 1.15 (9H, s); 1.4-1.7 (4H, m); 3-3.05 (2H, m); 3.4-3.45 (1H, m); 3.5-3.55 (2H, m); 4.4 (2H, broad s); 6.2-6.3 (2H, m); 6.4-6.5 (2H, m) |
| 30 | B (Halide displacement via alkoxy anion) | H | OCH₃ | 2-(isopropylamino)ethoxy | H |  | (as N-Boc protected) 1.15 (6H, d, J7 Hz); 1.45 (9H, s); 3.35-3.5 (2H, m); 3.8 (3H, s); 3.9-4.1 (2H, m); 4.3-4.45 (1H, m); 6.2 (1H, dd, J2 and 8 Hz); 6.3 (1H, d, J2 Hz); 6.8 (1H, m) |
| 31 | B (Halide displacement via alkoxy anion) | H | Cl | 2-(isopropylamino)ethoxy | H |  | (as N-Boc protected) 1.15 (6H, broad d, J7 Hz); 1.45 (9H, s); 3.35-3.5 (2H, m); 3.9-4.1 (2H, m); 4.3-4.45 (1H, m); 6.5 (1H, dd, J2 and 8 Hz); 6.7 (1H, d, J2 Hz); 6.8 (1H, d, J8 Hz) |
| 32 | C (Halide displacement) | __(H?) | OCH₃ | (4-CH₃)-piperazin-1-yl | H | 222 | 2.4 (3H, s); 2.5-2.7 (4H, m); 2.9-3.1 (4H, m); 3.8 (3H, s); 6.2-6.4 (2H, m); 6.8-6.9 (1H, m) |
| 33 | C (Halide displacement) | H | OCH₃ | 4-(tert-butoxycarbonyl)piperazin-1-yl | H |  | (as N-Boc protected) 1.4 (9H, s); 2.8-2.9 (4H, m); 3.5-3.6 94H, m); 3.75 (3H, s); 6.1-6.25 (2H, m); 6.65-6.8 (1H, m) |
| 34 | C (Halide displacement) | H | H | 4-(tert-butoxycarbonyl)piperazin-1-yl | H | 278 | (as N-Boc protected) 1.4 (9H, s); 2.85-2.95 (4H, m); 3.4 (2H, broad s); 3.45-3.55 (4H, m); 6.6 (2H, d, J8 Hz); 6.75 (2H, d, J8 Hz) |
| 35 | C (Halide displacement) | H | H | 4-(isopropyl)-piperazin-1-yl | H | 220 | 1.0 (6H, d, J7 Hz); 2.55-2.7 (6H, m); 2.95-3.05 (4H, m, 3.35 (2H, broad s); |

-continued

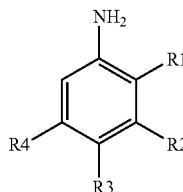

| Ex. | Method | R1 | R2 | R3 | R4 | MS | NMR |
|---|---|---|---|---|---|---|---|
| | | | | | | | 6.5-6.65 (2H, m); 6.7-6.8 (2H, m) |
| 36 | D (piperazine alkylation) | H | H | 4-(carbamoylmethyl)piperazin-1-yl | H | 235 | 2.6-2.7 (4H, m); 2.9-3.1 (4H, m); 3.4 (2H, broad s); 5.4 (1H, broad s); 6.55 (2H, d, J8 Hz); 66.7 (2H, d, J8 Hz); 7 (1H, broad s) |
| 37 | D (piperazine alkylation) | H | H | 4-(cyclohexylmethyl)-piperazin-1-yl | H | 274 | 0.7-0.9 (2H, m); 1.1-1.3 (3H, m); 1.4-1.5 (1H, m); 1.6-1.8 (5H, m); 2.1 (2H, d, J7 Hz); 2.4-2.55 (4H, m); 2.9-3 (4H, m); 3.35 (2H, broad s); 6.5-6.65 (2H, m); 7.8-7.9 (2H, m) |
| 38 | D (pipererazine alkylation) | H | H | 4-(((3-Cl)phenyl)-methyl)-piperazin-1-yl | H | 302/304 | See specific example |
| 39 | D (piperazine alkylation) | H | H | 4-(((3-cyano)-phenyl)-methyl)-piperazin-1-yl | H | 293 | 2.5-2.6 (4H, m); 2.9-3.1 (4H, m); 3.5 (2H, s); 6.5–6.6 (2H, m); 6.7-6.8 (2H, m); 7.3-7.4 (1H, m); 7.5-7.6 (2H, m); 7.6 (1H, m) |
| 40 | D (piperazine alkylation) | H | H | 4-(((3-OCH$_3$)-phenyl)-methyl)-piperazin-1-yl | H | | 2.5-2.6 (4H, m); 2.9-3.1 (4H, m); 3.45 (2H, s); 3.75 (3H, s); 6.5-6.6 (2H, m); 6.7-6.8 (3H, m); 6.8-6.9 (2H, m); 7.2-7.3 (1H, m) |
| 41 | C (Halide displacement) | H | Cl | (4-CH$_3$)-piperazin-1-yl | H | | 2.35 (3H, s); 2.5-2.7 (4H, m); 2.9-3 (4H, m); 3.5 (2H, broad s); 6.5 (1H, dd, J2 and 8 Hz); 6.7 (1H, d, J2 hz); 6.9 (1H, d, J8 Hz) |
| 42 | C (Halide displacement) | H | OCH$_3$ | 4-(isopropyl)-piperazin-1-yl | H | | 1.1 (6H, d, J7 Hz); 2.6-2.7 (6H, m); 2.9-3.1 (4H, m); 3.75 (3H, s); 6.15-6.3 (2H, m); 6.7 (1H, d, J8 Hz) |
| 43 | C (Halide displacement) | H | F | 4-(isopropyl)-piperazin-1-yl | H | | 1.1 (6H, d, J7 Hz); 2.6-2.7 (6H, m); 2.9-3 (4H, m); 3.5 (H, broad s); 6.3-6.4 (2H, m); 6.7-6.8 (1H, m) |
| 44 | C (Halide displacement) | H | (4-CH$_3$)-piperazin-1-yl | H | H | 192 | 2.25 (3H, s); 2.45-2.5 (4H, m); 3.1-3.2 (4H, m); 3.6 (2H, broad s); 6.1 (1H, dd, J2 and 8 Hz); 6.2 (1H, m; 6.3 (1H, d, J2 and 8 Hz); 6.95 (1H, t, J8 Hz) |
| 45 | C (Halide displace- | CH$_3$ | H | (4-CH$_3$)-piperazin-1-yl | H | 206 | 2.1 (3H, s); 2.3 (3H, s); 2.5-2.6 (4H, m); 2.9-3.1 (4H, m); |

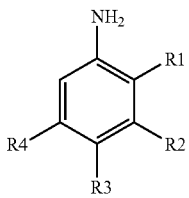

| Ex. | Method | R1 | R2 | R3 | R4 | MS | NMR |
|---|---|---|---|---|---|---|---|
| | ment) | | | | | | 6.5-6.6 (1H, m); 6.6–6.7 (2H, m) |
| 46 | D (piperazine alkylation) | H | H | (4-(2-dimethylaminoethyl))-piperazin-1-yl | H | 249 | 2.2 (6H, s); 2.3-2.4 (2H, m); 2.4-2.5 (2H, m); 2.5-2.6 (4H, m); 2.95-3.05 (4H, m); 6.55 (2H, d, J8 Hz); 6.75 (2H, d, J8 Hz) |
| 47 | D (piperazine alkylation) | H | H | (4-((2-methoxy)ethyl))-piperazin-1-yl | H | | 2.5-2.6 (6H, m); 2.95-3.05 (4H, m); 3.3 (3H, s); 3.5 (2H, t, J7 Hz); 6.55 (2H, d, J8 Hz); 6.75 (2H, d, J8 Hz) |
| 48 | D (piperazine alkylation) | H | H | (4-(3-dimethylaminopropyl))piperazin-1-yl | H | | See specific example |
| 49 | E (amide formation) | H | H | (N-(2-diethylamino)-ethyl)-(N-methyl))carbamoyl | H | 250 | dmso-$d_6$: 0.8-1.0 (6H, m); 2.3-2.6 (6H, m); 3.0 (3H, broad s); 3.35-3.5 (2H, m); 5.45 (2H, broad s); 6.5 (2H, d, J8 Hz); 7.1 (2H, d, J8 Hz) |
| 50 | E (amide formation) | H | (N-(2-dimethylamino)-ethyl)-carbamoyl | H | H | 208 | See specific example |
| 51 | E (amide formation) | H | (N-(2-diethylamino)-ethyl)-(N-methyl))-carbamoyl | H | H | 250 | dmso-$d_6$: 0.8-1.0 (6H, 2 broad m); 2.2-2.8 (4H, 2 broad m); 2.9-3.0 (3H, 2 broad s); 3.2-3.5 (2H, 2 broad m); 5.2 (2H, broad s); 6.4 (1H, d, J8 Hz); 6.5 (1H, d, J2 Hz); 6.6 (1H, dd, J2 and 8 Hz); 7.05 (1H, m) |

Carboxamide Synthesis

General Scheme

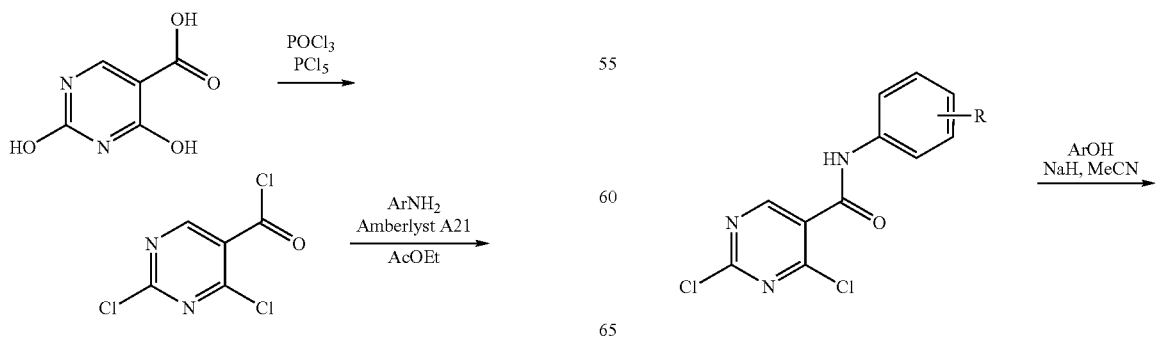

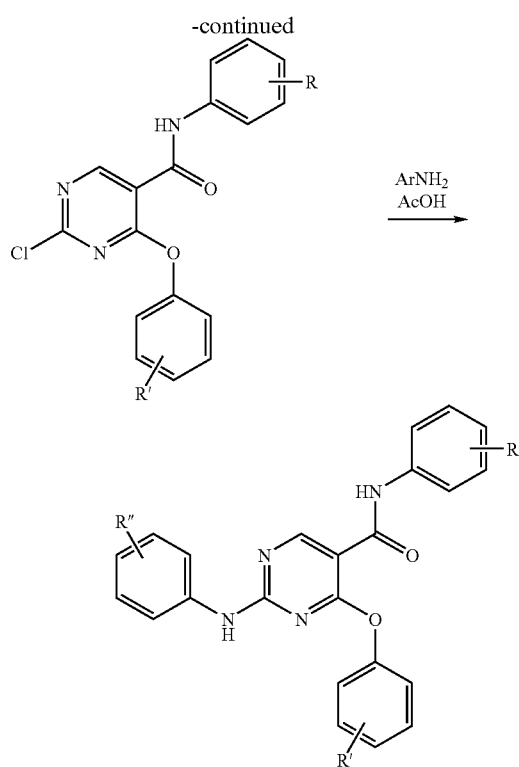

2,4-Dichloropyrimidine-5-carbonyl chloride

Prepared according to GB 1,182,086: uracil-5-carboxylic acid monohydrate (15.1 g, 86.7 mmol) was added in one portion to a suspension of phosphorus pentachloride (72.2 g, 346.7 mmol) in phosphorus oxychloride (50 mL). More phosphorus oxychloride (20 mL) was added. The reaction mixture was then heated up to 75° C. and gradually to reflux overnight. The phosphorus oxychloride was then distilled off. The mixture was filtered, the precipitate washed with ethyl acetate and the filtrate was concentrated in vacuo to give the title compound (18.3 g) as a yellow oil $^1$H NMR (400 MHz, CDCl$_3$): 9.26 (1H); $^{13}$C NMR (400 MHz, CDCl$_3$): 126.44, 161.34, 162.19, 163.94, 164.43

2,4-Dichloropyrimidine-5-N-(2',6'-dimethylphenyl)carboxamide

Amberlyst A-21 ion exchange resin (1.8 g) was added to a solution of 2,4-dichloropyrimidine-5-carbonyl chloride (18.3 g, 86.6 mmol) in ethyl acetate (400 mL). More ethyl acetate (50 mL) was added and 2,6-dimethylaniline (10.5 g, 10.7 mL, 86.6 mmol) was added dropwise at room temperature. The reaction mixture was heated at 50° C. overnight then cooled and quenched with water and extracted extracted with ethyl acetate (3×100 mL). The organic layer was washed with 1 N HCl (30 mL), 1 M NaOH (30 mL) and brine (30 mL). The organic layer was then dried on sodium sulfate, filtered and concentrated in vacuo. The crude product was washed with dichloromethane (2×30 mL) to afford the title compound as a pale yellow solid. $^1$H NMR (400 MHz, CDCl$_3$): 9.08 (1H, s), 7.71 (1H, s), 7.15-7.23 (3H, m), 2.32 (6H,s); $^{13}$C NMR (400 MHz, CDCl$_3$): 19.12, 127.56, 128.78, 129.00, 132.75, 135.81, 158.61, 160.25, 162.23, 162.41; MS: 296 [M+H$^+$]

2,4-Dichloropyrimidine-5-N-(2',6'-dichlorophenyl)carboxamide

Amberlyst A-21 ion exchange resin (2.14 g) was added to a solution of 2,4-dichloropyrimidine-5-carbonyl chloride (21.4 g, 101.2 mmol) in ethyl acetate (200 mL). The mixture was heated at 60° C. A solution of 2,6-dichloro aniline (19.68 g, 121.5 mmol) in ethyl acetate (200 mL) was added dropwise and the reaction mixture was heated at 60° C. overnight. The mixture was quenched with water and the organic layer extracted with ethyl acetate (3×100 mL), washed with 1 N HCl (30 mL), 1 M NaOH (30 mL) and brine (30 mL). The organic layer was then dried on sodium sulfate, filtered and concentrated in vacuo. The crude product was washed with dichloromethane (2×30 mL) to afford 2,4-dichloro-5-N-[2,6-dichlorophenyl]pyrimidine as a pale yellow solid. $^1$H NMR (400 MHz, CDCl$_3$): 10.88 (1H, s), 9.01 (1H, s), 7.63 (2H, d, J 8.1 Hz), 7.44 (1H, t, J 8.1 Hz); $^{13}$C NMR (400 MHz, CDCl$_3$): 128.5, 128.7, 130.0, 131.32, 133.5, 158.8, 159.5, 159.9, 160.3; MS: 336 [M+H$^+$]

2-Chloro-4-(3-chlorophenoxy)-5N-(2',6'-dichlorophenyl)carboxamide

3-Chlorophenol (0.651 g, 535 mL, 5.06 mmol) was added at 0° C. to a suspension of sodium hydride 60% dispersion in mineral oil (0.203 g, 5.06 mmol) in acetonitrile (10 mL). The mixture was stirred at 0° C. for 1 h. The phenoxide solution was then added dropwise at 0° C. to a solution of 2,4-dichloro-5-(2,6-dimethylphenyl)-carbamoylpyrimidine (1.50 g, 5.06 mmol) in acetonitrile (50 mL) (in other examples where poor solubility of the phenoxide is observed, N,N-dimethylformamide can be added to increase solubility). The reaction mixture was stirred at 0° C. for 2 h. The reaction mixture was diluted with ethyl acetate (150 mL) and washed with water (100 mL) and then brine (100 mL). The organic layer was dried on sodium sulfate, filtered and concentrated in vacuo. The crude product was washed with cyclohexane (2×20 mL) to the title compound as a white solid. Alternatively, the product can be purified by column chromatography eluting with ethyl acetate/cyclohexane mixtures. $^1$H NMR (400 MHz, CDCl$_3$): 9.33 (1H, s), 8.60 (1H, s), 7.45 (1H, dd, J 8.1 Hz), 7.10-7.44 (5H, m), 2.30 (6H, s); $^{13}$C NMR (400 MHz, CDCl$_3$): 19.66, 112.94, 120.03, 122.25, 127.50, 127.87, 128.41, 130.88, 133.08, 135.10, 135.44, 151.00, 159.03, 162.24, 165.94; MS: 388 [M+H$^+$]

2-(3-Fluoro-4-(3-(4-methylpiperazino)propoxy))phenylamino-4-(3-chloro-phenoxy)-5-N-(2',6'-dichlorophenyl)carboxamide A solution of 3-fluoro-4-(3-(4-methylpiperazino)propoxy) aniline (50.4 mg) in acetic acid (2 mL) was added to a solution of 2-chloro-4-((2-methoxy)phenoxy)-5-N-(2',6'-dichlorophenyl)carboxamide (80.0 mg) in acetic acid (1 mL). The mixture was heated in a sealed tube at 80° C. overnight. The solvent was distilled off and the residue dissolved in DCM (2 mL) and washed with 1M NaOH (1 mL). The two layers were separated and the organic layer concentrated under vacuum. The crude mixture was purified by flash column chromatography (eluent: DCM/MeOH 95/5) to afford the title product as a pale yellow solid. $^1$H NMR (400 MHz, CDCl$_3$): 9.16 (1H, s), 8.12 (1H, s), 7.00-7.45 (10H, m), 4.02 (2H, dd, J 6.3, 6.4 Hz), 3.79 (3H, s), 2.35-2.60 (10H, m), 2.32 (3H, s), 1.90 (2H, m); MS: 655 [M+H$^+$]

1-(Hydroxyphenyl)-4-(tertbutyloxycarbonyl)piperazine 1-(4-Hydroxyphenyl)piperazine (5 g, 28 mmol), triethylamine (5.8 ml, 42 mmol) and di-tert-butyldicarbonate (6.12 g, 28 mmol) were stirred overnight at room temperature in THF (30 mL). Ethyl acetate (100 mL) was then added to the solution. The organic layer was washed with 1M NaOH (50 mL) and water (50 mL). The organic layer was then dried (MgSO$_4$), filtered and evaporated under vacuum to give the title compound as a white solid. $^1$H NMR (400 MHz, CDCl$_3$): 7.75 (4H, q, J 16 Hz), 3.40 (4H, t, J 4 Hz), 2.90 (4H, t, J 4Hz), 1.40 (9H, s); MS: 279 [M+H$^+$] 10%, 223[M+H$^+$−tBu] 100%

2-(3-Fluoro-4-(4-methylpiperazino)phenylamino)-4-(4-(N-tert-butoxycarbonylpiperazino)phenoxy)-5-N-(2',6'-dichlorophenyl)carboxamide 2-Chloro-4-(4-(N-tert-butoxycarbonylpiperazino)phenoxy)-5-N-(2',6'-dichlorophenyl)carboxamide (144 mg, 0.25 mmol) and 3-fluoro-4-(4-methylpiperazino)-aniline (52.3 mg, 0.25 mmol) were placed in a pressure tube and acetic acid (5 mL) was added. The mixture was stirred at 80° C. for 4 h. It was then carefully neutralized using solid Na$_2$CO$_3$ and further adjusted to pH 12 using 5N NaOH. This was then extracted with ethyl acetate (10 mL). The organic layer was dried over sodium sulphate, filtered and evaporated under vacuum. The crude compound was purified by flash chromatography eluting with dichloromethane/methanol (95/5) to yield the title compound. $^1$H NMR (400 MHz, CDCl$_3$): 9.11 (1H, s), 9.01 (1H, s), 7.34 (2H, d, J 8 Hz), 7.15 (4H, m), 6.97 (2H, d, J=12 Hz), 6.69 (2H, bs), 3.57 (4H, dd, J 8 Hz, 4 Hz), 3.13 (4H, dd, J 8 Hz, 4 Hz), 2.99 (4H, bs), 2.61 (4H, bs), 2.35 (3H, s), 1.45 (9H, s); MS: 751 [M+H$^+$]

2-(3-Fluoro-4-(4-methylpiperazino)phenylamino)-4-(piperazino)phenoxy)-5-N-(2',6'-dichlorophenyl)carboxamide 2-(3-Fluoro-4-(4-methylpiperazino)phenylamino)-4-(4-(N-tert-butoxycarbonyl-piperazino)phenoxy)-5-N-(2',6'-dichlorophenyl)carboxamide (1.0 g, 1.3 mmol) was placed in a solution of trifluoroacetic acid (10 mL) and dichloromethane (40 mL). The solution was stirred overnight at room temperature. It was then evaporated to dryness under reduced pressure. The crude was taken up in dichloromethane (30 mL) and extracted with water (30 mL). 1N NaOH (20 mL) was then added to the aqueous layer. This was then extracted three times with dichloromethane (50 mL). The dichloromethane layer was dried (Na$_2$SO$_4$), filtered and evaporated to dryness under vacuum to give the title compound as a white solid. $^1$H NMR (400 MHz, CDCl$_3$): 9.18 (1H, s), 9.10 (1H, s), 7.42 (2H, d, J 8 Hz), 7.22 (4H, m), 7.05 (2H, d, J=9Hz), 6.85 (2H, bs), 3.20 (4H, dd, J 5 Hz, 3 Hz), 3.05 (8H, m), 2.60 (4H, bs), 2.35 (3H, s); MS: 651 [M+H$^+$]

The following compounds were prepared using the above carboxamide synthesis:

| No. | Name | LC purity | LC Rt | Mass found |
|---|---|---|---|---|
| 1 | 1,1-dimethylethyl 2-(4-((2-((3,5-bis(methyloxy)-4-((3-(1-piperazinyl)propyl)oxy)phenyl)amino)-5-(((2,6-dimethylphenyl)amino)carbonyl)-4-pyrimidinyl)oxy)-phenyl)ethylcarbamate | 92.3 | 1.33 | 756, 328 |
| 2 | 1,1-dimethylethyl 2-(4-((5-(((2,6-dimethylphenyl)amino)-carbonyl)-2-((3-(methyloxy)-4-(1-piperazinyl)phenyl)-amino)-4-pyrimidinyl)oxy)phenyl)ethylcarbamate | 91.4 | 1.43 | 668 |
| 3 | 1,1-dimethylethyl 4-(4-((4-((4-chlorophenyl)oxy)-5-(((2,6-dimethylphenyl)amino)carbonyl)-2-pyrimidinyl)-amino)phenyl)-1-piperazinecarboxylate | 90.5 | 1.63 | 629, 573 |
| 4 | 1,1-dimethylethyl 4-(4-((5-(((2,6-dimethylphenyl)amino)-carbonyl)-2-((4-(4-methyl-1-piperazinyl)phenyl)amino)-4-pyrimidinyl)oxy)phenyl)-1-piperazinecarboxylate | 97.4 | 1.44 | 368, 693, 347 |
| 5 | 2-((3-(((2-(diethylamino)ethyl)(methyl)amino)carbonyl)-phenyl)amino)-N-(2,6-dimethylphenyl)-4-((2-(methyloxy)-4-propylphenyl)oxy)-5-pyrimidinecarboxamide | 94 | 1.56 | 320, 639 |
| 6 | 2-((3-(((2-(diethylamino)ethyl)(methyl)amino)carbonyl)-phenyl)amino)-N-(2,6-dimethylphenyl)-4-((2-(ethyloxy)-phenyl)oxy)-5-pyrimidinecarboxamide | 93 | 1.41 | 611, 306 |
| 7 | 2-((3-(((2-(dimethylamino)ethyl)amino)sulfonyl)phenyl)-amino)-N-(2,6-dimethylphenyl)-4-((2-(ethyloxy)phenyl)-oxy)-5-pyrimidinecarboxamide | 96 | 1.36 | 605 |
| 8 | 2-((3-(((2-(dimethylamino)ethyl)amino)sulfonyl)phenyl)-amino)-N-(2,6-dimethylphenyl)-4-((2-(methyloxy)-4-propylphenyl)oxy)-5-pyrimidinecarboxamide | 94 | 1.49 | 633, 317, 256 |
| 9 | 2-((3-((difluoromethyl)oxy)-4-(4-methyl-1-piperazinyl)-phenyl)amino)-N-(2,6-dimethylphenyl)-4-((2-(ethyloxy)-phenyl)oxy)-5-pyrimidinecarboxamide | 100 | 1.47 | 310, 619 |
| 10 | 2-((3,4-bis(methyloxy)-5-((2-(4-methyl-1-piperazinyl)-ethyl)oxy)phenyl)amino)-N-(2,6-dimethylphenyl)-4-((2-(methyloxy)-4-propylphenyl)oxy)-5-pyrimidinecarboxamide | 98 | 1.47 | 343, 685 |
| 11 | 2-((3,4-bis(methyloxy)-5-((2-(4-methyl-1-piperazinyl)-ethyl)oxy)phenyl)amino)-N-(2,6-dimethylphenyl)-4-((2-(ethyloxy)phenyl)oxy)-5-pyrimidinecarboxamide | 97 | 1.33 | 329, 657 |
| 12 | 2-((3,4-bis(methyloxy)-5-((3-(4-methyl-1-piperazinyl)-propyl)oxy)phenyl)amino)-N-(2,6-dimethylphenyl)-4-((2-(methyloxy)-4-propylphenyl)oxy)-5-pyrimidinecarboxamide | 100 | 1.44 | 350, 699 |
| 13 | 2-((3,4-bis(methyloxy)-5-((3-(4-methyl-1-piperazinyl)-propyl)oxy)phenyl)amino)-N-(2,6-dimethylphenyl)-4-((2-(ethyloxy)phenyl)oxy)-5-pyrimidinecarboxamide | 97 | 1.31 | 336, 671 |
| 14 | 2-((3,5-bis(methyloxy)-4-((2-(4-methyl-1-piperazinyl)-ethyl)oxy)phenyl)amino)-N-(2,6-dimethylphenyl)-4-((2-(ethyloxy)phenyl)oxy)-5-pyrimidinecarboxamide | 97 | 1.27 | 657 |
| 15 | 2-((3,5-bis(methyloxy)-4-((2-(4-methyl-1-piperazinyl)-ethyl)oxy)phenyl)amino)-N-(2,6-dimethylphenyl)-4-((2-(methyloxy)-4-propylphenyl)oxy)-5-pyrimidinecarboxamide | 100 | 1.41 | 343, 685 |

-continued

| No. | Name | LC purity | LC Rt | Mass found |
|---|---|---|---|---|
| 16 | 2-((3,5-bis(methyloxy)-4-((3-(4-methyl-1-piperazinyl)-propyl)oxy)phenyl)amino)-N-(2,6-dimethylphenyl)-4-(phenyloxy)-5-pyrimidinecarboxamide | 94.3 | 1.25 | 314, 627 |
| 17 | 2-((3,5-bis(methyloxy)-4-((3-(4-methyl-1-piperazinyl)-propyl)oxy)phenyl)amino)-4-((3-(2-(diethylamino)ethyl)-phenyl)oxy)-N-(2,6-dimethylphenyl)-5-pyrimidinecarboxamide | 77.6 | 1.04 | 363, 765, 840, 726 |
| 18 | 2-((3,5-bis(methyloxy)-4-((3-(4-methyl-1-piperazinyl)-propyl)oxy)phenyl)amino)-N-(2,6-dimethylphenyl)-4-((2-fluorophenyl)oxy)-5-pyrimidinecarboxamide | 83.4 | 1.21 | 323, 645 |
| 19 | 2-((3,5-bis(methyloxy)-4-((3-(4-methyl-1-piperazinyl)-propyl)oxy)phenyl)amino)-N-(2,6-dichlorophenyl)-4-((2-(methyloxy)phenyl)oxy)-5-pyrimidinecarboxamide | 100 | 1.66 | 697/699 |
| 20 | 2-((3,5-bis(methyloxy)-4-((3-(4-methyl-1-piperazinyl)-propyl)oxy)phenyl)amino)-N-(2,6-dichlorophenyl)-4-(phenyloxy)-5-pyrimidinecarboxamide | 97.2 | 1.69 | 667/669 |
| 21 | 2-((3,5-bis(methyloxy)-4-((3-(4-methyl-1-piperazinyl)-propyl)oxy)phenyl)amino)-N-(2,6-dimethylphenyl)-4-((2-(methyloxy)phenyl)oxy)-5-pyrimidinecarboxamide | 97.8 | 1.22 | 329, 657 |
| 22 | 2-((3,5-bis(methyloxy)-4-((3-(4-methyl-1-piperazinyl)-propyl)oxy)phenyl)amino)-N-(2,6-dichlorophenyl)-4-((2-fluorophenyl)oxy)-5-pyrimidinecarboxamide | 100 | 1.24 | 685/687, 343 |
| 23 | 2-((3,5-bis(methyloxy)-4-((3-(4-methyl-1-piperazinyl)-propyl)oxy)phenyl)amino)-N-(2,6-dichlorophenyl)-4-(2-naphthalenyloxy)-5-pyrimidinecarboxamide | 100 | 1.33 | 717/719, 380, 359 |
| 24 | 2-((3,5-bis(methyloxy)-4-((3-(4-methyl-1-piperazinyl)-propyl)oxy)phenyl)amino)-N-(2,6-dimethylphenyl)-4-((4-(1-piperazinyl)phenyl)oxy)-5-pyrimidinecarboxamide | 93.8 | 1.02 | 356, 711 |
| 25 | 2-((3,5-bis(methyloxy)-4-((3-(4-methyl-1-piperazinyl)-propyl)oxy)phenyl)amino)-N-(2,6-dichlorophenyl)-4-((4-(1-piperazinyl)phenyl)oxy)-5-pyrimidinecarboxamide | 100 | 1.45 | 751/753 |
| 26 | 2-((3,5-bis(methyloxy)-4-((3-(4-methyl-1-piperazinyl)-propyl)oxy)phenyl)amino)-N-(2,6-dichlorophenyl)-4-((3-(methyloxy)phenyl)oxy)-5-pyrimidinecarboxamide | 98.8 | 1.2 | 697/699 |
| 27 | 2-((3,5-bis(methyloxy)-4-((3-(4-methyl-1-piperazinyl)-propyl)oxy)phenyl)amino)-N-(2,6-dimethylphenyl)-4-((4-fluorophenyl)oxy)-5-pyrimidinecarboxamide | 100 | 1.23 | 645, 323, 344 |
| 28 | 2-((3,5-bis(methyloxy)-4-((3-(4-methyl-1-piperazinyl)-propyl)oxy)phenyl)amino)-4-((3-(3-(diethylamino)-3-oxopropyl)phenyl)oxy)-N-(2,6-dimethylphenyl)-5-pyrimidinecarboxamide | 90.3 | 1.24 | 754, 377, 317 |
| 29 | 2-((3,5-bis(methyloxy)-4-((3-(4-methyl-1-piperazinyl)-propyl)oxy)phenyl)amino)-N-(2,6-dimethylphenyl)-4-((2-((trifluoromethyl)oxy)phenyl)oxy)-5-pyrimidinecarboxamide | 95.5 | 1.36 | 356, 711 |
| 30 | 2-((3,5-bis(methyloxy)-4-(4-methyl-1-piperazinyl)-phenyl)amino)-N-(2,6-dimethylphenyl)-4-(phenyloxy)-5-pyrimidinecarboxamide | 100 | 1.29 | 569, 285 |
| 31 | 2-((3-chloro-4-((2-(4-(1-methylethyl)-1-piperazinyl)-ethyl)oxy)phenyl)amino)-N-(2,6-dimethylphenyl)-4-((2-(methyloxy)-4-propylphenyl)oxy)-5-pyrimidinecarboxamide | 93 | 1.42 | 687, 344 |
| 32 | 2-((3-chloro-4-((2-(4-(1-methylethyl)-1-piperazinyl)-ethyl)oxy)phenyl)amino)-N-(2,6-dimethylphenyl)-4-((2-(ethyloxy)phenyl)oxy)-5-pyrimidinecarboxamide | 86 | 1.31 | 659, 330 |
| 33 | 2-((3-chloro-4-(4-(1-methylethyl)-1-piperazinyl)phenyl)-amino)-N-(2,6-dimethylphenyl)-4-((2-(ethyloxy)phenyl)-oxy)-5-pyrimidinecarboxamide | 85 | 1.49 | 308, 615 |
| 34 | 2-((3-chloro-4-(4-(1-methylethyl)-1-piperazinyl)phenyl)-amino)-N-(2,6-dimethylphenyl)-4-((4-(phenyloxy)-phenyl)oxy)-5-pyrimidinecarboxamide | 100 | 1.64 | 332, 663 |
| 35 | 2-((3-chloro-4-(4-(1-methylethyl)-1-piperazinyl)phenyl)-amino)-N-(2,6-dimethylphenyl)-4-((2-(methyloxy)-4-(2-propenyl)phenyl)oxy)-5-pyrimidinecarboxamide | 98 | 1.57 | 321, 641 |
| 36 | 2-((3-chloro-4-(4-(1-methylethyl)-1-piperazinyl)phenyl)-amino)-N-(2,6-dimethylphenyl)-4-((4-((phenylmethyl)-oxy)phenyl)oxy)-5-pyrimidinecarboxamide | 100 | 1.64 | 339, 677 |
| 37 | 2-((3-chloro-4-(4-(1-methylethyl)-1-piperazinyl)phenyl)-amino)-4-((2-((dimethylamino)carbonyl)-4-(methyloxy)-phenyl)oxy)-N-(2,6-dimethylphenyl)-5-pyrimidinecarboxamide | 98 | 1.29 | 336, 672 |
| 38 | 2-((3-chloro-4-(4-(1-methylethyl)-1-piperazinyl)phenyl)-amino)-4-((2-((cyclopropylmethyl)oxy)phenyl)oxy)-N-(2,6-dimethylphenyl)-5-pyrimidinecarboxamide | 92 | 1.51 | 641, 321 |
| 39 | 2-((3-chloro-4-(4-(1-methylethyl)-1-piperazinyl)phenyl)-amino)-4-((4-((1E)-3-(diethylamino)-3-oxo-1-propenyl)-2-(methyloxy)phenyl)oxy)-N-(2,6-dimethylphenyl)-5-pyrimidinecarboxamide | 88 | 1.43 | 726 |

-continued

| No. | Name | LC purity | LC Rt | Mass found |
|---|---|---|---|---|
| 40 | 2-((3-chloro-4-(4-(1-methylethyl)-1-piperazinyl)phenyl)-amino)-N-(2,6-dimethylphenyl)-4-((2-(methyloxy)-4-propylphenyl)oxy)-5-pyrimidinecarboxamide | 100 | 1.56 | 322, 643 |
| 41 | 2-((3-chloro-4-(4-methyl-1-piperazinyl)phenyl)amino)-N-(2,6-dimethylphenyl)-4-((2-(ethyloxy)phenyl)oxy)-5-pyrimidinecarboxamide | 98 | 1.42 | 294, 587 |
| 42 | 2-((3-chloro-4-(4-methyl-1-piperazinyl)phenyl)amino)-N-(2,6-dimethylphenyl)-4-((2-(methyloxy)-4-propylphenyl)-oxy)-5-pyrimidinecarboxamide | 98 | 1.55 | 308, 615 |
| 43 | 2-((4-(((2-(diethylamino)ethyl)(methyl)amino)carbonyl)-phenyl)amino)-N-(2,6-dimethylphenyl)-4-((2-(ethyloxy)-phenyl)oxy)-5-pyrimidinecarboxamide | 95 | 1.35 | 611 |
| 44 | 2-((4-(((2-(diethylamino)ethyl)(methyl)amino)carbonyl)-phenyl)amino)-N-(2,6-dimethylphenyl)-4-((2-(methyloxy)-4-propylphenyl)oxy)-5-pyrimidinecarboxamide | 100 | 1.46 | 639, 284, 320 |
| 45 | 2-((4-((3-(4-(2-(dimethylamino)ethyl)-1-piperazinyl)-propyl)oxy)-3-fluorophenyl)amino)-N-(2,6-dimethylphenyl)-4-((2-(ethyloxy)phenyl)oxy)-5-pyrimidinecarboxamide | 100 | 1.25 | 344, 686 |
| 46 | 2-((4-((3-(4-(2-(dimethylamino)ethyl)-1-piperazinyl)-propyl)oxy)-3-fluorophenyl)amino)-N-(2,6-dimethylphenyl)-4-((2-(methyloxy)-4-propylphenyl)oxy)-5-pyrimidinecarboxamide | 100 | 1.35 | 358, 714 |
| 47 | 2-((4-((3-(diethylamino)propyl)oxy)-3-fluorophenyl)-amino)-N-(2,6-dimethylphenyl)-4-(phenyloxy)-5-pyrimidinecarboxamide | 93.1 | 1.39 | 558, 279 |
| 48 | 2-((4-(1-(3-(dimethylamino)propyl)-4-piperidinyl)-phenyl)amino)-N-(2,6-dimethylphenyl)-4-((2-(ethyloxy)-phenyl)oxy)-5-pyrimidinecarboxamide | 95 | 1.26 | 623, 312 |
| 49 | 2-((4-(1-(3-(dimethylamino)propyl)-4-piperidinyl)-phenyl)amino)-N-(2,6-dimethylphenyl)-4-((2-(methyloxy)-4-propylphenyl)oxy)-5-pyrimidinecarboxamide | 95 | 1.35 | 651, 326 |
| 50 | 2-((4-(2-(diethylamino)ethyl)phenyl)amino)-N-(2,6-dimethylphenyl)-4-((2-(ethyloxy)phenyl)oxy)-5-pyrimidinecarboxamide | 95 | 1.43 | 277, 554 |
| 51 | 2-((4-(2-(diethylamino)ethyl)phenyl)amino)-N-(2,6-dimethylphenyl)-4-((2-(methyloxy)-4-propylphenyl)oxy)-5-pyrimidinecarboxamide | 96 | 1.55 | 291, 582 |
| 52 | 2-((4-(4-(2-(dimethylamino)ethyl)-1-piperazinyl)phenyl)-amino)-N-(2,6-dimethylphenyl)-4-((2-(ethyloxy)phenyl)-oxy)-5-pyrimidinecarboxamide | 97 | 1.28 | 305, 610 |
| 53 | 2-((4-(4-(2-(dimethylamino)ethyl)-1-piperazinyl)phenyl)-amino)-N-(2,6-dimethylphenyl)-4-((2-(methyloxy)-4-propylphenyl)oxy)-5-pyrimidinecarboxamide | 100 | 1.3 | 638, 297, 320 |
| 54 | 2-((4-(4-(2-(dimethylamino)ethyl)-1-piperazinyl)phenyl)-amino)-N-(2,6-dimethylphenyl)-4-((pentafluorophenyl)-oxy)-5-pyrimidinecarboxamide | 93 | 1.3 | 656, 328 |
| 55 | 2-((4-(4-(2-(dimethylamino)ethyl)-1-piperazinyl)phenyl)-amino)-N-(2,6-dimethylphenyl)-4-((2-(trifluoromethyl)-phenyl)oxy)-5-pyrimidinecarboxamide | 100 | 1.29 | 317, 634 |
| 56 | 2-((4-(4-(2-(dimethylamino)ethyl)-1-piperazinyl)phenyl)-amino)-N-(2,6-dimethylphenyl)-4-((2-methyl-1,3-benzothiazol-5-yl)oxy)-5-pyrimidinecarboxamide | 100 | 1.14 | 637 |
| 57 | 2-((4-(4-(2-(dimethylamino)ethyl)-1-piperazinyl)phenyl)-amino)-4-((2,2-dimethyl-2,3-dihydro-1-benzofuran-7-yl)-oxy)-N-(2,6-dimethylphenyl)-5-pyrimidinecarboxamide | 97 | 1.28 | 318, 636 |
| 58 | 2-((4-(4-(2-amino-2-oxoethyl)-1-piperazinyl)phenyl)-amino)-N-(2,6-dimethylphenyl)-4-((2-(ethyloxy)phenyl)-oxy)-5-pyrimidinecarboxamide | 97 | 1.32 | 298, 596 |
| 59 | 2-((4-(4-(2-amino-2-oxoethyl)-1-piperazinyl)phenyl)-amino)-N-(2,6-dimethylphenyl)-4-((2-(methyloxy)-4-propylphenyl)oxy)-5-pyrimidinecarboxamide | 100 | 1.42 | 312, 624 |
| 60 | 2-((4-(4-(2-aminoethyl)-1-piperazinyl)phenyl)amino)-N-(2,6-dimethylphenyl)-4-((2-(ethyloxy)phenyl)oxy)-5-pyrimidinecarboxamide | 84 | 1.22 | 283, 582 |
| 61 | 2-((4-(4-(2-aminoethyl)-1-piperazinyl)phenyl)amino)-N-(2,6-dimethylphenyl)-4-((2-(methyloxy)-4-propylphenyl)-oxy)-5-pyrimidinecarboxamide | 91 | 1.31 | 297, 219, 610 |
| 62 | 2-((4-(4-(3-(dimethylamino)propyl)-1-piperazinyl)-phenyl)amino)-N-(2,6-dimethylphenyl)-4-((2-(ethyloxy)-phenyl)oxy)-5-pyrimidinecarboxamide | 100 | 1.28 | 312, 624 |
| 63 | 2-((4-(4-(3-(dimethylamino)propyl)-1-piperazinyl)-phenyl)amino)-N-(2,6-dimethylphenyl)-4-((2-(methyloxy)-4-propylphenyl)oxy)-5-pyrimidinecarboxamide | 100 | 1.37 | 326, 652 |

-continued

| No. | Name | LC purity | LC Rt | Mass found |
|---|---|---|---|---|
| 64 | 2-((4-(4-(3-(dimethylamino)propyl)-1-piperazinyl)-phenyl)amino)-N-(2,6-dimethylphenyl)-4-((2-(trifluoromethyl)phenyl)oxy)-5-pyrimidinecarboxamide | 100 | 1.29 | 324, 648 |
| 65 | 2-((4-(4-(3-(dimethylamino)propyl)-1-piperazinyl)-phenyl)amino)-N-(2,6-dimethylphenyl)-4-((2-(5-isoxazolyl)phenyl)oxy)-5-pyrimidinecarboxamide | 100 | 1.16 | 647, 241 |
| 66 | 2-((4-(4-(3-(dimethylamino)propyl)-1-piperazinyl)-phenyl)amino)-4-((2,2-dimethyl-2,3-dihydro-1-benzofuran-7-yl)oxy)-N-(2,6-dimethylphenyl)-5-pyrimidinecarboxamide | 100 | 1.28 | 325, 650 |
| 67 | 2-((4-(4-(3-(dimethylamino)propyl)-1-piperazinyl)-phenyl)amino)-N-(2,6-dimethylphenyl)-4-((2-methyl-1,3-benzothiazol-5-yl)oxy)-5-pyrimidinecarboxamide | 100 | 1.13 | 651, 304 |
| 68 | 2-(1,3-benzothiazol-6-ylamino)-N-(2,6-dimethylphenyl)-4-((2-(ethyloxy)phenyl)oxy)-5-pyrimidinecarboxamide | 97 | 1.64 | 512 |
| 69 | 2-(1,3-benzothiazol-6-ylamino)-N-(2,6-dimethylphenyl)-4-((2-(methyloxy)-4-propylphenyl)oxy)-5-pyrimidinecarboxamide | 100 | 1.8 | 540 |
| 70 | 2,6-dichloro-N-(2-((3-fluoro-4-((3-(4-methyl-1-piperazinyl)propyl)oxy)phenyl)amino)-4-((2-(methyloxy)phenyl)oxy)-5-pyrimidinyl)benzamide | 100 | 1.21 | 328, 655/657 |
| 71 | 2,6-dichloro-N-(4-((2-(methyloxy)phenyl)oxy)-2-((4-(4-methyl-1-piperazinyl)phenyl)amino)-5-pyrimidinyl)-benzamide | 100 | 1.21 | 290, 579/581 |
| 72 | 2-[3-Difluoromethoxy-4-(4-methyl-piperazin-1-yl)-phenylamino]-4-(2-methoxy-4-propyl-phenoxy)-pyrimidine-5-carboxylic acid (2,6-dimethyl-phenyl)-amide | 99 | 1.58 | 324, 647 |
| 73 | 2-amino-N-(2,6-dimethylphenyl)-4-((2-(ethyloxy)-phenyl)oxy)-5-pyrimidinecarboxamide | 96 | 1.34 | 379, 757, 779 |
| 74 | 4-((2-((cyclopropylmethyl)oxy)phenyl)oxy)-N-(2,6-dimethylphenyl)-2-((4-(4-(1-methylethyl)-1-piperazinyl)-phenyl)amino)-5-pyrimidinecarboxamide | 100 | 1.43 | 607, 304 |
| 75 | 4-((2-((cyclopropylmethyl)oxy)phenyl)oxy)-N-(2,6-dimethylphenyl)-2-((3,4,5-tris(methyloxy)phenyl)amino)-5-pyrimidinecarboxamide | 96 | 1.73 | 571 |
| 76 | 4-((2-((cyclopropylmethyl)oxy)phenyl)oxy)-N-(2,6-dimethylphenyl)-2-((4-(4-methyl-1-piperazinyl)phenyl)-amino)-5-pyrimidinecarboxamide | 100 | 1.37 | 579, 310, 290 |
| 77 | 4-((2-((cyclopropylmethyl)oxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.31 | 655, 328, 348 |
| 78 | 4-((2-((cyclopropylmethyl)oxy)phenyl)oxy)-N-(2,6-dimethylphenyl)-2-((3-fluoro-4-((3-(1-piperidinyl)-propyl)oxy)phenyl)amino)-5-pyrimidinecarboxamide | 87 | 1.51 | 640 |
| 79 | 4-((2-((cyclopropylmethyl)oxy)phenyl)oxy)-N-(2,6-dimethylphenyl)-2-((3-fluoro-4-(4-methyl-1-piperazinyl)-phenyl)amino)-5-pyrimidinecarboxamide | 100 | 1.41 | 597, 299, 319 |
| 80 | 4-((2-(((dimethylamino)carbonyl)-4-(methyloxy)phenyl)-oxy)-N-(2,6-dimethylphenyl)-2-((3-fluoro-4-(4-methyl-1-piperazinyl)phenyl)amino)-5-pyrimidinecarboxamide | 89 | 1.21 | 628, 335, 314 |
| 81 | 4-((2-(((dimethylamino)carbonyl)-4-(methyloxy)phenyl)-oxy)-N-(2,6-dimethylphenyl)-2-((4-(4-(1-methylethyl)-1-piperazinyl)phenyl)amino)-5-pyrimidinecarboxamide | 100 | 1.23 | 319, 638 |
| 82 | 4-((2-(((dimethylamino)carbonyl)-4-(methyloxy)phenyl)-oxy)-N-(2,6-dimethylphenyl)-2-((3-fluoro-4-((3-(1-piperidinyl)propyl)oxy)phenyl)amino)-5-pyrimidinecarboxamide | 98 | 1.34 | 336, 671 |
| 83 | 4-((2-(((dimethylamino)carbonyl)-4-(methyloxy)phenyl)-oxy)-N-(2,6-dimethylphenyl)-2-((3-fluoro-4-((3-(4-methyl-1-piperazinyl)propyl)oxy)phenyl)amino)-5-pyrimidinecarboxamide | 97 | 1.19 | 343, 686 |
| 84 | 4-((2-(((dimethylamino)carbonyl)-4-(methyloxy)phenyl)-oxy)-N-(2,6-dimethylphenyl)-2-((3,4,5-tris(methyloxy)-phenyl)amino)-5-pyrimidinecarboxamide | 84 | 1.41 | 602, 624, 481 |
| 85 | 4-((2-(((dimethylamino)carbonyl)phenyl)oxy)-N-(2,6-dimethylphenyl)-2-((4-(4-methyl-1-piperazinyl)phenyl)-amino)-5-pyrimidinecarboxamide | 100 | 1.13 | 602, 580 |
| 86 | 4-((2-(((dimethylamino)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 97 | 1.11 | 656, 678 |
| 87 | 4-((2-(((dimethylamino)carbonyl)phenyl)oxy)-N-(2,6-dimethylphenyl)-2-((3-fluoro-4-((3-(1-piperidinyl)-propyl)oxy)phenyl)amino)-5-pyrimidinecarboxamide | 96 | 1.26 | 641, 663 |
| 88 | 4-((2-(((dimethylamino)carbonyl)phenyl)oxy)-N-(2,6-dimethylphenyl)-2-((3-fluoro-4-(4-methyl-1-piperazinyl)-phenyl)amino)-5-pyrimidinecarboxamide | 98 | 1.18 | 598, 620, 477, 406 |

-continued

| No. | Name | LC purity | LC Rt | Mass found |
|---|---|---|---|---|
| 89 | 4-((2-((dimethylamino)carbonyl)phenyl)oxy)-N-(2,6-dimethylphenyl)-2-((4-(4-(1-methylethyl)-1-piperazinyl)-phenyl)amino)-5-pyrimidinecarboxamide | 100 | 1.18 | 608, 630, 416, 487 |
| 90 | 4-((2-(aminocarbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 91.8 | 1.33 | 628 |
| 91 | 4-((2-(aminocarbonyl)phenyl)oxy)-N-(2,6-dimethylphenyl)-2-((4-(4-methyl-1-piperazinyl)phenyl)-amino)-5-pyrimidinecarboxamide | 97.9 | 1.41 | 552 |
| 92 | 4-((2-(cyclopentyloxy)phenyl)oxy)-N-(2,6-dimethylphenyl)-2-((4-(4-(1-methylethyl)-1-piperazinyl)-phenyl)amino)-5-pyrimidinecarboxamide | 100 | 1.51 | 311, 277, 621 |
| 93 | 4-((2-(cyclopentyloxy)phenyl)oxy)-N-(2,6-dimethylphenyl)-2-((4-(4-methyl-1-piperazinyl)phenyl)-amino)-5-pyrimidinecarboxamide | 100 | 1.4 | 693, 615 |
| 94 | 4-((2-(cyclopentyloxy)phenyl)oxy)-N-(2,6-dimethylphenyl)-2-((3-fluro-4-((3-(4-methyl-1-piperazinyl)propyl)oxy)phenyl)amino)-5-pyrimidinecarboxamide | 95 | 1.35 | 669, 692, 301 |
| 95 | 4-((2-(cyclopentyloxy)phenyl)oxy)-N-(2,6-dimethylphenyl)-2-((3-fluro-4-((3-(1-piperidinyl)-propyl)oxy)phenyl)amino)-5-pyrimidinecarboxamide | 97 | 1.54 | 654, 293 |
| 96 | 4-((2-(cyclopentyloxy)phenyl)oxy)-N-(2,6-dimethylphenyl)-2-((3-fluro-4-(4-methyl-1-piperazinyl)-phenyl)amino)-5-pyrimidinecarboxamide | 98 | 1.47 | 611, 633 |
| 97 | 4-((2,2-dimethyl-2,3-dihydro-1-benzofuran-7-yl)oxy)-N-(2,6-dimethylphenyl)-2-((4-(4-methyl-1-piperazinyl)-phenyl)amino)-5-pyrimidinecarboxamide | 90 | 1.39 | 290, 579 |
| 98 | 4-((2,2-dimethyl-2,3-dihydro-1-benzofuran-7-yl)oxy)-N-(2,6-dimethylphenyl)-2-((4-(4-(1-methylethyl)-1-piperazinyl)phenyl)amino)-5-pyrimidinecarboxamide | 100 | 1.42 | 607 |
| 99 | 4-((2,2-dimethyl-2,3-dihydro-1-benzofuran-7-yl)oxy)-N-(2,6-dimethylphenyl)-2-((3-fluro-4-((3-(4-methyl-1-piperazinyl)propyl)oxy)phenyl)amino)-5-pyrimidinecarboxamide | 100 | 1.3 | 655, 328, 348 |
| 100 | 4-((2,2-dimethyl-2,3-dihydro-1-benzofuran-7-yl)oxy)-N-(2,6-dimethylphenyl)-2-((3-fluro-4-(4-methyl-1-piperazinyl)phenyl)amino)-5-pyrimidinecarboxamide | 98 | 1.42 | 299, 597 |
| 101 | 4-((2,2-dimethyl-2,3-dihydro-1-benzofuran-7-yl)oxy)-N-(2,6-dimethylphenyl)-2-((3-fluoro-4-((3-(1-piperidinyl)-propyl)oxy)phenyl)amino)-5-pyrimidinecarboxamide | 100 | 1.5 | 640 |
| 102 | 4-((2,2-dimethyl-2,3-dihydro-1-benzofuran-7-yl)oxy)-N-(2,6-dimethylphenyl)-2-((3-(methyloxy)-4-(4-methyl-1-piperazinyl)phenyl)amino)-5-pyrimidinecarboxamide | 100 | 1.38 | 609 |
| 103 | 4-((2,2-dimethyl-2,3-dihydro-1-benzofuran-7-yl)oxy)-N-(2,6-dimethylphenyl)-2-((3-fluoro-4-((3-(4-morpholinyl)-propyl)oxy)phenyl)amino)-5-pyrimidinecarboxamide | 100 | 1.38 | 642, 322, 261 |
| 104 | 4-((2,3-dichlorophenyl)oxy)-N-(2,6-dimethylphenyl)-2-((4-(4-(1-methylethyl)-1-piperazinyl)phenyl)amino)-5-pyrimidinecarboxamide | 93 | 1.44 | 303, 605/607 |
| 105 | 4-((2,4-dichlorophenyl)oxy)-N-(2,6-dimethylphenyl)-2-((3-(methyloxy)-4-(4-methyl-1-piperazinyl)phenyl)-amino)-5-pyrimidinecarboxamide | 100 | 1.38 | 607/609, 324, 304 |
| 106 | 4-((2,4-dichlorophenyl)oxy)-N-(2,6-dimethylphenyl)-2-((3-fluoro-4-((3-(4-methyl-1-piperazinyl)propyl)oxy)-phenyl)amino)-5-pyrimidinecarboxamide | 96.9 | 1.32 | 653/655, 327, 347 |
| 107 | 4-((2,4-dichlorophenyl)oxy)-N-(2,6-dimethylphenyl)-2-((3-fluoro-4-((3-(1-piperidinyl)propyl)oxy)phenyl)-amino)-5-pyrimidinecarboxamide | 100 | 1.52 | 638/640, 319 |
| 108 | 4-((2,4-dichlorophenyl)oxy)-N-(2,6-dimethylphenyl)-2-((3-fluoro-4-(4-methyl-1-piperazinyl)phenyl)amino)-5-pyrimidinecarboxamide | 100 | 1.43 | 318, 595/597, 298 |
| 109 | 4-((2,4-dichlorophenyl)oxy)-N-(2,6-dimethylphenyl)-2-((4-(4-(1-methylethyl)-1-piperazinyl)phenyl)amino)-5-pyrimidinecarboxamide | 100 | 1.42 | 303, 605/607, 323 |
| 110 | 4-((2,4-dichlorophenyl)oxy)-N-(2,6-dimethylphenyl)-2-((4-(4-methyl-1-piperazinyl)phenyl)amino)-5-pyrimidinecarboxamide | 100 | 1.39 | 309, 289, 577/579 |
| 111 | 4-((2,6-bis(methyloxy)phenyl)oxy)-N-(2,6-dimethylphenyl)-2-(3-fluoro-4-((3-(1-piperidinyl)propyl)oxy)-phenyl)amino)-5-pyrimidinecarboxamide | 95 | 1.44 | 315, 630 |
| 112 | 4-((2,6-bis(methyloxy)phenyl)oxy)-N-(2,6-dimethylphenyl)-2-((4-(4-methyl-1-piperazinyl)phenyl)-amino)-5-pyrimidinecarboxamide | 100 | 1.31 | 285, 569 |
| 113 | 4-((2,6-bis(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.28 | 323, 645 |

-continued

| No. | Name | LC purity | LC Rt | Mass found |
|---|---|---|---|---|
| 114 | 4-((2,6-bis(methyloxy)phenyl)oxy)-N-(2,6-dimethylphenyl)-2-((3-fluoro-4-(4-methyl-1-piperazinyl)-phenyl)amino)-5-pyrimidinecarboxamide | 85 | 1.36 | 294, 587 |
| 115 | 4-((2,6-bis(methyloxy)phenyl)oxy)-N-(2,6-dimethylphenyl)-2-((4-(4-(1-methylethyl)-1-piperazinyl)phenyl)amino)-5-pyrimidinecarboxamide | 90 | 1.37 | 299, 597 |
| 116 | 4-((2-chloro-4-((diethylamino)carbonyl)phenyl)oxy)-2-((4-(4-(2-(dimethylamino)ethyl)-1-piperazinyl)phenyl)-amino)-N-(2,6-dimethylphenyl)-5-pyrimidinecarboxamide | 97 | 1.26 | 350, 370, 699 |
| 117 | 4-((2-chloro-4-((diethylamino)carbonyl)phenyl)oxy)-2-((4-(4-(3-(dimethylamino)propyl)-1-piperazinyl)phenyl)-amino)-N-(2,6-dimethylphenyl)-5-pyrimidinecarboxamide | 93 | 1.28 | 357, 713 |
| 118 | 4-((2-chloro-4-((diethylamino)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 92 | 1.26 | 718, 299, 551 |
| 119 | 4-((2-chloro-4-((diethylamino)carbonyl)phenyl)oxy)-N-(2,6-dimethylphenyl)-2-((3-fluoro-4-(4-methyl-1-piperazinyl)phenyl)amino)-5-pyrimidinecarboxamide | 90 | 1.36 | 660 |
| 120 | 4-((2-chloro-4-((diethylamino)carbonyl)phenyl)oxy)-N-(2,6-dimethylphenyl)-2-((4-(4-(1-methylethyl)-1-piperazinyl)phenyl)amino)-5-pyrimidinecarboxamide | 95 | 1.41 | 670, 335 |
| 121 | 4-((2-chloro-4-((diethylamino)carbonyl)phenyl)oxy)-N-(2,6-dimethylphenyl)-2-((3-fluoro-4-((3-(1-piperidinyl)-propyl)oxy)phenyl)amino)-5-pyrimidinecarboxamide | 97 | 1.46 | 703/705, 352 |
| 122 | 4-((2-chloro-4-((diethylamino)carbonyl)phenyl)oxy)-N-(2,6-dimethylphenyl)-2-((4-(4-methyl-1-piperazinyl)-phenyl)amino)-5-pyrimidinecarboxamide | 100 | 1.37 | 321, 642/644 |
| 123 | 4-((2-chloro-4-(trifluoromethyl)phenyl)oxy)-2-((4-(4-(3-(dimethylamino)propyl)-1-piperazinyl)phenyl)amino)-N-(2,6-dimethylphenyl)-5-pyrimidinecarboxamide | 90 | 1.27 | 682, 319, 341 |
| 124 | 4-((2-chloro-4-(trifluoromethyl)phenyl)oxy)-N-(2,6-dimethylphenyl)-2-((4-(4-methyl-1-piperazinyl)phenyl)-amino)-5-pyrimidinecarboxamide | 86 | 1.43 | 611, 326 |
| 125 | 4-((2-chloro-4-(trifluoromethyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 86 | 1.36 | 687, 344, 364 |
| 126 | 4-((2-chloro-4-(trifluoromethyl)phenyl)oxy)-N-(2,6-dimethylphenyl)-2-((3-fluoro-4-(4-methyl-1-piperazinyl)phenyl)amino)-5-pyrimidinecarboxamide | 95 | 1.46 | 629 |
| 127 | 4-((2-chloro-4-(trifluoromethyl)phenyl)oxy)-N-(2,6-dimethylphenyl)-2-((4-(4-(1-methylethyl)-1-piperazinyl)-phenyl)amino)-5-pyrimidinecarboxamide | 97 | 1.43 | 639, 320 |
| 128 | 4-((2-chloro-4-fluorophenyl)oxy)-2-((4-(4-(2-(dimethylamino)ethyl)-1-piperazinyl)phenyl)amino)-N-(2,6-dimethylphenyl)-5-pyrimidinecarboxamide | 87 | 1.27 | 309, 618/620 |
| 129 | 4-((2-chloro-4-fluorophenyl)oxy)-2-((4-(4-(3-(dimethylamino)propyl)-1-piperazinyl)phenyl)amino)-N-(2,6-dimethylphenyl)-5-pyrimidinecarboxamide | 97 | 1.28 | 316, 632/634 |
| 130 | 4-((2-chloro-4-fluorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.3 | 319, 637/639 |
| 131 | 4-((2-chloro-4-fluorophenyl)oxy)-N-(2,6-dimethylphenyl)-2-((3-fluoro-4-((3-(1-piperidinyl)-propyl)oxy)phenyl)amino)-5-pyrimidinecarboxamide | 100 | 1.49 | 622/624, 311 |
| 132 | 4-((2-chloro-4-fluorophenyl)oxy)-N-(2,6-dimethylphenyl)-2-((3-fluoro-4-(4-methyl-1-piperazinyl)-phenyl)amino)-5-pyrimidinecarboxamide | 96 | 1.4 | 579/581, 290 |
| 133 | 4-((2-chloro-4-fluorophenyl)oxy)-N-(2,6-dimethylphenyl)-2-((4-(4-methyl-1-piperazinyl)phenyl)-amino)-5-pyrimidinecarboxamide | 90 | 1.38 | 561/563, 281 |
| 134 | 4-((2-chloro-4-fluorophenyl)oxy)-N-(2,6-dimethylphenyl)-2-((4-(4-(1-methylethyl)-1-piperazinyl)phenyl)amino)-5-pyrimidinecarboxamide | 86 | 1.41 | 295, 589/591 |
| 135 | 4-((2-chloro-4-methylphenyl)oxy)-2-((4-(4-(3-(dimethylamino)propyl)-1-piperazinyl)phenyl)amino)-N-(2,6-dimethylphenyl)-5-pyrimidinecarboxamide | 100 | 1.27 | 314, 628/630 |
| 136 | 4-((2-chloro-4-methylphenyl)oxy)-N-(2,6-dimethylphenyl)-2-((3-fluoro-4-((3-(4-methyl-1-piperazinyl)propyl)oxy)phenyl)amino)-5-pyrimidine-carboxamide | 100 | 1.33 | 317, 633/635 |
| 137 | 4-((2-chloro-4-methylphenyl)oxy)-N-(2,6-dimethylphenyl)-2-((3-fluoro-4-((3-(1-piperidinyl)-propyl)oxy)phenyl)amino)-5-pyrimidinecarboxamide | 97 | 1.53 | 618/620, 309 |
| 138 | 4-((2-chloro-4-methylphenyl)oxy)-N-(2,6-dimethylphenyl)-2-((3-fluoro-4-(4-methyl-1-piperazinyl)-phenyl)amino)-5-pyrimidinecarboxamide | 94 | 1.44 | 575/577, 288 |

| No. | Name | LC purity | LC Rt | Mass found |
|---|---|---|---|---|
| 139 | 4-((2-chloro-4-methylphenyl)oxy)-N-(2,6-dimethylphenyl)-2-((4-(4-methyl-1-piperazinyl)phenyl)amino)-5-pyrimidinecarboxamide | 100 | 1.39 | 279, 557/559 |
| 140 | 4-((2-chloro-4-methylphenyl)oxy)-N-(2,6-dimethylphenyl)-2-((4-(4-(1-methylethyl)-1-piperazinyl)phenyl)amino)-5-pyrimidinecarboxamide | 97 | 1.44 | 313, 585/587 |
| 141 | 4-((2-chlorophenyl)oxy)-N-(2,6-dimethylphenyl)-2-((3-(methyloxy)-4-(4-methyl-1-piperazinyl)phenyl)amino)-5-pyrimidinecarboxamide | 100 | 1.32 | 573/575, 287, 307 |
| 142 | 4-((2-chlorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 98 | 1.26 | 310, 619/621, 330 |
| 143 | 4-((2-chlorophenyl)oxy)-N-(2,6-dimethylphenyl)-2-((3-fluoro-4-((3-(1-piperidinyl)propyl)oxy)phenyl)amino)-5-pyrimidinecarboxamide | 98.4 | 1.44 | 604/606, 302 |
| 144 | 4-((2-chlorophenyl)oxy)-N-(2,6-dimethylphenyl)-2-((3-fluoro-4-(4-methyl-1-piperazinyl)phenyl)amino)-5-pyrimidinecarboxamide | 98.7 | 1.33 | 281, 561/563, 301 |
| 145 | 4-((2-chlorophenyl)oxy)-N-(2,6-dimethylphenyl)-2-((4-(4-(1-methylethyl)-1-piperazinyl)phenyl)amino)-5-pyrimidinecarboxamide | 85.8 | 1.37 | 286, 571/573, 306 |
| 146 | 4-((2-chlorophenyl)oxy)-N-(2,6-dimethylphenyl)-2-((4-(4-methyl-1-piperazinyl)phenyl)amino)-5-pyrimidinecarboxamide | 97.7 | 1.31 | 292, 543/545, 272 |
| 147 | 4-((3-(2-(diethylamino)ethyl)phenyl)oxy)-N-(2,6-dimethylphenyl)-2-((4-(4-methyl-1-piperazinyl)phenyl)amino)-5-pyrimidinecarboxamide | 93.9 | 1.07 | 325, 608, 722 |
| 148 | 4-((3-(2-(diethylamino)ethyl)phenyl)oxy)-N-(2,6-dimethylphenyl)-2-((3-(methyloxy)-4-(4-methyl-1-piperazinyl)phenyl)amino)-5-pyrimidinecarboxamide | 82.6 | 1.07 | 319, 752, 677, 638 |
| 149 | 4-((3-(2-(diethylamino)ethyl)phenyl)oxy)-N-(2,6-dimethylphenyl)-2-((4-(1-piperazinyl)phenyl)amino)-5-pyrimidinecarboxamide | 96.1 | 1.11 | 318, 594 |
| 150 | 4-((3-(2-aminoethyl)phenyl)oxy)-N-(2,6-dichlorophenyl)-2-(phenylamino)-5-pyrimidinecarboxamide | 98.1 | 1.24 | 494/496 |
| 151 | 4-((3-(2-aminoethyl)phenyl)oxy)-N-(2,6-dimethylphenyl)-2-(phenylamino)-5-pyrimidinecarboxamide | 95.3 | 1.22 | 454, 248 |
| 152 | 4-((3-(3-(diethylamino)-3-oxopropyl)phenyl)oxy)-N-(2,6-dimethylphenyl)-2-((4-(4-methyl-1-piperazinyl)phenyl)amino)-5-pyrimidinecarboxamide | 96.7 | 1.29 | 278, 636, 318 |
| 153 | 4-((3-(3-(diethylamino)-3-oxopropyl)phenyl)oxy)-N-(2,6-dimethylphenyl)-2-((3-(methyloxy)-4-(4-methyl-1-piperazinyl)phenyl)amino)-5-pyrimidinecarboxamide | 96.6 | 1.31 | 666, 333 |
| 154 | 4-((3-(3-(diethylamino)-3-oxopropyl)phenyl)oxy)-N-(2,6-dimethylphenyl)-2-((3-fluoro-4-(4-methyl-1-piperazinyl)phenyl)amino)-5-pyrimidinecarboxamide | 96 | 1.35 | 654, 327 |
| 155 | 4-((3-(3-(diethylamino)-3-oxopropyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 91.3 | 1.25 | 712, 356, 296 |
| 156 | 4-((3-(3-(diethylamino)-3-oxopropyl)phenyl)oxy)-N-(2,6-dimethylphenyl)-2-((3-fluoro-4-((3-(1-piperidinyl)propyl)oxy)phenyl)amino)-5-pyrimidinecarboxamide | 95.1 | 1.35 | 654, 327, 287 |
| 157 | 4-((3-(3-(diethylamino)-3-oxopropyl)phenyl)oxy)-N-(2,6-dimethylphenyl)-2-((4-(((2R)-2-pyrrolidinylmethyl)oxy)phenyl)amino)-5-pyrimidinecarboxamide | 86.5 | 1.32 | 637 |
| 158 | 4-((3-(3-amino-3-oxopropyl)phenyl)oxy)-2-((3-chloro-4-(4-(1-methylethyl)-1-piperazinyl)phenyl)amino)-N-(2,6-dimethylphenyl)-5-pyrimidinecarboxamide | 100 | 1.28 | 252, 642, 321 |
| 159 | 4-((3-(3-amino-3-oxopropyl)phenyl)oxy)-N-(2,6-dimethylphenyl)-2-((3,4,5-tris(methyloxy)phenyl)amino)-5-pyrimidinecarboxamide | 100 | 1.35 | 572 |
| 160 | 4-((3-(3-amino-3-oxopropyl)phenyl)oxy)-N-(2,6-dimethylphenyl)-2-((4-(4-methyl-1-piperazinyl)phenyl)amino)-5-pyrimidinecarboxamide | 100 | 1.19 | 221, 580, 290 |
| 161 | 4-((3-(3-amino-3-oxopropyl)phenyl)oxy)-N-(2,6-dimethylphenyl)-2-((3-fluoro-4-((3-(1-piperidinyl)propyl)oxy)phenyl)amino)-5-pyrimidinecarboxamide | 97 | 1.27 | 641, 252, 321 |
| 162 | 4-((3-(3-amino-3-oxopropyl)phenyl)oxy)-N-(2,6-dimethylphenyl)-2-((3-fluoro-4-(4-methyl-1-piperazinyl)phenyl)amino)-5-pyrimidinecarboxamide | 97 | 1.16 | 598, 299 |
| 163 | 4-((3-(3-amino-3-oxopropyl)phenyl)oxy)-N-(2,6-dimethylphenyl)-2-((4-(4-(1-methylethyl)-1-piperazinyl)phenyl)amino)-5-pyrimidinecarboxamide | 100 | 1.22 | 235, 608, 304 |
| 164 | 4-((3-(3-amino-3-oxopropyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.17 | 259, 656, 328 |

| No. | Name | LC purity | LC Rt | Mass found |
|---|---|---|---|---|
| 165 | 4-((3,3'-bis(methyloxy)-1,1'-biphenyl-4-yl)oxy)-N-(2,6-dimethylphenyl)-2-((3,4,5-tris(methyloxy)phenyl)amino)-5-pyrimidinecarboxamide | 94 | 1.8 | 637 |
| 166 | 4-((3,4'-bis(methyloxy)-1,1'-biphenyl-4-yl)oxy)-N-(2,6-dimethylphenyl)-2-((3-fluoro-4-((3-(4-methyl-1-piperazinyl)propyl)oxy)phenyl)amino)-5-pyrimidinecarboxamide | 96 | 1.4 | 361, 721 |
| 167 | 4-((3,4'-bis(methyloxy)-1,1'-biphenyl-4-yl)oxy)-N-(2,6-dimethylphenyl)-2-((3,4,5-tris(methyloxy)phenyl)amino)-5-pyrimidinecarboxamide | 94 | 1.74 | 637 |
| 168 | 4-((3,4-dichlorophenyl)oxy)-N-(2,6-dimethylphenyl)-2-((3-(methyloxy)-4-(4-methyl-1-piperazinyl)phenyl)amino)-5-pyrimidinecarboxamide | 100 | 1.4 | 607/609, 324, 304 |
| 169 | 4-((3,4-dichlorophenyl)oxy)-N-(2,6-dimethylphenyl)-2-((3-fluoro-4-((3-(1-piperidinyl)propyl)oxy)phenyl)amino)-5-pyrimidinecarboxamide | 100 | 1.52 | 638/640, 319 |
| 170 | 4-((3,4-dichlorophenyl)oxy)-N-(2,6-dimethylphenyl)-2-((3-fluoro-4-(4-methyl-1-piperazinyl)phenyl)amino)-5-pyrimidinecarboxamide | 100 | 1.43 | 318, 595/597, 339 |
| 171 | 4-((3,4-dichlorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 96.6 | 1.32 | 327, 653/655, 347 |
| 172 | 4-((3,4-dichlorophenyl)oxy)-N-(2,6-dimethylphenyl)-2-((4-(4-(1-methylethyl)-1-piperazinyl)phenyl)amino)-5-pyrimidinecarboxamide | 98.5 | 1.44 | 605/607, 323 |
| 173 | 4-((3,4-dichlorophenyl)oxy)-N-(2,6-dimethylphenyl)-2-((4-(4-methyl-1-piperazinyl)phenyl)amino)-5-pyrimidinecarboxamide | 100 | 1.39 | 577/579 |
| 174 | 4-((3'-chloro-3-(methyloxy)-1,1'-biphenyl-4-yl)oxy)-N-(2,6-dimethylphenyl)-2-((3-fluoro-4-((3-(4-methyl-1-piperazinyl)propyl)oxy)phenyl)amino)-5-pyrimidinecarboxamide | 84 | 1.47 | 363, 725 |
| 175 | 4-((3-chlorophenyl)oxy)-N-(2,6-dimethylphenyl)-2-((3-(methyloxy)-4-(4-methyl-1-piperazinyl)phenyl)amino)-5-pyrimidinecarboxamide | 97.8 | 1.31 | 573, 287, 307 |
| 176 | 4-((3-chlorophenyl)oxy)-N-(2,6-dimethylphenyl)-2-((3-fluoro-4-(4-methyl-1-piperazinyl)phenyl)amino)-5-pyrimidinecarboxamide | 98.1 | 1.37 | 561, 301, 281 |
| 177 | 4-((3-chlorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 97.2 | 1.25 | 310, 619 |
| 178 | 4-((3-chlorophenyl)oxy)-N-(2,6-dimethylphenyl)-2-((3-fluoro-4-((3-(1-piperidinyl)propyl)oxy)phenyl)amino)-5-pyrimidinecarboxamide | 94.1 | 1.45 | 604, 302 |
| 179 | 4-((3-chlorophenyl)oxy)-N-(2,6-dimethylphenyl)-2-((4-(4-(1-methylethyl)-1-piperazinyl)phenyl)amino)-5-pyrimidinecarboxamide | 96.8 | 1.37 | 571, 286, 306 |
| 180 | 4-((3-chlorophenyl)oxy)-N-(2,6-dimethylphenyl)-2-((4-(4-methyl-1-piperazinyl)phenyl)amino)-5-pyrimidinecarboxamide | 98 | 1.33 | 543, 292, 272 |
| 181 | 4-((3'-cyano-3-(methyloxy)-1,1'-biphenyl-4-yl)oxy)-N-(2,6-dimethylphenyl)-2-((3,4,5-tris(methyloxy)phenyl)amino)-5-pyrimidinecarboxamide | 100 | 1.67 | 632 |
| 182 | 4-((4-((1E)-3-(diethylamino)-3-oxo-1-propenyl)-2-(methyloxy)phenyl)oxy)-N-(2,6-dimethylphenyl)-2-((4-(4-methyl-1-piperazinyl)phenyl)amino)-5-pyrimidinecarboxamide | 97 | 1.39 | 332, 664 |
| 183 | 4-((4-((1E)-3-(diethylamino)-3-oxo-1-propenyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 96 | 1.33 | 370, 740 |
| 184 | 4-((4-((1E)-3-(diethylamino)-3-oxo-1-propenyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide | 94 | 1.49 | 363, 725 |
| 185 | 4-((4-((1E)-3-(diethylamino)-3-oxo-1-propenyl)-2-(methyloxy)phenyl)oxy)-N-(2,6-dimethylphenyl)-2-((3-fluoro-4-(4-methyl-1-piperazinyl)phenyl)amino)-5-pyrimidinecarboxamide | 96 | 1.41 | 341, 682 |
| 186 | 4-((4-((1E)-3-(diethylamino)-3-oxo-1-propenyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide | 98 | 1.39 | 692 |
| 187 | 4-((4-((1E)-3-(diethylamino)-3-oxo-1-propenyl)-2-(methyloxy)phenyl)oxy)-N-(2,6-dimethylphenyl)-2-((3,4,5-tris(methyloxy)phenyl)amino)-5-pyrimidinecarboxamide | 93 | 1.52 | 656 |
| 188 | 4-((4-(2-(diethylamino)ethyl)oxy)phenyl)oxy)-N-(2,6-dimethylphenyl)-2-((4-(4-methyl-1-piperazinyl)phenyl)amino)-5-pyrimidinecarboxamide | 100 | 1.09 | 312, 333, 624 |

-continued

| No. | Name | LC purity | LC Rt | Mass found |
|---|---|---|---|---|
| 189 | 4-((4-((diethylamino)carbonyl)-2-(methyloxy)phenyl)-oxy)-2-((4-(4-(3-(dimethylamino)propyl)-1-piperazinyl)-phenyl)amino)-N-(2,6-dimethylphenyl)-5-pyrimidinecarboxamide | 96 | 1.24 | 355, 709 |
| 190 | 4-((4-((diethylamino)carbonyl)-2-(methyloxy)phenyl)-oxy)-N-(2,6-dimethylphenyl)-2-((4-(4-methyl-1-piperazinyl)phenyl)amino)-5-pyrimidinecarboxamide | 96 | 1.32 | 319, 638 |
| 191 | 4-((4-((diethylamino)carbonyl)-2-(methyloxy)phenyl)-oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.26 | 714, 357 |
| 192 | 4-((4-((diethylamino)carbonyl)-2-(methyloxy)phenyl)-oxy)-N-(2,6-dimethylphenyl)-2-((3-fluoro-4-((3-(1-piperidinyl)propyl)oxy)phenyl)amino)-5-pyrimidinecarboxamide | 100 | 1.43 | 699, 350 |
| 193 | 4-((4-((diethylamino)carbonyl)-2-(methyloxy)phenyl)-oxy)-N-(2,6-dimethylphenyl)-2-((3-fluoro-4-(4-methyl-1-piperazinyl)phenyl)amino)-5-pyrimidinecarboxamide | 100 | 1.34 | 328, 656 |
| 194 | 4-((4-((diethylamino)carbonyl)-2-(methyloxy)phenyl)-oxy)-N-(2,6-dimethylphenyl)-2-((4-(4-(1-methylethyl)-1-piperazinyl)phenyl)amino)-5-pyrimidinecarboxamide | 90 | 1.39 | 333, 666 |
| 195 | 4-((4-(1,3-benzodioxol-5-yl)-2-(methyloxy)phenyl)oxy)-N-(2,6-dimethylphenyl)-2-((3,4,5-tris(methyloxy)-phenyl)amino)-5-pyrimidinecarboxamide | 100 | 1.75 | 651 |
| 196 | 4-((4-(1,3-benzodioxol-5-yl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 93 | 1.36 | 735, 389 |
| 197 | 4-((4-(2-aminoethyl)-2-(methyloxy)phenyl)oxy)-N-(2,6-dimethylphenyl)-2-((4-(4-(1-methylethyl)-1-piperazinyl)-phenyl)amino)-5-pyrimidinecarboxamide | 92 | 1.08 | 610 |
| 198 | 4-((4-(2-aminoethyl)-2-(methyloxy)phenyl)oxy)-N-(2,6-dimethylphenyl)-2-((4-(4-methyl-1-piperazinyl)phenyl)-amino)-5-pyrimidinecarboxamide | 98 | 1.05 | 582, 604 |
| 199 | 4-((4-(2-aminoethyl)-2-(methyloxy)phenyl)oxy)-N-(2,6-dimethylphenyl)-2-((3-(methyloxy)-4-(4-methyl-1-piperazinyl)phenyl)amino)-5-pyrimidinecarboxamide | 90 | 1.06 | 612, 634 |
| 200 | 4-((4-(2-aminoethyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 94 | 1.05 | 658, 681 |
| 201 | 4-((4-(2-aminoethyl)-2-(methyloxy)phenyl)oxy)-N-(2,6-dimethylphenyl)-2-((3-fluoro-4-((3-(1-piperidinyl)-propyl)oxy)phenyl)amino)-5-pyrimidinecarboxamide | 100 | 1.12 | 643, 666 |
| 202 | 4-((4-(2-aminoethyl)-2-(methyloxy)phenyl)oxy)-N-(2,6-dimethylphenyl)-2-((3,4,5-tris(methyloxy)phenyl)amino)-5-pyrimidinecarboxamide | 100 | 1.22 | 287, 574 |
| 203 | 4-((4-(2-aminoethyl)-2,6-bis(methyloxy)phenyl)oxy)-2-((4-(4-(2-(dimethylamino)ethyl)-1-piperazinyl)phenyl)-amino)-N-(2,6-dimethylphenyl)-5-pyrimidinecarboxamide | 84 | 1.07 | 335, 669 |
| 204 | 4-((4-(2-aminoethyl)-2,6-bis(methyloxy)phenyl)oxy)-N-(2,6-dimethylphenyl)-2-((4-(4-methyl-1-piperazinyl)-phenyl)amino)-5-pyrimidinecarboxamide | 96 | 1.1 | 612, 306 |
| 205 | 4-((4-(2-aminoethyl)-2,6-bis(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.05 | 345, 688 |
| 206 | 4-((4-(2-aminoethyl)-2,6-bis(methyloxy)phenyl)oxy)-N-(2,6-dimethylphenyl)-2-((3-fluoro-4-((3-(1-piperidinyl)-propyl)oxy)phenyl)amino)-5-pyrimidinecarboxamide | 92 | 1.12 | 337, 673 |
| 207 | 4-((4-(2-aminoethyl)-2,6-bis(methyloxy)phenyl)oxy)-N-(2,6-dimethylphenyl)-2-((3-fluoro-4-(4-methyl-1-piperazinyl)phenyl)amino)-5-pyrimidinecarboxamide | 100 | 1.12 | 315, 630 |
| 208 | 4-((4-(2-aminoethyl)-2,6-bis(methyloxy)phenyl)oxy)-N-(2,6-dimethylphenyl)-2-((4-(4-(1-methylethyl)-1-piperazinyl)phenyl)amino)-5-pyrimidinecarboxamide | 100 | 1.12 | 320, 640 |
| 209 | 4-((4-(2-aminoethyl)phenyl)oxy)-2-((3,5-bis(methyloxy)-4-((3-(1-piperazinyl)propyl)oxy)phenyl)amino)-N-(2,6-dimethylphenyl)-5-pyrimidinecarboxamide | 98.1 | 1.02 | 328, 656 |
| 210 | 4-((4-(2-aminoethyl)phenyl)oxy)-N-(2,6-dimethylphenyl)-2-((3-(methyloxy)-4-(1-piperazinyl)-phenyl)amino)-5-pyrimidinecarboxamide | 95.2 | 1.03 | 284, 305.568 |
| 211 | 4-((4-(2-aminoethyl)phenyl)oxy)-N-(2,6-dimethylphenyl)-2-((4-(1-piperazinyl)phenyl)amino)-5-pyrimidinecarboxamide | 91.6 | 1.07 | 281, 538 |
| 212 | 4-((4-(2-aminoethyl)phenyl)oxy)-N-(2,6-dimethylphenyl)-2-((4-(4-methyl-1-piperazinyl)phenyl)-amino)-5-pyrimidinecarboxamide | 97.7 | 1.09 | 228, 552 |
| 213 | 4-((4-(3-(diethylamino)-3-oxopropyl)-2-(methyloxy)-phenyl)oxy)-N-(2,6-dimethylphenyl)-2-((4-(4-(1-methylethyl)-1-piperazinyl)phenyl)amino)-5-pyrimidinecarboxamide | 93 | 1.36 | 694, 716 |

-continued

| No. | Name | LC purity | LC Rt | Mass found |
|---|---|---|---|---|
| 214 | 4-((4-(3-(diethylamino)-3-oxopropyl)-2-(methyloxy)-phenyl)oxy)-N-(2,6-dimethylphenyl)-2-((4-(4-methyl-1-piperazinyl)phenyl)amino)-5-pyrimidinecarboxamide | 95 | 1.31 | 666, 688 |
| 215 | 4-((4-(3-(diethylamino)-3-oxopropyl)-2-(methyloxy)-phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.25 | 742, 764 |
| 216 | 4-((4-(3-(diethylamino)-3-oxopropyl)-2-(methyloxy)-phenyl)oxy)-N-(2,6-dimethylphenyl)-2-((3-fluoro-4-((3-(1-piperidinyl)propyl)oxy)phenyl)amino)-5-pyrimidinecarboxamide | 98 | 1.42 | 727, 749 |
| 217 | 4-((4-(3-(diethylamino)-3-oxopropyl)-2-(methyloxy)-phenyl)oxy)-N-(2,6-dimethylphenyl)-2-((3-fluoro-4-(4-methyl-1-piperazinyl)phenyl)amino)-5-pyrimidinecarboxamide | 98 | 1.33 | 684, 706 |
| 218 | 4-((4-(3-(diethylamino)propyl)-2-(methyloxy)phenyl)-oxy)-N-(2,6-dimethylphenyl)-2-((3-fluoro-4-(4-methyl-1-piperazinyl)phenyl)amino)-5-pyrimidinecarboxamide | 83 | 1.18 | 335, 670 |
| 219 | 4-((4-(3-(diethylamino)propyl)-2-(methyloxy)phenyl)-oxy)-N-(2,6-dimethylphenyl)-2-((4-(4-(1-methylethyl)-1-piperazinyl)phenyl)amino)-5-pyrimidinecarboxamide | 91 | 1.19 | 340, 680 |
| 220 | 4-((4-(acetylamino)phenyl)oxy)-N-(2,6-dimethylphenyl)-2-((3-(methyloxy)-4-(4-methyl-1-piperazinyl)phenyl)-amino)-5-pyrimidinecarboxamide | 95.1 | 1.13 | 596 |
| 221 | 4-((4-(acetylamino)phenyl)oxy)-N-(2,6-dimethylphenyl)-2-((4-(4-methyl-1-piperazinyl)phenyl)amino)-5-pyrimidinecarboxamide | 96.9 | 1.12 | 566 |
| 222 | 4-((4-(acetylamino)phenyl)oxy)-N-(2,6-dimethylphenyl)-2-((4-(1-piperazinyl)phenyl)amino)-5-pyrimidinecarboxamide | 94.2 | 1.14 | 552, 297, 318 |
| 223 | 4-((4-(aminocarbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 89.7 | 1.1 | 335, 628 |
| 224 | 4-((4-(aminocarbonyl)phenyl)oxy)-N-(2,6-dimethylphenyl)-2-((3-fluoro-4-(4-methyl-1-piperazinyl)-phenyl)amino)-5-pyrimidinecarboxamide | 100 | 1.14 | 570, 306, 285 |
| 225 | 4-((4-(aminocarbonyl)phenyl)oxy)-N-(2,6-dimethylphenyl)-2-((4-(4-methyl-1-piperazinyl)phenyl)-amino)-5-pyrimidinecarboxamide | 92.1 | 1.12 | 552, 297, 276 |
| 226 | 4-((4-(aminocarbonyl)phenyl)oxy)-N-(2,6-dimethylphenyl)-2-((4-(4-(1-methylethyl)-1-piperazinyl)-phenyl)amino)-5-pyrimidinecarboxamide | 92.6 | 1.16 | 580, 311, 290 |
| 227 | 4-((4'-(dimethylamino)-3-(methyloxy)-1,1'-biphenyl-4-yl)oxy)-N-(2,6-dimethylphenyl)-2-((3,4,5-tris(methyloxy)phenyl)amino)-5-pyrimidinecarboxamide | 98 | 1.41 | 325, 650 |
| 228 | 4-((4-bromo-2-(methyloxy)phenyl)oxy)-2-((3-chloro-4-(4-(1-methylethyl)-1-piperazinyl)phenyl)amino)-N-(2,6-dimethylphenyl)-5-pyrimidinecarboxamide | 100 | 1.5 | 341, 678/680 |
| 229 | 4-((4-bromo-2-(methyloxy)phenyl)oxy)-2-((4-(4-(2-(dimethylamino)ethyl)-1-piperazinyl)phenyl)amino)-N-(2,6-dimethylphenyl)-5-pyrimidinecarboxamide | 100 | 1.27 | 338, 674/676 |
| 230 | 4-((4-bromo-2-(methyloxy)phenyl)oxy)-2-((4-(4-(3-(dimethylamino)propyl)-1-piperazinyl)phenyl)amino)-N-(2,6-dimethylphenyl)-5-pyrimidinecarboxamide | 95 | 1.26 | 345, 688/690 |
| 231 | 4-((4-bromo-2-(methyloxy)phenyl)oxy)-N-(2,6-dimethylphenyl)-2-((4-(4-methyl-1-piperazinyl)phenyl)-amino)-5-pyrimidinecarboxamide | 95 | 1.38 | 617/619 |
| 232 | 4-((4-bromo-2-(methyloxy)phenyl)oxy)-N-(2,6-dimethylphenyl)-2-((3,4,5-tris(methyloxy)phenyl)amino)-5-pyrimidinecarboxamide | 100 | 1.71 | 609/611 |
| 233 | 4-((4-bromo-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.33 | 348, 693/695 |
| 234 | 4-((4-bromo-2-(methyloxy)phenyl)oxy)-N-(2,6-dimethylphenyl)-2-((3-fluoro-4-(4-methyl-1-piperazinyl)-phenyl)amino)-5-pyrimidinecarboxamide | 100 | 1.44 | 319, 635/637 |
| 235 | 4-((4-bromo-2-(methyloxy)phenyl)oxy)-N-(2,6-dimethylphenyl)-2-((3-fluoro-4-((3-(1-piperidinyl)-propyl)oxy)phenyl)amino)-5-pyrimidinecarboxamide | 98 | 1.54 | 341, 678/680 |
| 236 | 4-((4-bromo-2-(methyloxy)phenyl)oxy)-N-(2,6-dimethylphenyl)-2-((4-(4-(1-methylethyl)-1-piperazinyl)-phenyl)amino)-5-pyrimidinecarboxamide | 100 | 1.45 | 324, 645/647 |
| 237 | 4-((4-bromo-2-chlorophenyl)oxy)-2-((4-(4-(2-(dimethylamino)ethyl)-1-piperazinyl)phenyl)amino)-N-(2,6-dimethylphenyl)-5-pyrimidinecarboxamide | 100 | 1.3 | 340, 677/679/681 |
| 238 | 4-((4-bromo-2-chlorophenyl)oxy)-2-((4-(4-(3-(dimethylamino)propyl)-1-piperazinyl)phenyl)amino)-N-(2,6-dimethylphenyl)-5-pyrimidinecarboxamide | 100 | 1.29 | 347, 691/693/695 |

-continued

| No. | Name | LC purity | LC Rt | Mass found |
|---|---|---|---|---|
| 239 | 4-((4-bromo-2-chlorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 97 | 1.36 | 350, 698/670 |
| 240 | 4-((4-bromo-2-chlorophenyl)oxy)-N-(2,6-dimethylphenyl)-2-((3-fluoro-4-((3-(1-piperidinyl)-propyl)oxy)phenyl)amino)-5-pyrimidinecarboxamide | 93 | 1.53 | 681/683/685, 342 |
| 241 | 4-((4-bromo-2-chlorophenyl)oxy)-N-(2,6-dimethylphenyl)-2-((3-fluoro-4-(4-methyl-1-piperazinyl)-phenyl)amino)-5-pyrimidinecarboxamide | 97 | 1.45 | 638/640/642, 321 |
| 242 | 4-((4-bromo-2-chlorophenyl)oxy)-N-(2,6-dimethylphenyl)-2-((4-(4-methyl-1-piperazinyl)phenyl)-amino)-5-pyrimidinecarboxamide | 100 | 1.41 | 312, 621/623 |
| 243 | 4-((4-bromo-2-chlorophenyl)oxy)-N-(2,6-dimethylphenyl)-2-((4-(4-(1-methylethyl)-1-piperazinyl)-phenyl)amino)-5-pyrimidinecarboxamide | 96 | 1.46 | 326, 648/650/652 |
| 244 | 4-((4-chloro-2-(methyloxy)phenyl)oxy)-N-(2,6-dimethylphenyl)-2-((4-(4-methyl-1-piperazinyl)phenyl)-amino)-5-pyrimidinecarboxamide | 100 | 1.34 | 573, 307, 287 |
| 245 | 4-((4-chloro-2-(methyloxy)phenyl)oxy)-N-(2,6-dimethylphenyl)-2-((4-(4-(1-methylethyl)-1-piperazinyl)-phenyl)amino)-5-pyrimidinecarboxamide | 88.6 | 1.39 | 601, 301 |
| 246 | 4-((4-chloro-2-(methyloxy)phenyl)oxy)-N-(2,6-dimethylphenyl)-2-((3-fluoro-4-(4-methyl-1-piperazinyl)-phenyl)amino)-5-pyrimidinecarboxamide | 91.3 | 1.31 | 591, 632 |
| 247 | 4-((4-chloro-2-(methyloxy)phenyl)oxy)-N-(2,6-dimethylphenyl)-2-((3-fluoro-4-((3-(1-piperidinyl)-propyl)oxy)phenyl)amino)-5-pyrimidinecarboxamide | 90.9 | 1.4 | 634 |
| 248 | 4-((4-chloro-2-(methyloxy)phenyl)oxy)-N-(2,6-dimethylphenyl)-2-((3-(methyloxy)-4-(4-methyl-1-piperazinyl)phenyl)amino)-5-pyrimidinecarboxamide | 98.8 | 1.28 | 603 |
| 249 | 4-((4'-chloro-3-(methyloxy)-1,1'-biphenyl-4-yl)oxy)-N-(2,6-dimethylphenyl)-2-((3-fluoro-4-((3-(4-methyl-1-piperazinyl)propyl)oxy)phenyl)amino)-5-pyrimidinecarboxamide | 96 | 1.48 | 363, 725 |
| 250 | 4-((4'-chloro-3-(methyloxy)-1,1'-biphenyl-4-yl)oxy)-N-(2,6-dimethylphenyl)-2-((3,4,5-tris(methyloxy)phenyl)-amino)-5-pyrimidinecarboxamide | 85 | 1.85 | 641 |
| 251 | 4-((4-chlorophenyl)oxy)-N-(2,6-dimethylphenyl)-2-((4-(1-piperazinyl)phenyl)amino)-5-pyrimidinecarboxamide | 100 | 1.28 | 529 |
| 252 | 4-((4-chlorophenyl)oxy)-N-(2,6-dimethylphenyl)-2-((4-(4-(1-methylethyl)-1-piperazinyl)phenyl)amino)-5-pyrimidinecarboxamide | 95.4 | 1.33 | 571 |
| 253 | 4-((4-chlorophenyl)oxy)-N-(2,6-dimethylphenyl)-2-((4-(4-methyl-1-piperazinyl)phenyl)amino)-5-pyrimidinecarboxamide | 97.3 | 1.28 | 543 |
| 254 | 4-((5-((1E)-3-(diethylamino)-3-oxo-1-propenyl)-2-(methyloxy)phenyl)oxy)-N-(2,6-dimethylphenyl)-2-((4-(4-methyl-1-piperazinyl)phenyl)amino)-5-pyrimidinecarboxamide | 98 | 1.3 | 664 |
| 255 | 4-((5-((1E)-3-(diethylamino)-3-oxo-1-propenyl)-2-(methyloxy)phenyl)oxy)-N-(2,6-dimethylphenyl)-2-((3-fluoro-4-((3-(4-methyl-1-piperazinyl)propyl)oxy)phenyl)-amino)-5-pyrimidinecarboxamide | 99 | 1.25 | 740 |
| 256 | 4-((5-((1E)-3-(diethylamino)-3-oxo-1-propenyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide | 100 | 1.4 | 725, 747 |
| 257 | 4-((5-((1E)-3-(diethylamino)-3-oxo-1-propenyl)-2-(methyloxy)phenyl)oxy)-N-(2,6-dimethylphenyl)-2-((3-fluoro-4-(4-methyl-1-piperazinyl)phenyl)amino)-5-pyrimidinecarboxamide | 90 | 1.33 | 682, 704 |
| 258 | 4-((5-((1E)-3-(diethylamino)-3-oxo-1-propenyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide | 96 | 1.4 | 346, 692 |
| 259 | 4-((5-((1E)-3-(diethylamino)-3-oxo-1-propenyl)-2-(methyloxy)phenyl)oxy)-2-((4-(4-(2-(dimethylamino)-ethyl)-1-piperazinyl)phenyl)amino)-N-(2,6-dimethylphenyl)-5-pyrimidinecarboxamide | 87 | 1.29 | 721 |
| 260 | 4-((5-(3-(diethylamino)-3-oxopropyl)-2-(methyloxy)-phenyl)oxy)-N-(2,6-dimethylphenyl)-2-((4-(4-methyl-1-piperazinyl)phenyl)amino)-5-pyrimidinecarboxamide | 100 | 1.33 | 333, 273, 666 |
| 261 | 4-((5-(3-(diethylamino)-3-oxopropyl)-2-(methyloxy)-phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.28 | 371, 742, 311 |
| 262 | 4-((5-(3-(diethylamino)-3-oxopropyl)-2-(methyloxy)-phenyl)oxy)-N-(2,6-dimethylphenyl)-2-((3-fluoro-4-(4-methyl-1-piperazinyl)phenyl)amino)-5-pyrimidinecarboxamide | 100 | 1.36 | 342, 684 |

| No. | Name | LC purity | LC Rt | Mass found |
|---|---|---|---|---|
| 263 | 4-((5-(3-(diethylamino)-3-oxopropyl)-2-(methyloxy)-phenyl)oxy)-N-(2,6-dimethylphenyl)-2-((3-fluoro-4-((3-(1-piperidinyl)propyl)oxy)phenyl)amino)-5-pyrimidinecarboxamide | 92 | 1.42 | 364, 727 |
| 264 | 4-((5-(3-(diethylamino)-3-oxopropyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide | 89 | 1.37 | 347, 287, 694 |
| 265 | 4-((5-(3-(diethylamino)-3-oxopropyl)-2-(methyloxy)phenyl)oxy)-2-((4-(4-(2-(dimethylamino)ethyl)-1-piperazinyl)phenyl)amino)-N-(2,6-dimethylphenyl)-5-pyrimidinecarboxamide | 88 | 1.23 | 723, 745 |
| 266 | 4-(1,3-benzodioxol-5-yloxy)-2-((3,5-bis(methyloxy)-4-((3-(4-methyl-1-piperazinyl)propyl)oxy)phenyl)amino)-N-(2,6-dimethylphenyl)-5-pyrimidinecarboxamide | 100 | 1.24 | 671, 334 |
| 267 | 4-(1,3-benzodioxol-5-yloxy)-N-(2,6-dimethylphenyl)-2-((3-fluoro-4-(4-methyl-1-piperazinyl)phenyl)amino)-5-pyrimidinecarboxamide | 99 | 1.32 | 571, 306, 286 |
| 268 | 4-(1,3-benzodioxol-5-yloxy)-N-(2,6-dimethylphenyl)-2-((4-(((2R)-2-pyrrolidinylmethyl)oxy)phenyl)amino)-5-pyrimidinecarboxamide | 91.4 | 1.32 | 554, 298 |
| 269 | 4-(1,3-benzodioxol-5-yloxy)-N-(2,6-dimethylphenyl)-2-((4-(4-methyl-1-piperazinyl)phenyl)amino)-5-pyrimidinecarboxamide | 100 | 1.27 | 297, 553 |
| 270 | 4-(3,4-Dichloro-phenoxy)-2-[4-(pyrrolidin-2-ylmethoxy)-phenylamino]-pyrimidine-5-carboxylic acid (2,6-dimethyl-phenyl)-amide | 94.8 | 1.43 | 578/580 |
| 271 | 4-(3-fluoro-phenoxy)-2-[4-(pyrrolidin-2-ylmethoxy)-phenylamino]-pyrimidine-5-carboxylic acid (2,6-dimethyl-phenyl)-amide | 85.3 | 1.32 | 528 |
| 272 | N-(2,6-dichlorophenyl)-2-((3-(methyloxy)-4-((2-(4-methyl-1-piperazinyl)ethyl)oxy)phenyl)amino)-4-((2-(methyloxy)phenyl)oxy)-5-pyrimidinecarboxamide | 94 | 1.21 | 347, 653/655 |
| 273 | N-(2,6-dichlorophenyl)-2-((3-(methyloxy)-4-((3-(4-methyl-1-piperazinyl)propyl)oxy)phenyl)amino)-4-((2-(methyloxy)phenyl)oxy)-5-pyrimidinecarboxamide | 94.9 | 1.22 | 334, 355, 667/669 |
| 274 | N-(2,6-dichlorophenyl)-2-((3-(methyloxy)-4-((3-(4-methyl-1-piperazinyl)propyl)oxy)phenyl)amino)-4-((4-(1-piperazinyl)phenyl)oxy)-5-pyrimidinecarboxamide | 99.7 | 1.05 | 382, 361, 721/723 |
| 275 | N-(2,6-dichlorophenyl)-2-((3-(methyloxy)-4-((3-(4-methyl-1-piperazinyl)propyl)oxy)phenyl)amino)-4-((3-(methyloxy)phenyl)oxy)-5-pyrimidinecarboxamide | 100 | 1.18 | 667/669 |
| 276 | N-(2,6-dichlorophenyl)-2-((3-(methyloxy)-4-(4-methyl-1-piperazinyl)phenyl)amino)-4-((2-(methyloxy)phenyl)-oxy)-5-pyrimidinecarboxamide | 100 | 1.29 | 609/611, 325 |
| 277 | N-(2,6-dichlorophenyl)-2-((3-(methyloxy)-4-(4-methyl-1-piperazinyl)phenyl)amino)-4-(2-naphthalenyloxy)-5-pyrimidinecarboxamide | 100 | 1.32 | 629/631 |
| 278 | N-(2,6-dichlorophenyl)-2-((3-fluoro-4-((3-(1-piperidinyl)propyl)oxy)phenyl)amino)-4-(phenyloxy)-5-pyrimidinecarboxamide | 92.9 | 1.41 | 610/612 |
| 279 | N-(2,6-dichlorophenyl)-2-((3-fluoro-4-((3-(1-piperidinyl)propyl)oxy)phenyl)amino)-4-((2-(methyloxy)phenyl)oxy)-5-pyrimidinecarboxamide | 98.2 | 1.37 | 640/642 |
| 280 | N-(2,6-dichlorophenyl)-2-((3-fluoro-4-((3-(1-piperidinyl)propyl)oxy)phenyl)amino)-4-((4-(1-piperazinyl)phenyl)oxy)-5-pyrimidinecarboxamide | 100 | 1.15 | 347, 694/696, 368 |
| 281 | N-(2,6-dichlorophenyl)-2-((3-fluoro-4-((3-(1-piperidinyl)propyl)oxy)phenyl)amino)-4-(2-naphthalenyloxy)-5-pyrimidinecarboxamide | 98 | 1.44 | 660/662 |
| 282 | N-(2,6-dichlorophenyl)-2-((3-fluoro-4-((3-(4-methyl-1-piperazinyl)propyl)oxy)phenyl)amino)-4-(phenyloxy)-5-pyrimidinecarboxamide | 98 | 1.24 | 625/627, 333, 313 |
| 283 | N-(2,6-dichlorophenyl)-2-((3-fluoro-4-((3-(4-methyl-1-piperazinyl)propyl)oxy)phenyl)amino)-4-((2-(methyloxy)phenyl)oxy)-5-pyrimidinecarboxamide | 100 | 1.19 | 655/657 |
| 284 | N-(2,6-dichlorophenyl)-2-((3-fluoro-4-((3-(4-methyl-1-piperazinyl)propyl)oxy)phenyl)amino)-4-((4-(1-piperazinyl)phenyl)oxy)-5-pyrimidinecarboxamide | 100 | 1.08 | 355, 375, 709/711 |
| 285 | N-(2,6-dichlorophenyl)-2-((3-fluoro-4-((3-(4-methyl-1-piperazinyl)propyl)oxy)phenyl)amino)-4-((3-(methyloxy)phenyl)oxy)-5-pyrimidinecarboxamide | 100 | 1.19 | 655/657 |
| 286 | N-(2,6-dichlorophenyl)-2-((3-fluoro-4-((3-(4-methyl-1-piperazinyl)propyl)oxy)phenyl)amino)-4-(2-naphthalenyloxy)-5-pyrimidinecarboxamide | 95 | 1.25 | 675/677 |
| 287 | N-(2,6-dichlorophenyl)-2-((3-fluoro-4-(4-methyl-1-piperazinyl)phenyl)amino)-4-(phenyloxy)-5-pyrimidinecarboxamide | 89.5 | 1.32 | 567/569 |

| No. | Name | LC purity | LC Rt | Mass found |
|---|---|---|---|---|
| 288 | N-(2,6-dichlorophenyl)-2-((3-fluoro-4-(4-methyl-1-piperazinyl)phenyl)amino)-4-((2-(methyloxy)phenyl)oxy)-5-pyrimidinecarboxamide | 100 | 1.27 | 597/599 |
| 289 | N-(2,6-dichlorophenyl)-2-((3-fluoro-4-(4-methyl-1-piperazinyl)phenyl)amino)-4-((4-(1-piperazinyl)phenyl)oxy)-5-pyrimidinecarboxamide | 100 | 1.11 | 346, 651/653, 326 |
| 290 | N-(2,6-dichlorophenyl)-2-((3-fluoro-4-(4-methyl-1-piperazinyl)phenyl)amino)-4-((4-(1-piperazinyl)phenyl)oxy)-5-pyrimidinecarboxamide | 100 | 1.11 | 346, 651/653, 326 |
| 291 | N-(2,6-dichlorophenyl)-2-((3-fluoro-4-(4-methyl-1-piperazinyl)phenyl)amino)-4-((3-(methyloxy)phenyl)oxy)-5-pyrimidinecarboxamide | 100 | 1.27 | 597/599 |
| 292 | N-(2,6-dichlorophenyl)-2-((3-fluoro-4-(4-methyl-1-piperazinyl)phenyl)amino)-4-(2-naphthalenyloxy)-5-pyrimidinecarboxamide | 98.4 | 1.34 | 617/619 |
| 293 | N-(2,6-dichlorophenyl)-2-((4-((3-(diethylamino)propyl)oxy)-3-fluorophenyl)amino)-4-(phenyloxy)-5-pyrimidinecarboxamide | 97 | 1.39 | 598/600 |
| 294 | N-(2,6-dichlorophenyl)-2-((4-(4-(1-methylethyl)-1-piperazinyl)phenyl)amino)-4-((4-(1-piperazinyl)phenyl)oxy)-5-pyrimidinecarboxamide | 100 | 1.1 | 331, 661/663 |
| 295 | N-(2,6-dichlorophenyl)-2-((4-(4-(1-methylethyl)-1-piperazinyl)phenyl)amino)-4-((3-(methyloxy)phenyl)oxy)-5-pyrimidinecarboxamide | 100 | 1.29 | 607/609 |
| 296 | N-(2,6-dichlorophenyl)-2-((4-(4-(1-methylethyl)-1-piperazinyl)phenyl)amino)-4-(phenyloxy)-5-pyrimidinecarboxamide | 96.3 | 1.27 | 577/579 |
| 297 | N-(2,6-dichlorophenyl)-2-((4-(4-(1-methylethyl)-1-piperazinyl)phenyl)amino)-4-((2-(methyloxy)phenyl)oxy)-5-pyrimidinecarboxamide | 92.4 | 1.28 | 607/609 |
| 298 | N-(2,6-dichlorophenyl)-2-((4-(4-methyl-1-piperazinyl)phenyl)amino)-4-(phenyloxy)-5-pyrimidinecarboxamide | 97.1 | 1.75 | 549/551 |
| 299 | N-(2,6-dichlorophenyl)-2-((4-(4-methyl-1-piperazinyl)phenyl)amino)-4-2-naphthalenyloxy)-5-pyrimidinecarboxamide | 98.8 | 1.37 | 599/601 |
| 300 | N-(2,6-dichlorophenyl)-2,4-bis((3-(methyloxy)phenyl)oxy)-5-pyrimidinecarboxamide | 100 | 2.06 | 512/514 |
| 301 | N-(2,6-dichlorophenyl)-4-((2-(methyloxy)phenyl)oxy)-2-((4-(4-methyl-1-piperazinyl)phenyl)amino)-5-pyrimidinecarboxamide | 98 | 1.75 | 579/581 |
| 302 | N-(2,6-dichlorophenyl)-4-((2-fluorophenyl)oxy)-2-((3-(methyloxy)-4-(4-methyl-1-piperazinyl)phenyl)amino)-5-pyrimidinecarboxamide | 98.6 | 1.28 | 597/599 |
| 303 | N-(2,6-dichlorophenyl)-4-((2-fluorophenyl)oxy)-2-((3-(methyloxy)-4-((3-(4-methyl-1-piperazinyl)propyl)oxy)phenyl)amino)-5-pyrimidinecarboxamide | 100 | 1.21 | 655/657, 328, 348 |
| 304 | N-(2,6-dichlorophenyl)-4-((2-fluorophenyl)oxy)-2-((4-(4-methyl-1-piperazinyl)phenyl)amino)-5-pyrimidinecarboxamide | 96.6 | 1.28 | 567/569 |
| 305 | N-(2,6-dichlorophenyl)-4-((4-(1-piperazinyl)phenyl)oxy)-2-((3,4,5-tris(methyloxy)phenyl)amino)-5-pyrimidinecarboxamide | 100 | 1.19 | 625/627, 334, 313 |
| 306 | N-(2,6-dimethylphenyl)-2-((3-(methyloxy)-4-(((4-methyl-1-piperazinyl)acetyl)amino)phenyl)amino)-4-((2-(methyloxy)-4-propylphenyl)oxy)-5-pyrimidinecarboxamide | 100 | 1.43 | 668 |
| 307 | N-(2,6-dimethylphenyl)-2-((3-(methyloxy)-4-((2-(4-methyl-1-piperazinyl)ethyl)oxy)phenyl)amino)-4-(phenyloxy)-5-pyrimidinecarboxamide | 100 | 1.17 | 583 |
| 308 | N-(2,6-dimethylphenyl)-2-((3-(methyloxy)-4-((2-(4-methyl-1-piperazinyl)ethyl)oxy)phenyl)amino)-4-((2-(methyloxy)phenyl)oxy)-5-pyrimidinecarboxamide | 94.5 | 1.19 | 327, 307, 613 |
| 309 | N-(2,6-dimethylphenyl)-2-((3-(methyloxy)-4-((2-(4-methyl-1-piperazinyl)ethyl)oxy)phenyl)amino)-4-((4-(1-piperazinyl)phenyl)oxy)-5-pyrimidinecarboxamide | 99.1 | 1 | 667, 334 |
| 310 | N-(2,6-dimethylphenyl)-2-((3-(methyloxy)-4-((3-(4-methyl-1-piperazinyl)propyl)oxy)phenyl)amino)-4-(phenyloxy)-5-pyrimidinecarboxamide | 100 | 1.17 | 597 |
| 311 | N-(2,6-dimethylphenyl)-2-((3-(methyloxy)-4-((3-(4-methyl-1-piperazinyl)propyl)oxy)phenyl)amino)-4-((2-(methyloxy)phenyl)oxy)-5-pyrimidinecarboxamide | 93.2 | 1.2 | 314, 334, 627 |
| 312 | N-(2,6-dimethylphenyl)-2-((3-(methyloxy)-4-((3-(4-methyl-1-piperazinyl)propyl)oxy)phenyl)amino)-4-((4-(1-piperazinyl)phenyl)oxy)-5-pyrimidinecarboxamide | 99.2 | 1 | 681, 341 |
| 313 | N-(2,6-dimethylphenyl)-2-((3-(methyloxy)-4-((3-(4-methyl-1-piperazinyl)propyl)oxy)phenyl)amino)-4-((3-(methyloxy)phenyl)oxy)-5-pyrimidinecarboxamide | 100 | 1.23 | 627, 314, 334 |
| 314 | N-(2,6-dimethylphenyl)-2-((3-(methyloxy)-4-((3-(4-methyl-1-piperazinyl)propyl)oxy)phenyl)amino)-4-((2-((trifluoromethyl)oxy)phenyl)oxy)-5-pyrimidinecarboxamide | 100 | 1.31 | 681, 341, 361 |
| 315 | N-(2,6-dimethylphenyl)-2-((3-(methyloxy)-4-(1-piperazinyl)phenyl)amino)-4-((2-(methyloxy)-4-propylphenyl)oxy)-5-pyrimidinecarboxamide | 95 | 1.45 | 299, 597 |

-continued

| No. | Name | LC purity | LC Rt | Mass found |
|---|---|---|---|---|
| 316 | N-(2,6-dimethylphenyl)-2-((3-(methyloxy)-4-(4-methyl-1-piperazinyl)phenyl)amino)-4-((2-(methyloxy)phenyl)oxy)-5-pyrimidinecarboxamide | 93.8 | 1.28 | 305, 569 |
| 317 | N-(2,6-dimethylphenyl)-2-((3-(methyloxy)-4-(4-methyl-1-piperazinyl)phenyl)amino)-4-((2-((phenylmethyl)oxy)phenyl)oxy)-5-pyrimidinecarboxamide | 92.1 | 1.43 | 645, 344, 323 |
| 318 | N-(2,6-dimethylphenyl)-2-((3-(methyloxy)-4-(4-methyl-1-piperazinyl)phenyl)amino)-4-((2-(methyloxy)-4-propylphenyl)oxy)-5-pyrimidinecarboxamide | 96 | 1.45 | 327, 306, 611 |
| 319 | N-(2,6-dimethylphenyl)-2-((3-(methyloxy)-4-(4-methyl-1-piperazinyl)phenyl)amino)-4-(((2-(methyloxy)phenyl)methyl)oxy)-5-pyrimidinecarboxamide | 83 | 1.38 | 583 |
| 320 | N-(2,6-dimethylphenyl)-2-((3-fluoro-4-(((1-methyl-3-piperidinyl)methyl)oxy)phenyl)amino)-4-((2-(methyloxy)-4-propylphenyl)oxy)-5-pyrimidinecarboxamide | 87 | 1.57 | 314, 628 |
| 321 | N-(2,6-dimethylphenyl)-2-((3-fluoro-4-(((2S)-2-pyrrolidinylmethyl)oxy)phenyl)amino)-4-((2-(methyloxy)-4-propylphenyl)oxy)-5-pyrimidinecarboxamide | 98 | 1.51 | 300, 600 |
| 322 | N-(2,6-dimethylphenyl)-2-((3-fluoro-4-((2-(1-piperazinyl)ethyl)oxy)phenyl)amino)-4-((2-(methyloxy)-4-propylphenyl)oxy)-5-pyrimidinecarboxamide | 93 | 1.37 | 315, 629 |
| 323 | N-(2,6-dimethylphenyl)-2-((3-fluoro-4-((2-(1-piperidinyl)ethyl)oxy)phenyl)amino)-4-((2-(methyloxy)-4-propylphenyl)oxy)-5-pyrimidinecarboxamide | 100 | 1.59 | 314, 628 |
| 324 | N-(2,6-dimethylphenyl)-2-((3-fluoro-4-((2-(1-pyrrolidinyl)ethyl)oxy)phenyl)amino)-4-((2-(methyloxy)-4-propylphenyl)oxy)-5-pyrimidinecarboxamide | 98 | 1.56 | 307, 614 |
| 325 | N-(2,6-dimethylphenyl)-2-((3-fluoro-4-((2-(4-(1-methylethyl)-1-piperazinyl)ethyl)oxy)phenyl)amino)-4-((2-(methyloxy)-4-propylphenyl)oxy)-5-pyrimidinecarboxamide | 98 | 1.38 | 336, 671 |
| 326 | N-(2,6-dimethylphenyl)-2-((3-fluoro-4-((2-(4-methyl-1-piperazinyl)ethyl)oxy)phenyl)amino)-4-((2-(methyloxy)-4-propylphenyl)oxy)-5-pyrimidinecarboxamide | 100 | 1.38 | 322, 643 |
| 327 | N-(2,6-dimethylphenyl)-2-((3-fluoro-4-((2-(4-morpholinyl)ethyl)oxy)phenyl)amino)-4-((2-(methyloxy)-4-propylphenyl)oxy)-5-pyrimidinecarboxamide | 85 | 1.53 | 315, 630 |
| 328 | N-(2,6-dimethylphenyl)-2-((3-fluoro-4-((3-(1-piperidinyl)propyl)oxy)phenyl)amino)-4-(phenyloxy)-5-pyrimidinecarboxamide | 98.7 | 1.4 | 570, 285 |
| 329 | N-(2,6-dimethylphenyl)-2-((3-fluoro-4-((3-(1-piperidinyl)propyl)oxy)phenyl)amino)-4-((4-(methyloxy)phenyl)oxy)-5-pyrimidinecarboxamide | 98.9 | 1.36 | 600 |
| 330 | N-(2,6-dimethylphenyl)-2-((3-fluoro-4-((3-(1-piperidinyl)propyl)oxy)phenyl)amino)-4-((2-(methyloxy)phenyl)oxy)-5-pyrimidinecarboxamide | 100 | 1.44 | 600, 300 |
| 331 | N-(2,6-dimethylphenyl)-2-((3-fluoro-4-((3-(1-piperidinyl)propyl)oxy)phenyl)amino)-4-((2-((phenylmethyl)oxy)phenyl)oxy)-5-pyrimidinecarboxamide | 97.7 | 1.54 | 676, 339, 359 |
| 332 | N-(2,6-dimethylphenyl)-2-((3-fluoro-4-((3-(1-piperidinyl)propyl)oxy)phenyl)amino)-4-((2-((1-methylethyl)oxy)phenyl)oxy)-5-pyrimidinecarboxamide | 99 | 1.48 | 628 |
| 333 | N-(2,6-dimethylphenyl)-2-((3-fluoro-4-((3-(1-piperidinyl)propyl)oxy)phenyl)amino)-4-((2-(methyloxy)-4-propylphenyl)oxy)-5-pyrimidinecarboxamide | 93.6 | 1.57 | 322, 642 |
| 334 | N-(2,6-dimethylphenyl)-2-((3-fluoro-4-((3-(1-piperidinyl)propyl)oxy)phenyl)amino)-4-((4-(phenyloxy)phenyl)oxy)-5-pyrimidinecarboxamide | 100 | 1.56 | 662 |
| 335 | N-(2,6-dimethylphenyl)-2-((3-fluoro-4-((3-(1-piperidinyl)propyl)oxy)phenyl)amino)-4-((2-(methyloxy)-4-(2-propenyl)phenyl)oxy)-5-pyrimidinecarboxamide | 88 | 1.52 | 640, 320 |
| 336 | N-(2,6-dimethylphenyl)-2-((3-fluoro-4-((3-(1-piperidinyl)propyl)oxy)phenyl)amino)-4-((4-((phenylmethyl)oxy)phenyl)oxy)-5-pyrimidinecarboxamide | 100 | 1.6 | 328, 676 |
| 337 | N-(2,6-dimethylphenyl)-2-((3-fluoro-4-((3-(1-piperidinyl)propyl)oxy)phenyl)amino)-4-((2-(propyloxy)phenyl)oxy)-5-pyrimidinecarboxamide | 100 | 1.48 | 628, 651, 315 |
| 338 | N-(2,6-dimethylphenyl)-2-((3-fluoro-4-((3-(1-piperidinyl)propyl)oxy)phenyl)amino)-4-((2-(5-isoxazolyl)phenyl)oxy)-5-pyrimidinecarboxamide | 93 | 1.4 | 319, 637, 258 |
| 339 | N-(2,6-dimethylphenyl)-2-((3-fluoro-4-((3-(1-piperidinyl)propyl)oxy)phenyl)amino)-4-((pentafluorophenyl)oxy)-5-pyrimidinecarboxamide | 88 | 1.5 | 660 |
| 340 | N-(2,6-dimethylphenyl)-2-((3-fluoro-4-((3-(1-piperidinyl)propyl)oxy)phenyl)amino)-4-((4-(1H-1,2,4-triazol-1-yl)phenyl)oxy)-5-pyrimidinecarboxamide | 100 | 1.31 | 637, 319 |

-continued

| No. | Name | LC purity | LC Rt | Mass found |
|-----|------|-----------|-------|------------|
| 341 | N-(2,6-dimethylphenyl)-2-((3-fluoro-4-((3-(1-piperidinyl)propyl)oxy)phenyl)amino)-4-((2-(trifluoromethyl)phenyl)oxy)-5-pyrimidinecarboxamide | 92 | 1.48 | 638 |
| 342 | N-(2,6-dimethylphenyl)-2-((3-fluoro-4-((3-(1-piperidinyl)propyl)oxy)phenyl)amino)-4-((2-methyl-1,3-benzothiazol-5-yl)oxy)-5-pyrimidinecarboxamide | 100 | 1.33 | 321, 641 |
| 343 | N-(2,6-dimethylphenyl)-2-((3-fluoro-4-((3-(1-pyrrolidinyl)propyl)oxy)phenyl)amino)-4-((2-(methyloxy)-4-propylphenyl)oxy)-5-pyrimidinecarboxamide | 100 | 1.59 | 314, 628 |
| 344 | N-(2,6-dimethylphenyl)-2-((3-fluoro-4-((3-(4-(2-(methyloxy)ethyl)-1-piperazinyl)propyl)oxy)phenyl)-amino)-4-((2-(methyloxy)-4-propylphenyl)oxy)-5-pyrimidinecarboxamide | 95 | 1.37 | 351, 701 |
| 345 | N-(2,6-dimethylphenyl)-2-((3-fluoro-4-((3-(4-methyl-1-piperazinyl)propyl)oxy)phenyl)amino)-4-((2-fluorophenyl)oxy)-5-pyrimidinecarboxamide | 97.1 | 1.24 | 302, 603, 322 |
| 346 | N-(2,6-dimethylphenyl)-2-((3-fluoro-4-((3-(4-methyl-1-piperazinyl)propyl)oxy)phenyl)amino)-4-(phenyloxy)-5-pyrimidinecarboxamide | 100 | 1.21 | 293, 585, 313 |
| 347 | N-(2,6-dimethylphenyl)-2-((3-fluoro-4-((3-(4-methyl-1-piperazinyl)propyl)oxy)phenyl)amino)-4-((4-(methyloxy)phenyl)oxy)-5-pyrimidinecarboxamide | 100 | 1.18 | 615 |
| 348 | N-(2,6-dimethylphenyl)-2-((3-fluoro-4-((3-(4-methyl-1-piperazinyl)propyl)oxy)phenyl)amino)-4-((3-fluorophenyl)oxy)-5-pyrimidinecarboxamide | 89.3 | 1.29 | 603 |
| 349 | N-(2,6-dimethylphenyl)-2-((3-fluoro-4-((3-(4-methyl-1-piperazinyl)propyl)oxy)phenyl)amino)-4-((3-(methyloxy)phenyl)oxy)-5-pyrimidinecarboxamide | 100 | 1.27 | 615, 308, 329 |
| 350 | N-(2,6-dimethylphenyl)-2-((3-fluoro-4-((3-(4-methyl-1-piperazinyl)propyl)oxy)phenyl)amino)-4-((4-fluoro-phenyl)oxy)-5-pyrimidinecarboxamide | 100 | 1.21 | 603, 302, 322 |
| 351 | N-(2,6-dimethylphenyl)-2-((3-fluoro-4-((3-(4-methyl-1-piperazinyl)propyl)oxy)phenyl)amino)-4-((2-(methyloxy)phenyl)oxy)-5-pyrimidinecarboxamide | 100 | 1.24 | 615, 308, 328 |
| 352 | N-(2,6-dimethylphenyl)-2-((3-fluoro-4-((3-(4-methyl-1-piperazinyl)propyl)oxy)phenyl)amino)-4-((2-((trifluoromethyl)oxy)phenyl)oxy)-5-pyrimidinecarboxamide | 98.4 | 1.31 | 669, 335, 355 |
| 353 | N-(2,6-dimethylphenyl)-2-((3-fluoro-4-((3-(4-methyl-1-piperazinyl)propyl)oxy)phenyl)amino)-4-((3-(2-oxo-1-pyrrolidinyl)phenyl)oxy)-5-pyrimidinecarboxamide | 82 | 1.19 | 668 |
| 354 | N-(2,6-dimethylphenyl)-2-((3-fluoro-4-((3-(4-methyl-1-piperazinyl)propyl)oxy)phenyl)amino)-4-((2-((phenylmethyl)oxy)phenyl)oxy)-5-pyrimidinecarboxamide | 98.2 | 1.32 | 691, 346, 367 |
| 355 | N-(2,6-dimethylphenyl)-2-((3-fluoro-4-((3-(4-methyl-1-piperazinyl)propyl)oxy)phenyl)amino)-4-((2-((1-methylethyl)oxy)phenyl)oxy)-5-pyrimidinecarboxamide | 97.4 | 1.29 | 643 |
| 356 | N-(2,6-dimethylphenyl)-2-((3-fluoro-4-((3-(4-methyl-1-piperazinyl)propyl)oxy)phenyl)amino)-4-((2-(methyloxy)-4-propylphenyl)oxy)-5-pyrimidinecarboxamide | 95.5 | 1.37 | 329, 657 |
| 357 | N-(2,6-dimethylphenyl)-2-((3-fluoro-4-((3-(4-methyl-1-piperazinyl)propyl)oxy)phenyl)amino)-4-(((2-(methyloxy)phenyl)methyl)oxy)-5-pyrimidinecarboxamide | 88 | 1.33 | 629 |
| 358 | N-(2,6-dimethylphenyl)-2-((3-fluoro-4-((3-(4-methyl-1-piperazinyl)propyl)oxy)phenyl)amino)-4-((4-(phenyloxy)phenyl)oxy)-5-pyrimidinecarboxamide | 100 | 1.41 | 339, 677 |
| 359 | N-(2,6-dimethylphenyl)-2-((3-fluoro-4-((3-(4-methyl-1-piperazinyl)propyl)oxy)phenyl)amino)-4-((2-(methyloxy)-4-(2-propenyl)phenyl)oxy)-5-pyrimidinecarboxamide | 79 | 1.4 | 328, 655 |
| 360 | N-(2,6-dimethylphenyl)-2-((3-fluoro-4-((3-(4-methyl-1-piperazinyl)propyl)oxy)phenyl)amino)-4-((4-((phenylmethyl)oxy)phenyl)oxy)-5-pyrimidinecarboxamide | 100 | 1.41 | 346, 691 |
| 361 | N-(2,6-dimethylphenyl)-2-((3-fluoro-4-((3-(4-methyl-1-piperazinyl)propyl)oxy)phenyl)amino)-4-((2-(propyloxy)phenyl)oxy)-5-pyrimidinecarboxamide | 100 | 1.29 | 322, 643, 665 |
| 362 | N-(2,6-dimethylphenyl)-2-((3-fluoro-4-((3-(4-methyl-1-piperazinyl)propyl)oxy)phenyl)amino)-4-((3-(methyloxy)-4'-(trifluoromethyl)-1,1'-biphenyl-4-yl)oxy)-5-pyrimidinecarboxamide | 86 | 1.46 | 759, 380, 401 |
| 363 | N-(2,6-dimethylphenyl)-2-((3-fluoro-4-((3-(4-methyl-1-piperazinyl)propyl)oxy)phenyl)amino)-4-((4-(1H-indol-5-yl)-2-(methyloxy)phenyl)oxy)-5-pyrimidinecarboxamide | 94 | 1.39 | 365, 730 |
| 364 | N-(2,6-dimethylphenyl)-2-((3-fluoro-4-((3-(4-methyl-1-piperazinyl)propyl)oxy)phenyl)amino)-4-((2-(methyloxy)-4-(3-thienyl)phenyl)oxy)-5-pyrimidinecarboxamide | 89 | 1.37 | 349, 697 |

| No. | Name | LC purity | LC Rt | Mass found |
|---|---|---|---|---|
| 365 | N-(2,6-dimethylphenyl)-2-((3-fluoro-4-((3-(4-methyl-1-piperazinyl)propyl)oxy)phenyl)amino)-4-((2-(methyloxy)-4-(3-pyridinyl)phenyl)oxy)-5-pyrimidinecarboxamide | 95 | 1.1 | 692, 367, 346 |
| 366 | N-(2,6-dimethylphenyl)-2-((3-fluoro-4-((3-(4-methyl-1-piperazinyl)propyl)oxy)phenyl)amino)-4-((4-(1H-1,2,4-triazol-1-yl)phenyl)oxy)-5-pyrimidinecarboxamide | 93 | 1.19 | 326, 652 |
| 367 | N-(2,6-dimethylphenyl)-2-((3-fluoro-4-((3-(4-methyl-1-piperazinyl)propyl)oxy)phenyl)amino)-4-((2-(trifluoromethyl)phenyl)oxy)-5-pyrimidinecarboxamide | 100 | 1.3 | 653, 327 |
| 368 | N-(2,6-dimethylphenyl)-2-((3-fluoro-4-((3-(4-methyl-1-piperazinyl)propyl)oxy)phenyl)amino)-4-((2-methyl-1,3-benzothiazol-5-yl)oxy)-5-pyrimidinecarboxamide | 100 | 1.17 | 329, 656 |
| 369 | N-(2,6-dimethylphenyl)-2-((3-fluoro-4-((3-(4-methyl-1-piperazinyl)propyl)oxy)phenyl)amino)-4-((2-(5-isoxazolyl)phenyl)oxy)-5-pyrimidinecarboxamide | 100 | 1.18 | 266, 652 |
| 370 | N-(2,6-dimethylphenyl)-2-((3-fluoro-4-((3-(4-morpholinyl)propyl)oxy)phenyl)amino)-4-((2-(methyloxy)-4-propylphenyl)oxy)-5-pyrimidinecarboxamide | 100 | 1.55 | 322, 644, 408 |
| 371 | N-(2,6-dimethylphenyl)-2-((3-fluoro-4-((3-piperidinylmethyl)oxy)phenyl)amino)-4-((2-(methyloxy)-4-propylphenyl)oxy)-5-pyrimidinecarboxamide | 95 | 1.55 | 307, 614 |
| 372 | N-(2,6-dimethylphenyl)-2-((3-fluoro-4-((3R,5S)-3,4,5-trimethyl-1-piperazinyl)phenyl)amino)-4-((2-(methyloxy)-4-propylphenyl)oxy)-5-pyrimidinecarboxamide | 97 | 1.5 | 314, 627, 253 |
| 373 | N-(2,6-dimethylphenyl)-2-((3-fluoro-4-((4-(1H-imidazol-1-yl)butyl)oxy)phenyl)amino)-4-((2-(methyloxy)-4-propylphenyl)oxy)-5-pyrimidinecarboxamide | 100 | 1.58 | 320, 639 |
| 374 | N-(2,6-dimethylphenyl)-2-((3-fluoro-4-((octahydro-2H-quinolizin-1-ylmethyl)oxy)phenyl)amino)-4-((2-(methyloxy)-4-propylphenyl)oxy)-5-pyrimidinecarboxamide | 66 | 6.36 | 334, 668 |
| 375 | N-(2,6-dimethylphenyl)-2-((3-fluoro-4-(4-methyl-1-piperazinyl)phenyl)amino)-4-((2-fluorophenyl)oxy)-5-pyrimidinecarboxamide | 94.8 | 1.32 | 545, 293, 273 |
| 376 | N-(2,6-dimethylphenyl)-2-((3-fluoro-4-(4-methyl-1-piperazinyl)phenyl)amino)-4-((4-(methyloxy)phenyl)-oxy)-5-pyrimidinecarboxamide | 99.6 | 1.27 | 557 |
| 377 | N-(2,6-dimethylphenyl)-2-((3-fluoro-4-(4-methyl-1-piperazinyl)phenyl)amino)-4-(phenyloxy)-5-pyrimidinecarboxamide | 100 | 1.28 | 527, 568 |
| 378 | N-(2,6-dimethylphenyl)-2-((3-fluoro-4-(4-methyl-1-piperazinyl)phenyl)amino)-4-((4-fluorophenyl)oxy)-5-pyrimidinecarboxamide | 94.5 | 1.36 | 545, 293, 273 |
| 379 | N-(2,6-dimethylphenyl)-2-((3-fluoro-4-(4-methyl-1-piperazinyl)phenyl)amino)-4-((3-fluorophenyl)oxy)-5-pyrimidinecarboxamide | 100 | 1.32 | 545 |
| 380 | N-(2,6-dimethylphenyl)-2-((3-fluoro-4-(4-methyl-1-piperazinyl)phenyl)amino)-4-((3-(methyloxy)phenyl)-oxy)-5-pyrimidinecarboxamide | 100 | 1.36 | 557, 299, 279 |
| 381 | N-(2,6-dimethylphenyl)-2-((3-fluoro-4-(4-methyl-1-piperazinyl)phenyl)amino)-4-((2-((trifluoromethyl)oxy)-phenyl)oxy)-5-pyrimidinecarboxamide | 100 | 1.42 | 611, 326, 306 |
| 382 | N-(2,6-dimethylphenyl)-2-((3-fluoro-4-(4-methyl-1-piperazinyl)phenyl)amino)-4-((2-(methyloxy)phenyl)-oxy)-5-pyrimidinecarboxamide | 100 | 1.35 | 557, 299, 279 |
| 383 | N-(2,6-dimethylphenyl)-2-((3-fluoro-4-(4-methyl-1-piperazinyl)phenyl)amino)-4-((3-(2-oxo-1-pyrrolidinyl)-phenyl)oxy)-5-pyrimidinecarboxamide | 95.7 | 1.25 | 610 |
| 384 | N-(2,6-dimethylphenyl)-2-((3-fluoro-4-(4-methyl-1-piperazinyl)phenyl)amino)-4-((2-((phenylmethyl)oxy)-phenyl)oxy)-5-pyrimidinecarboxamide | 98.8 | 1.46 | 633, 442, 338 |
| 385 | N-(2,6-dimethylphenyl)-2-((3-fluoro-4-(4-methyl-1-piperazinyl)phenyl)amino)-4-((2-((1-methylethyl)oxy)-phenyl)oxy)-5-pyrimidinecarboxamide | 100 | 1.41 | 585 |
| 386 | N-(2,6-dimethylphenyl)-2-((3-fluoro-4-(4-methyl-1-piperazinyl)phenyl)amino)-4-((2-(methyloxy)-4-propylphenyl)oxy)-5-pyrimidinecarboxamide | 94.3 | 1.47 | 599, 408, 320, 300 |
| 387 | N-(2,6-dimethylphenyl)-2-((3-fluoro-4-(4-methyl-1-piperazinyl)phenyl)amino)-4-((2-(methyloxy)-4-(2-propenyl)phenyl)oxy)-5-pyrimidinecarboxamide | 100 | 1.45 | 597, 319, 299 |
| 388 | N-(2,6-dimethylphenyl)-2-((3-fluoro-4-(4-methyl-1-piperazinyl)phenyl)amino)-4-((4-((phenylmethyl)oxy)-phenyl)oxy)-5-pyrimidinecarboxamide | 90 | 1.54 | 317, 633 |
| 389 | N-(2,6-dimethylphenyl)-2-((3-fluoro-4-(4-methyl-1-piperazinyl)phenyl)amino)-4-((4-(phenyloxy)phenyl)-oxy)-5-pyrimidinecarboxamide | 98 | 1.51 | 310, 619 |

| No. | Name | LC purity | LC Rt | Mass found |
|---|---|---|---|---|
| 390 | N-(2,6-dimethylphenyl)-2-((3-fluoro-4-(4-methyl-1-piperazinyl)phenyl)amino)-4-((2-(propyloxy)phenyl)oxy)-5-pyrimidinecarboxamide | 100 | 1.4 | 585, 607 |
| 391 | N-(2,6-dimethylphenyl)-2-((3-fluoro-4-(4-methyl-1-piperazinyl)phenyl)amino)-4-((4-(1H-1,2,4-triazol-1-yl)phenyl)oxy)-5-pyrimidinecarboxamide | 100 | 1.25 | 594, 297 |
| 392 | N-(2,6-dimethylphenyl)-2-((3-fluoro-4-(4-methyl-1-piperazinyl)phenyl)amino)-4-((2-(trifluoromethyl)phenyl)oxy)-5-pyrimidinecarboxamide | 98 | 1.41 | 298, 595 |
| 393 | N-(2,6-dimethylphenyl)-2-((3-fluoro-4-(4-methyl-1-piperazinyl)phenyl)amino)-4-((2-methyl-1,3-benzothiazol-5-yl)oxy)-5-pyrimidinecarboxamide | 100 | 1.24 | 300, 598, 239 |
| 394 | N-(2,6-dimethylphenyl)-2-((3-fluoro-4-(4-methyl-1-piperazinyl)phenyl)amino)-4-((2-(5-isoxazolyl)phenyl)oxy)-5-pyrimidinecarboxamide | 100 | 1.26 | 594, 237, 473 |
| 395 | N-(2,6-dimethylphenyl)-2-((4-((2-((1-methylethyl)amino)ethyl)oxy)-3-(methyloxy)phenyl)amino)-4-((2-(methyloxy)-4-propylphenyl)oxy)-5-pyrimidinecarboxamide | 100 | 1.53 | 307, 614 |
| 396 | N-(2,6-dimethylphenyl)-2-((4-((3-(4-(1-methylethyl)-1-piperazinyl)propyl)oxy)-3-(methyloxy)phenyl)amino)-4-((2-(methyloxy)-4-propylphenyl)oxy)-5-pyrimidinecarboxamide | 96 | 1.39 | 349, 697 |
| 397 | N-(2,6-dimethylphenyl)-2-((4-(1-(1-methylethyl)-4-piperidinyl)phenyl)amino)-4-((2-(methyloxy)-4-propylphenyl)oxy)-5-pyrimidinecarboxamide | 100 | 1.54 | 608 |
| 398 | N-(2,6-dimethylphenyl)-2-((4-(2-(3,4-dimethyl-1-piperazinyl)-2-oxoethyl)phenyl)amino)-4-((2-(methyloxy)-4-propylphenyl)oxy)-5-pyrimidinecarboxamide | 93 | 1.45 | 319, 637 |
| 399 | N-(2,6-dimethylphenyl)-2-((4-(2-(3,4-dimethyl-1-piperazinyl)-2-oxoethyl)phenyl)amino)-4-((2-(ethyloxy)phenyl)oxy)-5-pyrimidinecarboxamide | 90 | 1.34 | 305, 609 |
| 400 | N-(2,6-dimethylphenyl)-2-((4-(2-(3,4-dimethyl-1-piperazinyl)ethyl)phenyl)amino)-4-((2-(ethyloxy)phenyl)oxy)-5-pyrimidinecarboxamide | 100 | 1.23 | 298, 595 |
| 401 | N-(2,6-dimethylphenyl)-2-((4-(2-(3,4-dimethyl-1-piperazinyl)ethyl)phenyl)amino)-4-((2-(methyloxy)-4-propylphenyl)oxy)-5-pyrimidinecarboxamide | 97 | 1.32 | 312, 623, 251 |
| 402 | N-(2,6-dimethylphenyl)-2-((4-(3,4-dimethyl-1-piperazinyl)-3-fluorophenyl)amino)-4-((2-(methyloxy)-4-propylphenyl)oxy)-5-pyrimidinecarboxamide | 97 | 1.49 | 613, 307, 246 |
| 403 | N-(2,6-dimethylphenyl)-2-((4-(3,4-dimethyl-1-piperazinyl)-3-fluorophenyl)amino)-4-((2-(ethyloxy)phenyl)oxy)-5-pyrimidinecarboxamide | 93 | 1.38 | 585, 232, 293 |
| 404 | N-(2,6-dimethylphenyl)-2-((4-(3,4-dimethyl-1-piperazinyl)phenyl)amino)-4-((2-(methyloxy)-4-propylphenyl)oxy)-5-pyrimidinecarboxamide | 100 | 1.49 | 298, 595 |
| 405 | N-(2,6-dimethylphenyl)-2-((4-(3,4-dimethyl-1-piperazinyl)phenyl)amino)-4-((2-(ethyloxy)phenyl)oxy)-5-pyrimidinecarboxamide | 100 | 1.38 | 284, 567 |
| 406 | N-(2,6-dimethylphenyl)-2-((4-(4-(1-methylethyl)-1-piperazinyl)phenyl)amino)-4-((4-(methyloxy)phenyl)oxy)-5-pyrimidinecarboxamide | 100 | 1.31 | 567, 304, 384 |
| 407 | N-(2,6-dimethylphenyl)-2-((4-(4-(1-methylethyl)-1-piperazinyl)phenyl)amino)-4-(phenyloxy)-5-pyrimidinecarboxamide | 98.5 | 1.19 | 615 |
| 408 | N-(2,6-dimethylphenyl)-2-((4-(4-(1-methylethyl)-1-piperazinyl)phenyl)amino)-4-((3-(methyloxy)phenyl)oxy)-5-pyrimidinecarboxamide | 95.2 | 1.37 | 567, 304, 284 |
| 409 | N-(2,6-dimethylphenyl)-2-((4-(4-(1-methylethyl)-1-piperazinyl)phenyl)amino)-4-((2-(methyloxy)phenyl)oxy)-5-pyrimidinecarboxamide | 100 | 1.35 | 284, 305, 567 |
| 410 | N-(2,6-dimethylphenyl)-2-((4-(4-(1-methylethyl)-1-piperazinyl)phenyl)amino)-4-((2-((trifluoromethyl)oxy)phenyl)oxy)-5-pyrimidinecarboxamide | 100 | 1.46 | 621, 311, 321 |
| 411 | N-(2,6-dimethylphenyl)-2-((4-(4-(1-methylethyl)-1-piperazinyl)phenyl)amino)-4-((3-(2-oxo-1-pyrrolidinyl)phenyl)oxy)-5-pyrimidinecarboxamide | 91.4 | 1.27 | 620 |
| 412 | N-(2,6-dimethylphenyl)-2-((4-(4-(1-methylethyl)-1-piperazinyl)phenyl)amino)-4-((2-((phenylmethyl)oxy)phenyl)oxy)-5-pyrimidinecarboxamide | 100 | 1.47 | 322, 643, 343 |
| 413 | N-(2,6-dimethylphenyl)-2-((4-(4-(1-methylethyl)-1-piperazinyl)phenyl)amino)-4-((2-(methyloxy)-4-propylphenyl)oxy)-5-pyrimidinecarboxamide | 99 | 1.49 | 305, 609, 326 |
| 414 | N-(2,6-dimethylphenyl)-2-((4-(4-(1-methylethyl)-1-piperazinyl)phenyl)amino)-4-((4-(phenyloxy)phenyl)oxy)-5-pyrimidinecarboxamide | 100 | 1.5 | 629, 315, 335 |

| No. | Name | LC purity | LC Rt | Mass found |
|---|---|---|---|---|
| 415 | N-(2,6-dimethylphenyl)-2-((4-(4-(1-methylethyl)-1-piperazinyl)phenyl)amino-4-((2-(methyloxy)-4-(2-propenyl)phenyl)oxy)-5-pyrimidinecarboxamide | 87 | 1.51 | 304, 607 |
| 416 | N-(2,6-dimethylphenyl)-2-((4-(4-(1-methylethyl)-1-piperazinyl)phenyl)amino)-4-((4-((phenylmethyl)oxy)-phenyl)oxy)-5-pyrimidinecarboxamide | 100 | 1.57 | 322, 643 |
| 417 | N-(2,6-dimethylphenyl)-2-((4-(4-(1-methylethyl)-1-piperazinyl)phenyl)amino)-4-((2-(propyloxy)phenyl)-oxy)-5-pyrimidinecarboxamide | 100 | 1.47 | 298, 595 |
| 418 | N-(2,6-dimethylphenyl)-2-((4-(4-(1-methylethyl)-1-piperazinyl)phenyl)amino)-4-((pentafluorophenyl)oxy)-5-pyrimidinecarboxamide | 88 | 1.45 | 627 |
| 419 | N-(2,6-dimethylphenyl)-2-((4-(4-(1-methylethyl)-1-piperazinyl)phenyl)amino)-4-((4-(1H-1,2,4-triazol-1-yl)-phenyl)oxy)-5-pyrimidinecarboxamide | 100 | 1.24 | 302, 604 |
| 420 | N-(2,6-dimethylphenyl)-2-((4-(4-(1-methylethyl)-1-piperazinyl)phenyl)amino)-4-((2-(trifluoromethyl)-phenyl)oxy)-5-pyrimidinecarboxamide | 91 | 1.41 | 303, 605 |
| 421 | N-(2,6-dimethylphenyl)-2-((4-(4-(2-(ethylamino)ethyl)-1-piperazinyl)phenyl)amino)-4-((2-(methyloxy)-4-propylphenyl)oxy)-5-pyrimidinecarboxamide | 94 | 1.34 | 638, 297, 320 |
| 422 | N-(2,6-dimethylphenyl)-2-((4-(4-(2-(ethylamino)ethyl)-1-piperazinyl)phenyl)amino)-4-((ethyloxy)phenyl)oxy)-5-pyrimidinecarboxamide | 90 | 1.26 | 326, 305, 610 |
| 423 | N-(2,6-dimethylphenyl)-2-((4-(4-(2-(methyloxy)ethyl)-1-piperazinyl)phenyl)amino)-4-((2-(methyloxy)-4-propylphenyl)oxy)-5-pyrimidinecarboxamide | 100 | 1.52 | 313, 625 |
| 424 | N-(2,6-dimethylphenyl)-2-((4-(4-methyl-1-piperazinyl)-phenyl)amino)-4-(phenyloxy)-5-pyrimidinecarboxamide | 100 | 1.29 | 275, 509, 255 |
| 425 | N-(2,6-dimethylphenyl)-2-((4-(4-methyl-1-piperazinyl)-phenyl)amino)-4-((4-(1-piperazinyl)phenyl)oxy)-5-pyrimidinecarboxamide | 94.1 | 1.06 | 318, 297, 707, 593 |
| 426 | N-(2,6-dimethylphenyl)-2-((4-(4-methyl-1-piperazinyl)-phenyl)amino)-4-(2-naphthalenyloxy)-5-pyrimidinecarboxamide | 96.5 | 1.35 | 300, 559 |
| 427 | N-(2,6-dimethylphenyl)-2-((4-(4-methyl-1-piperazinyl)-phenyl)amino)-4-(phenylsulfanyl)-5-pyrimidinecarboxamide | 92.9 | 1.3 | 168, 525 |
| 428 | N-(2,6-dimethylphenyl)-2-((4-(4-methyl-1-piperazinyl)-phenyl)amino)-4-((3-(2-oxo-1-pyrrolidinyl)phenyl)oxy)-5-pyrimidinecarboxamide | 90.8 | 1.23 | 592 |
| 429 | N-(2,6-dimethylphenyl)-2-((4-(4-methyl-1-piperazinyl)-phenyl)amino)-4-((2-((phenylmethyl)oxy)phenyl)oxy)-5-pyrimidinecarboxamide | 100 | 1.41 | 329, 615 |
| 430 | N-(2,6-dimethylphenyl)-2-((4-(4-methyl-1-piperazinyl)-phenyl)amino)-4-((4-(phenyloxy)phenyl)oxy)-5-pyrimidinecarboxamide | 100 | 1.49 | 301, 601 |
| 431 | N-(2,6-dimethylphenyl)-2-((4-(4-methyl-1-piperazinyl)-phenyl)amino)-4-((4-((phenylmethyl)oxy)phenyl)oxy)-5-pyrimidinecarboxamide | 98 | 1.51 | 308, 615 |
| 432 | N-(2,6-dimethylphenyl)-2-((4-(4-methyl-1-piperazinyl)-phenyl)amino)-4-((2-(propyloxy)phenyl)oxy)-5-pyrimidinecarboxamide | 100 | 1.36 | 657, 589 |
| 433 | N-(2,6-dimethylphenyl)-2-((4-(4-methyl-1-piperazinyl)-phenyl)amino)-4-((pentafluorophenyl)oxy)-5-pyrimidinecarboxamide | 100 | 1.41 | 599, 300 |
| 434 | N-(2,6-dimethylphenyl)-2-((4-(4-methyl-1-piperazinyl)-phenyl)amino)-4-((4-(1H-1,2,4-triazol-1-yl)phenyl)oxy)-5-pyrimidinecarboxamide | 88 | 1.21 | 288, 576 |
| 435 | N-(2,6-dimethylphenyl)-2-((4-(4-methyl-1-piperazinyl)-phenyl)amino)-4-((2-(trifluoromethyl)phenyl)oxy)-5-pyrimidinecarboxamide | 97 | 1.36 | 577, 309 |
| 436 | N-(2,6-dimethylphenyl)-4-(((2-(methyloxy)phenyl)-methyl)oxy)-2-((4-(4-methyl-1-piperazinyl)phenyl)-amino)-5-pyrimidinecarboxamide | 89 | 1.4 | 553 |
| 437 | N-(2,6-dimethylphenyl)-4-((1-methylethyl)oxy)-2-((4-(4-(1-methylethyl)-1-piperazinyl)phenyl)amino)-5-pyrimidinecarboxamide | 94 | 1.26 | 231, 503, 252 |
| 438 | N-(2,6-dimethylphenyl)-4-((2-((1-methylethyl)oxy)-phenyl)oxy)-2-((4-(4-(1-methylethyl)-1-piperazinyl)-phenyl)amino)-5-pyrimidinecarboxamide | 96.3 | 1.42 | 595 |
| 439 | N-(2,6-dimethylphenyl)-4-((2-((1-methylethyl)oxy)-phenyl)oxy)-2-((4-(4-methyl-1-piperazinyl)phenyl)-amino)-5-pyrimidinecarboxamide | 99 | 1.37 | 567 |
| 440 | N-(2,6-dimethylphenyl)-4-((2-((1-methylethyl)oxy)-phenyl)oxy)-2-((3-(methyloxy)-4-(4-methyl-1-piperazinyl)phenyl)amino)-5-pyrimidinecarboxamide | 100 | 1.38 | 597 |

-continued

| No. | Name | LC purity | LC Rt | Mass found |
|---|---|---|---|---|
| 441 | N-(2,6-dimethylphenyl)-4-((2-(5-isoxazolyl)phenyl)oxy)-2-((4-(4-methyl-1-piperazinyl)phenyl)amino)-5-pyrimidinecarboxamide | 95 | 1.28 | 288, 576, 228 |
| 442 | N-(2,6-dimethylphenyl)-4-((2-(5-isoxazolyl)phenyl)oxy)-2-((4-(4-(1-methylethyl)-1-piperazinyl)phenyl)amino)-5-pyrimidinecarboxamide | 100 | 133 | 302, 242, 604 |
| 443 | N-(2,6-dimethylphenyl)-4-((2-(ethyloxy)phenyl)oxy)-2-((3-((3-(1-piperidinyl)propyl)oxy)phenyl)amino)-5-pyrimidinecarboxamide | 89 | 1.53 | 596, 298 |
| 444 | N-(2,6-dimethylphenyl)-4-((2-(ethyloxy)phenyl)oxy)-2-((3-((3-(4-methyl-1-piperazinyl)propyl)oxy)phenyl)-amino)-5-pyrimidinecarboxamide | 94 | 1.35 | 306, 611 |
| 445 | N-(2,6-dimethylphenyl)-4-((2-(ethyloxy)phenyl)oxy)-2-((3-(methyloxy)-4-(4-methyl-1-piperazinyl)phenyl)-amino)-5-pyrimidinecarboxamide | 99.5 | 1.34 | 583, 292, 312 |
| 446 | N-(2,6-dimethylphenyl)-4-((2-(ethyloxy)phenyl)oxy)-2-((3-(methyloxy)-4-(1-piperazinyl)phenyl)amino)-5-pyrimidinecarboxamide | 86 | 1.32 | 569 |
| 447 | N-(2,6-dimethylphenyl)-4-((2-(ethyloxy)phenyl)oxy)-2-((3-(methyloxy)-4-(((4-methyl-1-piperazinyl)acetyl)-amino)phenyl)amino)-5-pyrimidinecarboxamide | 100 | 1.32 | 640 |
| 448 | N-(2,6-dimethylphenyl)-4-((2-(ethyloxy)phenyl)oxy)-2-((3-(methyloxy)-4-(((2S)-2-pyrrolidinylmethyl)oxy)-phenyl)amino)-5-pyrimidinecarboxamide | 87 | 1.39 | 292, 584 |
| 449 | N-(2,6-dimethylphenyl)-4-((2-(ethyloxy)phenyl)oxy)-2-((3,4,5-tris(methyloxy)phenyl)amino)-5-pyrimidinecarboxamide | 100 | 1.63 | 545 |
| 450 | N-(2,6-dimethylphenyl)-4-((2-(ethyloxy)phenyl)oxy)-2-((3-fluoro-4-((3-(4-methyl-1-piperazinyl)propyl)oxy)-phenyl)amino)-5-pyrimidinecarboxamide | 96 | 1.28 | 315, 335, 629 |
| 451 | N-(2,6-dimethylphenyl)-4-((2-(ethyloxy)phenyl)oxy)-2-((3-fluoro-4-((3-(1-piperidinyl)propyl)oxy)phenyl)-amino)-5-pyrimidinecarboxamide | 95.2 | 1.46 | 614, 307 |
| 452 | N-(2,6-dimethylphenyl)-4-((2-(ethyloxy)phenyl)oxy)-2-((3-fluoro-4-(4-methyl-1-piperazinyl)phenyl)amino)-5-pyrimidinecarboxamide | 96.1 | 1.34 | 306, 571, 286 |
| 453 | N-(2,6-dimethylphenyl)-4-((2-(ethyloxy)phenyl)oxy)-2-((3-fluoro-4-((2-(1-piperidinyl)ethyl)oxy)phenyl)amino)-5-pyrimidinecarboxamide | 93 | 1.44 | 600 |
| 454 | N-(2,6-dimethylphenyl)-4-((2-(ethyloxy)phenyl)oxy)-2-((3-fluoro-4-((3-(4-morpholinyl)propyl)oxy)phenyl)-amino)-5-pyrimidinecarboxamide | 100 | 1.44 | 308, 616 |
| 455 | N-(2,6-dimethylphenyl)-4-((2-(ethyloxy)phenyl)oxy)-2-((3-fluoro-4-(((1-methyl-3-piperidinyl)methyl)oxy)-phenyl)amino)-5-pyrimidinecarboxamide | 100 | 1.47 | 300, 600 |
| 456 | N-(2,6-dimethylphenyl)-4-((2-(ethyloxy)phenyl)oxy)-2-((3-fluoro-4-((2-(4-methyl-1-piperazinyl)ethyl)oxy)-phenyl)amino)-5-pyrimidinecarboxamide | 100 | 1.28 | 615 |
| 457 | N-(2,6-dimethylphenyl)-4-((2-(ethyloxy)phenyl)oxy)-2-((3-fluoro-4-((2-(1-pyrrolidinyl)ethyl)oxy)phenyl)-amino)-5-pyrimidinecarboxamide | 100 | 1.42 | 586 |
| 458 | N-(2,6-dimethylphenyl)-4-((2-(ethyloxy)phenyl)oxy)-2-((3-fluoro-4-((3-(1-pyrrolidinyl)propyl)oxy)phenyl)-amino)-5-pyrimidinecarboxamide | 97 | 1.47 | 300, 600 |
| 459 | N-(2,6-dimethylphenyl)-4-((2-(ethyloxy)phenyl)oxy)-2-((3-fluoro-4-((2-(4-morpholinyl)ethyl)oxy)phenyl)-amino)-5-pyrimidinecarboxamide | 86 | 1.37 | 602, 624 |
| 460 | N-(2,6-dimethylphenyl)-4-((2-(ethyloxy)phenyl)oxy)-2-((3-fluoro-4-((2-(4-(1-methylethyl)-1-piperazinyl)ethyl)-oxy)phenyl)amino)-5-pyrimidinecarboxamide | 100 | 1.28 | 322, 643, 665 |
| 461 | N-(2,6-dimethylphenyl)-4-((2-(ethyloxy)phenyl)oxy)-2-((3-fluoro-4-((2-(1-piperazinyl)ethyl)oxy)phenyl)amino)-5-pyrimidinecarboxamide | 85 | 1.26 | 301, 601 |
| 462 | N-(2,6-dimethylphenyl)-4-((2-(ethyloxy)phenyl)oxy)-2-((3-fluoro-4-(((2R)-2-pyrrolidinylmethyl)oxy)phenyl)-amino)-5-pyrimidinecarboxamide | 91 | 1.39 | 572, 594 |
| 463 | N-(2,6-dimethylphenyl)-4-((2-(ethyloxy)phenyl)oxy)-2-((3-fluoro-4-(((2S)-2-pyrrolidinylmethyl)oxy)phenyl)-amino)-5-pyrimidinecarboxamide | 86 | 1.4 | 572 |
| 464 | N-(2,6-dimethylphenyl)-4-((2-(ethyloxy)phenyl)oxy)-2-((3-fluoro-4-((3R,5S)-3,4,5-trimethyl-1-piperazinyl)-phenyl)amino)-5-pyrimidinecarboxamide | 95 | 1.4 | 599, 239, 300 |
| 465 | N-(2,6-dimethylphenyl)-4-((2-(ethyloxy)phenyl)oxy)-2-((3-fluoro-4-((octahydro-2H-quinolizin-1-ylmethyl)oxy)-phenyl)amino)-5-pyrimidinecarboxamide | 70 | 5.85 | 320, 640 |

-continued

| No. | Name | LC purity | LC Rt | Mass found |
|---|---|---|---|---|
| 466 | N-(2,6-dimethylphenyl)-4-((2-(ethyloxy)phenyl)oxy)-2-((3-fluoro-4-((4-(1H-imidazol-1-yl)butyl)oxy)phenyl)-amino)-5-pyrimidinecarboxamide | 94 | 1.48 | 306, 611 |
| 467 | N-(2,6-dimethylphenyl)-4-((2-(ethyloxy)phenyl)oxy)-2-((3-fluoro-4-((3-(4-(2-(methyloxy)ethyl)-1-piperazinyl)propyl)oxy)phenyl)amino)-5-pyrimidinecarboxamide | 100 | 1.28 | 337, 673 |
| 468 | N-(2,6-dimethylphenyl)-4-((2-(ethyloxy)phenyl)oxy)-2-(4-((2-(4-methyl-1-piperazinyl)ethyl)oxy)phenyl)-amino)-5-pyrimidinecarboxamide | 100 | 1.25 | 597, 319, 299 |
| 469 | N-(2,6-dimethylphenyl)-4-((2-(ethyloxy)phenyl)oxy)-2-((4-((2-((1-methylethyl)amino)ethyl)oxy)-3-(methyloxy)-phenyl)amino)-5-pyrimidinecarboxamide | 93 | 1.42 | 293, 586 |
| 470 | N-(2,6-dimethylphenyl)-4-((2-(ethyloxy)phenyl)oxy)-2-((4-((3-(4-(1-methylethyl)-1-piperazinyl)propyl)oxy)-3-(methyloxy)phenyl)amino)-5-pyrimidinecarboxamide | 98 | 1.28 | 335, 669 |
| 471 | N-(2,6-dimethylphenyl)-4-((2-(ethyloxy)phenyl)oxy)-2-((4-(1-(1-methylethyl)-4-piperidinyl)phenyl)amino)-5-pyrimidinecarboxamide | 100 | 1.44 | 290, 580 |
| 472 | N-(2,6-dimethylphenyl)-4-((2-(ethyloxy)phenyl)oxy)-2-((4-(1-methyl-4-piperidinyl)phenyl)amino)-5-pyrimidinecarboxamide | 100 | 1.37 | 552 |
| 473 | N-(2,6-dimethylphenyl)-4-((2-(ethyloxy)phenyl)oxy)-2-((4-(2-(4-methyl-1-piperazinyl)-2-oxoethyl)phenyl)-amino)-5-pyrimidinecarboxamide | 100 | 1.32 | 298, 595 |
| 474 | N-(2,6-dimethylphenyl)-4-((2-(ethyloxy)phenyl)oxy)-2-((4-(2-(4-methyl-1-piperazinyl)ethyl)phenyl)amino)-5-pyrimidinecarboxamide | 100 | 1.21 | 581, 291, 230 |
| 475 | N-(2,6-dimethylphenyl)-4-((2-(ethyloxy)phenyl)oxy)-2-((4-(4-(1-methylethyl)-1-piperazinyl)phenyl)amino)-5-pyrimidinecarboxamide | 87 | 1.38 | 291, 581, 311 |
| 476 | N-(2,6-dimethylphenyl)-4-((2-(ethyloxy)phenyl)oxy)-2-((4-(4-(2-(methyloxy)ethyl)-1-piperazinyl)phenyl)-amino)-5-pyrimidinecarboxamide | 100 | 1.39 | 299, 597 |
| 477 | N-(2,6-dimethylphenyl)-4-((2-(ethyloxy)phenyl)oxy)-2-((4-(4-methyl-1-piperazinyl)phenyl)amino)-5-pyrimidinecarboxamide | 99.5 | 1.31 | 297, 553 |
| 478 | N-(2,6-dimethylphenyl)-4-((2-(ethyloxy)phenyl)oxy)-2-((6-(4-methyl-1-piperazinyl)-3-pyridinyl)amino)-5-pyrimidinecarboxamide | 100 | 1.24 | 554, 298, 277 |
| 479 | N-(2,6-dimethylphenyl)-4-((2-(ethyloxy)phenyl)oxy)-2-((6-(4-morpholinyl)-3-pyridinyl)amino)-5-pyrimidine-carboxamide | 96 | 1.37 | 541 |
| 480 | N-(2,6-dimethylphenyl)-4-((2-(methyloxy)-4-(2-propenyl)phenyl)oxy)-2-((4-(4-methyl-1-piperazinyl)-phenyl)amino)-5-pyrimidinecarboxamide | 100 | 1.42 | 579, 310, 290 |
| 481 | N-(2,6-dimethylphenyl)-4-((2-(methyloxy)-4-(2-propenyl)phenyl)oxy)-2-((3,4,5-tris(methyloxy)phenyl)-amino)-5-pyrimidinecarboxamide | 100 | 1.78 | 571 |
| 482 | N-(2,6-dimethylphenyl)-4-((2-(methyloxy)-4-(3-pyridinyl)phenyl)oxy)-2-((3,4,5-tris(methyloxy)phenyl)-amino)-5-pyrimidinecarboxamide | 88 | 1.25 | 304, 608 |
| 483 | N-(2,6-dimethylphenyl)-4-((2-(methyloxy)-4-(3-thienyl)-phenyl)oxy)-2-((3,4,5-tris(methyloxy)phenyl)amino)-5-pyrimidinecarboxamide | 100 | 1.76 | 613 |
| 484 | N-(2,6-dimethylphenyl)-4-((2-(methyloxy)-4-propylphenyl)oxy)-2-((4-(4-methyl-1-piperazinyl)-phenyl)amino)-5-pyrimidinecarboxamide | 96 | 1.43 | 321, 581, 291 |
| 485 | N-(2,6-dimethylphenyl)-4-((2-(methyloxy)-4-propylphenyl)oxy)-2-((3,4,5-tris(methyloxy)phenyl)-amino)-5-pyrimidinecarboxamide | 98 | 1.84 | 573 |
| 486 | N-(2,6-dimethylphenyl)-4-((2-(methyloxy)-4-propylphenyl)oxy)-2-((4-((2-(4-methyl-1-piperazinyl)-ethyl)oxy)phenyl)amino)-5-pyrimidinecarboxamide | 96 | 1.39 | 313, 625 |
| 487 | N-(2,6-dimethylphenyl)-4-((2-(methyloxy)-4-propylphenyl)oxy)-2-((4-(1-methyl-4-piperidinyl)-phenyl)amino)-5-pyrimidinecarboxamide | 93 | 1.52 | 290, 580 |
| 488 | N-(2,6-dimethylphenyl)-4-((2-(methyloxy)-4-propylphenyl)oxy)-2-((3-((3-(1-piperidinyl)propyl)oxy)-phenyl)amino)-5-pyrimidinecarboxamide | 100 | 1.67 | 312, 624 |
| 489 | N-(2,6-dimethylphenyl)-4-((2-(methyloxy)-4-propylphenyl)oxy)-2-((3-((3-(4-methyl-1-piperazinyl)-propyl)oxy)phenyl)amino)-5-pyrimidinecarboxamide | 87 | 1.47 | 320, 639 |
| 490 | N-(2,6-dimethylphenyl)-4-((2-(methyloxy)-4-propylphenyl)oxy)-2-((3-(methyloxy)-4-(((2S)-2-pyrrolidinylmethyl)oxy)phenyl)amino)-5-pyrimidinecarboxamide | 95 | 1.54 | 306, 612 |
| 491 | N-(2,6-dimethylphenyl)-4-((2-(methyloxy)-4-propylphenyl)oxy)-2-((4-(2-(4-methyl-1-piperazinyl)-2-oxoethyl)phenyl)amino)-5-pyrimidinecarboxamide | 95 | 1.43 | 312, 623 |

| No. | Name | LC purity | LC Rt | Mass found |
|---|---|---|---|---|
| 492 | N-(2,6-dimethylphenyl)-4-((2-(methyloxy)-4-propylphenyl)oxy)-2-((4-(2-(4-methyl-1-piperazinyl)-ethyl)phenyl)amino)-5-pyrimidinecarboxamide | 100 | 1.31 | 305, 609, 244 |
| 493 | N-(2,6-dimethylphenyl)-4-((2-(methyloxy)phenyl)oxy)-2-((4-(((2S)-2-pyrrolidinylmethyl)oxy)phenyl)amino)-5-pyrimidinecarboxamide | 92.2 | 1.3 | 540, 291, 270 |
| 494 | N-(2,6-dimethylphenyl)-4-((2-(methyloxy)phenyl)oxy)-2-((4-(4-methyl-1-piperazinyl)phenyl)amino)-5-pyrimidinecarboxamide | 96.6 | 1.27 | 290, 539 |
| 495 | N-(2,6-dimethylphenyl)-4-((2-(methyloxy)phenyl)oxy)-2-(phenylamino)-5-pyrimidinecarboxamide | 84.1 | 1.68 | 441 |
| 496 | N-(2,6-dimethylphenyl)-4-((2-ethylphenyl)oxy)-2-((3-(methyloxy)-4-(4-methyl-1-piperazinyl)phenyl)amino)-5-pyrimidinecarboxamide | 90.9 | 1.33 | 567 |
| 497 | N-(2,6-dimethylphenyl)-4-((2-ethylphenyl)oxy)-2-((3-fluoro-4-(4-methyl-1-piperazinyl)phenyl)amino)-5-pyrimidinecarboxamide | 99.6 | 1.35 | 555, 596 |
| 498 | N-(2,6-dimethylphenyl)-4-((2-ethylphenyl)oxy)-2-((3-fluoro-4-((3-(1-piperidinyl)propyl)oxy)phenyl)amino)-5-pyrimidinecarboxamide | 85.9 | 1.44 | 598 |
| 499 | N-(2,6-dimethylphenyl)-4-((2-ethylphenyl)oxy)-2-((4-(4-(1-methylethyl)-1-piperazinyl)phenyl)amino)-5-pyrimidinecarboxamide | 98.9 | 1.66 | 565 |
| 500 | N-(2,6-dimethylphenyl)-4-((2-ethylphenyl)oxy)-2-((4-(4-methyl-1-piperazinyl)phenyl)amino)-5-pyrimidinecarboxamide | 97.6 | 1.31 | 537 |
| 501 | N-(2,6-dimethylphenyl)-4-((2-fluorophenyl)oxy)-2-((3-(methyloxy)-4-((2-(4-methyl-1-piperazinyl)ethyl)oxy)-phenyl)amino)-5-pyrimidinecarboxamide | 96.4 | 1.2 | 321, 301, 601 |
| 502 | N-(2,6-dimethylphenyl)-4-((2-fluorophenyl)oxy)-2-((3-(methyloxy)-4-((3-(4-methyl-1-piperazinyl)propyl)oxy)-phenyl)amino)-5-pyrimidinecarboxamide | 93.4 | 1.21 | 615, 308, 328 |
| 503 | N-(2,6-dimethylphenyl)-4-((2-fluorophenyl)oxy)-2-((3-(methyloxy)-4-(4-methyl-1-piperazinyl)phenyl)amino)-5-pyrimidinecarboxamide | 90.2 | 1.26 | 557, 279, 299 |
| 504 | N-(2,6-dimethylphenyl)-4-((2-fluorophenyl)oxy)-2-((4-(4-methyl-1-piperazinyl)phenyl)amino)-5-pyrimidinecarboxamide | 93.1 | 1.28 | 527, 284 |
| 505 | N-(2,6-dimethylphenyl)-4-((2-methyl-1,3-benzothiazol-5-yl)oxy)-2-((4-(4-methyl-1-piperazinyl)phenyl)amino)-5-pyrimidinecarboxamide | 100 | 1.21 | 291, 580, 230 |
| 506 | N-(2,6-dimethylphenyl)-4-((2-methyl-1,3-benzothiazol-5-yl)oxy)-2-((4-(4-(1-methylethyl)-1-piperazinyl)phenyl)-amino)-5-pyrimidinecarboxamide | 100 | 1.26 | 305, 608 |
| 507 | N-(2,6-dimethylphenyl)-4-((2'-methyl-3-(methyloxy)-1,1'-biphenyl-4-yl)oxy)-2-((3,4,5-tris(methyloxy)phenyl)-amino)-5-pyrimidinecarboxamide | 100 | 1.83 | 621, 643 |
| 508 | N-(2,6-dimethylphenyl)-4-((3-(methyloxy)-1,1'-biphenyl-4-yl)oxy)-2-((3,4,5-tris(methyloxy)phenyl)amino)-5-pyrimidinecarboxamide | 88 | 1.82 | 607 |
| 509 | N-(2,6-dimethylphenyl)-4-((3-(methyloxy)-4'-(trifluoromethyl)-1,1'-biphenyl-4-yl)oxy)-2-((3,4,5-tris(methyloxy)phenyl)amino)-5-pyrimidinecarboxamide | 90 | 1.89 | 675 |
| 510 | N-(2,6-dimethylphenyl)-4-((3-fluorophenyl)oxy)-2-((3-(methyloxy)-4-(4-methyl-1-piperazinyl)phenyl)amino)-5-pyrimidinecarboxamide | 100 | 1.3 | 557, 299, 279 |
| 511 | N-(2,6-dimethylphenyl)-4-((3-fluorophenyl)oxy)-2-((3-fluoro-4-((3-(1-piperidinyl)propyl)oxy)phenyl)amino)-5-pyrimidinecarboxamide | 95.9 | 1.4 | 588 |
| 512 | N-(2,6-dimethylphenyl)-4-((3-fluorophenyl)oxy)-2-((4-(4-(1-methylethyl)-1-piperazinyl)phenyl)amino)-5-pyrimidinecarboxamide | 90.4 | 1.37 | 555 |
| 513 | N-(2,6-dimethylphenyl)-4-((3-fluorophenyl)oxy)-2-((4-(4-methyl-1-piperazinyl)phenyl)amino)-5-pyrimidinecarboxamide | 100 | 1.3 | 527, 284 |
| 514 | N-(2,6-dimethylphenyl)-4-((4-((phenylmethyl)oxy)-phenyl)oxy)-2-((3,4,5-tris(methyloxy)phenyl)amino)-5-pyrimidinecarboxamide | 100 | 1.81 | 607 |
| 515 | N-(2,6-dimethylphenyl)-4-((4-(1H-indol-5-yl)-2-(methyloxy)phenyl)oxy)-2-((3,4,5-tris(methyloxy)-phenyl)amino)-5-pyrimidinecarboxamide | 100 | 1.67 | 646 |
| 516 | N-(2,6-dimethylphenyl)-4-((4-(4-methyl-1-piperazinyl)-phenyl)amino)-2-(phenylsulfanyl)-5-pyrimidinecarboxamide | 96.4 | 1.3 | 283, 525 |
| 517 | N-(2,6-dimethylphenyl)-4-((4-(methyloxy)phenyl)oxy)-2-((4-(1-piperazinyl)phenyl)amino)-5-pyrimidinecarboxamide | 92.9 | 1.24 | 283, 525 |
| 518 | N-(2,6-dimethylphenyl)-4-((4-(methyloxy)phenyl)oxy)-2-((4-(4-methyl-1-piperazinyl)phenyl)amino)-5-pyrimidinecarboxamide | 95.2 | 1.22 | 539 |
| 519 | N-(2,6-dimethylphenyl)-4-((4-(phenyloxy)phenyl)oxy)-2-((3,4,5-tris(methyloxy)phenyl)amino)-5-pyrimidinecarboxamide | 100 | 1.81 | 593 |

| No. | Name | LC purity | LC Rt | Mass found |
|---|---|---|---|---|
| 520 | N-(2,6-dimethylphenyl)-4-((4-fluorophenyl)oxy)-2-((3-(methyloxy)-4-(4-methyl-1-piperazinyl)phenyl)amino)-5-pyrimidinecarboxamide | 96.7 | 1.32 | 557, 299, 279 |
| 521 | N-(2,6-dimethylphenyl)-4-((4-fluorophenyl)oxy)-2-((3-fluoro-4-((3-(1-piperidinyl)propyl)oxy)phenyl)amino)-5-pyrimidinecarboxamide | 98.8 | 1.45 | 588 |
| 522 | N-(2,6-dimethylphenyl)-4-((4-fluorophenyl)oxy)-2-((4-(((2R)-2-pyrrolidinylmethyl)oxy)phenyl)amino)-5-pyrimidinecarboxamide | 82.2 | 1.32 | 528 |
| 523 | N-(2,6-dimethylphenyl)-4-((4-fluorophenyl)oxy)-2-((4-(4-methyl-1-piperazinyl)phenyl)amino)-5-pyrimidinecarboxamide | 100 | 1.27 | 527, 284 |
| 524 | 5-iodo-4-((2-(methyloxy)phenyl)oxy)-N-(4-(4-methyl-1-piperazinyl)phenyl)-2-pyrimidinamine | 100 | 1.29 | 517, 519 |
| 525 | 5-(((2,6-dimethylphenyl)amino)methyl)-4-((2-(methyloxy)phenyl)oxy)-N-(3,4,5-tris(methyloxy)phenyl)-2-pyrimidinamine | 91 | 1.22 | 517, 259 |
| 526 | N-(2,6-dimethylphenyl)-2,4-bis(phenylamino)-5-pyrimidinecarboxamide | 100 | 1.55 | 410 |
| 527 | N-(2,6-dimethylphenyl)-2-((3-fluoro-4-((3-(4-methyl-1-piperazinyl)propyl)oxy)phenyl)amino)-4-(phenylamino)-5-pyrimidinecarboxamide | 100 | 1.19 | 584, 292 |
| 528 | 5-((E)-2-(2-chlorophenyl)ethenyl)-4-((2-(methyloxy)phenyl)oxy)-N-(4-(4-methyl-1-piperazinyl)phenyl)-2-pyrimidinamine | 91 | 1.42 | 528, 53 |
| 529 | 5-((E)-2-(2-chlorophenyl)ethenyl)-4-((2-(methyloxy)phenyl)oxy)-N-(4-(4-methyl-1-piperazinyl)phenyl)-2-pyrimidinamine | 91 | 1.42 | 528, 530 |
| 530 | methyl (2E)-3-(4-((2-(methyloxy)phenyl)oxy)-2-((4-(4-methyl-1-piperazinyl)phenyl)amino)-5-pyrimidinyl)-2-propenoate | 100 | 1.19 | 476 |
| 531 | 5-((Z)-2-(2-chlorophenyl)-1-fluoroethenyl)-4-((2-(methyloxy)phenyl)oxy)-N-(4-(4-methyl-1-piperazinyl)phenyl)-2-pyrimidinamine | 90.2 | 1.55 | 546 |
| 532 | N-(2,6-dimethylphenyl)-2-((4-(4-methyl-1-piperazinyl)phenyl)amino)-4-(phenylamino)-5-pyrimidinecarboxamide | 100 | 1.2 | 508, 254 |
| 533 | N-(2,6-dimethylphenyl)-2-((3-fluoro-4-((3-(1-piperidinyl)propyl)oxy)phenyl)amino)-4-(phenylamino)-5-pyrimidinecarboxamide | 100 | 1.31 | 569, 285 |
| 534 | N-(2,6-dimethylphenyl)-2-((3-fluoro-4-(4-methyl-1-piperazinyl)phenyl)amino)-4-(phenylamino)-5-pyrimidinecarboxamide | 100 | 1.22 | 526, 263 |
| 535 | N-(2,6-dimethylphenyl)-2-((4-(4-(1-methylethyl)-1-piperazinyl)phenyl)amino)-4-(phenylamino)-5-pyrimidinecarboxamide | 92.6 | 4.39 | 536 |
| 536 | 2-((4-(4-(2-(dimethylamino)ethyl)-1-piperazinyl)phenyl)amino)-N-(2,6-dimethylphenyl)-4-(phenylamino)-5-pyrimidinecarboxamide | 100 | 1.13 | 565, 583 |
| 537 | 2-((4-(4-(3-(dimethylamino)propyl)-1-piperazinyl)phenyl)amino)-N-(2,6-dimethylphenyl)-4-(phenylamino)-5-pyrimidinecarboxamide | 100 | 1.12 | 579, 290 |
| 538 | 2-((4-(((2-(dimethylamino)ethyl)amino)carbonyl)phenyl)amino)-N-(2,6-dimethylphenyl)-4-(phenylamino)-5-pyrimidinecarboxamide | 100 | 1.2 | 524, 262 |
| 539 | N-(2,6-dimethylphenyl)-2-((4-(4-methyl-1-piperazinyl)phenyl)amino)-4-((3-((1,1,2,2-tetrafluoroethyl)oxy)phenyl)oxy)-5-pyrimidinecarboxamide | 94.2 | 1.39 | 625, 313 |
| 540 | N-(2,6-dimethylphenyl)-2-((3-fluoro-4-(3-(1-piperidinyl)propyl)oxy)phenyl)amino)-4-((3-((1,1,2,2-tetrafluoroethyl)oxy)phenyl)oxy)-5-pyrimidinecarboxamide | 96.9 | 1.5 | 686, 343 |
| 541 | N-(2,6-dimethylphenyl)-2-((3-fluoro-4-(4-methyl-1-piperazinyl)phenyl)amino)-4-((3-((1,1,2,2-tetrafluoroethyl)oxy)phenyl)oxy)-5-pyrimidinecarboxamide | 91.4 | 1.43 | 643, 322 |
| 542 | N-(2,6-dimethylphenyl)-2-((4-(4-(1-methylethyl)-1-piperazinyl)phenyl)amino)-4-((3-((1,1,2,2-tetrafluoroethyl)oxy)phenyl)oxy)-5-pyrimidinecarboxamide | 96.2 | 1.43 | 653, 327 |
| 543 | 2-((4-(diethylamino)butyl)amino)-N-(2,6-dimethylphenyl)-4-((2-(ethyloxy)phenyl)oxy)-5-pyrimidinecarboxamide | 100 | 1.29 | 506 |

| No. | Name | LC purity | LC Rt | Mass found |
|---|---|---|---|---|
| 544 | N-(2,6-dimethylphenyl)-4-((2-(ethyloxy)phenyl)oxy)-2-((2-(4-(phenylmethyl)-1-piperazinyl)ethyl)amino)-5-pyrimidinecarboxamide | 100 | 1.3 | 581, 291 |
| 545 | N-(2,6-dimethylphenyl)-2-((4-(4-methyl-1-piperazinyl)phenyl)amino)-4-(1-naphthalenyloxy)-5-pyrimidinecarboxamide | 100 | 1.33 | 559, 280 |
| 546 | N-(2,6-dimethylphenyl)-2-((4-(4-(1-methylethyl)-1-piperazinyl)phenyl)amino)-4-((2-(methyloxy)-4-(3-(((1R)-1-methylpropyl)amino)-3-oxopropyl)phenyl)oxy)-5-pyrimidinecarboxamide | 100 | 1.87 | 694, 347 |
| 547 | N-(2,6-dimethylphenyl)-4-((2-(methyloxy)-4-((1E)-3-oxo-3-((phenylmethyl)amino)-1-propenyl)phenyl)oxy)-2-(phenylamino)-5-pyrimidinecarboxamide | 91.2 | 1.57 | 600, 300 |
| 548 | N-(2,6-dimethylphenyl)-2-((3-fluoro-4-(4-methyl-1-piperazinyl)phenyl)amino)-4-((2-(methyloxy)-4-(3-(((1R)-1-methylpropyl)amino)-3-oxopropyl)phenyl)oxy)-5-pyrimidinecarboxamide | 100 | 1.33 | 684, 342 |
| 549 | N-(2,6-dimethylphenyl)-4-((2-(methyloxy)-4-(3-(((1S)-1-methylpropyl)amino)-3-oxopropyl)phenyl)oxy)-2-((4-(4-methyl-1-piperazinyl)phenyl)amino)-5-pyrimidinecarboxamide | 100 | 1.3 | 666, 333 |
| 550 | N-(2,6-dimethylphenyl)-2-((3-fluoro-4-((3-(4-methyl-1-piperazinyl)propyl)oxy)phenyl)amino)-4-((2-(methyloxy)-4-(3-(((1S)-1-methylpropyl)amino)-3-oxopropyl)phenyl)oxy)-5-pyrimidinecarboxamide | 100 | 1.27 | 742, 371 |
| 551 | N-(2,6-dimethylphenyl)-2-((3-fluoro-4-((3-(1-piperidinyl)propyl)oxy)phenyl)amino)-4-((2-(methyloxy)-4-(3-(((1S)-1-methylpropyl)amino)-3-oxopropyl)phenyl)oxy)-5-pyrimidinecarboxamide | 100 | 1.41 | 727, 364 |
| 552 | N-(2,6-dimethylphenyl)-2-((3-fluoro-4-(4-methyl-1-piperazinyl)phenyl)amino)-4-((2-(methyloxy)-4-(3-(((1S)-1-methylpropyl)amino)-3-oxopropyl)phenyl)oxy)-5-pyrimidinecarboxamide | 100 | 1.32 | 684 |
| 553 | N-(2,6-dimethylphenyl)-2-((4-(4-(1-methylethyl)-1-piperazinyl)phenyl)amino)-4-((2-(methyloxy)-4-(3-(((1S)-1-methylpropyl)amino)-3-oxopropyl)phenyl)oxy)-5-pyrimidinecarboxamide | 100 | 1.33 | 694 |
| 554 | 4-(3-(acetylamino)phenyl)oxy)-N-(2,6-dimethylphenyl)-2-((4-(4-(1-methylethyl)-1-piperazinyl)phenyl)amino)-5-pyrimidinecarboxamide | 86.5 | 1.19 | 594 |
| 555 | 2-((4-(diethylamino)butyl)amino)-N-(2,6-dimethylphenyl)-4-((2-(methyloxy)-4-propylphenyl)oxy)-5-pyrimidinecarboxamide | 89 | 1.47 | 534, 267 |
| 556 | N-(2,6-dimethylphenyl)-4-((2-(ethyloxy)phenyl)oxy)-2-((3-fluoro-4-((3-(1H-imidazol-1-yl)propyl)oxy)phenyl)amino)-5-pyrimidinecarboxamide | 100 | 1.45 | 597, 299 |
| 557 | 4-((3-((aminocarbonyl)amino)phenyl)oxy)-N-(2,6-dimethylphenyl)-2-((4-(4-methyl-1-piperazinyl)phenyl)amino)-5-pyrimidinecarboxamide | 84.8 | 1.11 | 567 |
| 558 | 4-((3-((aminocarbonyl)amino)phenyl)oxy)-N-(2,6-dimethylphenyl)-2-((3-fluoro-4-((3-(1-piperidinyl)propyl)oxy)phenyl)amino)-5-pyrimidinecarboxamide | 82.9 | 1.25 | 628, 314 |
| 559 | 4-((4-((butyloxy)methyl)-2-(methyloxy)phenyl)oxy)-N-(2,6-dimethylphenyl)-2-((3-fluoro-4-((3-(1H-imidazol-1-yl)propyl)oxy)phenyl)amino)-5-pyrimidinecarboxamide | 96.6 | 1.53 | 669 |
| 560 | 4-((4-((butyloxy)methyl)-2-(methyloxy)phenyl)oxy)-N-(2,6-dimethylphenyl)-2-((4-(4-methyl-1-piperazinyl)phenyl)amino)-5-pyrimidinecarboxamide | 100 | 1.48 | 625 |
| 561 | 4-((4-((butyloxy)methyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.4 | 701, 351 |
| 562 | 4-((4-((butyloxy)methyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide | 100 | 1.59 | 686, 343 |
| 563 | 4-((4-((butyloxy)methyl)-2-(methyloxy)phenyl)oxy)-N-(2,6-dimethylphenyl)-2-((3-fluoro-4-(4-methyl-1-piperazinyl)phenyl)amino)-5-pyrimidinecarboxamide | 100 | 1.51 | 643 |
| 564 | 4-((4-((butyloxy)methyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide | 100 | 1.56 | 653, 327 |

| No. | Name | LC purity | LC Rt | Mass found |
|---|---|---|---|---|
| 565 | 4-((4-((butyloxy)methyl-2-(methyloxy)phenyl)oxy)-2-((4-(4-(3-(dimethylamino)propyl)-1-piperazinyl)phenyl)amino)-N-(2,6-dimethylphenyl)-5-pyrimidinecarboxamide | 100 | 1.37 | 696, 348 |
| 566 | 4-((4-((butyloxy)methyl-2-(methyloxy)phenyl)oxy)-N-(2,6-dimethylphenyl)-2-((3-fluoro-4-((3-(4-(2-(methyloxy)ethyl)-1-piperazinyl)propyl)oxy)phenyl)amino)-5-pyrimidinecarboxamide | 100 | 1.47 | 745, 373 |
| 567 | N-(2,6-dimethylphenyl)-2-((3-fluoro-4-((3-(4-methyl-1-piperazinyl)propyl)oxy)phenyl)amino)-4-((3-(4-morpholinyl)phenyl)oxy)-5-pyrimidinecarboxamide | 100 | 1.22 | 670, 335 |
| 568 | N-(2,6-dimethylphenyl)-2-((3-fluoro-4-((3-(1-piperidinyl)propyl)oxy)phenyl)amino)-4-((3-(4-morpholinyl)phenyl)oxy)-5-pyrimidinecarboxamide | 100 | 1.39 | 655, 328 |
| 569 | 2-((4-(4-(3-(dimethylamino)propyl)-1-piperazinyl)phenyl)amino)-N-(2,6-dimethylphenyl)-4-((3-(4-morpholinyl)phenyl)oxy)-5-pyrimidinecarboxamide | 100 | 1.18 | 665, 333 |
| 570 | 4-((3-(acetylamino)phenyl)oxy)-N-(2,6-dimethylphenyl)-2-((3-fluoro-4-((3-(1-piperidinyl)propyl)oxy)phenyl)amino)-5-pyrimidinecarboxamide | 86.5 | 1.25 | 627 |
| 571 | 4-((3-(acetylamino)phenyl)oxy)-N-(2,6-dimethylphenyl)-2-((3-fluoro-4-(4-methyl-1-piperazinyl)phenyl)amino)-5-pyrimidinecarboxamide | 89.3 | 1.18 | 584 |
| 572 | 4-((3-(acetylamino)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 94.8 | 1.17 | 642, 334 1 |
| 573 | 2-((3,5-bis(methyloxy)-4-((3-(4-methyl-1-piperazinyl)propyl)oxy)phenyl)amino)-4-((4-(3-(diethylamino)-3-oxopropyl)-2-(methyloxy)phenyl)oxy)-N-(2,6-dimethylphenyl)-5-pyrimidinecarboxamide | 96.7 | 1.29 | 784, 392 |
| 574 | 4-((4-(3-(diethylamino)-3-oxopropyl)-2-(methyloxy)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 100 | 1.31 | 756, 378 |
| 575 | 2-((4-(diethylamino)butyl)amino)-4-((4-(3-(diethylamino)-3-oxopropyl)-2-(methyloxy)phenyl)oxy)-N-(2,6-dimethylphenyl)-5-pyrimidinecarboxamide | 100 | 1.27 | 619, 310 |
| 576 | N-(2,6-dichlorophenyl)-4-((4-(3-(diethylamino)-3-oxopropyl)-2-(methyloxy)phenyl)oxy)-2-((3-fluoro-4-((3-(4-methyl-1-piperazinyl)propyl)oxy)phenyl)amino)-5-pyrimidinecarboxamide | 100 | 1.29 | 782, 784 |
| 577 | N-(2,6-dichlorophenyl)-4-((4-(3-(diethylamino)-3-oxopropyl)-2-(methyloxy)phenyl)oxy)-2-((3-fluoro-4-((3-(1-piperidinyl)propyl)oxy)phenyl)amino)-5-pyrimidinecarboxamide | 94.7 | 1.45 | 767, 769 |
| 578 | 2-((3-chloro-4-(4-(1-methylethyl)-1-piperazinyl)phenyl)amino)-4-((4-(3-(diethylamino)-3-oxopropyl)-2-(methyloxy)phenyl)oxy)-N-(2,6-dimethylphenyl)-5-pyrimidinecarboxamide | 91.9 | 1.45 | 728, 730 |
| 579 | 4-((2-chloro-4-(2-(diethylamino)-2-oxoethyl)phenyl)oxy)-N-(2,6-dimethylphenyl)-2-((4-(4-methyl-1-piperazinyl)phenyl)amino)-5-pyrimidinecarboxamide | 100 | 1.34 | 656, 658 |
| 580 | 4-((2-chloro-4-(2-(diethylamino)-2-oxoethyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 97 | 1.27 | 732, 734 |
| 581 | 4-((2-chloro-4-(2-(diethylamino)-2-oxoethyl)phenyl)oxy)-N-(2,6-dimethylphenyl)-2-((3-fluoro-4-((3-(1-piperidinyl)propyl)oxy)phenyl)amino)-5-pyrimidinecarboxamide | 100 | 1.42 | 717, 719 |
| 582 | 4-((2-chloro-4-(2-(diethylamino)-2-oxoethyl)phenyl)oxy)-N-(2,6-dimethylphenyl)-2-((3-fluoro-4-(4-methyl-1-piperazinyl)phenyl)amino)-5-pyrimidinecarboxamide | 100 | 1.33 | 674, 676 |
| 583 | 4-((2-chloro-4-(2-(diethylamino)-2-oxoethyl)phenyl)oxy)-N-(2,6-dimethylphenyl)-2-((4-(4-(1-methylethyl)-1-piperazinyl)phenyl)amino)-5-pyrimidinecarboxamide | 98 | 1.38 | 684, 686 |

-continued

| No. | Name | LC purity | LC Rt | Mass found |
|---|---|---|---|---|
| 584 | 4-((2-chloro-4-(2-(diethylamino)-2-oxoethyl)phenyl)oxy)-2-((4-(4-(3-(dimethylamino)propyl)-1-piperazinyl)phenyl)amino)-N-(2,6-dimethylphenyl)-5-pyrimidinecarboxamide | 100 | 1.25 | 727, 729 |
| 585 | 2-((4-(((2-(dimethylamino)ethyl)amino)carbonyl)phenyl)amino)-4-((2,2-dimethyl-2,3-dihydro-1-benzofuran-7-yl)oxy)-N-(2,6-dimethylphenyl)-5-pyrimidinecarboxamide | 98.5 | 1.32 | 595 |
| 586 | 2-((3,5-bis(methyloxy)-4-((3-(4-methyl-1-piperazinyl)propyl)oxy)phenyl)amino)-4-((2,2-dimethyl-2,3-dihydro-1-benzofuran-7-yl)oxy)-N-(2,6-dimethylphenyl)-5-pyrimidinecarboxamide | 100 | 1.3 | 697, 349 |
| 587 | 4-((2,2-dimethyl-2,3-dihydro-1-benzofuran-7-yl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 93.5 | 1.31 | 669, 335 |
| 588 | N-(2,6-dimethylphenyl)-2-((3-fluoro-4-(4-methyl-1-piperazinyl)phenyl)amino)-4-((2-(methyloxy)-5-(3-oxo-3-((phenylmethyl)amino)propyl)phenyl)oxy)-5-pyrimidinecarboxamide | 100 | 1.33 | 718, 359 |
| 589 | N-(2,6-dimethylphenyl)-2-((3-fluoro-4-((3-(1-piperidinyl)propyl)oxy)phenyl)amino)-4-((2-(methyloxy)-5-(3-oxo-3-((phenylmethyl)amino)propyl)phenyl)oxy)-5-pyrimidinecarboxamide | 100 | 1.41 | 761, 381 |
| 590 | N-(2,6-dimethylphenyl)-2-((3-fluoro-4-(4-methyl-1-piperazinyl)phenyl)amino)-4-((2-(methyloxy)-5-((1E)-3-oxo-3-((phenylmethyl)amino)-1-propenyl)phenyl)oxy)-5-pyrimidinecarboxamide | 100 | 1.4 | 716, 358 |
| 591 | N-(2,6-dimethylphenyl)-2-((3-fluoro-4-((3-(4-methyl-1-piperazinyl)propyl)oxy)phenyl)amino)-4-((2-(methyloxy)-5-((1E)-3-oxo-3-((phenylmethyl)amino)-1-propenyl)phenyl)oxy)-5-pyrimidinecarboxamide | 100 | 1.31 | 774, 387 |
| 592 | N-(2,6-dimethylphenyl)-4-((2-(methyloxy)-5-((1E)-3-oxo-3-((phenylmethyl)amino)-1-propenyl)phenyl)oxy)-2-((4-(4-methyl-1-piperazinyl)phenyl)amino)-5-pyrimidinecarboxamide | 100 | 1.36 | 698, 349 |
| 593 | N-(2,6-dimethylphenyl)-4-((3-(2-(3-methyl-1,2,4-oxadiazol-5-yl)ethyl)phenyl)oxy)-2-((4-(4-methyl-1-piperazinyl)phenyl)amino)-5-pyrimidinecarboxamide | 97.2 | 1.28 | 619, 310 |
| 594 | N-(2,6-dimethylphenyl)-2-((3-fluoro-4-((3-(4-methyl-1-piperazinyl)propyl)oxy)phenyl)amino)-4-((3-(2-(3-methyl-1,2,4-oxadiazol-5-yl)ethyl)phenyl)oxy)-5-pyrimidinecarboxamide | 100 | 1.23 | 695, 348 |
| 595 | N-(2,6-dimethylphenyl)-2-((3-fluoro-4-((3-(1-piperidinyl)propyl)oxy)phenyl)amino)-4-((3-(2-(3-methyl-1,2,4-oxadiazol-5-yl)ethyl)phenyl)oxy)-5-pyrimidinecarboxamide | 100 | 1.39 | 680 |
| 596 | N-(2,6-dimethylphenyl)-2-((3-fluoro-4-(4-methyl-1-piperazinyl)phenyl)amino)-4-((3-(2-(3-methyl-1,2,4-oxadiazol-5-yl)ethyl)phenyl)oxy)-5-pyrimidinecarboxamide | 100 | 1.31 | 637 |
| 597 | N-(2,6-dimethylphenyl)-2-((4-(4-(1-methylethyl)-1-piperazinyl)phenyl)amino)-4-((3-(2-(3-methyl-1,2,4-oxadiazol-5-yl)ethyl)phenyl)oxy)-5-pyrimidinecarboxamide | 96.9 | 1.33 | 647 |
| 598 | 2-((4-(4-(3-(dimethylamino)propyl)-1-piperazinyl)phenyl)amino)-N-(2,6-dimethylphenyl)-4-((3-(2-(3-methyl-1,2,4-oxadiazol-5-yl)ethyl)phenyl)oxy)-5-pyrimidinecarboxamide | 98 | 1.21 | 690, 345 |
| 599 | N-(2,6-dimethylphenyl)-2-((4-(4-methyl-1-piperazinyl)phenyl)amino)-4-((3-((trifluoromethyl)oxy)phenyl)oxy)-5-pyrimidinecarboxamide | 94.6 | 1.39 | 680 |
| 600 | N-(2,6-dimethylphenyl)-2-((3-fluoro-4-((3-(4-methyl-1-piperazinyl)propyl)oxy)phenyl)amino)-4-((3-((trifluoromethyl)oxy)phenyl)oxy)-5-pyrimidinecarboxamide | 87.9 | 1.33 | 669, 335 |
| 601 | N-(2,6-dimethylphenyl)-2-((3-fluoro-4-((3-(1-piperidinyl)propyl)oxy)phenyl)amino)-4-((3-((trifluoromethyl)oxy)phenyl)oxy)-5-pyrimidinecarboxamide | 100 | 1.51 | 654, 327 |
| 602 | N-(2,6-dimethylphenyl)-2-((3-fluoro-4-(4-methyl-1-piperazinyl)phenyl)amino)-4-((3-((trifluoromethyl)oxy)phenyl)oxy)-5-pyrimidinecarboxamide | 97.6 | 1.43 | 611, 306 |

-continued

| No. | Name | LC purity | LC Rt | Mass found |
|---|---|---|---|---|
| 603 | N-(2,6-dimethylphenyl)-2-((4-(4-(1-methylethyl)-1-piperazinyl)phenyl)amino)-4-((3-((trifluoromethyl)oxy)phenyl)oxy)-5-pyrimidinecarboxamide | 88.9 | 1.44 | 621, 311 |
| 604 | 2-((4-(4-(3-(dimethylamino)propyl)-1-piperazinyl)phenyl)amino)-N-(2,6-dimethylphenyl)-4-((3-((trifluoromethyl)oxy)phenyl)oxy)-5-pyrimidinecarboxamide | 90.3 | 1.3 | 664, 332 |
| 605 | N-(2,6-dimethylphenyl)-2-((3-fluoro-4-((3-(1-piperidinyl)propyl)oxy)phenyl)amino)-4-((4-((trifluoromethyl)oxy)phenyl)oxy)-5-pyrimidinecarboxamide | 95.5 | 1.52 | 654 |
| 606 | N-(2,6-dimethylphenyl)-2-((4-(4-methyl-1-piperazinyl)phenyl)amino)-4-((3-(2-phenyl-4-pyrimidinyl)phenyl)oxy)-5-pyrimidinecarboxamide | 94.7 | 1.47 | 663 |
| 607 | N-(2,6-dimethylphenyl)-2-((3-fluoro-4-((3-(1-piperidinyl)propyl)oxy)phenyl)amino)-4-((3-(2-phenyl-4-pyrimidinyl)phenyl)oxy)-5-pyrimidinecarboxamide | 100 | 1.59 | 724, 362 |
| 608 | N-(2,6-dimethylphenyl)-2-((4-(4-(1-methylethyl)-1-piperazinyl)phenyl)amino)-4-((3-(2-phenyl-4-pyrimidinyl)phenyl)oxy)-5-pyrimidinecarboxamide | 97 | 1.54 | 691 |
| 609 | 2-((4-(((2-(diethylamino)ethyl)(methyl)amino)carbonyl)phenyl)amino)-N-(2,6-dimethylphenyl)-4-((2-(methyloxy)phenyl)oxy)-5-pyrimidinecarboxamide | 100 | 1.3 | 597, 299 |
| 610 | N-(2,6-dimethylphenyl)-2-((3-fluoro-4-(((1-methyl-3-piperidinyl)methyl)oxy)phenyl)amino)-4-((2-(methyloxy)phenyl)oxy)-5-pyrimidinecarboxamide | 100 | 1.37 | 586, 293 |
| 611 | N-(2,6-dimethylphenyl)-2-((4-(3,4-dimethyl-1-piperazinyl)-3-fluorophenyl)amino)-4-((2-(methyloxy)phenyl)oxy)-5-pyrimidinecarboxamide | 100 | 1.34 | 571 |
| 612 | N-(2,6-dimethylphenyl)-2-((3-fluoro-4-((2-(4-(1-methylethyl)-1-piperazinyl)ethyl)oxy)phenyl)amino)-4-((2-(methyloxy)phenyl)oxy)-5-pyrimidinecarboxamide | 100 | 1.24 | 629, 315 |
| 613 | 2-((3,4-bis(methyloxy)-5-((3-(4-methyl-1-piperazinyl)propyl)oxy)phenyl)amino)-N-(2,6-dimethylphenyl)-4-((2-(methyloxy)phenyl)oxy)-5-pyrimidinecarboxamide | 100 | 1.23 | 657, 329 |
| 614 | N-(2,6-dimethylphenyl)-2-((3-fluoro-4-((2-(4-(1-methylethyl)-1-piperazinyl)ethyl)oxy)phenyl)amino)-4-((2-(methyloxy)-4-(4-morpholinylcarbonyl)phenyl)oxy)-5-pyrimidinecarboxamide | 93.8 | 1.15 | 742, 371 |
| 615 | N-(2,6-dimethylphenyl)-2-((4-(3,4-dimethyl-1-piperazinyl)-3-fluorophenyl)amino)-4-((2-(methyloxy)-4-(4-morpholinylcarbonyl)phenyl)oxy)-5-pyrimidinecarboxamide | 100 | 1.23 | 684, 343 |
| 616 | N-(2,6-dimethylphenyl)-4-((2-(methyloxy)phenyl)oxy)-2-((3-((3-(1-piperidinyl)propyl)oxy)phenyl)amino)-5-pyrimidinecarboxamide | 100 | 1.43 | 582, 291 |
| 617 | 4-((2-chloro-4-((diethylamino)carbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 100 | 1.28 | 732, 366 |
| 618 | 4-((2-chloro-4-((diethylamino)carbonyl)phenyl)oxy)-N-(2,6-dimethylphenyl)-2-((3-((3-(1-piperidinyl)propyl)oxy)phenyl)amino)-5-pyrimidinecarboxamide | 100 | 1.42 | 685, 687 |
| 619 | 2-((3,4-bis(methyloxy)-5-((3-(4-methyl-1-piperazinyl)propyl)oxy)phenyl)amino)-4-((2-chloro-4-((diethylamino)carbonyl)phenyl)oxy)-N-(2,6-dimethylphenyl)-5-pyrimidinecarboxamide | 100 | 1.26 | 760, 762 |
| 620 | 4-((4-((2-(diethylamino)-2-oxoethyl)oxy)-2-(methyloxy)phenyl)oxy)-2-((4-(4-(3-(dimethylamino)propyl)-1-piperazinyl)phenyl)amino)-N-(2,6-dimethylphenyl)-5-pyrimidinecarboxamide | 99 | 1.2 | 739, 370 |
| 621 | 4-((4-((2-(diethylamino)-2-oxoethyl)oxy)-2-(methyloxy)phenyl)oxy)-2-((4-(4-(2-(diethylamino)ethyl)-1-piperazinyl)phenyl)amino)-N-(2,6-dimethylphenyl)-5-pyrimidinecarboxamide | 94.4 | 1.21 | 725, 363 |
| 622 | 4-((4-(3-(diethylamino)-3-oxopropyl)-2-(methyloxy)phenyl)oxy)-N-(2,6-dimethylphenyl)-2-((3-((3-(1-piperidinyl)propyl)oxy)phenyl)amino)-5-pyrimidinecarboxamide | 95.6 | 6.19 | 709, 355 |

| No. | Name | LC purity | LC Rt | Mass found |
|---|---|---|---|---|
| 623 | 4-((4-(3-(diethylamino)-3-oxopropyl)-2-(methyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 90.3 | 6.05 | 713, 357 |
| 624 | 2-((3,4-bis(methyloxy)-5-((3-(4-methyl-1-piperazinyl)propyl)oxy)phenyl)amino)-4-((4-(3-(diethylamino)-3-oxopropyl)-2-(methyloxy)phenyl)oxy)-N-(2,6-dimethylphenyl)-5-pyrimidinecarboxamide | 97.5 | 5.41 | 784, 392 |
| 625 | N-(2,6-dimethylphenyl)-2-((3-fluoro-4-((2-(4-(1-methylethyl)-1-piperazinyl)ethyl)oxy)phenyl)amino)-4-((4-(1H-imidazol-2-yl)phenyl)oxy)-5-pyrimidinecarboxamide | 100 | 1 | 665, 333 |
| 626 | N-(2,6-dimethylphenyl)-2-((4-(3,4-dimethyl-1-piperazinyl)-3-fluorophenyl)amino)-4-((4-(1H-imidazol-1-yl)phenyl)oxy)-5-pyrimidinecarboxamide | 100 | 1.07 | 607, 304 |
| 627 | N-(2,6-dimethylphenyl)-2-((3-((3-(1-piperidinyl)propyl)oxy)phenyl)amino)-4-((4-(1H-pyrrol-1-yl)phenyl)oxy)-5-pyrimidinecarboxamide | 100 | 1.51 | 617 |
| 628 | N-(2,6-dimethylphenyl)-2-((3-fluoro-4-((3-(1-piperidinyl)propyl)oxy)phenyl)amino)-4-((4-(1H-pyrrol-1-yl)phenyl)oxy)-5-pyrimidinecarboxamide | 100 | 1.48 | 635 |
| 629 | N-(2,6-dimethylphenyl)-2-((3-fluoro-4-((2-(4-(1-methylethyl)-1-piperazinyl)ethyl)oxy)phenyl)amino)-4-((4-(1H-pyrrol-1-yl)phenyl)oxy)-5-pyrimidinecarboxamide | 100 | 1.29 | 664, 332 |
| 630 | N-(2,6-dimethylphenyl)-2-((3-fluoro-4-(((1-methyl-3-piperidinyl)methyl)oxy)phenyl)amino)-4-((4-(1H-pyrrol-1-yl)phenyl)oxy)-5-pyrimidinecarboxamide | 91.7 | 1.41 | 621, 311 |
| 631 | N-(2,6-dichlorophenyl)-4-((2,2-dimethyl-2,3-dihydro-1-benzofuran-7-yl)oxy)-2-((3-fluoro-4-((3-(1-piperidinyl)propyl)oxy)phenyl)amino)-5-pyrimidinecarboxamide | 100 | 1.46 | 680, 682 |
| 632 | N-(2,6-dichlorophenyl)-4-((2,2-dimethyl-2,3-dihydro-1-benzofuran-7-yl)oxy)-2-((3-fluoro-4-((3-(4-methyl-1-piperazinyl)propyl)oxy)phenyl)amino)-5-pyrimidinecarboxamide | 100 | 1.28 | 695, 697 |
| 633 | 4-((4-(3-(diethylamino)-3-oxopropyl)-2-(methyloxy)phenyl)oxy)-N-(2,6-dimethylphenyl)-2-((4-(3,4-dimethyl-1-piperazinyl)-3-fluorophenyl)amino)-5-pyrimidinecarboxamide | 100 | 1.37 | 698 |
| 634 | 2-((4-(((2-(diethylamino)ethyl)(methyl)amino)carbonyl)phenyl)amino)-4-((4-(3-(diethylamino)-3-oxopropyl)-2-(methyloxy)phenyl)oxy)-N-(2,6-dimethylphenyl)-5-pyrimidinecarboxamide | 100 | 1.35 | 724, 362 |
| 635 | 4-((2-chloro-4-((diethylamino)carbonyl)phenyl)oxy)-N-(2,6-dichlorophenyl)-2-((3-fluoro-4-((3-(1-piperidinyl)propyl)oxy)phenyl)amino)-5-pyrimidinecarboxamide | 94.6 | 1.38 | 743, 745 |
| 636 | 2-((4-(diethylamino)butyl)amino)-N-(2,6-dimethylphenyl)-4-((2-(methyloxy)-4-(3-oxo-3-(1-pyrrolidinyl)propyl)phenyl)oxy)-5-pyrimidinecarboxamide | 97.8 | 1.19 | 617, 309 |
| 637 | N-(2,6-dimethylphenyl)-2-((4-(4-(1-methylethyl)-1-piperazinyl)phenyl)amino)-4-((2-(methyloxy)-4-(3-oxo-3-(1-pyrrolidinyl)propyl)phenyl)oxy)-5-pyrimidinecarboxamide | 100 | 1.3 | |
| 638 | 2-((3,4-bis(methyloxy)-5-((3-(4-methyl-1-piperazinyl)propyl)oxy)phenyl)amino)-N-(2,6-dimethylphenyl)-4-((3-(2-methyl-1,3-thiazol-4-yl)phenyl)oxy)-5-pyrimidinecarboxamide | 100 | 1.37 | 724, 302 |
| 639 | N-(2,6-dimethylphenyl)-2-((3-fluoro-4-((3-(4-methyl-1-piperazinyl)propyl)oxy)phenyl)amino)-4-((3-(2-methyl-1,3-thiazol-4-yl)phenyl)oxy)-5-pyrimidinecarboxamide | 100 | 1.35 | 682, 281 |
| 640 | N-(2,6-dimethylphenyl)-2-((3-fluoro-4-((3-(1-piperidinyl)propyl)oxy)phenyl)amino)-4-((3-(2-methyl-1,3-thiazol-4-yl)phenyl)oxy)-5-pyrimidinecarboxamide | 93.5 | 1.53 | 667, 274 |
| 641 | N-(2,6-dimethylphenyl)-4-((3-(2-methyl-1,3-thiazol-4-yl)phenyl)oxy)-2-((3-((3-(1-piperidinyl)propyl)oxy)phenyl)amino)-5-pyrimidinecarboxamide | 98 | 1.56 | 649, 265 |
| 642 | 2-((4-(((2-(diethylamino)ethyl)(methyl)amino)carbonyl)phenyl)amino)-N-(2,6-dimethylphenyl)-4-((3-(2-methyl-1,3-thiazol-4-yl)phenyl)oxy)-5-pyrimidinecarboxamide | 96.6 | 1.45 | 664, 333 |

| No. | Name | LC purity | LC Rt | Mass found |
|---|---|---|---|---|
| 643 | N-(2,6-dimethylphenyl)-2-((3-fluoro-4-((2-(4-(1-methylethyl)-1-piperazinyl)ethyl)oxy)phenyl)amino)-4-((3-2-methyl-1,3-thiazol-4-yl)phenyl)oxy)-5-pyrimidinecarboxamide | 93.6 | 1.38 | 696, 349 |
| 644 | N-(2,6-dimethylphenyl)-2-((3-fluoro-4-(((1-methyl-3-piperidinyl)methyl)oxy)phenyl)amino)-4-((3-(2-methyl-1,3-thiazol-4-yl)phenyl)oxy)-5-pyrimidinecarboxamide | 95.1 | 1.5 | 653, 267 |
| 645 | N-(2,6-dimethylphenyl)-2-((4-(3,4-dimethyl-1-piperazinyl)-3-fluorophenyl)amino)-4-((3-(2-methyl-1,3-thiazol-4-yl)phenyl)oxy)-5-pyrimidinecarboxamide | 98.5 | 1.47 | 638, 259 |
| 646 | N-(2,6-dimethylphenyl)-2-((3-fluoro-4-((2-(4-(1-methylethyl)-1-piperazinyl)ethyl)oxy)phenyl)amino)-4-((3-(2-phenyl-1,3-thiazol-4-yl)phenyl)oxy)-5-pyrimidinecarboxamide | 84.8 | 1.59 | 758, 380 |
| 647 | 2-((3,4-bis(methyloxy)-5-((3-(4-methyl-1-piperazinyl)propyl)oxy)phenyl)amino)-N-(2,6-dimethylphenyl)-4-((3-(2-phenyl-1,3-thiazol-4-yl)phenyl)oxy)-5-pyrimidinecarboxamide | 87.7 | 1.61 | 786, 394 |
| 648 | N-(2,6-dimethylphenyl)-2-((3-fluoro-4-(3-(1-piperidinyl)propyl)oxy)phenyl)amino)-4-((4-(1H-imidazol-1-yl)phenyl)oxy)-5-pyrimidinecarboxamide | 86.7 | 1.1 | 635, 318 |
| 649 | N-(2,6-dimethylphenyl)-4-((4-(1H-imidazol-1-yl)phenyl)oxy)-2-((3-((3-(1-piperidinyl)propyl)oxy)phenyl)amino)-5-pyrimidinecarboxamide | 92.7 | 1.09 | 618, 310 |
| 650 | N-(2,6-dimethylphenyl)-2-((3-fluoro-4-((2-(4-(1-methylethyl)-1-piperazinyl)ethyl)oxy)phenyl)amino)-4-((4-(1H-imidazol-1-yl)phenyl)oxy)-5-pyrimidinecarboxamide | 97.7 | 1.03 | 665, 333 |
| 651 | N-(2,6-dimethylphenyl)-2-((3-fluoro-4-((3-(4-methyl-1-piperazinyl)propyl)oxy)phenyl)amino)-4-((4-(1H-imidazol-1-yl)phenyl)oxy)-5-pyrimidinecarboxamide | 87.7 | 1.02 | 651, 326 |
| 652 | N-(2,6-dimethylphenyl)-4-((4-(3-(4-(1-methylethyl)-1-piperazinyl)-3-oxopropyl)-2-(methyloxy)phenyl)oxy)-2-((3-((3-(1-piperidinyl)propyl)oxy)phenyl)amino)-5-pyrimidinecarboxamide | 100 | 1.25 | 764, 383 |
| 653 | N-(2,6-dimethylphenyl)-2-((3-fluoro-4-((3-(1-piperidinyl)propyl)oxy)phenyl)amino)-4-((4-(3-(4-(1-methylethyl)-1-piperazinyl)-3-oxopropyl)-2-(methyloxy)phenyl)oxy)-5-pyrimidinecarboxamide | 95 | 1.22 | 782, 392 |
| 654 | N-(2,6-dimethylphenyl)-2-((3-fluoro-4-((3-(4-methyl-1-piperazinyl)propyl)oxy)phenyl)amino)-4-((4-(3-(4-(1-methylethyl)-1-piperazinyl)-3-oxopropyl)-2-(methyloxy)phenyl)oxy)-5-pyrimidinecarboxamide | 97.3 | 1.13 | 797, 399 |
| 655 | 2-((4-(diethylamino)butyl)amino)-4-((2,2-dimethyl-2,3-dihydro-1-benzofuran-7-yl)oxy)-N-(2,6-dimethylphenyl)-5-pyrimidinecarboxamide | 100 | 1.43 | 532, 267 |
| 656 | N-(2,6-dimethylphenyl)-4-((2-(methyloxy)-5-(3-oxo-3-((phenylmethyl)amino)propyl)phenyl)oxy)-2-((4-(4-methyl-1-piperazinyl)phenyl)amino)-5-pyrimidinecarboxamide | 88 | 1.33 | 700, 350 |
| 657 | N-(2,6-dimethylphenyl)-2-((3-fluoro-4-((3-(4-methyl-1-piperazinyl)propyl)oxy)phenyl)amino)-4-((2-(methyloxy)-5-(3-oxo-3-((phenylmethyl)amino)propyl)phenyl)oxy)-5-pyrimidinecarboxamide | 91 | 1.29 | 776, 388 |
| 658 | N-(2,6-dimethylphenyl)-2-((4-(4-(1-methylethyl)-1-piperazinyl)phenyl)amino)-4-((2-(methyloxy)-5-(3-oxo-3-((phenylmethyl)amino)propyl)phenyl)oxy)-5-pyrimidinecarboxamide | 87 | 1.35 | 728 |
| 659 | N-(2,6-dimethylphenyl)-4-((2-(methyloxy)-5-(3-oxo-3-((phenylmethyl)amino)propyl)phenyl)oxy)-2-(phenylamino)-5-pyrimidinecarboxamide | 100 | 1.52 | 602 |
| 660 | N-(2,6-dimethylphenyl)-2-((3-fluoro-4-((3-(4-methyl-1-piperazinyl)propyl)oxy)phenyl)amino)-4-((2-(methyloxy)-4-(3-oxo-3-(1-pyrrolidinyl)propyl)phenyl)oxy)-5-pyrimidinecarboxamide | 92 | 1.22 | 740 |
| 661 | N-(2,6-dimethylphenyl)-2-((3-fluoro-4-((3-(1-piperidinyl)propyl)oxy)phenyl)amino)-4-((2-(methyloxy)-4-(3-oxo-3-(1-pyrrolidinyl)propyl)phenyl)oxy)-5-pyrimidinecarboxamide | 100 | 1.36 | 725 |
| 662 | N-(2,6-dimethylphenyl)-4-((2-(methyloxy)-4-(3-oxo-3-(1-pyrrolidinyl)propyl)phenyl)oxy)-2-(phenylamino)-5-pyrimidinecarboxamide | 86 | 1.47 | 566 |

-continued

| No. | Name | LC purity | LC Rt | Mass found |
|---|---|---|---|---|
| 663 | N-(2,6-dimethylphenyl)-4-((2-(methyloxy)-4-(3-oxo-3-(1-pyrrolidinyl)propyl)phenyl)oxy)-2-(phenylamino)-5-pyrimidinecarboxamide | 86 | 1.35 | 728 |
| 664 | N-(2,6-dimethylphenyl)-2-((2-hydroxypropyl)amino)-4-((2-(methyloxy)-4-(3-oxo-3-(1-pyrrolidinyl)propyl)phenyl)oxy)-5-pyrimidinecarboxamide | 100 | 1.21 | 548 |
| 665 | 2-((3,4-bis(methyloxy)-5-((3-(4-methyl-1-piperazinyl)propyl)oxy)phenyl)amino)-N-(2,6-dimethylphenyl)-4-((2-(methyloxy)-4-(3-(4-morpholinyl)-3-oxopropyl)phenyl)oxy)-5-pyrimidinecarboxamide | 100 | 1.19 | 798, 399 |
| 666 | N-(2,6-dimethylphenyl)-2-((3-fluoro-4-((3-(4-methyl-1-piperazinyl)propyl)oxy)phenyl)amino)-4-((2-(methyloxy)-4-(4-morpholinyl)-3-oxopropyl)phenyl)oxy)-5-pyrimidinecarboxamide | 100 | 1.18 | 756 |
| 667 | N-(2,6-dimethylphenyl)-2-((3-fluoro-4-((3-(1-piperidinyl)propyl)oxy)phenyl)amino)-4-((2-(methyloxy)-4-(4-morpholinyl)-3-oxopropyl)phenyl)oxy)-5-pyrimidinecarboxamide | 91 | 1.32 | 741 |
| 668 | N-(2,6-dimethylphenyl)-4-((2-(methyloxy)-4-(3-(4-morpholinyl)-3-oxopropyl)phenyl)oxy)-2-((3-((3-(1-piperidinyl)propyl)oxy)phenyl)amino)-5-pyrimidinecarboxamide | 100 | 1.32 | 723 |
| 669 | 2-((4-(((2-(diethylamino)ethyl)(methyl)amino)carbonyl)phenyl)amino)-N-(2,6-dimethylphenyl)-4-((2-(methyloxy)-4-(3-(4-morpholinyl)-3-oxopropyl)phenyl)oxy)-5-pyrimidinecarboxamide | 100 | 1.26 | 738, 369 |
| 670 | N-(2,6-dimethylphenyl)-2-((3-fluoro-4-((2-(4-(1-methylethyl)-1-piperazinyl)ethyl)oxy)phenyl)amino)-4-((2-(methyloxy)-4-(3-(4-morpholinyl)-3-oxopropyl)phenyl)oxy)-5-pyrimidinecarboxamide | 100 | 1.2 | 770 |
| 671 | 4-(1,1'-biphenyl-3-yloxy)-2-((3,4-bis(methyloxy)-5-((3-(4-methyl-1-piperazinyl)propyl)oxy)phenyl)amino)-N-(2,6-dimethylphenyl)-5-pyrimidinecarboxamide | 94 | 1.36 | 703 |
| 672 | 4-(1,1'-biphenyl-3-yloxy)-N-(2,6-dimethylphenyl)-2-((3-fluoro-4-((3-(4-methyl-1-piperazinyl)propyl)oxy)phenyl)amino)-5-pyrimidinecarboxamide | 93 | 1.34 | 661 |
| 673 | 4-(1,1'-biphenyl-3-yloxy)-N-(2,6-dimethylphenyl)-2-((3-fluoro-4-((3-(1-piperidinyl)propyl)oxy)phenyl)amino)-5-pyrimidinecarboxamide | 93 | 1.51 | 646 |
| 674 | 4-(1,1'-biphenyl-3-yloxy)-N-(2,6-dimethylphenyl)-2-((3-((3-(1-piperidinyl)propyl)oxy)phenyl)amino)-5-pyrimidinecarboxamide | 95 | 1.55 | 628 |
| 675 | 4-(1,1'-biphenyl-3-yloxy)-2-((4-(((2-(diethylamino)ethyl)(methyl)amino)carbonyl)phenyl)amino)-N-(2,6-dimethylphenyl)-5-pyrimidinecarboxamide | 96 | 1.45 | 643 |
| 676 | 4-(1,1'-biphenyl-3-yloxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 95 | 1.37 | 675 |
| 677 | N-(2,6-dimethylphenyl)-2-((3-fluoro-4-((3-(4-methyl-1-piperazinyl)propyl)oxy)phenyl)amino)-4-((2-(methyloxy)-4-(4-morpholinylcarbonyl)phenyl)oxy)-5-pyrimidinecarboxamide | 95 | 1.24 | 728 |
| 678 | N-(2,6-dimethylphenyl)-2-((3-fluoro-4-((3-(1-piperidinyl)propyl)oxy)phenyl)amino)-4-((2-(methyloxy)-4-(4-morpholinylcarbonyl)phenyl)oxy)-5-pyrimidinecarboxamide | 94 | 1.26 | 713 |
| 679 | 2-((3,4-bis(methyloxy)-5-((3-(4-methyl-1-piperazinyl)propyl)oxy)phenyl)amino)-N-(2,6-dimethylphenyl)-4-((2-(methyloxy)-4-(4-morpholinylcarbonyl)phenyl)oxy)-5-pyrimidinecarboxamide | 100 | 1.14 | 770 |
| 680 | 4-((4-((2-(diethylamino)ethyl)oxy)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 89 | 1.14 | 730, 365 |
| 681 | 4-((4-((2-(diethylamino)ethyl)oxy)-2-(methyloxy)phenyl)oxy)-N-(2,6-dimethylphenyl)-2-((4-(4-(1-methylethyl)-1-piperazinyl)phenyl)amino)-5-pyrimidinecarboxamide | 100 | 1.16 | 796, 342 |

| No. | Name | LC purity | LC Rt | Mass found |
|---|---|---|---|---|
| 682 | 4-((4-((2-(diethylamino)ethyl)oxy)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide | 96 | 1.22 | 715, 358 |
| 683 | 4-((4-((2-(diethylamino)ethyl)oxy)-2-(methyloxy)phenyl)oxy)-2-((4-(4-(2-(dimethylamino)ethyl-1-piperazinyl)phenyl)amino)-N-(2,6-dimethylphenyl)-5-pyrimidinecarboxamide | 93 | 1.09 | 711, 356 |
| 684 | 4-((4-((2-(diethylamino)ethyl)oxy)-2-(methyloxy)phenyl)oxy)-2-((4-(4-(3-(dimethylamino)propyl)-1-piperazinyl)phenyl)amino)-N-(2,6-dimethylphenyl)-5-pyrimidinecarboxamide | 90 | 1.1 | 725, 363 |
| 685 | 4-((4-((2-(diethylamino)-2-oxoethyl)oxy)-2-(methyloxy)phenyl)oxy)-N-(2,6-dimethylphenyl)-2-((4-(4-methyl-1-piperazinyl)phenyl)amino)-5-pyrimidinecarboxamide | 100 | 1.28 | 744 |
| 686 | 4-((4-((2-(diethylamino)-2-oxoethyl)oxy)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.23 | 744 |
| 687 | 4-((4-((2-(diethylamino)-2-oxoethyl)oxy)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide | 97 | 1.4 | 729 |
| 688 | 4-((4-((2-(diethylamino)-2-oxoethyl)oxy)-2-(methyloxy)phenyl)oxy)-N-(2,6-dimethylphenyl)-2-((3-fluoro-4-(4-methyl-1-piperazinyl)phenyl)amino)-5-pyrimidinecarboxamide | 97 | 1.3 | 686 |
| 689 | 4-((4-((2-(diethylamino)-2-oxoethyl)oxy)-2-(methyloxy)phenyl)oxy)-N-(2,6-dimethylphenyl)-2-((4-(4-(1-methylethyl)-1-piperazinyl)phenyl)amino)-5-pyrimidinecarboxamide | 100 | 1.35 | 696 |
| 690 | 2-((3,4-bis(methyloxy)-5-((3-(4-methyl-1-piperazinyl)propyl)oxy)phenyl)amino)-4-((2-chloro-4-(1-pyrrolidinylcarbonyl)phenyl)oxy)-N-(2,6-dimethylphenyl)-5-pyrimidinecarboxamide | 100 | 1.22 | 758 |
| 691 | 4-((2-chloro-4-(1-pyrrolidinylcarbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.22 | 716, 718 |
| 692 | 4-((2-chloro-4-(1-pyrrolidinylcarbonyl)phenyl)oxy)-N-(2,6-dimethylphenyl)-2-((3-fluoro-4-((3-(1-piperidinyl)propyl)oxy)phenyl)amino)-5-pyrimidinecarboxamide | 100 | 1.38 | 701, 703 |
| 693 | 4-((2-chloro-4-(1-pyrrolidinylcarbonyl)phenyl)oxy)-N-(2,6-dimethylphenyl)-2-((3-((3-(1-piperidinyl)propyl)oxy)phenyl)amino)-5-pyrimidinecarboxamide | 100 | 1.37 | 683, 685 |
| 694 | 4-((2-chloro-4-(1-pyrrolidinylcarbonyl)phenyl)oxy)-2-((4-(((2-(diethylamino)ethyl)(methyl)amino)carbonyl)phenyl)amino)-N-(2,6-dimethylphenyl)-5-pyrimidinecarboxamide | 93 | 1.3 | 698, 700 |
| 695 | 4-((2-chloro-4-(1-pyrrolidinylcarbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 100 | 1.24 | 730, 732 |
| 696 | 4-((2-chloro-4-(1-pyrrolidinylcarbonyl)phenyl)oxy)-N-(2,6-dimethylphenyl)-2-((4-(3,4-dimethyl-1-piperazinyl)-3-fluorophenyl)amino)-5-pyrimidinecarboxamide | 100 | 1.31 | 672, 674 |
| 697 | 4-((2-chloro-4-((diethylamino)carbonyl)phenyl)oxy)-N-(2,6-dichlorophenyl)-2-((3-fluoro-4-((3-(4-methyl-1-piperazinyl)propyl)oxy)phenyl)amino)-5-pyrimidinecarboxamide | 95 | 1.26 | 758, 760 |
| 698 | N-(2,6-dichlorophenyl)-4-((2-(ethyloxy)phenyl)oxy)-2-((3-fluoro-4-((3-(4-methyl-1-piperazinyl)propyl)oxy)phenyl)amino)-5-pyrimidinecarboxamide | 87 | 1.3 | 669, 671 |
| 699 | N-(2,6-dichlorophenyl)-4-((2-(ethyloxy)phenyl)oxy)-2-((3-fluoro-4-((3-(1-piperidinyl)propyl)oxy)phenyl)amino)-5-pyrimidinecarboxamide | 92 | 1.47 | 654, 656 |
| 700 | N-(2,6-dichlorophenyl)-2-((3-fluoro-4-((3-(4-methyl-1-piperazinyl)propyl)oxy)phenyl)amino)-4-((2-(methyloxy)-4-propylphenyl)oxy)-5-pyrimidinecarboxamide | 100 | 1.35 | 697, 699 |

-continued

| No. | Name | LC purity | LC Rt | Mass found |
|---|---|---|---|---|
| 701 | N-(2,6-dichlorophenyl)-2-((3-fluoro-4-((3-(1-piperidinyl)propyl)oxy)phenyl)amino)-4-((2-(methyloxy)-4-propylphenyl)oxy)-5-pyrimidinecarboxamide | 94 | 1.56 | 682, 684 |
| 702 | N-(2,6-dichlorophenyl)-4-((4-((diethylamino)carbonyl)-2-(methyloxy)phenyl)oxy)-2-((3-fluoro-4-((3-(4-methyl-1-piperazinyl)propyl)oxy)phenyl)amino)-5-pyrimidinecarboxamide | 100 | 1.23 | 754, 756 |
| 703 | N-(2,6-dichlorophenyl)-4-((4-((diethylamino)carbonyl)-2-(methyloxy)phenyl)oxy)-2-((3-fluoro-4-((3-(1-piperidinyl)propyl)oxy)phenyl)amino)-5-pyrimidinecarboxamide | 100 | 1.39 | 739, 741 |
| 704 | N-(2,6-dimethylphenyl)-2-((4-(4-methyl-1-piperazinyl)phenyl)amino)-4-((3-(1H-pyrazol-3-yl)phenyl)oxy)-5-pyrimidinecarboxamide | 93 | 1.24 | 575, 227 |
| 705 | N-(2,6-dimethylphenyl)-2-((3-fluoro-4-((3-(4-methyl-1-piperazinyl)propyl)oxy)phenyl)amino)-4-((3-(1H-pyrazol-3-yl)phenyl)oxy)-5-pyrimidinecarboxamide | 100 | 1.19 | 651, 265 |
| 706 | N-(2,6-dimethylphenyl)-2-((3-fluoro-4-(4-methyl-1-piperazinyl)phenyl)amino)-4-((3-(1 H-pyrazol-3-yl)phenyl)oxy)-5-pyrimidinecarboxamide | 86 | 1.25 | 593, 236 |
| 707 | N-(2,6-dimethylphenyl)-2-((3-fluoro-4-((3-(1-piperidinyl)propyl)oxy)phenyl)amino)-4-((3-(1H-pyrazol-3-yl)phenyl)oxy)-5-pyrimidinecarboxamide | 98 | 1.33 | 636, 258 |
| 708 | N-(2,6-dimethylphenyl)-2-((4-(4-(1-methylethyl)-1-piperazinyl)phenyl)amino)-4-((3-(1H-pyrazol-3-yl)phenyl)oxy)-5-pyrimidinecarboxamide | 100 | 1.27 | 603, 302 |
| 709 | 2-((4-(4-(2-(dimethylamino)ethyl)-1-piperazinyl)phenyl)amino)-N-(2,6-dimethylphenyl)-4-((3-(1H-pyrazol-3-yl)phenyl)oxy)-5-pyrimidinecarboxamide | 88 | 1.17 | 632, 316 |
| 710 | 2-((4-(4-(3-(dimethylamino)propyl)-1-piperazinyl)phenyl)amino)-N-(2,6-dimethylphenyl)-4-((3-(1H-pyrazol-3-yl)phenyl)oxy)-5-pyrimidinecarboxamide | 96 | 1.18 | 646, 323 |
| 711 | 2-((4-(diethylamino)butyl)amino)-N-(2,6-dimethylphenyl)-4-((3-(1H-pyrazol-3-yl)phenyl)oxy)-5-pyrimidinecarboxamide | 93 | 1.17 | 528, 404 |
| 712 | N-(2,6-dimethylphenyl)-2-((4-(3,4-dimethyl-1-piperazinyl)-3-fluorophenyl)amino)-4-((3-(1H-pyrazol-3-yl)phenyl)oxy)-5-pyrimidinecarboxamide | 93 | 1.24 | 607, 304 |
| 713 | N-(2,6-dimethylphenyl)-4-((2-(ethyloxy)phenyl)oxy)-6-((4-(4-methyl-1-piperazinyl)phenyl)amino)-3-pyridinecarboxamide | 91 | 1.23 | 552, 276 |
| 714 | 4-((2-chloro-4-((diethylamino)carbonyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 100 | 1.39 | 689, 691 |
| 715 | 4-((2-chloro-4-((diethylamino)carbonyl)phenyl)oxy)-N-(2,6-dimethylphenyl)-2-((4-(3,4-dimethyl-1-piperazinyl)-3-fluorophenyl)amino)-5-pyrimidinecarboxamide | 91.4 | 1.47 | 674, 676 |
| 716 | 2-((3,5-bis(methyloxy)-4-((3-(4-methyl-1-piperazinyl)propyl)oxy)phenyl)amino)-4-((2-chloro-4-((diethylamino)carbonyl)phenyl)oxy)-N-(2,6-dimethylphenyl)-5-pyrimidinecarboxamide | 100 | 1.27 | 760, 762 |
| 717 | 4-((2-chloro-4-((diethylamino)carbonyl)phenyl)oxy)-N-(2,6-dimethylphenyl)-2-((3-(methyloxy)-4-((2-(4-methyl-1-piperazinyl)ethyl)oxy)phenyl)amino)-5-pyrimidinecarboxamide | 100 | 1.25 | 716, 718 |
| 718 | 4-((2-chloro-4-((diethylamino)carbonyl)phenyl)oxy)-N-(2,6-dimethylphenyl)-2-((3-(methyloxy)-4-methyl-1-piperazinyl)phenyl)amino)-5-pyrimidinecarboxamide | 100 | 1.33 | 672, 674 |
| 719 | 4-((2-chloro-4-((diethylamino)carbonyl)phenyl)oxy)-2-((3-((difluoromethyl)oxy)-4-(4-methyl-1-piperazinyl)phenyl)amino)-N-(2,6-dimethylphenyl)-5-pyrimidinecarboxamide | 100 | 1.41 | 708, 710 |
| 720 | 4-((2-chloro-4-((diethylamino)carbonyl)phenyl)oxy)-2-((3-chloro-4-(4-(1-methylethyl)-1-piperazinyl)phenyl)amino)-N-(2,6-dimethylphenyl)-5-pyrimidinecarboxamide | 100 | 1.44 | 704, 706 |
| 721 | N-(2,6-dimethylphenyl)-2-((4-(3,4-dimethyl-1-piperazinyl)-3-fluorophenyl)amino)-4-((2-(methyloxy)-4-(1-pyrrolidinylcarbonyl)phenyl)oxy)-5-pyrimidinecarboxamide | 100 | 1.28 | 668, 335 |

-continued

| No. | Name | LC purity | LC Rt | Mass found |
|---|---|---|---|---|
| 722 | N-(2,6-dimethylphenyl)-2-((3-fluoro-4-((3-(1-piperidinyl)propyl)oxy)phenyl)amino)-4-((2-(methyloxy)-4-(1-pyrrolidinylcarbonyl)phenyl)oxy)-5-pyrimidinecarboxamide | 100 | 1.32 | 697, 673 |
| 723 | N-(2,6-dimethylphenyl)-2-((3-fluoro-4-((3-(4-methyl-1-piperazinyl)propyl)oxy)phenyl)amino)-4-((2-(methyloxy)-4-(1-pyrrolidinylcarbonyl)phenyl)oxy)-5-pyrimidinecarboxamide | 100 | 1.18 | 712, 356 |
| 724 | 4-((3-(acetylamino)phenyl)oxy)-2-((4-(diethylamino)butyl)amino)-N-(2,6-dimethylphenyl)-5-pyrimidinecarboxamide | 100 | 1.09 | 519 |
| 725 | 4-((3-(acetylamino)phenyl)oxy)-N-(2,6-dimethylphenyl)-2-((4-(4-methyl-1-piperazinyl)phenyl)amino)-5-pyrimidinecarboxamide | 100 | 1.14 | 566, 283 |
| 726 | 4-((2-chloro-4-(1-pyrrolidinylcarbonyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 100 | 1.35 | 687, 689 |
| 727 | 2-((3,4-bis(methyloxy)-5-((3-(4-methyl-1-piperazinyl)propyl)oxy)phenyl)amino)-N-(2,6-dimethylphenyl)-4-((2-((1-methylethyl)oxy)phenyl)oxy)-5-pyrimidinecarboxamide | 100 | 1.31 | 685, 343 |
| 728 | N-(2,6-dimethylphenyl)-4-((2-((1-methylethyl)oxy)phenyl)oxy)-2-((3-((3-(1-piperidinyl)propyl)oxy)phenyl)amino)-5-pyrimidinecarboxamide | 100 | 1.52 | 610, 305 |
| 729 | 2-((4-(((2-(diethylamino)ethyl)(methyl)amino)carbonyl)phenyl)amino)-N-(2,6-dimethylphenyl)-4-((2-((1-methylethyl)oxy)phenyl)oxy)-5-pyrimidinecarboxamide | 100 | 1.39 | 625, 313 |
| 730 | N-(2,6-dimethylphenyl)-2-((3-fluoro-4-((2-(4-(1-methylethyl)-1-piperazinyl)ethyl)oxy)phenyl)amino)-4-((2-((1-methylethyl)oxy)phenyl)oxy)-5-pyrimidinecarboxamide | 100 | 1.33 | 657, 329 |
| 731 | N-(2,6-dimethylphenyl)-2-((3-fluoro-4-(((1-methyl-3-piperidinyl)methyl)oxy)phenyl)amino)-4-((2-((1-methylethyl)oxy)phenyl)oxy)-5-pyrimidinecarboxamide | 97.5 | 1.47 | 614, 307 |
| 732 | N-(2,6-dimethylphenyl)-2-((4-(3,4-dimethyl-1-piperazinyl)-3-fluorophenyl)amino)-4-((2-((1-methylethyl)oxy)phenyl)oxy)-5-pyrimidinecarboxamide | 100 | 1.42 | 599, 300 |
| 733 | 2-((3,4-bis(methyloxy)-5-((3-(4-methyl-1-piperazinyl)propyl)oxy)phenyl)amino)-N-(2,6-dimethylphenyl)-4-((2-(methyloxy)-4-(3-(((1R)-1-methylpropyl)amino)-3-oxopropyl)phenyl)oxy)-5-pyrimidinecarboxamide | 100 | 1.24 | 784, 332 |
| 734 | 2-((4-(((2-(diethylamino)ethyl)(methyl)amino)carbonyl)phenyl)amino)-N-(2,6-dimethylphenyl)-4-((2-(methyloxy)-4-(3-(((1R)-1-methylpropyl)amino)-3-oxopropyl)phenyl)oxy)-5-pyrimidinecarboxamide | 96.1 | 1.32 | 724, 363 |
| 735 | N-(2,6-dimethylphenyl)-2-((3-fluoro-4-((2-(4-(1-methylethyl)-1-piperazinyl)ethyl)oxy)phenyl)amino)-4-((2-(methyloxy)-4-(3-(((1R)-1-methylpropyl)amino)-3-oxopropyl)phenyl)oxy)-5-pyrimidinecarboxamide | 94.3 | 1.27 | 756, 379 |
| 736 | N-(2,6-dimethylphenyl)-2-((3-fluoro-4-(((1-methyl-3-piperidinyl)methyl)oxy)phenyl)amino)-4-((2-(methyloxy)-4-(3-(((1R)-1-methylpropyl)amino)-3-oxopropyl)phenyl)oxy)-5-pyrimidinecarboxamide | 93.9 | 1.35 | 713, 357 |
| 737 | N-(2,6-dimethylphenyl)-2-((4-(3,4-dimethyl-1-piperazinyl)-3-fluorophenyl)amino)-4-((2-(methyloxy)-4-(3-(((1R)-1-methylpropyl)amino)-3-oxopropyl)phenyl)oxy)-5-pyrimidinecarboxamide | 100 | 1.34 | 698, 350 |
| 738 | 4-((4-(4-(diethylamino)-4-oxobutyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.28 | 756, 378 |
| 739 | 4-((4-(4-(diethylamino)-4-oxobutyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide | 96.6 | 1.46 | 741, 371 |
| 740 | 4-((2-chloro-4-((diethylamino)carbonyl)phenyl)oxy)-2-((3-fluoro-4-((3-(4-methyl-1-piperazinyl)propyl)oxy)phenyl)amino)-N-(2-pyridinylmethyl)-5-pyrimidinecarboxamide | 90 | 0.91 | 705, 353 |

| No. | Name | LC purity | LC Rt | Mass found |
|---|---|---|---|---|
| 741 | 4-((2-chloro-4-((diethylamino)carbonyl)phenyl)oxy)-2-((3-fluoro-4-((3-(1-piperidinyl)propyl)oxy)phenyl)amino)-N-(2-pyridinylmethyl)-5-pyrimidinecarboxamide | 93.5 | 1.02 | 690, 345 |
| 742 | 2-((3-chloro-4-(4-(1-methylethyl)-1-piperazinyl)phenyl)amino)-4-((2,2-dimethyl-2,3-dihydro-1-benzofuran-7-yl)oxy)-N-(2,6-dimethylphenyl)-5-pyrimidinecarboxamide | 100 | 1.45 | 641 |
| 743 | 2-((4-(((2-(diethylamino)ethyl)(methyl)amino)carbonyl)phenyl)amino)-4-((2,2-dimethyl-2,3-dihydro-1-benzofuran-7-yl)oxy)-N-(2,6-dimethylphenyl)-5-pyrimidinecarboxamide | 98 | 1.47 | 637, 319 |
| 744 | 4-((2,2-dimethyl-2,3-dihydro-1-benzofuran-7-yl)oxy)-N-(2,6-dimethylphenyl)-2-((4-(3,4-dimethyl-1-piperazinyl)-3-fluorophenyl)amino)-5-pyrimidinecarboxamide | 95 | 1.48 | 611, 306 |
| 745 | 2-((3,4-bis(methyloxy)-5-((3-(4-methyl-1-piperazinyl)propyl)oxy)phenyl)amino)-4-((2,2-dimethyl-2,3-dihydro-1-benzofuran-7-yl)oxy)-N-(2,6-dimethylphenyl)-5-pyrimidinecarboxamide | 93 | 1.28 | 697, 349 |
| 746 | 4-((2,2-dimethyl-2,3-dihydro-1-benzofuran-7-yl)oxy)-N-(2,6-dimethylphenyl)-2-((3-fluoro-4-(((1-methyl-3-piperidinyl)methyl)oxy)phenyl)amino)-5-pyrimidinecarboxamide | 97 | 1.42 | 626 |
| 747 | 4-((2-chloro-4-((diethylamino)carbonyl)phenyl)oxy)-2-((3-fluoro-4-((3-(4-methyl-1-piperazinyl)propyl)oxy)phenyl)amino)-N-((1S)-1-phenylethyl)-5-pyrimidinecarboxamide | 98 | 1.25 | 18, 720 |
| 748 | 4-((2-chloro-4-((diethylamino)carbonyl)phenyl)oxy)-2-((3-fluoro-4-((3-(1-piperidinyl)propyl)oxy)phenyl)amino)-N-((1S)-1-phenylethyl)-5-pyrimidinecarboxamide | 92 | 1.4 | 703, 705 |
| 749 | -((2-chloro-4-((diethylamino)carbonyl)phenyl)oxy)-2-((3-fluoro-4-((3-(4-methyl-1-piperazinyl)propyl)oxy)phenyl)amino)-N-(4-fluorophenyl)-5-pyrimidinecarboxamide | 100 | 1.28 | 708, 710 |
| 750 | 4-((2-chloro-4-((diethylamino)carbonyl)phenyl)oxy)-N-(4-fluorophenyl)-2-((3-fluoro-4-((3-(1-piperidinyl)propyl)oxy)phenyl)amino)-5-pyrimidinecarboxamide | 100 | 1.46 | 693, 695 |
| 751 | 4-((2-chloro-4-((diethylamino)carbonyl)phenyl)oxy)-2-((3-fluoro-4-((3-(4-methyl-1-piperazinyl)propyl)oxy)phenyl)amino)-N-(2-fluorophenyl)-5-pyrimidinecarboxamide | 100 | 1.3 | 708, 710 |
| 752 | 4-((2-chloro-4-((diethylamino)carbonyl)phenyl)oxy)-N-(2-fluorophenyl)-2-((3-fluoro-4-((3-(1-piperidinyl)propyl)oxy)phenyl)amino)-5-pyrimidinecarboxamide | 100 | 1.46 | 693, 695 |
| 753 | 4-((2-chloro-4-((diethylamino)carbonyl)phenyl)oxy)-2-((3-fluoro-4-((3-(4-methyl-1-piperazinyl)propyl)oxy)phenyl)amino)-N-(2,4,6-trimethylphenyl)-5-pyrimidinecarboxamide | 100 | 1.3 | 732, 735 |
| 754 | 4-((2-chloro-4-((diethylamino)carbonyl)phenyl)oxy)-2-((3-fluoro-4-((3-(1-piperidinyl)propyl)oxy)phenyl)amino)-N-(2,4,6-trimethylphenyl)-5-pyrimidinecarboxamide | 98 | 1.46 | 717, 719 |
| 755 | 4-((2-chloro-4-((diethylamino)carbonyl)phenyl)oxy)-2-((3-fluoro-4-((3-(4-methyl-1-piperazinyl)propyl)oxy)phenyl)amino)-N-(2,4,6-trifluorophenyl)-5-pyrimidinecarboxamide | 100 | 1.23 | 744, 746 |
| 756 | 4-((2-chloro-4-((diethylamino)carbonyl)phenyl)oxy)-2-((3-fluoro-4-((3-(1-piperidinyl)propyl)oxy)phenyl)amino)-N-(2,4,6-trifluorophenyl)-5-pyrimidinecarboxamide | 100 | 1.36 | 729, 731 |
| 757 | 4-((4-(2-(diethylamino)-2-oxoethyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 92 | 4.67 | 728, 364 |
| 758 | 4-((4-(2-(diethylamino)-2-oxoethyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide | 99 | 5.57 | 713, 357 |

| No. | Name | LC purity | LC Rt | Mass found |
|---|---|---|---|---|
| 759 | 2-((4-(((2-(diethylamino)ethyl)(methyl)amino)carbonyl)phenyl)amino)-4-((4-(2-(diethylamino)-2-oxoethyl)-2-(methyloxy)phenyl)oxy)-N-(2,6-dimethylphenyl)-5-pyrimidinecarboxamide | 93.5 | 5.28 | 710, 355 |
| 760 | 4-((4-(2-(diethylamino)-2-oxoethyl)-2-(methyloxy)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 95.5 | 4.8 | 742, 371 |
| 761 | 4-((4-(2-(diethylamino)-2-oxoethyl)-2-(methyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 92.6 | 5.39 | 699, 350 |
| 762 | 4-((4-(2-(diethylamino)-2-oxoethyl)-2-(methyloxy)phenyl)oxy)-N-(2,6-dimethylphenyl)-2-((4-(3,4-dimethyl-1-piperazinyl)-3-fluorophenyl)amino)-5-pyrimidinecarboxamide | 97.1 | 5.35 | 684, 342 |
| 763 | 2-((3,4-bis(methyloxy)-5-((3-(4-methyl-1-piperazinyl)propyl)oxy)phenyl)amino)-4-((4-(2-(diethylamino)-2-oxoethyl)-2-(methyloxy)phenyl)oxy)-N-(2,6-dimethylphenyl)-5-pyrimidinecarboxamide | 91.8 | 4.76 | 770, 385 |
| 764 | N-(2,6-dimethylphenyl)-4-((2-(methyloxy)-4-(3-oxo-3-(1-pyrrolidinyl)propyl)phenyl)oxy)-2-((4-(4-methyl-1-piperazinyl)phenyl)amino)-5-pyrimidinecarboxamide | 95 | 1.26 | 664, 332 |
| 765 | 2-((3,4-bis(methyloxy)-5-((3-(4-methyl-1-piperazinyl)propyl)oxy)phenyl)amino)-N-(2,6-dimethylphenyl)-4-((4-(2-(3-methyl-1,2,4-oxadiazol-5-yl)ethyl)-2-(methyloxy)phenyl)oxy)-5-pyrimidinecarboxamide | 100 | 1.24 | 767, 384 |
| 766 | N-(2,6-dimethylphenyl)-2-((3-fluoro-4-((3-(4-methyl-1-piperazinyl)propyl)oxy)phenyl)amino)-4-((4-(2-(3-methyl-1,2,4-oxadiazol-5-yl)ethyl)-2-(methyloxy)phenyl)oxy)-5-pyrimidinecarboxamide | 100 | 1.24 | 725, 363 |
| 767 | N-(2,6-dimethylphenyl)-2-((3-fluoro-4-((3-(1-piperidinyl)propyl)oxy)phenyl)amino)-4-((4-(2-(3-methyl-1,2,4-oxadiazol-5-yl)ethyl)-2-(methyloxy)phenyl)oxy)-5-pyrimidinecarboxamide | 100 | 1.39 | 710, 355 |
| 768 | 2-((4-(((2-(diethylamino)ethyl)(methyl)amino)carbonyl)phenyl)amino)-N-(2,6-dimethylphenyl)-4-((4-(2-(3-methyl-1,2,4-oxadiazol-5-yl)ethyl)-2-(methyloxy)phenyl)oxy)-5-pyrimidinecarboxamide | 100 | 1.32 | 707, 354 |
| 769 | N-(2,6-dimethylphenyl)-2-((3-fluoro-4-((2-(4-(1-methylethyl)-1-piperazinyl)ethyl)oxy)phenyl)amino)-4-((4-(2-(3-methyl-1,2,4-oxadiazol-5-yl)ethyl)-2-(methyloxy)phenyl)oxy)-5-pyrimidinecarboxamide | 100 | 1.25 | 739, 370 |
| 770 | N-(2,6-dimethylphenyl)-2-((3-fluoro-4-(((1-methyl-3-piperidinyl)methyl)oxy)phenyl)amino)-4-((4-(2-(3-methyl-1,2,4-oxadiazol-5-yl)ethyl)-2-(methyloxy)phenyl)oxy)-5-pyrimidinecarboxamide | 100 | 1.37 | 696, 348 |
| 771 | N-(2,6-dimethylphenyl)-2-((4-(3,4-dimethyl-1-piperazinyl)-3-fluorophenyl)amino)-4-((4-(2-(3-methyl-1,2,4-oxadiazol-5-yl)ethyl)-2-(methyloxy)phenyl)oxy)-5-pyrimidinecarboxamide | 100 | 1.34 | 681, 341 |
| 772 | 4-((2-chloro-4-(2-(diethylamino)ethyl)phenyl)oxy)-N-(2,6-dimethylphenyl)-2-((3-fluoro-4-(4-methyl-1-piperazinyl)phenyl)amino)-5-pyrimidinecarboxamide | 86 | 1.15 | 774, 330 |
| 773 | 4-((2-chloro-4-(2-(diethylamino)ethyl)phenyl)oxy)-N-(2,6-dimethylphenyl)-2-((4-(4-(1-methylethyl)-1-piperazinyl)phenyl)amino)-5-pyrimidinecarboxamide | 100 | 1.15 | 784, 335 |
| 774 | 4-((2-chloro-4-(2-(diethylamino)ethyl)phenyl)oxy)-2-((4-(4-(3-(dimethylamino)propyl)-1-piperazinyl)phenyl)amino)-N-(2,6-dimethylphenyl)-5-pyrimidinecarboxamide | 92 | 1.11 | 713, 715 |
| 775 | 2-((4-(((2-(dimethylamino)ethyl)amino)carbonyl)phenyl)amino)-N-(2,6-dimethylphenyl)-4-((2-(methyloxy)-4-propylphenyl)oxy)-5-pyrimidinecarboxamide | 91 | 1.43 | 597, 299 |
| 776 | 2-((3-(((2-(dimethylamino)ethyl)amino)carbonyl)phenyl)amino)-N-(2,6-dimethylphenyl)-4-((2-(methyloxy)-4-propylphenyl)oxy)-5-pyrimidinecarboxamide | 93 | 1.51 | 597, 299 |

| No. | Name | LC purity | LC Rt | Mass found |
|---|---|---|---|---|
| 777 | 2-((4-(((2-(dimethylamino)ethyl)amino)carbonyl)phenyl)amino)-N-(2,6-dimethylphenyl)-4-((2-(ethyloxy)phenyl)oxy)-5-pyrimidinecarboxamide | 98 | 1.31 | 569, 285 |
| 778 | 2-((3-(((2-(dimethylamino)ethyl)amino)carbonyl)phenyl)amino)-N-(2,6-dimethylphenyl)-4-((2-(ethyloxy)phenyl)oxy)-5-pyrimidinecarboxamide | 100 | 1.36 | 569, 285 |
| 779 | 4-((2-chloro-4-(2-oxo-2-(1-pyrrolidinyl)ethyl)phenyl)oxy)-2-((4-(((2-(diethylamino)ethyl)(methyl)amino)carbonyl)phenyl)amino)-N-(2,6-dimethylphenyl)-5-pyrimidinecarboxamide | 86 | 1.32 | 712, 356 |
| 780 | 4-((2-chloro-4-(2-oxo-2-(1-pyrrolidinyl)ethyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 96 | 1.24 | 730, 732 |
| 781 | 4-((2-chloro-4-(2-oxo-2-(1-pyrrolidinyl)ethyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 100 | 1.26 | 744, 746 |
| 782 | 2-((4-(((2-(diethylamino)ethyl)(methyl)amino)carbonyl)phenyl)amino)-N-(2,6-dimethylphenyl)-4-((2-(methyloxy)-4-(1-pyrrolidinylcarbonyl)phenyl)oxy)-5-pyrimidinecarboxamide | 95 | 4.88 | 694, 347 |
| 783 | 2-((3,4-bis(methyloxy)-5-((3-(4-methyl-1-piperazinyl)propyl)oxy)phenyl)amino)-N-(2,6-dimethylphenyl)-4-((2-(methyloxy)-4-(1-pyrrolidinylcarbonyl)phenyl)oxy)-5-pyrimidinecarboxamide | 92 | 4.38 | 726, 363 |
| 784 | N-(2,6-dimethylphenyl)-2-((3-fluoro-4-((2-(4-(1-methylethyl)-1-piperazinyl)ethyl)oxy)phenyl)amino)-4-((2-(methyloxy)-4-(1-pyrrolidinylcarbonyl)phenyl)oxy)-5-pyrimidinecarboxamide | 98 | 4.48 | 726, 363 |
| 785 | 2-((3,4-bis(methyloxy)-5-((3-(4-methyl-1-piperazinyl)propyl)oxy)phenyl)amino)-N-(2,6-dimethylphenyl)-4-((2-(methyloxy)-4-((2-oxo-2-(1-pyrrolidinyl)ethyl)oxy)phenyl)oxy)-5-pyrimidinecarboxamide | 86 | 1.21 | 784, 392 |
| 786 | N-(2,6-dimethylphenyl)-2-((3-fluoro-4-((3-(4-methyl-1-piperazinyl)propyl)oxy)phenyl)amino)-4-((2-(methyloxy)-4-((2-oxo-2-(1-pyrrolidinyl)ethyl)oxy)phenyl)oxy)-5-pyrimidinecarboxamide | 100 | 1.21 | 742, 372 |
| 787 | N-(2,6-dimethylphenyl)-2-((3-fluoro-4-((3-(1-piperidinyl)propyl)oxy)phenyl)amino)-4-((2-(methyloxy)-4-((2-oxo-2-(1-pyrrolidinyl)ethyl)oxy)phenyl)oxy)-5-pyrimidinecarboxamide | 90 | 1.36 | 727, 364 |
| 788 | N-(2,6-dimethylphenyl)-2-((3-fluoro-4-((2-(4-(1-methylethyl)-1-piperazinyl)ethyl)oxy)phenyl)amino)-4-((2-(methyloxy)-4-((2-oxo-2-(1-pyrrolidinyl)ethyl)oxy)phenyl)oxy)-5-pyrimidinecarboxamide | 91 | 1.24 | 756, 379 |
| 789 | N-(2,6-dimethylphenyl)-2-((3-fluoro-4-(((1-methyl-3-piperidinyl)methyl)oxy)phenyl)amino)-4-((2-(methyloxy)-4-((2-oxo-2-(1-pyrrolidinyl)ethyl)oxy)phenyl)oxy)-5-pyrimidinecarboxamide | 92 | 1.32 | 713, 357 |
| 790 | N-(2,6-dimethylphenyl)-2-((4-(3,4-dimethyl-1-piperazinyl)-3-fluorophenyl)amino)-4-((2-(methyloxy)-4-((2-oxo-2-(1-pyrrolidinyl)ethyl)oxy)phenyl)oxy)-5-pyrimidinecarboxamide | 94 | 1.3 | 698, 350 |
| 791 | 4-((2-chloro-4-((diethylamino)carbonyl)phenyl)oxy)-2-((4-(((2-(diethylamino)ethyl)(methyl)amino)carbonyl)phenyl)amino)-N-(2,6-dimethylphenyl)-5-pyrimidinecarboxamide | 91 | 1.38 | 700, 703 |
| 792 | 2-((3,4-bis(methyloxy)-5-((3-(4-methyl-1-piperazinyl)propyl)oxy)phenyl)amino)-N-(2,6-dimethylphenyl)-4-((4-(((1-methylethyl)amino)carbonyl)-2-(methyloxy)phenyl)oxy)-5-pyrimidinecarboxamide | 100 | 1.23 | 742, 372 |

| No. | Name | LC purity | LC Rt | Mass found |
|---|---|---|---|---|
| 793 | N-(2,6-dimethylphenyl)-2-((3-fluoro-4-((3-(4-methyl-1-piperazinyl)propyl)oxy)phenyl)amino)-4-((4-(((1-methylethyl)amino)carbonyl)-2-(methyloxy)phenyl)oxy)-5-pyrimidinecarboxamide | 98 | 1.22 | 700, 351 |
| 794 | N-(2,6-dimethylphenyl)-2-((3-fluoro-4-((3-(1-piperidinyl)propyl)oxy)phenyl)amino)-4-((4-(((1-methylethyl)amino)carbonyl)-2-(methyloxy)phenyl)oxy)-5-pyrimidinecarboxamide | 97 | 1.37 | 685, 343 |
| 795 | N-(2,6-dimethylphenyl)-4-((4-(((1-methylethyl)amino)carbonyl)-2-(methyloxy)phenyl)oxy)-2-((3-((3-(1-piperidinyl)propyl)oxy)phenyl)amino)-5-pyrimidinecarboxamide | 92 | 1.39 | 667, 334 |
| 796 | 2-((4-(((2-(diethylamino)ethyl)(methyl)amino)carbonyl)phenyl)amino)-N-(2,6-dimethylphenyl)-4-((4-(((1-methylethyl)amino)carbonyl)-2-(methyloxy)phenyl)oxy)-5-pyrimidinecarboxamide | 91 | 1.29 | 682, 342 |
| 797 | N-(2,6-dimethylphenyl)-2-((3-fluoro-4-((2-(4-(1-methylethyl)-1-piperazinyl)ethyl)oxy)phenyl)amino)-4-((4-(((1-methylethyl)amino)carbonyl)-2-(methyloxy)phenyl)oxy)-5-pyrimidinecarboxamide | 100 | 1.23 | 714, 358 |
| 798 | N-(2,6-dimethylphenyl)-2-((3-fluoro-4-(((1-methyl-3-piperidinyl)methyl)oxy)phenyl)amino)-4-((4-(((1-methylethyl)amino)carbonyl)-2-(methyloxy)phenyl)oxy)-5-pyrimidinecarboxamide | 95 | 1.33 | 671, 336 |
| 799 | N-(2,6-dimethylphenyl)-2-((4-(3,4-dimethyl-1-piperazinyl)-3-fluorophenyl)amino)-4-((4-(((1-methylethyl)amino)carbonyl)-2-(methyloxy)phenyl)oxy)-5-pyrimidinecarboxamide | 96 | 1.3 | 656, 329 |
| 800 | 2-((3,4-bis(methyloxy)-5-((3-(4-methyl-1-piperazinyl)propyl)oxy)phenyl)amino)-4-((4-((cyclopentylamino)carbonyl)-2-(methyloxy)phenyl)oxy)-N-(2,6-dimethylphenyl)-5-pyrimidinecarboxamide | 94 | 1.27 | 768, 385 |
| 801 | 4-((4-((cyclopentylamino)carbonyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.26 | 726, 363 |
| 802 | 4-((4-((cyclopentylamino)carbonyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide | 100 | 1.42 | 711, 356 |
| 803 | 4-((4-((cyclopentylamino)carbonyl)-2-(methyloxy)phenyl)oxy)-N-(2,6-dimethylphenyl)-2-((3-((3-(1-piperidinyl)propyl)oxy)phenyl)amino)-5-pyrimidinecarboxamide | 98 | 1.45 | 693, 347 |
| 804 | 4-((4-((cyclopentylamino)carbonyl)-2-(methyloxy)phenyl)oxy)-2-((4-(((2-(diethylamino)ethyl)(methyl)amino)carbonyl)phenyl)amino)-N-(2,6-dimethylphenyl)-5-pyrimidinecarboxamide | 92 | 1.34 | 708, 355 |
| 805 | 4-((4-((cyclopentylamino)carbonyl)-2-(methyloxy)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 96 | 1.28 | 740, 371 |
| 806 | 4-((4-((cyclopentylamino)carbonyl)-2-(methyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 100 | 1.38 | 697, 349 |
| 807 | 4-((4-((cyclopentylamino)carbonyl)-2-(methyloxy)phenyl)oxy)-N-(2,6-dimethylphenyl)-2-((4-(3,4-dimethyl-1-piperazinyl)-3-fluorophenyl)amino)-5-pyrimidinecarboxamide | 100 | 1.36 | 682, 342 |
| 808 | 4-((4-(2-(diethylamino)-2-oxoethyl)-2-(methyloxy)phenyl)oxy)-N-(2,6-dimethylphenyl)-2-((3-((3-(1-piperidinyl)propyl)oxy)phenyl)amino)-5-pyrimidinecarboxamide | 97 | 1.42 | 695, 348 |
| 809 | 4-((2-chloro-4-((4-(1-methylethyl)-1-piperazinyl)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 109 | 773, 775 |

| No. | Name | LC purity | LC Rt | Mass found |
|---|---|---|---|---|
| 810 | 4-((2-chloro-4-((4-(1-methylethyl)-1-piperazinyl)carbonyl)phenyl)oxy)-N-(2,6-dimethylphenyl)-2-((3-fluoro-4-((3-(1-piperidinyl)propyl)oxy)phenyl)amino)-5-pyrimidinecarboxamide | 100 | 1.17 | 758, 760 |
| 811 | 4-((2-chloro-4-((4-(1-methylethyl)-1-piperazinyl)carbonyl)phenyl)oxy)-N-(2,6-dimethylphenyl)-2-((3-((3-(1-piperidinyl)propyl)oxy)phenyl)amino)-5-pyrimidinecarboxamide | 96 | 1.16 | 740, 742 |
| 812 | 4-((2-chloro-4-((4-(1-methylethyl)-1-piperazinyl)carbonyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 100 | 1.16 | 744, 746 |
| 813 | 4-((2-chloro-4-((4-(1-methylethyl)-1-piperazinyl)carbonyl)phenyl)oxy)-N-(2,6-dimethylphenyl)-2-((4-(3,4-dimethyl-1-piperazinyl)-3-fluorophenyl)amino)-5-pyrimidinecarboxamide | 92 | 1.14 | 729, 731 |
| 814 | 2-((3,4-bis(methyloxy)-5-((3-(4-methyl-1-piperazinyl)propyl)oxy)phenyl)amino)-4-((2-chloro-4-(((2-(methyloxy)ethyl)amino)carbonyl)phenyl)oxy)-N-(2,6-dimethylphenyl)-5-pyrimidinecarboxamide | 95 | 1.18 | 762, 764 |
| 815 | 2-((4-(((2-(diethylamino)ethyl)(methyl)amino)carbonyl)phenyl)amino)-N-(2,6-dimethylphenyl)-4-((4-(3-(4-(1-methylethyl)-1-piperazinyl)-3-oxopropyl)-2-(methyloxy)phenyl)oxy)-5-pyrimidinecarboxamide | 90 | 1.11 | 779, 390 |
| 816 | N-(2,6-dimethylphenyl)-2-((3-fluoro-4-(((1-methyl-3-piperidinyl)methyl)oxy)phenyl)amino)-4-((4-(3-(4-(1-methylethyl)-1-piperazinyl)-3-oxopropyl)-2-(methyloxy)phenyl)oxy)-5-pyrimidinecarboxamide | 97 | 1.13 | 768, 384 |
| 817 | N-(2,6-dimethylphenyl)-2-((4-(3,4-dimethyl-1-piperazinyl)-3-fluorophenyl)amino)-4-((4-(3-(4-(1-methylethyl)-1-piperazinyl)-3-oxopropyl)-2-(methyloxy)phenyl)oxy)-5-pyrimidinecarboxamide | 97 | 1.13 | 753, 377 |
| 818 | 2-((3,4-bis(methyloxy)-5-((3-(4-methyl-1-piperazinyl)propyl)oxy)phenyl)amino)-4-((2-chloro-4-((cyclopentylamino)carbonyl)phenyl)oxy)-N-(2,6-dimethylphenyl)-5-pyrimidinecarboxamide | 91 | 4.89 | 772, 774 |
| 819 | 4-((2-chloro-4-((cyclopentylamino)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 92 | 4.83 | 730, 732 |
| 820 | 4-((2-chloro-4-((cyclopentylamino)carbonyl)phenyl)oxy)-N-(2,6-dimethylphenyl)-2-((3-fluoro-4-((3-(1-piperidinyl)propyl)oxy)phenyl)amino)-5-pyrimidinecarboxamide | 97 | 5.86 | 715, 717 |
| 821 | 4-((2-chloro-4-((cyclopentylamino)carbonyl)phenyl)oxy)-2-((4-(((2-(diethylamino)ethyl)(methyl)amino)carbonyl)phenyl)amino)-N-(2,6-dimethylphenyl)-5-pyrimidinecarboxamide | 97 | 5.44 | 712, 714 |
| 822 | 4-((2-chloro-4-((cyclopentylamino)carbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 91 | 4.95 | 744, 746 |
| 823 | 4-((2-chloro-4-((cyclopentylamino)carbonyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 91 | 5.7 | 701, 703 |
| 824 | 4-((2-chloro-4-(4-morpholinylcarbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 94 | 4.3 | 732, 734 |
| 825 | 4-((2-chloro-4-(4-morpholinylcarbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 92 | 4.4 | 746, 748 |
| 826 | 4-((2-chloro-4-(4-morpholinylcarbonyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 88 | 5.01 | 703, 705 |

| No. | Name | LC purity | LC Rt | Mass found |
|---|---|---|---|---|
| 827 | 4-((2-chloro-4-(((1-methylethyl)amino)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.24 | 704, 706 |
| 828 | 4-((2-chloro-4-(((1-methylethyl)amino)carbonyl)phenyl)oxy)-N-(2,6-dimethylphenyl)-2-((3-fluoro-4-((3-(1-piperidinyl)propyl)oxy)phenyl)amino)-5-pyrimidinecarboxamide | 91 | 1.4 | 689, 691 |
| 829 | 4-((2-chloro-4-(((1-methylethyl)amino)carbonyl)phenyl)oxy)-2-((4-(((2-(diethylamino)ethyl)(methyl)amino)carbonyl)phenyl)amino)-N-(2,6-dimethylphenyl)-5-pyrimidinecarboxamide | 92 | 1.32 | 686, 688 |
| 830 | 2-((3,4-bis(methyloxy)-5-((3-(4-methyl-1-piperazinyl)propyl)oxy)phenyl)amino)-4-((2-chloro-4-(((1-methylethyl)amino)carbonyl)phenyl)oxy)-N-(2,6-dimethylphenyl)-5-pyrimidinecarboxamide | 100 | 1.25 | 746, 748 |
| 831 | N-(2,6-dimethylphenyl)-4-((2-ethylimidazo[1,2-a]pyridin-8-yl)oxy)-2-((3-fluoro-4-((3-(4-methyl-1-piperazinyl)propyl)oxy)phenyl)amino)-5-pyrimidinecarboxamide | 86 | 1.05 | 653, 327 |
| 832 | 2-((4-(((2-(diethylamino)ethyl)(methyl)amino)carbonyl)phenyl)amino)-4-(3-(3-(diethylamino)-3-oxopropyl)phenyl)oxy)-N-(2,6-dimethylphenyl)-5-pyrimidinecarboxamide | 88 | 1.33 | 694, 348 |
| 833 | 2-((3,4-bis(methyloxy)-5-((3-(4-methyl-1-piperazinyl)propyl)oxy)phenyl)amino)-4-((3-(3-(diethylamino)-3-oxopropyl)phenyl)oxy)-N-(2,6-dimethylphenyl)-5-pyrimidinecarboxamide | 100 | 1.25 | 754, 378 |
| 834 | 4-((3-(3-(diethylamino)-3-oxopropyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 100 | 1.37 | 683, 342 |
| 835 | 4-((3-(3-(diethylamino)-3-oxopropyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 100 | 1.27 | 726, 364 |
| 836 | 4-((3-(3-(diethylamino)-3-oxopropyl)phenyl)oxy)-N-(2,6-dimethylphenyl)-2-((3-((3-(1-piperidinyl)propyl)oxy)phenyl)amino)-5-pyrimidinecarboxamide | 100 | 1.42 | 679, 340 |
| 837 | 4-((2-chloro-4-(4-morpholinylcarbonyl)phenyl)oxy)-N-(2,6-dimethylphenyl)-2-((4-(3,4-dimethyl-1-piperazinyl)-3-fluorophenyl)amino)-5-pyrimidinecarboxamide | 98 | 4.9 | 688, 690 |
| 838 | 4-((2-chloro-4-((diethylamino)carbonyl)phenyl)oxy)-N-(2,6-dichloro-4-fluorophenyl)-2-((3-fluoro-4-((3-(4-methyl-1-piperazinyl)propyl)oxy)phenyl)amino)-5-pyrimidinecarboxamide | 96 | 1.33 | 776, 778 |
| 839 | 4-((2-chloro-4-((diethylamino)carbonyl)phenyl)oxy)-N-(2,6-dichloro-4-fluorophenyl)-2-((3-fluoro-4-((3-(1-piperidinyl)propyl)oxy)phenyl)amino)-5-pyrimidinecarboxamide | 92 | 1.49 | 761, 763 |
| 840 | 4-((2-chloro-4-((diethylamino)carbonyl)phenyl)oxy)-N-(4-fluoro-2,6-dimethylphenyl)-2-((3-fluoro-4-((3-(4-methyl-1-piperazinyl)propyl)oxy)phenyl)amino)-5-pyrimidinecarboxamide | 95 | 1.3 | 738, 738 |
| 841 | 4-((2-chloro-4-((diethylamino)carbonyl)phenyl)oxy)-N-(4-fluoro-2,6-dimethylphenyl)-2-((3-fluoro-4-((3-(1-piperidinyl)propyl)oxy)phenyl)amino)-5-pyrimidinecarboxamide | 97 | 1.47 | 721, 723 |
| 842 | 4-((2-chloro-4-((diethylamino)carbonyl)phenyl)oxy)-2-((3-fluoro-4-((3-(4-methyl-1-piperazinyl)propyl)oxy)phenyl)amino)-N-((5-methyl-3-isoxazolyl)methyl)-5-pyrimidinecarboxamide | 88 | 1.12 | 709, 711 |
| 843 | 4-((2-chloro-4-((diethylamino)carbonyl)phenyl)oxy)-2-((3-fluoro-4-((3-(1-piperidinyl)propyl)oxy)phenyl)amino)-N-((5-methyl-3-isoxazolyl)methyl)-5-pyrimidinecarboxamide | 87 | 1.26 | 694, 696 |
| 844 | 4-((2-chloro-4-(((2-(methyloxy)ethyl)amino)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 100 | 1.19 | 720, 722 |

-continued

| No. | Name | LC purity | LC Rt | Mass found |
|---|---|---|---|---|
| 845 | 4-((2-chloro-4-(((2-(methyloxy)ethyl)amino)carbonyl)phenyl)oxy)-N-(2,6-dimethylphenyl)-2-((3-fluoro-4-((3-(1-piperidinyl)propyl)oxy)phenyl)amino)-5-pyrimidinecarboxamide | 100 | 1.33 | 705, 707 |
| 846 | 2-((3,4-bis(methyloxy)-5-((3-(4-methyl-1-piperazinyl)propyl)oxy)phenyl)amino)-4-((4-((diethylamino)carbonyl)-2-(methyloxy)phenyl)oxy)-N-(2,6-dimethylphenyl)-5-pyrimidinecarboxamide | 100 | 1.25 | 756, 379 |
| 847 | 4-((4-((diethylamino)carbonyl)-2-(methyloxy)phenyl)oxy)-N-(2,6-dimethylphenyl)-2-((3-((3-(1-piperidinyl)propyl)oxy)phenyl)amino)-5-pyrimidinecarboxamide | 100 | 1.39 | 681, 341 |
| 848 | 4-((4-((diethylamino)carbonyl)-2-(methyloxy)phenyl)oxy)-2-((4-(((2-(diethylamino)ethyl)(methyl)amino)carbonyl)phenyl)amino)-N-(2,6-dimethylphenyl)-5-pyrimidinecarboxamide | 100 | 1.32 | 696, 348 |
| 849 | 4-((4-((diethylamino)carbonyl)-2-(methyloxy)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 100 | 1.26 | 728, 365 |
| 850 | 4-((4-((diethylamino)carbonyl)-2-(methyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 99 | 1.36 | 685, 343 |
| 851 | 4-((4-((diethylamino)carbonyl)-2-(methyloxy)phenyl)oxy)-N-(2,6-dimethylphenyl)-2-((4-(3,4-dimethyl-1-piperazinyl)-3-fluorophenyl)amino)-5-pyrimidinecarboxamide | 87 | 1.35 | 670, 336 |
| 852 | 4-((4-(3-(cyclopentylamino)-3-oxopropyl)-2-(methyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 92.5 | 1.38 | 725, 363 |
| 853 | N-(2,6-dimethylphenyl)-2-((3-fluoro-4-(((1-methyl-3-piperidinyl)methyl)oxy)phenyl)amino)-4-((4-(3-((1-methylethyl)amino)-3-oxopropyl)-2-(methyloxy)phenyl)oxy)-5-pyrimidinecarboxamide | 91.3 | 1.34 | 699, 350 |
| 854 | N-(2,6-dimethylphenyl)-2-((4-(3,4-dimethyl-1-piperazinyl)-3-fluorophenyl)amino)-4-((2-(methyloxy)-4-(3-((2-(methyloxy)ethyl)amino)-3-oxopropyl)phenyl)oxy)-5-pyrimidinecarboxamide | 97 | 1.21 | 700, 351 |
| 855 | N-(2,6-dimethylphenyl)-2-((3-fluoro-4-((3-(4-methyl-1-piperazinyl)propyl)oxy)phenyl)amino)-4-((2-(methyloxy)-4-(3-((2-(methyloxy)ethyl)amino)-3-oxopropyl)phenyl)oxy)-5-pyrimidinecarboxamide | 92.1 | 1.14 | 744, 373 |
| 856 | 2-((3,4-bis(methyloxy)-5-((3-(4-methyl-1-piperazinyl)propyl)oxy)phenyl)amino)-N-(2,6-dimethylphenyl)-4-((4-(3-((1-methylethyl)amino)-3-oxopropyl)-2-(methyloxy)phenyl)oxy)-5-pyrimidinecarboxamide | 100 | 1.22 | 770, 385 |
| 857 | 4-((4-(3-(cyclopentylamino)-3-oxopropyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide | 100 | 1.43 | 739, 370 |
| 858 | 2-((3,4-bis(methyloxy)-5-((3-(4-methyl-1-piperazinyl)propyl)oxy)phenyl)amino)-4-((4-(3-(cyclopentylamino)-3-oxopropyl)-2-(methyloxy)phenyl)oxy)-N-(2,6-dimethylphenyl)-5-pyrimidinecarboxamide | 92.3 | 1.26 | 796, 398 |
| 859 | 4-((4-(3-(cyclopentylamino)-3-oxopropyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide | 97.7 | 1.28 | 754, 377 |
| 860 | 4-((4-(3-(cyclopentylamino)-3-oxopropyl)-2-(methyloxy)phenyl)oxy)-N-(2,6-dimethylphenyl)-2-((4-(3,4-dimethyl-1-piperazinyl)-3-fluorophenyl)amino)-5-pyrimidinecarboxamide | 95.6 | 1.37 | 710, 355 |
| 861 | N-(2,6-dimethylphenyl)-2-((4-(3,4-dimethyl-1-piperazinyl)-3-fluorophenyl)amino)-4-((4-(3-((1-methylethyl)amino)-3-oxopropyl)-2-(methyloxy)phenyl)oxy)-5-pyrimidinecarboxamide | 100 | 1.32 | 684, 342 |

| No. | Name | LC purity | LC Rt | Mass found |
|---|---|---|---|---|
| 862 | N-(2,6-dimethylphenyl)-2-((3-fluoro-4-((3-(1-piperidinyl)propyl)oxy)phenyl)amino)-4-((4-(3-((1-methylethyl)amino)-3-oxopropyl)-2-(methyloxy)phenyl)oxy)-5-pyrimidinecarboxamide | 100 | 1.37 | 713, 357 |
| 863 | N-(2,6-dimethylphenyl)-4-((2-(methyloxy)-4-((2-oxo-2-(1-pyrrolidinyl)ethyl)oxy)phenyl)oxy)-2-((3-((3-(1-piperidinyl)propyl)oxy)phenyl)amino)-5-pyrimidinecarboxamide | 95.2 | 1.36 | 709, 355 |
| 864 | N-(2,6-dimethylphenyl)-2-((3-fluoro-4-((3-(4-methyl-1-piperazinyl)propyl)oxy)phenyl)amino)-4-((2-(methyloxy)-4-((2-(4-morpholinyl)-2-oxoethyl)oxy)phenyl)oxy)-5-pyrimidinecarboxamide | 100 | 1.16 | 758, 379 |
| 865 | N-(2,6-dimethylphenyl)-2-((3-fluoro-4-((3-(1-piperidinyl)propyl)oxy)phenyl)amino)-4-((2-(methyloxy)-4-((2-(4-morpholinyl)-2-oxoethyl)oxy)phenyl)oxy)-5-pyrimidinecarboxamide | 100 | 1.29 | 743, 372 |
| 866 | N-(2,6-dimethylphenyl)-4-((2-(methyloxy)-4-((2-(4-morpholinyl)-2-oxoethyl)oxy)phenyl)oxy)-2-((3-((3-(1-piperidinyl)propyl)oxy)phenyl)amino)-5-pyrimidinecarboxamide | 100 | 1.29 | 725, 363 |
| 867 | 2-((4-(((2-(diethylamino)ethyl)(methyl)amino)carbonyl)phenyl)amino)-N-(2,6-dimethylphenyl)-4-((2-(methyloxy)-4-((2-(4-morpholinyl)-2-oxoethyl)oxy)phenyl)oxy)-5-pyrimidinecarboxamide | 100 | 1.21 | 740, 371 |
| 868 | N-(2,6-dimethylphenyl)-2-((3-fluoro-4-(((1-methyl-3-piperidinyl)methyl)oxy)phenyl)amino)-4-((2-(methyloxy)-4-(1-pyrrolidinylcarbonyl)phenyl)oxy)-5-pyrimidinecarboxamide | 98.9 | 1.3 | 683, 342 |
| 869 | 4-((2-chloro-4-(2-oxo-2-(1-pyrrolidinyl)ethyl)phenyl)oxy)-N-(2,6-dimethylphenyl)-2-((3-fluoro-4-((3-(1-piperidinyl)propyl)oxy)phenyl)amino)-5-pyrimidinecarboxamide | 92.5 | 1.37 | 715 |
| 870 | 4-((2-chloro-4-(2-oxo-2-(1-pyrrolidinyl)ethyl)phenyl)oxy)-N-(2,6-dimethylphenyl)-2-((4-(3,4-dimethyl-1-piperazinyl)-3-fluorophenyl)amino)-5-pyrimidinecarboxamide | 100 | 1.33 | 686, 688 |
| 871 | 2-((3,4-bis(methyloxy)-5-((3-(4-methyl-1-piperazinyl)propyl)oxy)phenyl)amino)-4-((2-chloro-4-(2-oxo-2-(1-pyrrolidinyl)ethyl)phenyl)oxy)-N-(2,6-dimethylphenyl)-5-pyrimidinecarboxamide | 100 | 1.25 | 772, 774 |
| 872 | 4-((2-chloro-4-(2-oxo-2-(1-pyrrolidinyl)ethyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 100 | 1.36 | 701, 703 |
| 873 | 4-((2-chloro-4-(2-(4-morpholinyl)-2-oxoethyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 100 | 1.22 | 760, 762 |
| 874 | 4-((2-chloro-4-(2-(4-morpholinyl)-2-oxoethyl)phenyl)oxy)-2-((4-(((2-(diethylamino)ethyl)(methyl)amino)carbonyl)phenyl)amino)-N-(2,6-dimethylphenyl)-5-pyrimidinecarboxamide | 95.8 | 1.26 | 728, 730 |
| 875 | 2-((3,4-bis(methyloxy)-5-((3-(4-methyl-1-piperazinyl)propyl)oxy)phenyl)amino)-4-((2-chloro-4-(2-(4-morpholinyl)-2-oxoethyl)phenyl)oxy)-N-(2,6-dimethylphenyl)-5-pyrimidinecarboxamide | 100 | 1.19 | 788, 790 |
| 876 | 4-((2-chloro-4-(2-(4-morpholinyl)-2-oxoethyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 93.3 | 1.27 | 717, 719 |
| 877 | 4-((2-chloro-4-(2-(4-morpholinyl)-2-oxoethyl)phenyl)oxy)-N-(2,6-dimethylphenyl)-2-((3-((3-(1-piperidinyl)propyl)oxy)phenyl)amino)-5-pyrimidinecarboxamide | 100 | 1.28 | 713, 715 |
| 878 | 4-((2-chloro-4-(2-(4-morpholinyl)-2-oxoethyl)phenyl)oxy)-N-(2,6-dimethylphenyl)-2-((3-fluoro-4-((3-(1-piperidinyl)propyl)oxy)phenyl)amino)-5-pyrimidinecarboxamide | 100 | 1.34 | 731, 733 |

| No. | Name | LC purity | LC Rt | Mass found |
|---|---|---|---|---|
| 879 | 4-((2-chloro-4-(((2-(methyloxy)ethyl)amino)carbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 100 | 1.21 | 734, 736 |
| 880 | 4-((2-chloro-4-(((2-(methyloxy)ethyl)amino)carbonyl)phenyl)oxy)-N-(2,6-dimethylphenyl)-2-((4-(3,4-dimethyl-1-piperazinyl)-3-fluorophenyl)amino)-5-pyrimidinecarboxamide | 95.7 | 1.23 | 676, 678 |
| 881 | 4-((2-chloro-4-((4-(1-methylethyl)-1-piperazinyl)carbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide | 87.5 | 1.08 | 787, 789 |
| 882 | 2-((3,4-bis(methyloxy)-5-((3-(4-methyl-1-piperazinyl)propyl)oxy)phenyl)amino)-N-(2,6-dimethylphenyl)-4-((2-(methyloxy)-4-(2-(4-morpholinyl)-2-oxoethyl)phenyl)oxy)-5-pyrimidinecarboxamide | 100 | 1.14 | 784, 392 |
| 883 | N-(2,6-dimethylphenyl)-2-((3-fluoro-4-((3-(1-piperidinyl)propyl)oxy)phenyl)amino)-4-((2-(methyloxy)-4-(2-(4-morpholinyl)-2-oxoethyl)phenyl)oxy)-5-pyrimidinecarboxamide | 93.5 | 1.14 | 742, 371 |
| 884 | N-(2,6-dimethylphenyl)-4-((2-(methyloxy)-4-(2-(4-morpholinyl)-2-oxoethyl)phenyl)oxy)-2-((3-((3-(1-piperidinyl)propyl)oxy)phenyl)amino)-5-pyrimidinecarboxamide | 94.3 | 1.29 | 709, 355 |
| 885 | 2-((3,4-bis(methyloxy)-5-((3-(4-methyl-1-piperazinyl)propyl)oxy)phenyl)amino)-4-((2-(methyloxy)-4-(3-(((1R)-1-methylpropyl)amino)-3-oxopropyl)phenyl)oxy)-N-(2,4,6-trimethylphenyl)-5-pyrimidinecarboxamide | 100 | 1.29 | 798, 399 |
| 886 | 2-((3-fluoro-4-((3-(4-methyl-1-piperazinyl)propyl)oxy)phenyl)amino)-4-((2-(methyloxy)-4-(3-(((1R)-1-methylpropyl)amino)-3-oxopropyl)phenyl)oxy)-N-(2,4,6-trimethylphenyl)-5-pyrimidinecarboxamide | 100 | 1.3 | 756, 379 |
| 887 | 2-((3-fluoro-4-((3-(1-piperidinyl)propyl)oxy)phenyl)amino)-4-((2-(methyloxy)-4-(3-(((1R)-1-methylpropyl)amino)-3-oxopropyl)phenyl)oxy)-N-(2,4,6-trimethylphenyl)-5-pyrimidinecarboxamide | 100 | 1.45 | 741, 371 |
| 888 | 4-((2-(methyloxy)-4-(3-(((1R)-1-methylpropyl)amino)-3-oxopropyl)phenyl)oxy)-2-((3-((3-(1-piperidinyl)propyl)oxy)phenyl)amino)-N-(2,4,6-trimethylphenyl)-5-pyrimidinecarboxamide | 100 | 1.45 | 723, 362 |
| 889 | 2-((4-(((2-(diethylamino)ethyl)(methyl)amino)carbonyl)phenyl)amino)-4-((2-(methyloxy)-4-(3-(((1R)-1-methylpropyl)amino)-3-oxopropyl)phenyl)oxy)-N-(2,4,6-trimethylphenyl)-5-pyrimidinecarboxamide | 96.1 | 1.38 | 738, 370 |
| 890 | 2-((4-(4-(1-methylethyl)-1-piperazinyl)phenyl)amino)-4-((2-(methyloxy)-4-(3-(((1R)-1-methylpropyl)amino)-3-oxopropyl)phenyl)oxy)-N-(2,4,6-trimethylphenyl)-5-pyrimidinecarboxamide | 94 | 1.4 | 708, 355 |
| 891 | N-(2,6-dimethylphenyl)-2-((3-fluoro-4-((3-(1-piperidinyl)propyl)oxy)phenyl)amino)-4-((2-(methyloxy)-4-(2-(4-morpholinyl)-2-oxoethyl)phenyl)oxy)-5-pyrimidinecarboxamide | 100 | 1.29 | 727, 364 |
| 892 | 2-((3,4-bis(methyloxy)-5-((3-(4-methyl-1-piperazinyl)propyl)oxy)phenyl)amino)-N-(2,6-dimethylphenyl)-4-((2-(methyloxy)-4-((2-(4-morpholinyl)-2-oxoethyl)oxy)phenyl)oxy)-5-pyrimidinecarboxamide | 91 | 1.17 | 800, 521 |
| 893 | N-(2,6-dimethylphenyl)-2-((3-fluoro-4-((2-(4-(1-methylethyl)-1-piperazinyl)ethyl)oxy)phenyl)amino)-4-((2-(methyloxy)-4-((2-(4-morpholinyl)-2-oxoethyl)oxy)phenyl)oxy)-5-pyrimidinecarboxamide | 100 | 1.17 | 772, 386 |
| 894 | N-(2,6-dimethylphenyl)-2-((3-fluoro-4-(((1-methyl-3-piperidinyl)methyl)oxy)phenyl)amino)-4-((2-(methyloxy)-4-((2-(4-morpholinyl)-2-oxoethyl)oxy)phenyl)oxy)-5-pyrimidinecarboxamide | 98 | 1.24 | 729, 365 |
| 895 | N-(2,6-dimethylphenyl)-2-((4-(3,4-dimethyl-1-piperazinyl)-3-fluorophenyl)amino)-4-((2-(methyloxy)-4-((2-(4-morpholinyl)-2-oxoethyl)oxy)phenyl)oxy)-5-pyrimidinecarboxamide | 100 | 1.21 | 714, 358 |

-continued

| No. | Name | LC purity | LC Rt | Mass found |
|---|---|---|---|---|
| 896 | 2-((4-(((2-(diethylamino)ethyl)(methyl)amino)carbonyl)phenyl)amino)-N-(2,6-dimethylphenyl)-4-((2-(methyloxy)-4-((2-oxo-2-(1-pyrrolidinyl)ethyl)oxy)phenyl)oxy)-5-pyrimidinecarboxamide | 100 | 1.25 | 724,363 |
| 897 | 4-((4-(3-(diethylamino)-3-oxopropyl)-2-(methyloxy)phenyl)oxy)-2-((3-(((2-(dimethylamino)ethyl)amino)carbonyl)phenyl)amino)-N-(2,6-dimethylphenyl)-5-pyrimidinecarboxamide | 97 | 1.29 | 682, 342 |
| 898 | 2-((4-(((2-(diethylamino)ethyl)(methyl)amino)carbonyl)phenyl)amino)-N-(2,6-dimethylphenyl)-4-((2-(methyloxy)-4-(2-(4-morpholinyl)-2-oxoethyl)phenyl)oxy)-5-pyrimidinecarboxamide | 100 | 1.23 | 724,362 |
| 899 | N-(2,6-dimethylphenyl)-2-((3-fluoro-4-((2-(4-(1-methylethyl)-1-piperazinyl)ethyl)oxy)phenyl)amino)-4-((2-(methyloxy)-4-(2-(4-morpholinyl)-2-oxoethyl)phenyl)oxy)-5-pyrimidinecarboxamide | 98 | 1.18 | 756 |
| 900 | N-(2,6-dimethylphenyl)-2-((3-fluoro-4-(((1-methyl-3-piperidinyl)methyl)oxy)phenyl)amino)-4-((2-(methyloxy)-4-(2-(4-morpholinyl)-2-oxoethyl)phenyl)oxy)-5-pyrimidinecarboxamide | 100 | 1.26 | 713 |
| 901 | N-(2,6-dimethylphenyl)-2-((4-(3,4-dimethyl-1-piperazinyl)-3-fluorophenyl)amino)-4-((2-(methyloxy)-4-(2-(4-morpholinyl)-2-oxoethyl)phenyl)oxy)-5-pyrimidinecarboxamide | 100 | 1.25 | 698, 349 |
| 902 | 2-((3,4-bis(methyloxy)-5-((3-(4-methyl-1-piperazinyl)propyl)oxy)phenyl)amino)-N-(2,6-dimethylphenyl)-4-((2-(methyloxy)-4-((2-(methyloxy)ethyl)amino)-2-oxoethyl)phenyl)oxy)-5-pyrimidinecarboxamide | 97 | 1.11 | 772, 387 |
| 903 | N-(2,6-dimethylphenyl)-2-((3-fluoro-4-((3-(4-methyl-1-piperazinyl)propyl)oxy)phenyl)amino)-4-((2-(methyloxy)-4-(2-((2-(methyloxy)ethyl)amino)-2-oxoethyl)phenyl)oxy)-5-pyrimidinecarboxamide | 98 | 1.11 | 730, 366 |
| 904 | N-(2,6-dimethylphenyl)-2-((3-fluoro-4-((3-(1-piperidinyl)propyl)oxy)phenyl)amino)-4-((2-(methyloxy)-4-(2-((2-(methyloxy)ethyl)amino)-2-oxoethyl)phenyl)oxy)-5-pyrimidinecarboxamide | 100 | 1.28 | 715, 358 |
| 905 | N-(2,6-dimethylphenyl)-4-((2-(methyloxy)-4-(2-((2-(methyloxy)ethyl)amino)-2-oxoethyl)phenyl)oxy)-2-((3-((3-(1-piperidinyl)propyl)oxy)phenyl)amino)-5-pyrimidinecarboxamide | 100 | 1.24 | 697, 349 |
| 906 | N-(2,6-dimethylphenyl)-2-((3-fluoro-4-((2-(4-(1-methylethyl)-1-piperazinyl)ethyl)oxy)phenyl)amino)-4-((2-(methyloxy)-4-(2-((2-(methyloxy)ethyl)amino)-2-oxoethyl)phenyl)oxy)-5-pyrimidinecarboxamide | 100 | 1.13 | 744, 373 |
| 907 | N-(2,6-dimethylphenyl)-2-((3-fluoro-4-(((1-methyl-3-piperidinyl)methyl)oxy)phenyl)amino)-4-((2-(methyloxy)-4-(2-((2-(methyloxy)ethyl)amino)-2-oxoethyl)phenyl)oxy)-5-pyrimidinecarboxamide | 95 | 1.21 | 701, 351 |
| 908 | N-(2,6-dimethylphenyl)-2-((4-(3,4-dimethyl-1-piperazinyl)-3-fluorophenyl)amino)-4-((2-(methyloxy)-4-(2-((2-(methyloxy)ethyl)amino)-2-oxoethyl)phenyl)oxy)-5-pyrimidinecarboxamide | 98 | 1.17 | 686, 344 |
| 909 | N-(2,6-dimethylphenyl)-2-((3-fluoro-4-((3-(4-methyl-1-piperazinyl)propyl)oxy)phenyl)amino)-4-((2-oxo-1,2,3,4-tetrahydro-7-quinolinyl)oxy)-5-pyrimidinecarboxamide | 97 | 1.13 | 654, 327 |
| 910 | N-(2,6-dimethylphenyl)-2-((4-(3,4-dimethyl-1-piperazinyl)-3-fluorophenyl)amino)-4-((2-oxo-1,2,3,4-tetrahydro-7-quinolinyl)oxy)-5-pyrimidinecarboxamide | 100 | 1.2 | 610, 305 |
| 911 | 2-((3,4-bis(methyloxy)-5-((3-(4-methyl-1-piperazinyl)propyl)oxy)phenyl)amino)-N-(2,6-dimethylphenyl)-4-((2-oxo-1,2,3,4-tetrahydro-7-quinolinyl)oxy)-5-pyrimidinecarboxamide | 90 | 1.13 | 696, 348 |
| 912 | N-(2,6-dimethylphenyl)-2-((3-fluoro-4-(((1-methyl-3-piperidinyl)methyl)oxy)phenyl)amino)-4-((2-oxo-1,2,3,4-tetrahydro-7-quinolinyl)oxy)-5-pyrimidinecarboxamide | 100 | 1.23 | 625, 313 |
| 913 | N-(2,6-dimethylphenyl)-2-((3-fluoro-4-((2-(4-(1-methylethyl)-1-piperazinyl)ethyl)oxy)phenyl)amino)-4-((2-oxo-1,2,3,4-tetrahydro-7-quinolinyl)oxy)-5-pyrimidinecarboxamide | 86 | 1.16 | 668, 33 |
| 914 | N-(2,6-dimethylphenyl)-2-((4-(3,4-dimethyl-1-piperazinyl)-3-fluorophenyl)amino)-4-((4-((4-(1-methylethyl)-1-piperazinyl)carbonyl)-2-(methyloxy)phenyl)oxy)-5-pyrimidinecarboxamide | 97 | 1.1 | 725, 363 |

-continued

| No. | Name | LC purity | LC Rt | Mass found |
|---|---|---|---|---|
| 915 | 2-((4-(((2-(diethylamino)ethyl)(methyl)amino)carbonyl)phenyl)amino)-N-(2,6-dimethylphenyl)-4-((4-((4-(1-methylethyl)-1-piperazinyl)carbonyl)-2-(methyloxy)phenyl)oxy)-5-pyrimidinecarboxamide | 91 | 1.1 | 751, 376 |
| 916 | 2-((3,4-bis(methyloxy)-5-((3-(4-methyl-1-piperazinyl)propyl)oxy)phenyl)amino)-N-(2,6-dimethylphenyl)-4-((2-(methyloxy)-4-(((2-(methyloxy)ethyl)amino)carbonyl)phenyl)oxy)-5-pyrimidinecarboxamide | 98 | 1.12 | 758, 380 |
| 917 | N-(2,6-dimethylphenyl)-2-((3-fluoro-4-((3-(1-piperidinyl)propyl)oxy)phenyl)amino)-4-((2-(methyloxy)-4-(((2-(methyloxy)ethyl)amino)carbonyl)phenyl)oxy)-5-pyrimidinecarboxamide | 90 | 1.25 | 701, 351 |
| 918 | N-(2,6-dimethylphenyl)-2-((3-fluoro-4-((3-(1-piperidinyl)propyl)oxy)phenyl)amino)-4-((4-((4-(1-methylethyl)-1-piperazinyl)carbonyl)-2-(methyloxy)phenyl)oxy)-5-pyrimidinecarboxamide | 88 | 1.13 | 754, 378 |
| 919 | N-(2,6-dimethylphenyl)-2-((3-fluoro-4-((2-(4-(1-methylethyl)-1-piperazinyl)ethyl)oxy)phenyl)amino)-4-((4-((4-(1-methylethyl)-1-piperazinyl)carbonyl)-2-(methyloxy)phenyl)oxy)-5-pyrimidinecarboxamide | 90 | 1.06 | 784, 392 |
| 920 | 4-((3-(3-(diethylamino)-3-oxopropyl)phenyl)oxy)-N-(2,6-dimethylphenyl)-2-((4-(4-(3,4-dimethyl-1-piperazinyl)-3-fluorophenyl)amino)-5-pyrimidinecarboxamide | 97 | 1.31 | 668, 335 |
| 921 | 4-((4-(3-(diethylamino)-3-oxopropyl)-2-(methyloxy)phenyl)oxy)-2-((4-(((2-(dimethylamino)ethyl)amino)carbonyl)phenyl)amino)-N-(2,6-dimethylphenyl)-5-pyrimidinecarboxamide | 97 | 1.32 | 682, 341 |
| 922 | N-(2,6-dimethylphenyl)-2-((3-fluoro-4-((3-(4-methyl-1-piperazinyl)propyl)oxy)phenyl)amino)-4-((4-(3-((1-methylethyl)amino)-3-oxopropyl)-2-(methyloxy)phenyl)oxy)-5-pyrimidinecarboxamide | 93 | 1.22 | 728, 364 |
| 923 | 2-((4-(((2-(diethylamino)ethyl)(methyl)amino)carbonyl)phenyl)amino)-N-(2,6-dimethylphenyl)-4-((4-(3-((1-methylethyl)amino)-3-oxopropyl)-2-(methyloxy)phenyl)oxy)-5-pyrimidinecarboxamide | 100 | 1.29 | 710, 355 |
| 924 | 4-((4-(3-(cyclopentylamino)-3-oxopropyl)-2-(methyloxy)phenyl)oxy)-2-((4-(((2-(diethylamino)ethyl)(methyl)amino)carbonyl)phenyl)amino)-N-(2,6-dimethylphenyl)-5-pyrimidinecarboxamide | 98 | 1.35 | 736, 368 |
| 925 | 2-((4-(((2-(diethylamino)ethyl)(methyl)amino)carbonyl)phenyl)amino)-N-(2,6-dimethylphenyl)-4-((2-(methyloxy)-4-(3-((2-(methyloxy)ethyl)amino)-3-oxopropyl)phenyl)oxy)-5-pyrimidinecarboxamide | 90 | 1.22 | 726, 364 |
| 926 | 2-((4-(((2-(diethylamino)ethyl)(methyl)amino)carbonyl)phenyl)amino)-N-(2,6-dimethylphenyl)-4-((2-oxo-1,2,3,4-tetrahydro-7-quinolinyl)oxy)-5-pyrimidinecarboxamide | 100 | 1.18 | 636, 319 |
| 927 | 2-((3,4-bis(methyloxy)-5-((3-(4-methyl-1-piperazinyl)propyl)oxy)phenyl)amino)-4-((4-((diethylamino)carbonyl)-2-(ethyloxy)phenyl)oxy)-N-(2,6-dimethylphenyl)-5-pyrimidinecarboxamide | 98 | 1.3 | 770, 385 |
| 928 | 4-((4-((diethylamino)carbonyl)-2-(ethyloxy)phenyl)oxy)-N-(2,6-dimethylphenyl)-2-((3-fluoro-4-((3-(1-piperidinyl)propyl)oxy)phenyl)amino)-5-pyrimidinecarboxamide | 91 | 1.46 | 713, 357 |
| 929 | 4-((4-((diethylamino)carbonyl)-2-(ethyloxy)phenyl)oxy)-2-((4-(((2-(diethylamino)ethyl)(methyl)amino)carbonyl)phenyl)amino)-N-(2,6-dimethylphenyl)-5-pyrimidinecarboxamide | 100 | 1.41 | 710, 355 |
| 930 | 4-((4-((diethylamino)carbonyl)-2-(ethyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide | 85 | 1.41 | 699, 350 |
| 931 | 4-((4-((diethylamino)carbonyl)-2-(ethyloxy)phenyl)oxy)-N-(2,6-dimethylphenyl)-2-((4-(3,4-dimethyl-1-piperazinyl)-3-fluorophenyl)amino)-5-pyrimidinecarboxamide | 100 | 1.41 | 684, 342 |

-continued

| No. | Name | LC purity | LC Rt | Mass found |
|---|---|---|---|---|
| 932 | N-(2,6-dimethylphenyl)-2-((3-fluoro-4-((3-(4-methyl-1-piperazinyl)propyl)oxy)phenyl)amino)-4-((2-(methyloxy)-4-(((2-(methyloxy)ethyl)amino)carbonyl)phenyl)oxy)-5-pyrimidinecarboxamide | 92 | 1.13 | 716, 359 |
| 933 | N-(2,6-dimethylphenyl)-4-((2-(methyloxy)-4-(((2-(methyloxy)ethyl)amino)carbonyl)phenyl)oxy)-2-((3-((3-(1-piperidinyl)propyl)oxy)phenyl)amino)-5-pyrimidinecarboxamide | 89 | 1.25 | 683, 342 |
| 934 | 2-((4-(((2-(diethylamino)ethyl)(methyl)amino)carbonyl)phenyl)amino)-N-(2,6-dimethylphenyl)-4-((2-(methyloxy)-4-(((2-(methyloxy)ethyl)amino)carbonyl)phenyl)oxy)-5-pyrimidinecarboxamide | 97 | 1.23 | 698 |
| 935 | N-(2,6-dimethylphenyl)-2-((3-fluoro-4-((2-(4-(1-methylethyl)-1-piperazinyl)ethyl)oxy)phenyl)amino)-4-((2-(methyloxy)-4-(((2-(methyloxy)ethyl)amino)carbonyl)phenyl)oxy)-5-pyrimidinecarboxamide | 88 | 1.11 | 730, 366 |
| 936 | N-(2,6-dimethylphenyl)-2-((3-fluoro-4-(((1-methyl-3-piperidinyl)methyl)oxy)phenyl)amino)-4-((2-(methyloxy)-4-(((2-(methyloxy)ethyl)amino)carbonyl)phenyl)oxy)-5-pyrimidinecarboxamide | 90 | 1.25 | |
| 937 | 2-((3-fluoro-4-((3-(4-methyl-1-piperazinyl)propyl)oxy)phenyl)amino)-4-((2-(methyloxy)-4-(3-(((1R)-1-methylpropyl)amino)-3-oxopropyl)phenyl)oxy)-N-(2,4,6-trifluorophenyl)-5-pyrimidinecarboxamide | 100 | 1.74 | 768 |
| 938 | 2-((3-fluoro-4-((3-(1-piperidinyl)propyl)oxy)phenyl)amino)-4-((2-(methyloxy)-4-(3-(((1R)-1-methylpropyl)amino)-3-oxopropyl)phenyl)oxy)-N-(2,4,6-trifluorophenyl)-5-pyrimidinecarboxamide | 100 | 1.88 | 753 |
| 939 | 4-((2-(methyloxy)-4-(3-(((1R)-1-methylpropyl)amino)-3-oxopropyl)phenyl)oxy)-2-((3-((3-(1-piperidinyl)propyl)oxy)phenyl)amino)-N-(2,4,6-trifluorophenyl)-5-pyrimidinecarboxamide | 100 | 1.87 | 735 |
| 940 | 2-((4-(((2-(diethylamino)ethyl)(methyl)amino)carbonyl)phenyl)amino)-4-((2-(methyloxy)-4-(3-(((1R)-1-methylpropyl)amino)-3-oxopropyl)phenyl)oxy)-N-(2,4,6-trifluorophenyl)-5-pyrimidinecarboxamide | 97.6 | 1.83 | 750 |
| 941 | 2-((3-fluoro-4-((2-(4-(1-methylethyl)-1-piperazinyl)ethyl)oxy)phenyl)amino)-4-((2-(methyloxy)-4-(3-(((1R)-1-methylpropyl)amino)-3-oxopropyl)phenyl)oxy)-N-(2,4,6-trifluorophenyl)-5-pyrimidinecarboxamide | 96.4 | 1.76 | 782 |
| 942 | 2-((3-fluoro-4-(((1-methyl-3-piperidinyl)methyl)oxy)phenyl)amino)-4-((2-(methyloxy)-4-(3-(((1R)-1-methylpropyl)amino)-3-oxopropyl)phenyl)oxy)-N-(2,4,6-trifluorophenyl)-5-pyrimidinecarboxamide | 100 | 1.86 | 739 |
| 943 | 2-((4-(3,4-dimethyl-1-piperazinyl)-3-fluorophenyl)amino)-4-((2-(methyloxy)-4-(3-(((1R)-1-methylpropyl)amino)-3-oxopropyl)phenyl)oxy)-N-(2,4,6-trifluorophenyl)-5-pyrimidinecarboxamide | 100 | 1.34 | 724, 504 |

LC Method:

Unless otherwise indicated all LC analyses were run on a Waters 2790 system with a Phenomenex Luna $C_8$ (3µ) reverse phase column (100×2 mm) run with a flow rate of 1.00 mL/min.

The mobile phase used solvent A ($H_2O$/0.1% TFA) and solvent B ($CH_3CN$/0.1% TFA) with a 9.5 min gradient from 5% to 95% $CH_3CN$. The gradient was followed by a 0.2 min return to 5% $CH_3CN$ and a 3.8 min flush. The peaks of interest eluted on the LC profiles at the times indicated.

LC-MS Method:
1. LCMS analyses were run on an Micromass Single Quadrupole LCMS system comprising an Agilent HP-1100 LC with a Hypersil BDS $C_{18}$ (5µ) reverse phase column (2.1× 50 mm)) run with a flow rate of 1.00 mL/min.
2. The mobile phase used solvent A ($H_2O$/0.1% TFA) and solvent B ($CH_3CN$/0.1% TFA) with a 2.1 min gradient from 0% to 95% $CH_3CN$. The gradient was followed by a 0.2 min return to 0% $CH_3CN$ and a 0.1 min flush.
3. The peaks of interest eluted on the LC profiles at the times indicated.

Proton NMR Spectra:

Unless otherwise indicated all $^1H$ NMR spectra were run on an Bruker Avance 400 MHz instrument. All observed protons are reported as parts per million (ppm) downfield from tet ramethylsilane (TMS) or other internal reference in the appropriate solvent indicated.

Biological Assays

The following assays can be employed to determine the degree of activity of a compound as a protein kinase inhibitor. Compounds described herein have been tested in one or more of these assays, and have shown activity. Representative compounds of the invention were tested and found to exhibit $IC_{50}$ values of at least <10 µM in any one of the described assays, thereby demonstrating and confirming the utility of the compounds of the invention as protein kinase inhibitors and in the prophylaxis and treatment of immune diseases, hyperproliferative disorders, etc.

LCK-Homogeneous Time Resolved Fluorescent (HTRF) Kinase Assay:

The LCK HTRF assay begins with LCK in the presence of ATP phosphorylating the biotinylated peptide Gastrin. The reaction incubates for 90 min. To quench the assay detection reagents are added which both stop the reaction by diluting out the enzyme and chelating the metals due to the presence of EDTA. Once the detection reagents are added the assay incubates for 30 min to allow for equilibration of the detection reagents.

The LCK HTRF assay is comprised of 10 µL of compound in 100% DMSO, 15 µL of ATP and biotinylated Gastrin, and 15 µL of LCK KD GST (225-509) for a final volume of 40 µL. The final concentration of gastrin is 1.2 µM. The final concentration of ATP is 0.5 µM (Km app=0.6 µM+/−0.1) and the final concentration of LCK is 250 pM. Buffer conditions are as follows: 50 mM HEPES pH 7.5, 50 mM NaCl, 20 mM MgCl, 5 mM MnCl, 2 mM DTT, 0.05% BSA.

The assay is quenched and stopped with 160 µL of detection reagent. Detection reagents are as follows: Buffer made of 50 mM Tris, pH 7.5, 100 mM NaCl, 3 mM EDTA, 0.05% BSA, 0.1% Tween20. Added to this buffer prior to reading is Steptavidin allophycocyanin (SA-APC) at a final conc in the assay of 0.0004 mg/mL, and europilated anti-phosphotyrosine Ab (Eu-anti-PY) at a final conc of 0.025 nM.

The assay plate is read in either a Discovery or a RubyStar. The eu-anti-PY is excited at 320 nm and emits at 615 nm to excite the SA-APC which in turn emits at 655 nm. The ratio of SA-APC at 655 nm (excited due to close proximity to the Eu-anti-PY because of phosphorylation of the peptide) to free Eu-anti-PY at 615 nm will give substrate phosphorylation.

Assays for other kinases are done in a similar way as described above, varying the concentrations of enzyme, peptide substrate, and ATP added to the reaction, depending on the specific activity of the kinase and measured Km's for the substrates.

The following compounds exhibit activity of better than 1 µM in the LCK-HTRF Kinase Assay:

1,1-dimethylethyl 4-(4-((5-(((2,6-dimethylphenyl)amino)carbonyl)-2-((4-(4-methyl-1-piperazinyl)phenyl)amino)-4-pyrimidinyl)oxy)phenyl)-1-piperazinecarboxylate;

2-((3-(((2-(diethylamino)ethyl)(methyl)amino)carbonyl)phenyl)amino)-N-(2,6-dimethylphenyl)-4-((2-(ethyloxy)phenyl)oxy)-5-pyrimidinecarboxamide;

2-((3-(((2-(diethylamino)ethyl)(methyl)amino)carbonyl)phenyl)amino)-N-(2,6-dimethylphenyl)-4-((2-(methyloxy)-4-propylphenyl)oxy)-5-pyrimidinecarboxamide;

2-((3-(((2-(dimethylamino)ethyl)amino)sulfonyl)phenyl)amino)-N-(2,6-dimethylphenyl)-4-((2-(methyloxy)-4-propylphenyl)oxy)-5-pyrimidinecarboxamide;

2-((3-(((2-(dimethylamino)ethyl)amino)sulfonyl)phenyl)amino)-N-(2,6-dimethylphenyl)-4-((2-(ethyloxy)phenyl)oxy)-5-pyrimidinecarboxamide;

2-((3-((difluoromethyl)oxy)-4-(4-methyl-1-piperazinyl)phenyl)amino)-N-(2,6-dimethylphenyl)-4-((2-(ethyloxy)phenyl)oxy)-5-pyrimidinecarboxamide;

2-((3,4-bis(methyloxy)-5-((2-(4-methyl-1-piperazinyl)ethyl)oxy)phenyl)amino)-N-(2,6-dimethylphenyl)-4-((2-(methyloxy)-4-propylphenyl)oxy)-5-pyrimidinecarboxamide;

2-((3,4-bis(methyloxy)-5-((2-(4-methyl-1-piperazinyl)ethyl)oxy)phenyl)amino)-N-(2,6-dimethylphenyl)-4-((2-(ethyloxy)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)-4-propylphenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(ethyloxy)phenyl)oxy)-5-pyrimidinecarboxamide;

2-((3,5-bis(methyloxy)-4-((2-(4-methyl-1-piperazinyl)ethyl)oxy)phenyl)amino)-N-(2,6-dimethylphenyl)-4-((2-(ethyloxy)phenyl)oxy)-5-pyrimidinecarboxamide;

2-((3,5-bis(methyloxy)-4-((3-(4-methyl-1-piperazinyl)propyl)oxy)phenyl)amino)-N-(2,6-dimethylphenyl)-4-(phenyloxy)-5-pyrimidinecarboxamide;

2-((3,5-bis(methyloxy)-4-((3-(4-methyl-1-piperazinyl)propyl)oxy)phenyl)amino)-N-(2,6-dimethylphenyl)-4-((2-fluorophenyl)oxy)-5-pyrimidinecarboxamide;

2-((3,5-bis(methyloxy)-4-((3-(4-methyl-1-piperazinyl)propyl)oxy)phenyl)amino)-N-(2,6-dichlorophenyl)-4-(2-naphthalenyloxy)-5-pyrimidinecarboxamide;

2-((3,5-bis(methyloxy)-4-((3-(4-methyl-1-piperazinyl)propyl)oxy)phenyl)amino)-N-(2,6-dichlorophenyl)-4-((2-fluorophenyl)oxy)-5-pyrimidinecarboxamide;

2-((3,5-bis(methyloxy)-4-((3-(4-methyl-1-piperazinyl)propyl)oxy)phenyl)amino)-N-(2,6-dichlorophenyl)-4-((4-(1-piperazinyl)phenyl)oxy)-5-pyrimidinecarboxamide;

2-((3,5-bis(methyloxy)-4-((3-(4-methyl-1-piperazinyl)propyl)oxy)phenyl)amino)-N-(2,6-dimethylphenyl)-4-((4-fluorophenyl)oxy)-5-pyrimidinecarboxamide;

2-((3,5-bis(methyloxy)-4-((3-(4-methyl-1-piperazinyl)propyl)oxy)phenyl)amino)-N-(2,6-dimethylphenyl)-4-((2-((trifluoromethyl)oxy)phenyl)oxy)-5-pyrimidinecarboxamide;

2-((3,5-bis(methyloxy)-4-((3-(4-methyl-1-piperazinyl)propyl)oxy)phenyl)amino)-4-((3-(3-(diethylamino)-3-oxopropyl)phenyl)oxy)-N-(2,6-dimethylphenyl)-5-pyrimidinecarboxamide;

2-((3,5-bis(methyloxy)-4-((3-(4-methyl-1-piperazinyl)propyl)oxy)phenyl)amino)-N-(2,6-dichlorophenyl)-4-((3-(methyloxy)phenyl)oxy)-5-pyrimidinecarboxamide;

2-((3,5-bis(methyloxy)-4-((3-(4-methyl-1-piperazinyl)propyl)oxy)phenyl)amino)-N-(2,6-dimethylphenyl)-4-((4-(1-piperazinyl)phenyl)oxy)-5-pyrimidinecarboxamide;

2-((3,5-bis(methyloxy)-4-((3-(4-methyl-1-piperazinyl)propyl)oxy)phenyl)amino)-N-(2,6-dimethylphenyl)-4-((2-(methyloxy)phenyl)oxy)-5-pyrimidinecarboxamide;

2-((3,5-bis(methyloxy)-4-((3-(4-methyl-1-piperazinyl)propyl)oxy)phenyl)amino)-N-(2,6-dichlorophenyl)-4-(phenyloxy)-5-pyrimidinecarboxamide;

2-((3,5-bis(methyloxy)-4-((3-(4-methyl-1-piperazinyl)propyl)oxy)phenyl)amino)-N-(2,6-dichlorophenyl)-4-((2-(methyloxy)phenyl)oxy)-5-pyrimidinecarboxamide;

2-((3,5-bis(methyloxy)-4-(4-methyl-1-piperazinyl)phenyl)amino)-N-(2,6-dimethylphenyl)-4-(phenyloxy)-5-pyrimidinecarboxamide;

2-((3-chloro-4-((2-(4-(1-methylethyl)-1-piperazinyl)ethyl)oxy)phenyl)amino)-N-(2,6-dimethylphenyl)-4-((2-(ethyloxy)phenyl)oxy)-5-pyrimidinecarboxamide;

2-((3-chloro-4-((2-(4-(1-methylethyl)-1-piperazinyl)ethyl)oxy)phenyl)amino)-N-2,6-dimethylphenyl)-4-((2-(methyloxy)-4-propylphenyl)oxy)-5-pyrimidinecarboxamide;

2-((3-chloro-4-(4-(1-methylethyl)-1-piperazinyl)phenyl)amino)-4-((4-((1E)-3-(diethylamino)-3-oxo-1-propenyl)-2-(methyloxy)phenyl)oxy)-N-(2,6-dimethylphenyl)-5-pyrimidinecarboxamide;

2-((3-chloro-4-(4-(1-methylethyl)-1-piperazinyl)phenyl)amino)-4-((2-((cyclopropylmethyl)oxy)phenyl)oxy)-N-(2,6-dimethylphenyl)-5-pyrimidinecarboxamide;

2-((3-chloro-4-(4-(1-methylethyl)-1-piperazinyl)phenyl)amino)-4-((2-((dimethylamino)carbonyl)-4-(methyloxy)phenyl)oxy)-N-(2,6-dimethylphenyl)-5-pyrimidinecarboxamide;

2-((3-chloro-4-(4-(1-methylethyl)-1-piperazinyl)phenyl)amino)-N-(2,6-dimethylphenyl)-4-((2-(methyloxy)-4-propylphenyl)oxy)-5-pyrimidinecarboxamide;

2-((3-chloro-4-(4-(1-methylethyl)-1-piperazinyl)phenyl)amino)-N-(2,6-dimethylphenyl)-4-((4-((phenylmethyl)oxy)phenyl)oxy)-5-pyrimidinecarboxamide;

2-((3-chloro-4-(4-(1-methylethyl)-1-piperazinyl)phenyl)amino)-N-(2,6-dimethylphenyl)-4-((2-(methyloxy)-4-(2-propenyl)phenyl)oxy)-5-pyrimidinecarboxamide;

2-((3-chloro-4-(4-(1-methylethyl)-1-piperazinyl)phenyl)amino)-N-(2,6-dimethylphenyl)-4-((4-(phenyloxy)phenyl)oxy)-5-pyrimidinecarboxamide;

2-((3-chloro-4-(4-(1-methylethyl)-1-piperazinyl)phenyl)amino)-N-(2,6-dimethylphenyl)-4-((2-(ethyloxy)phenyl)oxy)-5-pyrimidinecarboxamide;

2-((3-chloro-4-(4-methyl-1-piperazinyl)phenyl)amino)-N-(2,6-dimethylphenyl)-4-((2-(ethyloxy)phenyl)oxy)-5-pyrimidinecarboxamide;

2-((4-(((2-(diethylamino)ethyl)(methyl)amino)carbonyl)phenyl)amino)-N-(2,6-dimethylphenyl)-4-((2-(methyloxy)-4-propylphenyl)oxy)-5-pyrimidinecarboxamide;

2-((4-(((2-(diethylamino)ethyl)(methyl)amino)carbonyl)phenyl)amino)-N-(2,6-dimethylphenyl)-4-((2-(ethyloxy)phenyl)oxy)-5-pyrimidinecarboxamide;

2-((4-((3-(4-(2-(dimethylamino)ethyl)-1-piperazinyl)propyl)oxy)-3-fluorophenyl)amino)-N-(2,6-dimethylphenyl)-4-((2-(ethyloxy)phenyl)oxy)-5-pyrimidinecarboxamide;

2-((4-((3-(4-(2-(dimethylamino)ethyl)-1-piperazinyl)propyl)oxy)-3-fluorophenyl)amino)-N-(2,6-dimethylphenyl)-4-((2-(methyloxy)-4-propylphenyl)oxy)-5-pyrimidinecarboxamide;

2-((4-((3-(diethylamino)propyl)oxy)-3-fluorophenyl)amino)-N-(2,6-dimethylphenyl)-4-(phenyloxy)-5-pyrimidinecarboxamide;

2-((4-(1-(3-(dimethylamino)propyl)-4-piperidinyl)phenyl)amino)-N-(2,6-dimethylphenyl)-4-((2-(methyloxy)-4-propylphenyl)oxy)-5-pyrimidinecarboxamide;

2-((4-(1-(3-(dimethylamino)propyl)-4-piperidinyl)phenyl)amino)-N-(2,6-dimethylphenyl)-4-((2-(ethyloxy)phenyl)oxy)-5-pyrimidinecarboxamide;

2-((4-(2-(diethylamino)ethyl)phenyl)amino)-N-(2,6-dimethylphenyl)-4-((2-(methyloxy)-4-propylphenyl)oxy)-5-pyrimidinecarboxamide;

2-((4-(2-(diethylamino)ethyl)phenyl)amino)-N-(2,6-dimethylphenyl)-4-((2-(ethyloxy)phenyl)oxy)-5-pyrimidinecarboxamide;

2-((4-(4-(2-(dimethylamino)ethyl)-1-piperazinyl)phenyl)amino)-4-((2,2-dimethyl-2,3-dihydro-1-benzofuran-7-yl)oxy)-N-(2,6-dimethylphenyl)-5-pyrimidinecarboxamide;

2-((4-(4-(2-(dimethylamino)ethyl)-1-piperazinyl)phenyl)amino)-N-(2,6-dimethylphenyl)-4-((2-(methyloxy)-4-propylphenyl)oxy)-5-pyrimidinecarboxamide;

2-((4-(4-(2-(dimethylamino)ethyl)-1-piperazinyl)phenyl)amino)-N-(2,6-dimethylphenyl)-4-((2-(trifluoromethyl)phenyl)oxy)-5-pyrimidinecarboxamide;

2-((4-(4-(2-(dimethylamino)ethyl)-1-piperazinyl)phenyl)amino)-N-(2,6-dimethylphenyl)-4-((pentafluorophenyl)oxy)-5-pyrimidinecarboxamide;

2-((4-(4-(2-(dimethylamino)ethyl)-1-piperazinyl)phenyl)amino)-N-(2,6-dimethylphenyl)-4-((2-methyl-1,3-benzothiazol-5-yl)oxy)-5-pyrimidinecarboxamide;

2-((4-(4-(2-(dimethylamino)ethyl)-1-piperazinyl)phenyl)amino)-N-(2,6-dimethylphenyl)-4-((2-(ethyloxy)phenyl)oxy)-5-pyrimidinecarboxamide;

2-((4-(4-(2-amino-2-oxoethyl)-1-piperazinyl)phenyl)amino)-N-(2,6-dimethylphenyl)-4-((2-(methyloxy)-4-propylphenyl)oxy)-5-pyrimidinecarboxamide;

2-((4-(4-(2-amino-2-oxoethyl)-1-piperazinyl)phenyl)amino)-N-(2,6-dimethylphenyl)-4-((2-(ethyloxy)phenyl)oxy)-5-pyrimidinecarboxamide;

2-((4-(4-(2-aminoethyl)-1-piperazinyl)phenyl)amino)-N-(2,6-dimethylphenyl)-4-((2-(methyloxy)-4-propylphenyl)oxy)-5-pyrimidinecarboxamide;

2-((4-(4-(2-aminoethyl)-1-piperazinyl)phenyl)amino)-N-(2,6-dimethylphenyl)-4-((2-(ethyloxy)phenyl)oxy)-5-pyrimidinecarboxamide;

2-((4-(4-(3-(dimethylamino)propyl)-1-piperazinyl)phenyl)amino)-4-((2,2-dimethyl-2,3-dihydro-1-benzofuran-7-yl)oxy)-N-(2,6-dimethylphenyl)-5-pyrimidinecarboxamide;

2-((4-(4-(3-(dimethylamino)propyl)-1-piperazinyl)phenyl)amino)-N-(2,6-dimethylphenyl)-4-((2-(methyloxy)-4-propylphenyl)oxy)-5-pyrimidinecarboxamide;

2-((4-(4-(3-(dimethylamino)propyl)-1-piperazinyl)phenyl)amino)-N-(2,6-dimethylphenyl)-4-((2-(trifluoromethyl)phenyl)oxy)-5-pyrimidinecarboxamide;

2-((4-(4-(3-(dimethylamino)propyl)-1-piperazinyl)phenyl)amino)-N-(2,6-dimethylphenyl)-4-((2-(5-isoxazolyl)phenyl)oxy)-5-pyrimidinecarboxamide;

2-((4-(4-(3-(dimethylamino)propyl)-1-piperazinyl)phenyl)amino)-N-(2,6-dimethylphenyl)-4-((2-(ethyloxy)phenyl)oxy)-5-pyrimidinecarboxamide;

2-(1,3-benzothiazol-6-ylamino)-N-(2,6-dimethylphenyl)-4-((2-(ethyloxy)phenyl)oxy)-5-pyrimidinecarboxamide;

2-(1,3-benzothiazol-6-ylamino)-N-(2,6-dimethylphenyl)-4-((2-(methyloxy)-4-propylphenyl)oxy)-5-pyrimidinecarboxamide;

2,6-dichloro-N-(2-((3-fluoro-4-((3-(4-methyl-1-piperazinyl)propyl)oxy)phenyl)amino)-4-((2-(methyloxy)phenyl)oxy)-5-pyrimidinyl)benzamide;

2,6-dichloro-N-(4-((2-(methyloxy)phenyl)oxy)-2-((4-(4-methyl-1-piperazinyl)phenyl)amino)-5-pyrimidinyl)benzamide;

4-((2-((cyclopropylmethyl)oxy)phenyl)oxy)-N-(2,6-dimethylphenyl)-2-((3-fluoro-4-(4-methyl-1-piperazinyl)phenyl)amino)-5-pyrimidinecarboxamide;

4-((2-((cyclopropylmethyl)oxy)phenyl)oxy)-N-(2,6-dimethylphenyl)-2-((3-fluoro-4-(3-(1-piperidinyl)propyl)oxy)phenyl)amino)-5-pyrimidinecarboxamide;

4-((2-((cyclopropylmethyl)oxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-((cyclopropylmethyl)oxy)phenyl)oxy)-N-(2,6-dimethylphenyl)-2-((4-(4-methyl-1-piperazinyl)phenyl)amino)-5-pyrimidinecarboxamide;

4-((2-((cyclopropylmethyl)oxy)phenyl)oxy)-N-(2,6-dimethylphenyl)-2-((3,4,5-tris(methyloxy)phenyl)amino)-5-pyrimidinecarboxamide;

4-((2-((cyclopropylmethyl)oxy)phenyl)oxy)-N-(2,6-dimethylphenyl)-2-((4-(4-(1-methylethyl)-1-piperazinyl)phenyl)amino)-5-pyrimidinecarboxamide;

4-((2-((dimethylamino)carbonyl)-4-(methyloxy)phenyl)oxy)-N-(2,6-dimethylphenyl)-2-((3,4,5-tris(methyloxy)phenyl)amino)-5-pyrimidinecarboxamide;

4-((2-((dimethylamino)carbonyl)-4-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-((dimethylamino)carbonyl)-4-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-((dimethylamino)carbonyl)-4-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((2-((dimethylamino)carbonyl)-4-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((2-((dimethylamino)carbonyl)phenyl)oxy)-N-(2,6-dimethylphenyl)-2-((3-fluoro-4-(4-methyl-1-piperazinyl)phenyl)amino)-5-pyrimidinecarboxamide;

4-((2-((dimethylamino)carbonyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-((dimethylamino)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-((dimethylamino)carbonyl)phenyl)oxy)-N-(2,6-dimethylphenyl)-2((4-(4-methyl-1-piperazinyl)phenyl)amino)-5-pyrimidinecarboxamide;

4-((2-((dimethylamino)carbonyl)phenyl)oxy)-N-(2,6-dimethylphenyl)-2-((4-(4-(1-methylethyl)-1-piperazinyl)phenyl)amino)-5-pyrimidinecarboxamide;

4-((2-(aminocarbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-(aminocarbonyl)phenyl)oxy)-N-(2,6-dimethylphenyl)-2-((4-(4-methyl-1-piperazinyl)phenyl)amino)-5-pyrimidinecarboxamide;

4-((2-(cyclopentyloxy)phenyl)oxy)-N-(2,6-dimethylphenyl)-2-((3-fluoro-4-(4-methyl-1-piperazinyl)phenyl)amino)-5-pyrimidinecarboxamide;

4-((2-(cyclopentyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-(cyclopentyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-(cyclopentyloxy)phenyl)oxy)-N-(2,6-dimethylphenyl)-2-((4-(4-methyl-1-piperazinyl)phenyl)amino)-5-pyrimidinecarboxamide;

4-((2-(cyclopentyloxy)phenyl)oxy)-N-(2,6-dimethylphenyl)-2-((4-(4-(1-methylethyl)-1-piperazinyl)phenyl)amino)-5-pyrimidinecarboxamide;

4-((2,2-dimethyl-2,3-dihydro-1-benzofuran-7-yl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2,2-dimethyl-2,3-dihydro-1-benzofuran-7-yl)oxy)-N-(2,6-dimethylphenyl)-2-((4-(4-(1-methylethyl)-1-piperazinyl)phenyl)amino)-5-pyrimidinecarboxamide;

4-((2,2-dimethyl-2,3-dihydro-1-benzofuran-7-yl)oxy)-N-(2,6-dimethylphenyl)-2-((4-(4-methyl-1-piperazinyl)phenyl)amino)-5-pyrimidinecarboxamide;

4-((2,2-dimethyl-2,3-dihydro-1-benzofuran-7-yl)oxy)-N-(2,6-dimethylphenyl)-2-((3-fluoro-4-((3-(4-morpholinyl)propyl)oxy)phenyl)amino)-5-pyrimidinecarboxamide;

4-((2,2-dimethyl-2,3-dihydro-1-benzofuran-7-yl)oxy)-N-(2,6-dimethylphenyl)-2-((3-(methyloxy)-4-(4-methyl-1-piperazinyl)phenyl)amino)-5-pyrimidinecarboxamide;

4-((2,2-dimethyl-2,3-dihydro-1-benzofuran-7-yl)oxy)-N-(2,6-dimethylphenyl)-2-((3-fluoro-4-((3-(1-piperidinyl)propyl)oxy)phenyl)amino)-5-pyrimidinecarboxamide;

4-((2,2-dimethyl-2,3-dihydro-1-benzofuran-7-yl)oxy)-N-(2,6-dimethylphenyl)-2-((3-fluoro-4-(4-methyl-1-piperazinyl)phenyl)amino)-5-pyrimidinecarboxamide;

4-((2,3-dichlorophenyl)oxy)-N-(2,6-dimethylphenyl)-2-((4-(4-(1-methylethyl)-1-piperazinyl)phenyl)amino)-5-pyrimidinecarboxamide;

4-((2,4-dichlorophenyl)oxy)-N-(2,6-dimethylphenyl)-2-((3-(methyloxy)-4-(4-methyl-1-piperazinyl)phenyl)amino)-5-pyrimidinecarboxamide;

4-((2,4-dichlorophenyl)oxy)-N-(2,6-dimethylphenyl)-2-((3-fluoro-4-(4-methyl-1-piperazinyl)phenyl)amino)-5-pyrimidinecarboxamide;

4-((2,4-dichlorophenyl)oxy)-N-(2,6-dimethylphenyl)-2-((3-fluoro-4-((3-(1-piperidinyl)propyl)oxy)phenyl)amino)-5-pyrimidinecarboxamide;

4-((2,4-dichlorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2,4-dichlorophenyl)oxy)-N-(2,6-dimethylphenyl)-2-((4-(4-(1-methylethyl)-1-piperazinyl)phenyl)amino)-5-pyrimidinecarboxamide;

4-((2,4-dichlorophenyl)oxy)-N-(2,6-dimethylphenyl)-2-((4-(4-methyl-1-piperazinyl)phenyl)amino)-5-pyrimidinecarboxamide;

4-((2,6-bis(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((2,6-bis(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2,6-bis(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2,6-bis(methyloxy)phenyl)oxy)-N-(2,6-dimethylphenyl)-2-((4-(4-(1-methylethyl)-1-piperazinyl)phenyl)amino)-5-pyrimidinecarboxamide;

4-((2,6-bis(methyloxy)phenyl)oxy)-N-(2,6-dimethylphenyl)-2-((4-(4-methyl-1-piperazinyl)phenyl)amino)-5-pyrimidinecarboxamide;

4-((2-chloro-4-((diethylamino)carbonyl)phenyl)oxy)-2-((4-(4-(2-(dimethylamino)ethyl)-1-piperazinyl)phenyl)amino)-N-(2,6-dimethylphenyl)-5-pyrimidinecarboxamide;

4-((2-chloro-4-((diethylamino)carbonyl)phenyl)oxy)-2-((4-(4-(3-(dimethylamino)propyl)-1-piperazinyl)phenyl)amino)-N-(2,6-dimethylphenyl)-5-pyrimidinecarboxamide;

4-((2-chloro-4-((diethylamino)carbonyl)phenyl)oxy)-N-(2,6-dimethylphenyl)-2-((4-(4-methyl-1-piperazinyl)phenyl)amino)-5-pyrimidinecarboxamide;

4-((2-chloro-4-((diethylamino)carbonyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-((diethylamino)carbonyl)phenyl)oxy)-N-(2,6-dimethylphenyl)-2-((4-(4-(1-methylethyl)-1-piperazinyl)phenyl)amino)-5-pyrimidinecarboxamide;

4-((2-chloro-4-((diethylamino)carbonyl)phenyl)oxy)-N-(2,6-dimethylphenyl)-2-((3-fluoro-4-(4-methyl-1-piperazinyl)phenyl)amino)-5-pyrimidinecarboxamide;

4-((2-chloro-4-((diethylamino)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-(trifluoromethyl)phenyl)oxy)-2-((4-(4-(3-(dimethylamino)propyl)-1-piperazinyl)phenyl)amino)-N-(2,6-dimethylphenyl)-5-pyrimidinecarboxamide;

4-((2-chloro-4-(trifluoromethyl)phenyl)oxy)-N-(2,6-dimethylphenyl)-2-((4-(4-(1-methylethyl)-1-piperazinyl)phenyl)amino)-5-pyrimidinecarboxamide;

4-((2-chloro-4-(trifluoromethyl)phenyl)oxy)-N-(2,6-dimethylphenyl)-2-((3-fluoro-4-(4-methyl-1-piperazinyl)phenyl)amino)-5-pyrimidinecarboxamide;

4-((2-chloro-4-(trifluoromethyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-(trifluoromethyl)phenyl)oxy)-N-(2,6-dimethylphenyl)-2-((4-(4-methyl-1-piperazinyl)phenyl)amino)-5-pyrimidinecarboxamide;

4-((2-chloro-4-fluorophenyl)oxy)-2-((4-(4-(2-(dimethylamino)ethyl)-1-piperazinyl)phenyl)amino)-N-(2,6-dimethylphenyl)-5-pyrimidinecarboxamide;

4-((2-chloro-4-fluorophenyl)oxy)-2-((4-(4-(3-(dimethylamino)propyl)-1-piperazinyl)phenyl)amino)-N-(2,6-dimethylphenyl)-5-pyrimidinecarboxamide;

4-((2-chloro-4-fluorophenyl)oxy)-N-(2,6-dimethylphenyl)-2-((3-fluoro-4-(4-methyl-1-piperazinyl)phenyl)amino)-5-pyrimidinecarboxamide;

4-((2-chloro-4-fluorophenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-fluorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-fluorophenyl)oxy)-N-(2,6-dimethylphenyl)-2-((4-(4-(1-methylethyl)-1-piperazinyl)phenyl)amino)-5-pyrimidinecarboxamide;

4-((2-chloro-4-fluorophenyl)oxy)-N-(2,6-dimethylphenyl)-2-((4-(4-methyl-1-piperazinyl)phenyl)amino)-5-pyrimidinecarboxamide;

4-((2-chloro-4-methylphenyl)oxy)-2-((4-(4-(3-(dimethylamino)propyl)-1-piperazinyl)phenyl)amino)-N-(2,6-dimethylphenyl)-5-pyrimidinecarboxamide;

4-((2-chloro-4-methylphenyl)oxy)-N-(2,6-dimethylphenyl)-2-((3-fluoro-4-(4-methyl-1-piperazinyl)phenyl)amino)-5-pyrimidinecarboxamide;

4-((2-chloro-4-methylphenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-methylphenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-methylphenyl)oxy)-N-(2,6-dimethylphenyl)-2-((4-(4-(1-methylethyl)-1-piperazinyl)phenyl)amino)-5-pyrimidinecarboxamide;

4-((2-chloro-4-methylphenyl)oxy)-N-(2,6-dimethylphenyl)-2-((4-(4-methyl-1-piperazinyl)phenyl)amino)-5-pyrimidinecarboxamide;

4-((2-chlorophenyl)oxy)-N-(2,6-dimethylphenyl)-2-((3-(methyloxy)-4-(4-methyl-1-piperazinyl)phenyl)amino)-5-pyrimidinecarboxamide;

4-((2-chlorophenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chlorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chlorophenyl)oxy)-N-(2,6-dimethylphenyl)-2-((3-fluoro-4-(4-methyl-1-piperazinyl)phenyl)amino)-5-pyrimidinecarboxamide;

4-((2-chlorophenyl)oxy)-N-(2,6-dimethylphenyl)-2-((4-(4-(1-methylethyl)-1-piperazinyl)phenyl)amino)-5-pyrimidinecarboxamide;

4-((2-chlorophenyl)oxy)-N-(2,6-dimethylphenyl)-2-((4-(4-methyl-1-piperazinyl)phenyl)amino)-5-pyrimidinecarboxamide;

4-((3-(2-(diethylamino)ethyl)phenyl)oxy)-N-(2,6-dimethylphenyl)-2-((4-(4-methyl-1-piperazinyl)phenyl)amino)-5-pyrimidinecarboxamide;

4-((3-(2-(diethylamino)ethyl)phenyl)oxy)-N-(2,6-dimethylphenyl)-2-((3-(methyloxy)-4-(4-methyl-1-piperazinyl)phenyl)amino)-5-pyrimidinecarboxamide;

4-((3-(2-(diethylamino)ethyl)phenyl)oxy)-N-(2,6-dimethylphenyl)-2-((4-(1-piperazinyl)phenyl)amino)-5-pyrimidinecarboxamide;

4-((3-(2-aminoethyl)phenyl)oxy)-N-(2,6-dichlorophenyl)-2-(phenylamino)-5-pyrimidinecarboxamide;

4-((3-(2-aminoethyl)phenyl)oxy)-N-(2,6-dimethylphenyl)-2-(phenylamino)-5-pyrimidinecarboxamide;

4-((3-(3-(diethylamino)-3-oxopropyl)phenyl)oxy)-N-(2,6-dimethylphenyl)-2-((4-(4-methyl-1-piperazinyl)phenyl)amino)-5-pyrimidinecarboxamide;

4-((3-(3-(diethylamino)-3-oxopropyl)phenyl)oxy)-N-(2,6-dimethylphenyl)-2-((4-(((2R)-2-pyrrolidinylmethyl)oxy)phenyl)amino)-5-pyrimidinecarboxamide;

4-((3-(3-(diethylamino)-3-oxopropyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((3-(3-(diethylamino)-3-oxopropyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((3-(3-(diethylamino)-3-oxopropyl)phenyl)oxy)-N-(2,6-dimethylphenyl)-2-((3-fluoro-4-(4-methyl-1-piperazinyl)phenyl)amino)-5-pyrimidinecarboxamide;

4-((3-(3-(diethylamino)-3-oxopropyl)phenyl)oxy)-N-(2,6-dimethylphenyl)-2-((3-(methyloxy)-4-(4-methyl-1-piperazinyl)phenyl)amino)-5-pyrimidinecarboxamide;

4-((3-(3-amino-3-oxopropyl)phenyl)oxy)-2-((3-chloro-4-(4-(1-methylethyl)-1-piperazinyl)phenyl)amino)-N-(2,6-dimethylphenyl)-5-pyrimidinecarboxamide;

4-((3-(3-amino-3-oxopropyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((3-(3-amino-3-oxopropyl)phenyl)oxy)-N-(2,6-dimethylphenyl)-2-((4-(4-(1-methylethyl)-1-piperazinyl)phenyl)amino)-5-pyrimidinecarboxamide;

4-((3-(3-amino-3-oxopropyl)phenyl)oxy)-N-(2,6-dimethylphenyl)-2-((3-fluoro-4-(4-methyl-1-piperazinyl)phenyl)amino)-5-pyrimidinecarboxamide;

4-((3-(3-amino-3-oxopropyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((3-(3-amino-3-oxopropyl)phenyl)oxy)-N-(2,6-dimethylphenyl)-2-((4-(4-methyl-1-piperazinyl)phenyl)amino)-5-pyrimidinecarboxamide;

4-((3-(3-amino-3-oxopropyl)phenyl)oxy)-N-(2,6-dimethylphenyl)-2-((3,4,5-tris(methyloxy)phenyl)amino)-5-pyrimidinecarboxamide;

4-((3,3'-bis(methyloxy)-1,1'-biphenyl-4-yl)oxy)-N-(2,6-dimethylphenyl)-2-((3,4,5-tris(methyloxy)phenyl)amino)-5-pyrimidinecarboxamide;

4-((3,4'-bis(methyloxy)-1,1'-biphenyl-4-yl)oxy)-N-(2,6-dimethylphenyl)-2-((3,4,5-tris(methyloxy)phenyl)amino)-5-pyrimidinecarboxamide;

4-((3,4'-bis(methyloxy)-1,1'-biphenyl-4-yl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((3,4-dichlorophenyl)oxy)-N-(2,6-dimethylphenyl)-2-((3-(methyloxy)-4-(4-methyl-1-piperazinyl)phenyl)amino)-5-pyrimidinecarboxamide;

4-((3,4-dichlorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((3,4-dichlorophenyl)oxy)-N-(2,6-dimethylphenyl)-2-((3-fluoro-4-(4-methyl-1-piperazinyl)phenyl)amino)-5-pyrimidinecarboxamide;

4-((3,4-dichlorophenyl)oxy)-N-(2,6-dimethylphenyl)-2-((3-fluoro-4-((3-(1-piperidinyl)propyl)oxy)phenyl)amino)-5-pyrimidinecarboxamide;

4-((3,4-dichlorophenyl)oxy)-N-(2,6-dimethylphenyl)-2-((4-(((2S)-2-pyrrolidinylmethyl)oxy)phenyl)amino)-5-pyrimidinecarboxamide;

4-((3,4-dichlorophenyl)oxy)-N-(2,6-dimethylphenyl)-2-((4-(4-(1-methylethyl)-1-piperazinyl)phenyl)amino)-5-pyrimidinecarboxamide;

4-((3,4-dichlorophenyl)oxy)-N-(2,6-dimethylphenyl)-2-((4-(4-methyl-1-piperazinyl)phenyl)amino)-5-pyrimidinecarboxamide;

4-((3'-chloro-3-(methyloxy)-1,1'-biphenyl-4-yl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((3-chlorophenyl)oxy)-N-(2,6-dimethylphenyl)-2-((3-(methyloxy)-4-(4-methyl-1-piperazinyl)phenyl)amino)-5-pyrimidinecarboxamide;

4-((3-chlorophenyl)oxy)-N-(2,6-dimethylphenyl)-2-((3-fluoro-4-((3-(1-piperidinyl)propyl)oxy)phenyl)amino)-5-pyrimidinecarboxamide;

4-((3-chlorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((3-chlorophenyl)oxy)-N-(2,6-dimethylphenyl)-2-((3-fluoro-4-(4-methyl-1-piperazinyl)phenyl)amino)-5-pyrimidinecarboxamide;

4-((3-chlorophenyl)oxy)-N-(2,6-dimethylphenyl)-2-((4-(4-(1-methylethyl)-1-piperazinyl)phenyl)amino)-5-pyrimidinecarboxamide;

4-((3-chlorophenyl)oxy)-N-(2,6-dimethylphenyl)-2-((4-(4-methyl-1-piperazinyl)phenyl)amino)-5-pyrimidinecarboxamide;

4-((3'-cyano-3-(methyloxy)-1,1'-biphenyl-4-yl)oxy)-N-(2,6-dimethylphenyl)-2-((3,4,5-tris(methyloxy)phenyl)amino)-5-pyrimidinecarboxamide;

4-((4-((1E)-3-(diethylamino)-3-oxo-1-propenyl)-2-(methyloxy)phenyl)oxy)-N-(2,6-dimethylphenyl)-2-((3,4,5-tris(methyloxy)phenyl)amino)-5-pyrimidinecarboxamide;

4-((4-((1E)-3-(diethylamino)-3-oxo-1-propenyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((4-((1E)-3-(diethylamino)-3-oxo-1-propenyl)-2-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((4-((1E)-3-(diethylamino)-3-oxo-1-propenyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-((1E)-3-(diethylamino)-3-oxo-1-propenyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-((1E)-3-(diethylamino)-3-oxo-1-propenyl)-2-(methyloxy)phenyl)oxy)-N-(2,6-dimethylphenyl)-2-((4-(4-methyl-1-piperazinyl)phenyl)amino)-5-pyrimidinecarboxamide;

4-((4-((2-(diethylamino)ethyl)oxy)phenyl)oxy)-N-(2,6-dimethylphenyl)-2-((4-(4-methyl-1-piperazinyl)phenyl)amino)-5-pyrimidinecarboxamide;

4-((4-((diethylamino)carbonyl)-2-(methyloxy)phenyl)oxy)-2-((4-(4-(3-(dimethylamino)propyl)-1-piperazinyl)phenyl)amino)-N-(2,6-dimethylphenyl)-5-pyrimidinecarboxamide;

4-((4-((diethylamino)carbonyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((4-((diethylamino)carbonyl)-2-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((4-((diethylamino)carbonyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-((diethylamino)carbonyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-((diethylamino)carbonyl)-2-(methyloxy)phenyl)oxy)-N-(2,6-dimethylphenyl)-2-((4-(4-methyl-1-piperazinyl)phenyl)amino)-5-pyrimidinecarboxamide;

4-((4-(1,3-benzodioxol-5-yl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-(1,3-benzodioxol-5-yl)-2-(methyloxy)phenyl)oxy)-N-(2,6-dimethylphenyl)-2-((3,4,5-tris(methyloxy)phenyl)amino)-5-pyrimidinecarboxamide;

4-((4-(2-aminoethyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-(2-aminoethyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-(2-aminoethyl)-2-(methyloxy)phenyl)oxy)-N-(2,6-dimethylphenyl)-2-((3-(methyloxy)-4-(4-methyl-1-piperazinyl)phenyl)amino)-5-pyrimidinecarboxamide;

4-((4-(2-aminoethyl)-2-(methyloxy)phenyl)oxy)-N-(2,6-dimethylphenyl)-2-((4-(4-methyl-1-piperazinyl)phenyl)amino)-5-pyrimidinecarboxamide;

4-((4-(2-aminoethyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((4-(2-aminoethyl)-2-(methyloxy)phenyl)oxy)-N-(2,6-dimethylphenyl)-2-((3,4,5-tris(methyloxy)phenyl)amino)-5-pyrimidinecarboxamide;

4-((4-(2-aminoethyl)-2,6-bis(methyloxy)phenyl)oxy)-2-((4-(4-(2-(dimethylamino)ethyl)-1-piperazinyl)phenyl)amino)-N-(2,6-dimethylphenyl)-5-pyrimidinecarboxamide;

4-((4-(2-aminoethyl)-2,6-bis(methyloxy)phenyl)oxy)-N-(2,6-dimethylphenyl)-2-((4-(4-(1-methylethyl)-1-piperazinyl)phenyl)amino)-5-pyrimidinecarboxamide;

4-((4-(2-aminoethyl)-2,6-bis(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((4-(2-aminoethyl)-2,6-bis(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-(2-aminoethyl)-2,6-bis(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-(2-aminoethyl)-2,6-bis(methyloxy)phenyl)oxy)-N-(2,6-dimethylphenyl)-2-((4-(4-methyl-1-piperazinyl)phenyl)amino)-5-pyrimidinecarboxamide;

4-((4-(2-aminoethyl)phenyl)oxy)-N-(2,6-dimethylphenyl)-2-((4-(1-piperazinyl)phenyl)amino)-5-pyrimidinecarboxamide;

4-((4-(2-aminoethyl)phenyl)oxy)-N-(2,6-dimethylphenyl)-2-((4-(4-methyl-1-piperazinyl)phenyl)amino)-5-pyrimidinecarboxamide;

4-(4-(3-(diethylamino)-3-oxopropyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-(4-(3-(diethylamino)-3-oxopropyl)-2-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-(4-(3-(diethylamino)-3-oxopropyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-(4-(3-(diethylamino)-3-oxopropyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-(4-(3-(diethylamino)-3-oxopropyl)-2-(methyloxy)phenyl)oxy)-N-(2,6-dimethylphenyl)-2-((4-(4-methyl-1-piperazinyl)phenyl)amino)-5-pyrimidinecarboxamide;

4-((4-(3-(diethylamino)propyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((4-(3-(diethylamino)propyl)-2-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((4-(acetylamino)phenyl)oxy)-N-(2,6-dimethylphenyl)-2-((3-(methyloxy)-4-(4-methyl-1-piperazinyl)phenyl)amino)-5-pyrimidinecarboxamide;

4-((4-(acetylamino)phenyl)oxy)-N-(2,6-dimethylphenyl)-2-((4-(1-piperazinyl)phenyl)amino)-5-pyrimidinecarboxamide;

4-((4-(acetylamino)phenyl)oxy)-N-(2,6-dimethylphenyl)-2-((4-(4-methyl-1-piperazinyl)phenyl)amino)-5-pyrimidinecarboxamide;

4-((4-(aminocarbonyl)phenyl)oxy)-N-(2,6-dimethylphenyl)-2-((3-fluoro-4-(4-methyl-1-piperazinyl)phenyl)amino)-5-pyrimidinecarboxamide;

4-((4-(aminocarbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-(aminocarbonyl)phenyl)oxy)-N-(2,6-dimethylphenyl)-2-((4-(4-(1-methylethyl)-1-piperazinyl)phenyl)amino)-5-pyrimidinecarboxamide;

4-((4-(aminocarbonyl)phenyl)oxy)-N-(2,6-dimethylphenyl)-2-((4-(4-methyl-1-piperazinyl)phenyl)amino)-5-pyrimidinecarboxamide;

4-((4'-(dimethylamino)-3-(methyloxy)-1,1'-biphenyl-4-yl)oxy)-N-(2,6-dimethylphenyl)-2-((3,4,5-tris(methyloxy)phenyl)amino)-5-pyrimidinecarboxamide;

4-((4-bromo-2-(methyloxy)phenyl)oxy)-2-((3-chloro-4-(1-methylethyl)-1-piperazinyl)phenyl)amino)-N-(2,6-dimethylphenyl)-5-pyrimidinecarboxamide;

4-((4-bromo-2-(methyloxy)phenyl)oxy)-2-((4-(4-(2-(dimethylamino)ethyl)-1-piperazinyl)phenyl)amino)-N-(2,6-dimethylphenyl)-5-pyrimidinecarboxamide;

4-((4-bromo-2-(methyloxy)phenyl)oxy)-2-((4-(4-(3-(dimethylamino)propyl)-1-piperazinyl)phenyl)amino)-N-(2,6-dimethylphenyl)-5-pyrimidinecarboxamide;

4-((4-bromo-2-(methyloxy)phenyl)oxy)-N-(2,6-dimethylphenyl)-2-((3,4,5-tris(methyloxy)phenyl)amino)-5-pyrimidinecarboxamide;

4-((4-bromo-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-bromo-2-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((4-bromo-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-bromo-2-(methyloxy)phenyl)oxy)-N-(2,6-dimethylphenyl)-2-((4-(4-methyl-1-piperazinyl)phenyl)amino)-5-pyrimidinecarboxamide;

4-((4-bromo-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((4-bromo-2-chlorophenyl)oxy)-2-((4-(4-(2-(dimethylamino)ethyl)-1-piperazinyl)phenyl)amino)-N-(2,6-dimethylphenyl)-5-pyrimidinecarboxamide;

4-((4-bromo-2-chlorophenyl)oxy)-2-((4-(4-(3-(dimethylamino)propyl)-1-piperazinyl)phenyl)amino)-N-(2,6-dimethylphenyl)-5-pyrimidinecarboxamide;

4-((4-bromo-2-chlorophenyl)oxy)-N-(2,6-dimethylphenyl)-2-((3-fluoro-4-(4-methyl-1-piperazinyl)phenyl)amino)-5-pyrimidinecarboxamide;

4-((4-bromo-2-chlorophenyl)oxy)-N-(2,6-dimethylphenyl)-2-((3-fluoro-4-((3-(1-piperidinyl)propyl)oxy)phenyl)amino)-5-pyrimidinecarboxamide;

4-((4-bromo-2-chlorophenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-bromo-2-chlorophenyl)oxy)-N-(2,6-dimethylphenyl)-2-((4-(4-(1-methylethyl)-1-piperazinyl)phenyl)amino)-5-pyrimidinecarboxamide;

4-((4-bromo-2-chlorophenyl)oxy)-N-(2,6-dimethylphenyl)-2-((4-(4-methyl-1-piperazinyl)phenyl)amino)-5-pyrimidinecarboxamide;

4-((4-chloro-2-(methyloxy)phenyl)oxy)-N-(2,6-dimethylphenyl)-2-((3-(methyloxy)-4-(4-methyl-1-piperazinyl)phenyl)amino)-5-pyrimidinecarboxamide;

4-((4-chloro-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-chloro-2-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((4-chloro-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((4-chloro-2-(methyloxy)phenyl)oxy)-N-(2,6-dimethylphenyl)-2-((4-(4-methyl-1-piperazinyl)phenyl)amino)-5-pyrimidinecarboxamide;

4-((4'-chloro-3-(methyloxy)-1,1'-biphenyl-4-yl)oxy)-N-(2,6-dimethylphenyl)-2-((3,4,5-tris(methyloxy)phenyl)amino)-5-pyrimidinecarboxamide;

4-((4'-chloro-3-(methyloxy)-1,1'-biphenyl-4-yl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-chlorophenyl)oxy)-N-(2,6-dimethylphenyl)-2-((4-(1-piperazinyl)phenyl)amino)-5-pyrimidinecarboxamide;

4-((4-chlorophenyl)oxy)-N-(2,6-dimethylphenyl)-2-((4-(4-(1-methylethyl)-1-piperazinyl)phenyl)amino)-5-pyrimidinecarboxamide;

4-((4-chlorophenyl)oxy)-N-(2,6-dimethylphenyl)-2-((4-(4-methyl-1-piperazinyl)phenyl)amino)-5-pyrimidinecarboxamide;

4-((5-((1E)-3-(diethylamino)-3-oxo-1-propenyl)-2-(methyloxy)phenyl)oxy)-2-((4-(4-(2-(dimethylamino)ethyl)-1-piperazinyl)phenyl)amino)-N-(2,6-dimethylphenyl)-5-pyrimidinecarboxamide;

4-((5-((1E)-3-(diethylamino)-3-oxo-1-propenyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((5-((1E)-3-(diethylamino)-3-oxo-1-propenyl)-2-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((5-((1E)-3-(diethylamino)-3-oxo-1-propenyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((5-((1E)-3-(diethylamino)-3-oxo-1-propenyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((5-((1E)-3-(diethylamino)-3-oxo-1-propenyl)-2-(methyloxy)phenyl)oxy)-N-(2,6-dimethylphenyl)-2-((4-(4-methyl-1-piperazinyl)phenyl)amino)-5-pyrimidinecarboxamide;

4-((5-(3-(diethylamino)-3-oxopropyl)-2-(methyloxy)phenyl)oxy)-2-((4-(4-(2-(dimethylamino)ethyl)-1-piperazinyl)phenyl)amino)-N-(2,6-dimethylphenyl)-5-pyrimidinecarboxamide;

4-((5-(3-(diethylamino)-3-oxopropyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((5-(3-(diethylamino)-3-oxopropyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((5-(3-(diethylamino)-3-oxopropyl)-2-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((5-(3-(diethylamino)-3-oxopropyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((5-(3-(diethylamino)-3-oxopropyl)-2-(methyloxy)phenyl)oxy)-N-(2,6-dimethylphenyl)-2-((4-(4-methyl-1-piperazinyl)phenyl)amino)-5-pyrimidinecarboxamide;

4-(1,3-benzodioxol-5-yloxy)-2-((3,5-bis(methyloxy)-4-((3-(4-methyl-1-piperazinyl)propyl)oxy)phenyl)amino)-N-(2,6-dimethylphenyl)-5-pyrimidinecarboxamide;

4-(1,3-benzodioxol-5-yloxy)-N-(2,6-dimethylphenyl)-2-((3-fluoro-4-(4-methyl-1-piperazinyl)phenyl)amino)-5-pyrimidinecarboxamide;

4-(1,3-benzodioxol-5-yloxy)-N-(2,6-dimethylphenyl)-2-((4-(((2R)-2-pyrrolidinylmethyl)oxy)phenyl)amino)-5-pyrimidinecarboxamide;

4-(1,3-benzodioxol-5-yloxy)-N-(2,6-dimethylphenyl)-2-((4-(4-methyl-1-piperazinyl)phenyl)amino)-5-pyrimidinecarboxamide;

N-(2,6-dichlorophenyl)-2-((3-(methyloxy)-4-((2-(4-methyl-1-piperazinyl)ethyl)oxy)phenyl)amino)-4-((2-(methyloxy)phenyl)oxy)-5-pyrimidinecarboxamide;

N-(2,6-dichlorophenyl)-2-((3-(methyloxy)-4-((3-(4-methyl-1-piperazinyl)propyl)oxy)phenyl)amino)-4-((2-(methyloxy)phenyl)oxy)-5-pyrimidinecarboxamide;

N-(2,6-dichlorophenyl)-2-((3-(methyloxy)-4-((3-(4-methyl-1-piperazinyl)propyl)oxy)phenyl)amino)-4-((3-(methyloxy)phenyl)oxy)-5-pyrimidinecarboxamide;

N-(2,6-dichlorophenyl)-2-((3-(methyloxy)-4-((3-(4-methyl-1-piperazinyl)propyl)oxy)phenyl)amino)-4-((4-(1-piperazinyl)phenyl)oxy)-5-pyrimidinecarboxamide;

N-(2,6-dichlorophenyl)-2-((3-(methyloxy)-4-(4-methyl-1-piperazinyl)phenyl)amino)-4-(2-naphthalenyloxy)-5-pyrimidinecarboxamide;

N-(2,6-dichlorophenyl)-2-((3-(methyloxy)-4-(4-methyl-1-piperazinyl)phenyl)amino)-4-((2-(methyloxy)phenyl)oxy)-5-pyrimidinecarboxamide;

N-(2,6-dichlorophenyl)-2-((3-fluoro-4-((3-(1-piperidinyl)propyl)oxy)phenyl)amino)-4-(phenyloxy)-5-pyrimidinecarboxamide;

N-(2,6-dichlorophenyl)-2-((3-fluoro-4-((3-(1-piperidinyl)propyl)oxy)phenyl)amino)-4-(2-naphthalenyloxy)-5-pyrimidinecarboxamide;

N-(2,6-dichlorophenyl)-2-((3-fluoro-4-((3-(1-piperidinyl)propyl)oxy)phenyl)amino)-4-((4-(1-piperazinyl)phenyl)oxy)-5-pyrimidinecarboxamide;

N-(2,6-dichlorophenyl)-2-((3-fluoro-4-((3-(1-piperidinyl)propyl)oxy)phenyl)amino)-4-((2-(methyloxy)phenyl)oxy)-5-pyrimidinecarboxamide;

N-(2,6-dichlorophenyl)-2-((3-fluoro-4-((3-(4-methyl-1-piperazinyl)propyl)oxy)phenyl)amino)-4-(phenyloxy)-5-pyrimidinecarboxamide;

N-(2,6-dichlorophenyl)-2-((3-fluoro-4-((3-(4-methyl-1-piperazinyl)propyl)oxy)phenyl)amino)-4-((4-(1-piperazinyl)phenyl)oxy)-5-pyrimidinecarboxamide;

N-(2,6-dichlorophenyl)-2-((3-fluoro-4-((3-(4-methyl-1-piperazinyl)propyl)oxy)phenyl)amino)-4-(2-naphthalenyloxy)-5-pyrimidinecarboxamide;

N-(2,6-dichlorophenyl)-2-((3-fluoro-4-((3-(4-methyl-1-piperazinyl)propyl)oxy)phenyl)amino)-4-((3-(methyloxy)phenyl)oxy)-5-pyrimidinecarboxamide;

N-(2,6-dichlorophenyl)-2-((3-fluoro-4-((3-(4-methyl-1-piperazinyl)propyl)oxy)phenyl)amino)-4-((2-(methyloxy)phenyl)oxy)-5-pyrimidinecarboxamide;

N-(2,6-dichlorophenyl)-2-((3-fluoro-4-(4-methyl-1-piperazinyl)phenyl)amino)-4-((4-(1-piperazinyl)phenyl)oxy)-5-pyrimidinecarboxamide;

N-(2,6-dichlorophenyl)-2-((3-fluoro-4-(4-methyl-1-piperazinyl)phenyl)amino)-4-(phenyloxy)-5-pyrimidinecarboxamide;

N-(2,6-dichlorophenyl)-2-((3-fluoro-4-(4-methyl-1-piperazinyl)phenyl)amino)-4-(2-naphthalenyloxy)-5-pyrimidinecarboxamide;

N-(2,6-dichlorophenyl)-2-((3-fluoro-4-(4-methyl-1-piperazinyl)phenyl)amino)-4-((3-(methyloxy)phenyl)oxy)-5-pyrimidinecarboxamide;

N-(2,6-dichlorophenyl)-2-((3-fluoro-4-(4-methyl-1-piperazinyl)phenyl)amino)-4-((2-(methyloxy)phenyl)oxy)-5-pyrimidinecarboxamide;

N-(2,6-dichlorophenyl)-2-((4-((3-(diethylamino)propyl)oxy)-3-fluorophenyl)amino)-4-(phenyloxy)-5-pyrimidinecarboxamide;

N-(2,6-dichlorophenyl)-2-((4-(4-(1-methylethyl)-1-piperazinyl)phenyl)amino)-4-((4-(1-piperazinyl)phenyl)oxy)-5-pyrimidinecarboxamide;

N-(2,6-dichlorophenyl)-2-((4-(4-(1-methylethyl)-1-piperazinyl)phenyl)amino)-4-((2-(methyloxy)phenyl)oxy)-5-pyrimidinecarboxamide;

N-(2,6-dichlorophenyl)-2-((4-(4-(1-methylethyl)-1-piperazinyl)phenyl)amino)-4-(phenyloxy)-5-pyrimidinecarboxamide;

N-(2,6-dichlorophenyl)-2-((4-(4-(1-methylethyl)-1-piperazinyl)phenyl)amino)-4-((3-(methyloxy)phenyl)oxy)-5-pyrimidinecarboxamide;

N-(2,6-dichlorophenyl)-2-((4-(4-methyl-1-piperazinyl)phenyl)amino)-4-(2-naphthalenyloxy)-5-pyrimidinecarboxamide;

N-(2,6-dichlorophenyl)-2-((4-(4-methyl-1-piperazinyl)phenyl)amino)-4-(phenyloxy)-5-pyrimidinecarboxamide;

N-(2,6-dichlorophenyl)-4-((2-(methyloxy)phenyl)oxy)-2-((4-(4-methyl-1-piperazinyl)phenyl)amino)-5-pyrimidinecarboxamide;

N-(2,6-dichlorophenyl)-4-((2-fluorophenyl)oxy)-2-((3-(methyloxy)-4-(4-methyl-1-piperazinyl)phenyl)amino)-5-pyrimidinecarboxamide;

N-(2,6-dichlorophenyl)-4-((2-fluorophenyl)oxy)-2-((3-(methyloxy)-4-((3-(4-methyl-1-piperazinyl)propyl)oxy)phenyl)amino)-5-pyrimidinecarboxamide;

N-(2,6-dichlorophenyl)-4-((2-fluorophenyl)oxy)-2-((4-(4-methyl-1-piperazinyl)phenyl)amino)-5-pyrimidinecarboxamide;

N-(2,6-dichlorophenyl)-4-((4-(1-piperazinyl)phenyl)oxy)-2-((3,4,5-tris(methyloxy)phenyl)amino)-5-pyrimidinecarboxamide;

N-(2,6-dimethylphenyl)-2-((3-(methyloxy)-4-(((4-methyl-1-piperazinyl)acetyl)amino)phenyl)amino)-4-((2-(methyloxy)-4-propylphenyl)oxy)-5-pyrimidinecarboxamide;

N-(2,6-dimethylphenyl)-2-((3-(methyloxy)-4-((2-(4-methyl-1-piperazinyl)ethyl)oxy)phenyl)amino)-4-(phenyloxy)-5-pyrimidinecarboxamide;

N-(2,6-dimethylphenyl)-2-((3-(methyloxy)-4-((2-(4-methyl-1-piperazinyl)ethyl)oxy)phenyl)amino)-4-((2-(methyloxy)phenyl)oxy)-5-pyrimidinecarboxamide;

N-(2,6-dimethylphenyl)-2-((3-(methyloxy)-4-((2-(4-methyl-1-piperazinyl)ethyl)oxy)phenyl)amino)-4-((4-(1-piperazinyl)phenyl)oxy)-5-pyrimidinecarboxamide;

N-(2,6-dimethylphenyl)-2-((3-(methyloxy)-4-((3-(4-methyl-1-piperazinyl)propyl)oxy)phenyl)amino)-4-(phenyloxy)-5-pyrimidinecarboxamide;

N-(2,6-dimethylphenyl)-2-((3-(methyloxy)-4-((3-(4-methyl-1-piperazinyl)propyl)oxy)phenyl)amino)-4-((2-((trifluoromethyl)oxy)phenyl)oxy)-5-pyrimidinecarboxamide;

N-(2,6-dimethylphenyl)-2-((3-(methyloxy)-4-((3-(4-methyl-1-piperazinyl)propyl)oxy)phenyl)amino)-4-((3-(methyloxy)phenyl)oxy)-5-pyrimidinecarboxamide;

N-(2,6-dimethylphenyl)-2-((3-(methyloxy)-4-((3-(4-methyl-1-piperazinyl)propyl)oxy)phenyl)amino)-4-((4-(1-piperazinyl)phenyl)oxy)-5-pyrimidinecarboxamide;

N-(2,6-dimethylphenyl)-2-((3-(methyloxy)-4-((3-(4-methyl-1-piperazinyl)propyl)oxy)phenyl)amino)-4-((2-(methyloxy)phenyl)oxy)-5-pyrimidinecarboxamide;

N-(2,6-dimethylphenyl)-2-((3-(methyloxy)-4-(1-piperazinyl)phenyl)amino)-4-((2-(methyloxy)-4-propylphenyl)oxy)-5-pyrimidinecarboxamide;

N-(2,6-dimethylphenyl)-2-((3-(methyloxy)-4-(4-methyl-1-piperazinyl)phenyl)amino)-4-((2-(methyloxy)phenyl)oxy)-5-pyrimidinecarboxamide;

N-(2,6-dimethylphenyl)-2-((3-(methyloxy)-4-(4-methyl-1-piperazinyl)phenyl)amino)-4-((2-(methyloxy)-4-propylphenyl)oxy)-5-pyrimidinecarboxamide;

N-(2,6-dimethylphenyl)-2-((3-(methyloxy)-4-(4-methyl-1-piperazinyl)phenyl)amino)-4-((2-((phenylmethyl)oxy)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((2-(methyloxy)-4-propylphenyl)oxy)-5-pyrimidinecarboxamide;

N-(2,6-dimethylphenyl)-2-((3-fluoro-4-(((2S)-2-pyrrolidinylmethyl)oxy)phenyl)amino)-4-((2-(methyloxy)-4-propylphenyl)oxy)-5-pyrimidinecarboxamide;

N-(2,6-dimethylphenyl)-2-((3-fluoro-4-((2-(1-piperazinyl)ethyl)oxy)phenyl)amino)-4-((2-(methyloxy)-4-propylphenyl)oxy)-5-pyrimidinecarboxamide;

N-(2,6-dimethylphenyl)-2-((3-fluoro-4-((2-(1-piperidinyl)ethyl)oxy)phenyl)amino)-4-((2-(methyloxy)-4-propylphenyl)oxy)-5-pyrimidinecarboxamide;

N-(2,6-dimethylphenyl)-2-((3-fluoro-4-((2-(1-pyrrolidinyl)ethyl)oxy)phenyl)amino)-4-((2-(methyloxy)-4-propylphenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)-4-propylphenyl)oxy)-5-pyrimidinecarboxamide;

N-(2,6-dimethylphenyl)-2-((3-fluoro-4-((2-(4-methyl-1-piperazinyl)ethyl)oxy)phenyl)amino)-4-((2-(methyloxy)-4-propylphenyl)oxy)-5-pyrimidinecarboxamide;

N-(2,6-dimethylphenyl)-2-((3-fluoro-4-((2-(4-morpholinyl)ethyl)oxy)phenyl)amino)-4-((2-(methyloxy)-4-propylphenyl)oxy)-5-pyrimidinecarboxamide;

N-(2,6-dimethylphenyl)-2-((3-fluoro-4-((3-(1-piperidinyl)propyl)oxy)phenyl)amino)-4-((4-(methyloxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-(phenyloxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-propylphenyl)oxy)-5-pyrimidinecarboxamide;

N-(2,6-dimethylphenyl)-2-((3-fluoro-4-((3-(1-piperidinyl)propyl)oxy)phenyl)amino)-4-((2-((1-methylethyl)oxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-((phenylmethyl)oxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(propyloxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(trifluoromethyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((4-(1H-1,2,4-triazol-1-yl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((pentafluorophenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(5-isoxazolyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-methyl-1,3-benzothiazol-5-yl)oxy)-5-pyrimidinecarboxamide;

N-(2,6-dimethylphenyl)-2-((3-fluoro-4-((3-(1-piperidinyl)propyl)oxy)phenyl)amino)-4-((4-((phenylmethyl)oxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-(2-propenyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((4-(phenyloxy)phenyl)oxy)-5-pyrimidinecarboxamide;

N-(2,6-dimethylphenyl)-2-((3-fluoro-4-((3-(1-pyrrolidinyl)propyl)oxy)phenyl)amino)-4-((2-(methyloxy)-4-propylphenyl)oxy)-5-pyrimidinecarboxamide;

N-(2,6-dimethylphenyl)-2-((3-fluoro-4-((3-(4-(2-(methyloxy)ethyl)-1-piperazinyl)propyl)oxy)phenyl)amino)-4-((2-(methyloxy)-4-propylphenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((4-(methyloxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((4-fluorophenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-((trifluoromethyl)oxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-(((2-(methyloxy)phenyl)methyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-propylphenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-((1-methylethyl)oxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-((phenylmethyl)oxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(propyloxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-(phenylamino)-5-pyrimidinecarboxamide;

N-(2,6-dimethylphenyl)-2-((3-fluoro-4-((3-(4-methyl-1-piperazinyl)propyl)oxy)phenyl)amino)-4-((2-(trifluoromethyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((4-(1H-1,2,4-triazol-1-yl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(3-pyridinyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(3-thienyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((4-(1H-indol-5-yl)-2-(methyloxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((3-(methyloxy)-4'-(trifluoromethyl)-1,1'-biphenyl-4-yl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(5-isoxazolyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-methyl-1,3-benzothiazol-5-yl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((4-((phenylmethyl)oxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(2-propenyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((4-(phenyloxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((3-(2-oxo-1-pyrrolidinyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((3-(methyloxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((3-fluorophenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-(phenyloxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-fluorophenyl)oxy)-5-pyrimidinecarboxamide;

N-(2,6-dimethylphenyl)-2-((3-fluoro-4-((3-(4-morpholinyl)propyl)oxy)phenyl)amino)-4-((2-(methyloxy)-4-propylphenyl)oxy)-5-pyrimidinecarboxamide;

N-(2,6-dimethylphenyl)-2-((3-fluoro-4-((3-piperidinylmethyl)oxy)phenyl)amino)-4-((2-(methyloxy)-4-propylphenyl)oxy)-5-pyrimidinecarboxamide;

N-(2,6-dimethylphenyl)-2-((3-fluoro-4-((3R,5S)-3,4,5-trimethyl-1-piperazinyl)phenyl)amino)-4-((2-(methyloxy)-4-propylphenyl)oxy)-5-pyrimidinecarboxamide;

N-(2,6-dimethylphenyl)-2-((3-fluoro-4-((4-(1H-imidazol-1-yl)butyl)oxy)phenyl)amino)-4-((2-(methyloxy)-4-propylphenyl)oxy)-5-pyrimidinecarboxamide;

N-(2,6-dimethylphenyl)-2-((3-fluoro-4-((octahydro-2H-quinolizin-1-ylmethyl)oxy)phenyl)amino)-4-((2-(methyloxy)-4-propylphenyl)oxy)-5-pyrimidinecarboxamide;

N-(2,6-dimethylphenyl)-2-((3-fluoro-4-(4-methyl-1-piperazinyl)phenyl)amino)-4-((2-fluorophenyl)oxy)-5-pyrimidinecarboxamide;

N-(2,6-dimethylphenyl)-2-((3-fluoro-4-(4-methyl-1-piperazinyl)phenyl)amino)-4-(phenyloxy)-5-pyrimidinecarboxamide;

N-(2,6-dimethylphenyl)-2-((3-fluoro-4-(4-methyl-1-piperazinyl)phenyl)amino)-4-((2-(methyloxy)phenyl)oxy)-5-pyrimidinecarboxamide;

N-(2,6-dimethylphenyl)-2-((3-fluoro-4-(4-methyl-1-piperazinyl)phenyl)amino)-4-((2-((trifluoromethyl)oxy)phenyl)oxy)-5-pyrimidinecarboxamide;

N-(2,6-dimethylphenyl)-2-((3-fluoro-4-(4-methyl-1-piperazinyl)phenyl)amino)-4-((2-(methyloxy)-4-propylphenyl)oxy)-5-pyrimidinecarboxamide;

N-(2,6-dimethylphenyl)-2-((3-fluoro-4-(4-methyl-1-piperazinyl)phenyl)amino)-4-((2-((1-methylethyl)oxy)phenyl)oxy)-5-pyrimidinecarboxamide;

N-(2,6-dimethylphenyl)-2-((3-fluoro-4-(4-methyl-1-piperazinyl)phenyl)amino)-4-((2-((phenylmethyl)oxy)phenyl)oxy)-5-pyrimidinecarboxamide;

N-(2,6-dimethylphenyl)-2-((3-fluoro-4-(4-methyl-1-piperazinyl)phenyl)amino)-4-((2-(propyloxy)phenyl)oxy)-5-pyrimidinecarboxamide;

N-(2,6-dimethylphenyl)-2-((3-fluoro-4-(4-methyl-1-piperazinyl)phenyl)amino)-4-((2-(trifluoromethyl)phenyl)oxy)-5-pyrimidinecarboxamide;

N-(2,6-dimethylphenyl)-2-((3-fluoro-4-(4-methyl-1-piperazinyl)phenyl)amino)-4-((4-(1H-1,2,4-triazol-1-yl)phenyl)oxy)-5-pyrimidinecarboxamide;

N-(2,6-dimethylphenyl)-2-((3-fluoro-4-(4-methyl-1-piperazinyl)phenyl)amino)-4-((2-(5-isoxazolyl)phenyl)oxy)-5-pyrimidinecarboxamide;

N-(2,6-dimethylphenyl)-2-((3-fluoro-4-(4-methyl-1-piperazinyl)phenyl)amino)-4-((2-methyl-1,3-benzothiazol-5-yl)oxy)-5-pyrimidinecarboxamide;

N-(2,6-dimethylphenyl)-2-((3-fluoro-4-(4-methyl-1-piperazinyl)phenyl)amino)-4-((4-(phenyloxy)phenyl)oxy)-5-pyrimidinecarboxamide;

N-(2,6-dimethylphenyl)-2-((3-fluoro-4-(4-methyl-1-piperazinyl)phenyl)amino)-4-((4-((phenylmethyl)oxy)phenyl)oxy)-5-pyrimidinecarboxamide;

N-(2,6-dimethylphenyl)-2-((3-fluoro-4-(4-methyl-1-piperazinyl)phenyl)amino)-4-((2-(methyloxy)-4-(2-propenyl)phenyl)oxy)-5-pyrimidinecarboxamide;

N-(2,6-dimethylphenyl)-2-((3-fluoro-4-(4-methyl-1-piperazinyl)phenyl)amino)-4-((3-(2-oxo-1-pyrrolidinyl)phenyl)oxy)-5-pyrimidinecarboxamide;

N-(2,6-dimethylphenyl)-2-((3-fluoro-4-(4-methyl-1-piperazinyl)phenyl)amino)-4-((3-(methyloxy)phenyl)oxy)-5-pyrimidinecarboxamide;

N-(2,6-dimethylphenyl)-2-((3-fluoro-4-(4-methyl-1-piperazinyl)phenyl)amino)-4-((3-fluorophenyl)oxy)-5-pyrimidinecarboxamide;

N-(2,6-dimethylphenyl)-2-((3-fluoro-4-(4-methyl-1-piperazinyl)phenyl)amino)-4-((4-fluorophenyl)oxy)-5-pyrimidinecarboxamide;

N-(2,6-dimethylphenyl)-2-((3-fluoro-4-(4-methyl-1-piperazinyl)phenyl)amino)-4-((4-(methyloxy)phenyl)oxy)-5-pyrimidinecarboxamide;

N-(2,6-dimethylphenyl)-2-((4-((2-((1-methylethyl)amino)ethyl)oxy)-3-(methyloxy)phenyl)amino)-4-((2-(methyloxy)-4-propylphenyl)oxy)-5-pyrimidinecarboxamide;

N-(2,6-dimethylphenyl)-2-((4-((3-(4-(1-methylethyl)-1-piperazinyl)propyl)oxy)-3-(methyloxy)phenyl)amino)-4-((2-(methyloxy)-4-propylphenyl)oxy)-5-pyrimidinecarboxamide;   N-(2,6-dimethylphenyl)-2-((4-(1-(1-methylethyl)-4-piperidinyl)phenyl)amino)-4-((2-(methyloxy)-4-propylphenyl)oxy)-5-pyrimidinecarboxamide;

N-(2,6-dimethylphenyl)-2-((4-(2-(3,4-dimethyl-1-piperazinyl)-2-oxoethyl)phenyl)amino)-4-((2-(methyloxy)-4-propylphenyl)oxy)-5-pyrimidinecarboxamide;

N-(2,6-dimethylphenyl)-2-((4-(2-(3,4-dimethyl-1-piperazinyl)-2-oxoethyl)phenyl)amino)-4-((2-(ethyloxy)phenyl)oxy)-5-pyrimidinecarboxamide;

N-(2,6-dimethylphenyl)-2-((4-(2-(3,4-dimethyl-1-piperazinyl)ethyl)phenyl)amino)-4-((2-(methyloxy)-4-propylphenyl)oxy)-5-pyrimidinecarboxamide;

N-(2,6-dimethylphenyl)-2-((4-(2-(3,4-dimethyl-1-piperazinyl)ethyl)phenyl)amino)-4-((2-(ethyloxy)phenyl)oxy)-5-pyrimidinecarboxamide;

N-(2,6-dimethylphenyl)-2-((4-(3,4-dimethyl-1-piperazinyl)-3-fluorophenyl)amino)-4-((2-(ethyloxy)phenyl)oxy)-5-pyrimidinecarboxamide;

N-(2,6-dimethylphenyl)-2-((4-(3,4-dimethyl-1-piperazinyl)-3-fluorophenyl)amino)-4-((2-(methyloxy)-4-propylphenyl)oxy)-5-pyrimidinecarboxamide;

N-(2,6-dimethylphenyl)-2-((4-(3,4-dimethyl-1-piperazinyl)phenyl)amino)-4-((2-(ethyloxy)phenyl)oxy)-5-pyrimidinecarboxamide;

N-(2,6-dimethylphenyl)-2-((4-(3,4-dimethyl-1-piperazinyl)phenyl)amino)-4-((2-(methyloxy)-4-propylphenyl)oxy)-5-pyrimidinecarboxamide;

N-(2,6-dimethylphenyl)-2-((4-(4-(1-methylethyl)-1-piperazinyl)phenyl)amino)-4-((3-(methyloxy)phenyl)oxy)-5-pyrimidinecarboxamide;

N-(2,6-dimethylphenyl)-2-((4-(4-(1-methylethyl)-1-piperazinyl)phenyl)amino)-4-(phenyloxy)-5-pyrimidinecarboxamide;

N-(2,6-dimethylphenyl)-2-((4-(4-(1-methylethyl)-1-piperazinyl)phenyl)amino)-4-((2-(methyloxy)phenyl)oxy)-5-pyrimidinecarboxamide;

N-(2,6-dimethylphenyl)-2-((4-(4-(1-methylethyl)-1-piperazinyl)phenyl)amino)-4-((2-((trifluoromethyl)oxy)phenyl)oxy)-5-pyrimidinecarboxamide;

N-(2,6-dimethylphenyl)-2-((4-(4-(1-methylethyl)-1-piperazinyl)phenyl)amino)-4-((2-(methyloxy)-4-propylphenyl)oxy)-5-pyrimidinecarboxamide;

N-(2,6-dimethylphenyl)-2-((4-(4-(1-methylethyl)-1-piperazinyl)phenyl)amino)-4-((2-((phenylmethyl)oxy)phenyl)oxy)-5-pyrimidinecarboxamide;

N-(2,6-dimethylphenyl)-2-((4-(4-(1-methylethyl)-1-piperazinyl)phenyl)amino)-4-((2-(propyloxy)phenyl)oxy)-5-pyrimidinecarboxamide;

N-(2,6-dimethylphenyl)-2-((4-(4-(1-methylethyl)-1-piperazinyl)phenyl)amino)-4-((2-(trifluoromethyl)phenyl)oxy)-5-pyrimidinecarboxamide;

N-(2,6-dimethylphenyl)-2-((4-(4-(1-methylethyl)-1-piperazinyl)phenyl)amino)-4-((4-(1H-1,2,4-triazol-1-yl)phenyl)oxy)-5-pyrimidinecarboxamide;

N-(2,6-dimethylphenyl)-2-((4-(4-(1-methylethyl)-1-piperazinyl)phenyl)amino)-4-((pentafluorophenyl)oxy)-5-pyrimidinecarboxamide;

N-(2,6-dimethylphenyl)-2-((4-(4-(1-methylethyl)-1-piperazinyl)phenyl)amino)-4-((4-((phenylmethyl)oxy)phenyl)oxy)-5-pyrimidinecarboxamide;

N-(2,6-dimethylphenyl)-2-((4-(4-(1-methylethyl)-1-piperazinyl)phenyl)amino)-4-((2-(methyloxy)-4-(2-propenyl)phenyl)oxy)-5-pyrimidinecarboxamide;

N-(2,6-dimethylphenyl)-2-((4-(4-(1-methylethyl)-1-piperazinyl)phenyl)amino)-4-((4-(phenyloxy)phenyl)oxy)-5-pyrimidinecarboxamide;

N-(2,6-dimethylphenyl)-2-((4-(4-(1-methylethyl)-1-piperazinyl)phenyl)amino)-4-((3-(2-oxo-1-pyrrolidinyl)phenyl)oxy)-5-pyrimidinecarboxamide;

N-(2,6-dimethylphenyl)-2-((4-(4-(1-methylethyl)-1-piperazinyl)phenyl)amino)-4-((4-(methyloxy)phenyl)oxy)-5-pyrimidinecarboxamide;

N-(2,6-dimethylphenyl)-2-((4-(4-(2-(ethylamino)ethyl)-1-piperazinyl)phenyl)amino)-4-((2-(methyloxy)-4-propylphenyl)oxy)-5-pyrimidinecarboxamide;

N-(2,6-dimethylphenyl)-2-((4-(4-(2-(ethylamino)ethyl)-1-piperazinyl)phenyl)amino)-4-((2-(ethyloxy)phenyl)oxy)-5-pyrimidinecarboxamide;

N-(2,6-dimethylphenyl)-2-((4-(4-(2-(methyloxy)ethyl)-1-piperazinyl)phenyl)amino)-4-((2-(methyloxy)-4-propylphenyl)oxy)-5-pyrimidinecarboxamide;

N-(2,6-dimethylphenyl)-2-((4-(4-methyl-1-piperazinyl)phenyl)amino)-4-(phenyloxy)-5-pyrimidinecarboxamide;

N-(2,6-dimethylphenyl)-2-((4-(4-methyl-1-piperazinyl)phenyl)amino)-4-((4-(1-piperazinyl)phenyl)oxy)-5-pyrimidinecarboxamide;

N-(2,6-dimethylphenyl)-2-((4-(4-methyl-1-piperazinyl)phenyl)amino)-4-(phenylsulfanyl)-5-pyrimidinecarboxamide;

N-(2,6-dimethylphenyl)-2-((4-(4-methyl-1-piperazinyl)phenyl)amino)-4-((2-((phenylmethyl)oxy)phenyl)oxy)-5-pyrimidinecarboxamide;

N-(2,6-dimethylphenyl)-2-((4-(4-methyl-1-piperazinyl)phenyl)amino)-4-((2-(propyloxy)phenyl)oxy)-5-pyrimidinecarboxamide;

N-(2,6-dimethylphenyl)-2-((4-(4-methyl-1-piperazinyl)phenyl)amino)-4-((2-(trifluoromethyl)phenyl)oxy)-5-pyrimidinecarboxamide;

N-(2,6-dimethylphenyl)-2-((4-(4-methyl-1-piperazinyl)phenyl)amino)-4-((4-(1H-1,2,4-triazol-1-yl)phenyl)oxy)-5-pyrimidinecarboxamide;

N-(2,6-dimethylphenyl)-2-((4-(4-methyl-1-piperazinyl)phenyl)amino)-4-((pentafluorophenyl)oxy)-5-pyrimidinecarboxamide;

N-(2,6-dimethylphenyl)-2-((4-(4-methyl-1-piperazinyl)phenyl)amino)-4-((4-((phenylmethyl)oxy)phenyl)oxy)-5-pyrimidinecarboxamide;

N-(2,6-dimethylphenyl)-2-((4-(4-methyl-1-piperazinyl)phenyl)amino)-4-((4-(phenyloxy)phenyl)oxy)-5-pyrimidinecarboxamide;

N-(2,6-dimethylphenyl)-2-((4-(4-methyl-1-piperazinyl)phenyl)amino)-4-((3-(2-oxo-1-pyrrolidinyl)phenyl)oxy)-5-pyrimidinecarboxamide;

N-(2,6-dimethylphenyl)-2-((4-(4-methyl-1-piperazinyl)phenyl)amino)-4-(2-naphthalenyloxy)-5-pyrimidinecarboxamide;

N-(2,6-dimethylphenyl)-4-((1-methylethyl)oxy)-2-((4-(4-(1-methylethyl)-1-piperazinyl)phenyl)amino)-5-pyrimidinecarboxamide;

N-(2,6-dimethylphenyl)-4-((2-((1-methylethyl)oxy)phenyl)oxy)-2-((3-(methyloxy)-4-(4-methyl-1-piperazinyl)phenyl)amino)-5-pyrimidinecarboxamide;

N-(2,6-dimethylphenyl)-4-((2-((1-methylethyl)oxy)phenyl)oxy)-2-((4-(4-methyl-1-piperazinyl)phenyl)amino)-5-pyrimidinecarboxamide;

N-(2,6-dimethylphenyl)-4-((2-((1-methylethyl)oxy)phenyl)oxy)-2-((4-(4-(1-methylethyl)-1-piperazinyl)phenyl)amino)-5-pyrimidinecarboxamide;

N-(2,6-dimethylphenyl)-4-((2-(5-isoxazolyl)phenyl)oxy)-2-((4-(4-(1-methylethyl)-1-piperazinyl)phenyl)amino)-5-pyrimidinecarboxamide;

N-(2,6-dimethylphenyl)-4-((2-(5-isoxazolyl)phenyl)oxy)-2-((4-(4-methyl-1-piperazinyl)phenyl)amino)-5-pyrimidinecarboxamide;

N-(2,6-dimethylphenyl)-4-((2-(ethyloxy)phenyl)oxy)-2-((3-((3-(1-piperidinyl)propyl)oxy)phenyl)amino)-5-pyrimidinecarboxamide;

N-(2,6-dimethylphenyl)-4-((2-(ethyloxy)phenyl)oxy)-2-((3-((3-(4-methyl-1-piperazinyl)propyl)oxy)phenyl)amino)-5-pyrimidinecarboxamide;

N-(2,6-dimethylphenyl)-4-((2-(ethyloxy)phenyl)oxy)-2-((3-(methyloxy)-4-(4-methyl-1-piperazinyl)phenyl)amino)-5-pyrimidinecarboxamide;

N-(2,6-dimethylphenyl)-4-((2-(ethyloxy)phenyl)oxy)-2-((3-(methyloxy)-4-(((2S)-2-pyrrolidinylmethyl)oxy)phenyl)amino)-5-pyrimidinecarboxamide;

N-(2,6-dimethylphenyl)-4-((2-(ethyloxy)phenyl)oxy)-2-((3-(methyloxy)-4-(((4-methyl-1-piperazinyl)acetyl)amino)phenyl)amino)-5-pyrimidinecarboxamide;

N-(2,6-dimethylphenyl)-4-((2-(ethyloxy)phenyl)oxy)-2-((3-(methyloxy)-4-(1-piperazinyl)phenyl)amino)-5-pyrimidinecarboxamide;

N-(2,6-dimethylphenyl)-4-((2-(ethyloxy)phenyl)oxy)-2-((3,4,5-tris(methyloxy)phenyl)amino)-5-pyrimidinecarboxamide;

N-(2,6-dimethylphenyl)-4-((2-(ethyloxy)phenyl)oxy)-2-((3-fluoro-4-((2-(4-(1-methylethyl)-1-piperazinyl)ethyl)oxy)phenyl)amino)-5-pyrimidinecarboxamide;

N-(2,6-dimethylphenyl)-4-((2-(ethyloxy)phenyl)oxy)-2-((3-fluoro-4-(4-methyl-1-piperazinyl)phenyl)amino)-5-pyrimidinecarboxamide;

N-(2,6-dimethylphenyl)-4-((2-(ethyloxy)phenyl)oxy)-2-((3-fluoro-4-((3-(1-piperidinyl)propyl)oxy)phenyl)amino)-5-pyrimidinecarboxamide;

N-(2,6-dimethylphenyl)-4-((2-(ethyloxy)phenyl)oxy)-2-((3-fluoro-4-((3-(4-methyl-1-piperazinyl)propyl)oxy)phenyl)amino)-5-pyrimidinecarboxamide;

N-(2,6-dimethylphenyl)-4-((2-(ethyloxy)phenyl)oxy)-2-((3-fluoro-4-(((2R)-2-pyrrolidinylmethyl)oxy)phenyl)amino)-5-pyrimidinecarboxamide;

N-(2,6-dimethylphenyl)-4-((2-(ethyloxy)phenyl)oxy)-2-((3-fluoro-4-((2-(1-piperazinyl)ethyl)oxy)phenyl)amino)-5-pyrimidinecarboxamide;

N-(2,6-dimethylphenyl)-4-((2-(ethyloxy)phenyl)oxy)-2-((3-fluoro-4-((2-(4-morpholinyl)ethyl)oxy)phenyl)amino)-5-pyrimidinecarboxamide;

N-(2,6-dimethylphenyl)-4-((2-(ethyloxy)phenyl)oxy)-2-((3-fluoro-4-((3-(1-pyrrolidinyl)propyl)oxy)phenyl)amino)-5-pyrimidinecarboxamide;

N-(2,6-dimethylphenyl)-4-((2-(ethyloxy)phenyl)oxy)-2-((3-fluoro-4-((4-(1H-imidazol-1-yl)butyl)oxy)phenyl)amino)-5-pyrimidinecarboxamide;

N-(2,6-dimethylphenyl)-4-((2-(ethyloxy)phenyl)oxy)-2-((3-fluoro-4-((3-(4-(2-(methyloxy)ethyl)-1-piperazinyl)propyl)oxy)phenyl)amino)-5-pyrimidinecarboxamide;

N-(2,6-dimethylphenyl)-4-((2-(ethyloxy)phenyl)oxy)-2-((3-fluoro-4-((octahydro-2H-quinolizin-1-ylmethyl)oxy)phenyl)amino)-5-pyrimidinecarboxamide;

N-(2,6-dimethylphenyl)-4-((2-(ethyloxy)phenyl)oxy)-2-((3-fluoro-4-((3R,5S)-3,4,5-trimethyl-1-piperazinyl)phenyl)amino)-5-pyrimidinecarboxamide;

N-(2,6-dimethylphenyl)-4-((2-(ethyloxy)phenyl)oxy)-2-((3-fluoro-4-(((2S)-2-pyrrolidinylmethyl)oxy)phenyl)amino)-5-pyrimidinecarboxamide;

N-(2,6-dimethylphenyl)-4-((2-(ethyloxy)phenyl)oxy)-2-((3-fluoro-4-((2-(1-pyrrolidinyl)ethyl)oxy)phenyl)amino)-5-pyrimidinecarboxamide;

N-(2,6-dimethylphenyl)-4-((2-(ethyloxy)phenyl)oxy)-2-((3-fluoro-4-(((1-methyl-3-piperidinyl)methyl)oxy)phenyl)amino)-5-pyrimidinecarboxamide;

N-(2,6-dimethylphenyl)-4-((2-(ethyloxy)phenyl)oxy)-2-((3-fluoro-4-((3-(4-morpholinyl)propyl)oxy)phenyl)amino)-5-pyrimidinecarboxamide;

N-(2,6-dimethylphenyl)-4-((2-(ethyloxy)phenyl)oxy)-2-((3-fluoro-4-((2-(1-piperidinyl)ethyl)oxy)phenyl)amino)-5-pyrimidinecarboxamide;

N-(2,6-dimethylphenyl)-4-((2-(ethyloxy)phenyl)oxy)-2-((4-((2-(((1-methylethyl)amino)ethyl)oxy)-3-(methyloxy)phenyl)amino)-5-pyrimidinecarboxamide;

N-(2,6-dimethylphenyl)-4-((2-(ethyloxy)phenyl)oxy)-2-((4-((2-(4-methyl-1-piperazinyl)ethyl)oxy)phenyl)amino)-5-pyrimidinecarboxamide;

N-(2,6-dimethylphenyl)-4-((2-(ethyloxy)phenyl)oxy)-2-((4-((3-(4-(1-methylethyl)-1-piperazinyl)propyl)oxy)-3-(methyloxy)phenyl)amino)-5-pyrimidinecarboxamide;

N-(2,6-dimethylphenyl)-4-((2-(ethyloxy)phenyl)oxy)-2-((4-(1-(1-methylethyl)-4-piperidinyl)phenyl)amino)-5-pyrimidinecarboxamide;

N-(2,6-dimethylphenyl)-4-((2-(ethyloxy)phenyl)oxy)-2-((4-(1-methyl-4-piperidinyl)phenyl)amino)-5-pyrimidinecarboxamide;

N-(2,6-dimethylphenyl)-4-((2-(ethyloxy)phenyl)oxy)-2-((4-(2-(4-methyl-1-piperazinyl)-2-oxoethyl)phenyl)amino)-5-pyrimidinecarboxamide;

N-(2,6-dimethylphenyl)-4-((2-(ethyloxy)phenyl)oxy)-2-((4-(2-(4-methyl-1-piperazinyl)ethyl)phenyl)amino)-5-pyrimidinecarboxamide;

N-(2,6-dimethylphenyl)-4-((2-(ethyloxy)phenyl)oxy)-2-((4-(4-(1-methylethyl)-1-piperazinyl)phenyl)amino)-5-pyrimidinecarboxamide;

N-(2,6-dimethylphenyl)-4-((2-(ethyloxy)phenyl)oxy)-2-((4-(4-(2-(methyloxy)ethyl)-1-piperazinyl)phenyl)amino)-5-pyrimidinecarboxamide;

N-(2,6-dimethylphenyl)-4-((2-(ethyloxy)phenyl)oxy)-2-((4-(4-methyl-1-piperazinyl)phenyl)amino)-5-pyrimidinecarboxamide;

N-(2,6-dimethylphenyl)-4-((2-(ethyloxy)phenyl)oxy)-2-((6-(4-methyl-1-piperazinyl)-3-pyridinyl)amino)-5-pyrimidinecarboxamide;

N-(2,6-dimethylphenyl)-4-((2-(ethyloxy)phenyl)oxy)-2-((6-(4-morpholinyl)-3-pyridinyl)amino)-5-pyrimidinecarboxamide;

N-(2,6-dimethylphenyl)-4-((2-(methyloxy)-4-(2-propenyl)phenyl)oxy)-2-((3,4,5-tris(methyloxy)phenyl)amino)-5-pyrimidinecarboxamide;

N-(2,6-dimethylphenyl)-4-((2-(methyloxy)-4-(2-propenyl)phenyl)oxy)-2-((4-(4-methyl-1-piperazinyl)phenyl)amino)-5-pyrimidinecarboxamide;

N-(2,6-dimethylphenyl)-4-((2-(methyloxy)-4-(3-pyridinyl)phenyl)oxy)-2-((3,4,5-tris(methyloxy)phenyl)amino)-5-pyrimidinecarboxamide;

N-(2,6-dimethylphenyl)-4-((2-(methyloxy)-4-(3-thienyl)phenyl)oxy)-2-((3,4,5-tris(methyloxy)phenyl)amino)-5-pyrimidinecarboxamide;

N-(2,6-dimethylphenyl)-4-((2-(methyloxy)-4-propylphenyl)oxy)-2-((4-(4-methyl-1-piperazinyl)phenyl)amino)-5-pyrimidinecarboxamide;

N-(2,6-dimethylphenyl)-4-((2-(methyloxy)-4-propylphenyl)oxy)-2-((3-((3-(4-methyl-1-piperazinyl)propyl)oxy)phenyl)amino)-5-pyrimidinecarboxamide;

N-(2,6-dimethylphenyl)-4-((2-(methyloxy)-4-propylphenyl)oxy)-2-((3-((3-(1-piperidinyl)propyl)oxy)phenyl)amino)-5-pyrimidinecarboxamide;

N-(2,6-dimethylphenyl)-4-((2-(methyloxy)-4-propylphenyl)oxy)-2-((4-(2-(4-methyl-1-piperazinyl)-2-oxoethyl)phenyl)amino)-5-pyrimidinecarboxamide;

N-(2,6-dimethylphenyl)-4-((2-(methyloxy)-4-propylphenyl)oxy)-2-((4-(2-(4-methyl-1-piperazinyl)ethyl)phenyl)amino)-5-pyrimidinecarbox amide;

N-(2,6-dimethylphenyl)-4-((2-(methyloxy)-4-propylphenyl)oxy)-2-((3-(methyloxy)-4-(((2S)-2-pyrrolidinylmethyl)oxy)phenyl)amino)-5-pyrimidinecarboxamide;

N-(2,6-dimethylphenyl)-4-((2-(methyloxy)-4-propylphenyl)oxy)-2-((4-(1-methyl-4-piperidinyl)phenyl)amino)-5-pyrimidinecarboxamide;

N-(2,6-dimethylphenyl)-4-((2-(methyloxy)phenyl)oxy)-2-((4-(((2S)-2-pyrrolidinylmethyl)oxy)phenyl)amino)-5-pyrimidinecarboxamide;

N-(2,6-dimethylphenyl)-4-((2-(methyloxy)phenyl)oxy)-2-((4-(4-methyl-1-piperazinyl)phenyl)amino)-5-pyrimidinecarboxamide;

N-(2,6-dimethylphenyl)-4-((2-(methyloxy)phenyl)oxy)-2-(phenylamino)-5-pyrimidinecarboxamide;

N-(2,6-dimethylphenyl)-4-((2-ethylphenyl)oxy)-2-((3-(methyloxy)-4-(4-methyl-1-piperazinyl)phenyl)amino)-5-pyrimidinecarboxamide;

N-(2,6-dimethylphenyl)-4-((2-ethylphenyl)oxy)-2-((3-fluoro-4-((3-(1-piperidinyl)propyl)oxy)phenyl)amino)-5-pyrimidinecarboxamide;

N-(2,6-dimethylphenyl)-4-((2-ethylphenyl)oxy)-2-((3-fluoro-4-(4-methyl-1-piperazinyl)phenyl)amino)-5-pyrimidinecarboxamide;

N-(2,6-dimethylphenyl)-4-((2-ethylphenyl)oxy)-2-((4-(4-(1-methylethyl)-1-piperazinyl)phenyl)amino)-5-pyrimidinecarboxamide;

N-(2,6-dimethylphenyl)-4-((2-ethylphenyl)oxy)-2-((4-(4-methyl-1-piperazinyl)phenyl)amino)-5-pyrimidinecarboxamide;

N-(2,6-dimethylphenyl)-4-((2-fluorophenyl)oxy)-2-((3-(methyloxy)-4-(4-methyl-1-piperazinyl)phenyl)amino)-5-pyrimidinecarboxamide;

N-(2,6-dimethylphenyl)-4-((2-fluorophenyl)oxy)-2-((3-(methyloxy)-4-((3-(4-methyl-1-piperazinyl)propyl)oxy)phenyl)amino)-5-pyrimidinecarboxamide;

N-(2,6-dimethylphenyl)-4-((2-fluorophenyl)oxy)-2-((3-(methyloxy)-4-((2-(4-methyl-1-piperazinyl)ethyl)oxy)phenyl)amino)-5-pyrimidinecarboxamide;

N-(2,6-dimethylphenyl)-4-((2-fluorophenyl)oxy)-2-((4-(4-methyl-1-piperazinyl)phenyl)amino)-5-pyrimidinecarboxamide;

N-(2,6-dimethylphenyl)-4-((2-methyl-1,3-benzothiazol-5-yl)oxy)-2-((4-(4-(1-methylethyl)-1-piperazinyl)phenyl)amino)-5-pyrimidinecarboxamide;

N-(2,6-dimethylphenyl)-4-((2-methyl-1,3-benzothiazol-5-yl)oxy)-2-((4-(4-methyl-1-piperazinyl)phenyl)amino)-5-pyrimidinecarboxamide;

N-(2,6-dimethylphenyl)-4-((2'-methyl-3-(methyloxy)-1,1'-biphenyl-4-yl)oxy)-2-((3,4,5-tris(methyloxy)phenyl)amino)-5-pyrimidinecarboxamide;

N-(2,6-dimethylphenyl)-4-((3-(methyloxy)-4'-(trifluoromethyl)-1,1'-biphenyl-4-yl)oxy)-2-((3,4,5-tris(methyloxy)phenyl)amino)-5-pyrimidinecarboxamide;

N-(2,6-dimethylphenyl)-4-((3-fluorophenyl)oxy)-2-((3-(methyloxy)-4-(4-methyl-1-piperazinyl)phenyl)amino)-5-pyrimidinecarboxamide;

N-(2,6-dimethylphenyl)-4-((3-fluorophenyl)oxy)-2-((3-fluoro-4-((3-(1-piperidinyl)propyl)oxy)phenyl)amino)-5-pyrimidinecarboxamide;

N-(2,6-dimethylphenyl)-4-((3-fluorophenyl)oxy)-2-((4-(4-(1-methylethyl)-1-piperazinyl)phenyl)amino)-5-pyrimidinecarboxamide;

N-(2,6-dimethylphenyl)-4-((3-fluorophenyl)oxy)-2-((4-(4-methyl-1-piperazinyl)phenyl)amino)-5-pyrimidinecarboxamide;

N-(2,6-dimethylphenyl)-4-((4-((phenylmethyl)oxy)phenyl)oxy)-2-((3,4,5-tris(methyloxy)phenyl)amino)-5-pyrimidinecarboxamide;

N-(2,6-dimethylphenyl)-4-((4-(1H-indol-5-yl)-2-(methyloxy)phenyl)oxy)-2-((3,4,5-tris(methyloxy)phenyl)amino)-5-pyrimidinecarboxamide;

N-(2,6-dimethylphenyl)-4-((4-(methyloxy)phenyl)oxy)-2-((4-(1-piperazinyl)phenyl)amino)-5-pyrimidinecarboxamide;

N-(2,6-dimethylphenyl)-4-((4-(methyloxy)phenyl)oxy)-2-((4-(4-methyl-1-piperazinyl)phenyl)amino)-5-pyrimidinecarboxamide;

N-(2,6-dimethylphenyl)-4-((4-(phenyloxy)phenyl)oxy)-2-((3,4,5-tris(methyloxy)phenyl)amino)-5-pyrimidinecarboxamide;

N-(2,6-dimethylphenyl)-4-((4-fluorophenyl)oxy)-2-((3-(methyloxy)-4-(4-methyl-1-piperazinyl)phenyl)amino)-5-pyrimidinecarboxamide;

N-(2,6-dimethylphenyl)-4-((4-fluorophenyl)oxy)-2-((3-fluoro-4-((3-(1-piperidinyl)propyl)oxy)phenyl)amino)-5-pyrimidinecarboxamide;

N-(2,6-dimethylphenyl)-4-((4-fluorophenyl)oxy)-2-((4-(((2R)-2-pyrrolidinylmethyl)oxy)phenyl)amino)-5-pyrimidinecarboxamide; and N-(2,6-dimethylphenyl)-4-((4-fluorophenyl)oxy)-2-((4-(4-methyl-1-piperazinyl)phenyl)amino)-5-pyrimidinecarboxamide;

2,6-dimethylphenyl 2-((4-((2-(dimethylamino)ethyl)oxy)phenyl)amino)-4-pyrimidinyl(2-(4-morpholinyl)ethyl)carbamate;

2,6-dimethylphenyl 2-((3,5-bis(methyloxy)-4-((3-(4-methyl-1-piperazinyl)propyl)oxy)phenyl)amino)-4-pyrimidinyl(2,4-dimethylphenyl)carbamate;

2,4,6-trimethylphenyl 2-((3,4-bis(methyloxy)-5-((2-(4-methyl-1-piperazinyl)ethyl)oxy)phenyl)amino)-4-pyrimidinyl(2,4-bis(methyloxy)phenyl)carbamate;

2,6-dimethylphenyl 2,4-bis(methyloxy)phenyl(2-((4-(((2-(dimethylamino)ethyl)amino)carbonyl)phenyl)amino)-4-pyrimidinyl)carbamate;

2,6-dimethylphenyl 2,4-bis(methyloxy)phenyl(2-((4-((3-(4-(1-methylethyl)-1-piperazinyl)propyl)oxy)-3-(methyloxy)phenyl)amino)-4-pyrimidinyl)carbamate;

2,6-dimethylphenyl 2,4-bis(methyloxy)phenyl(2-((3-(((2-(diethylamino)ethyl)(methyl)amino)carbonyl)phenyl)amino)-4-pyrimidinyl)carbamate;

2,6-dimethylphenyl 2,4-bis(methyloxy)phenyl(2-((3-(((2-(dimethylamino)ethyl)amino)sulfonyl)phenyl)amino)-4-pyrimidinyl)carbamate;

2,6-dimethylphenyl 2,4-bis(methyloxy)phenyl(2-((4-((2-(diethylamino)ethyl)oxy)phenyl)amino)-4-pyrimidinyl)carbamate;

2,6-dimethylphenyl 2,4-bis(methyloxy)phenyl(2-((3-chloro-4-((2-((1-methylethyl)amino)ethyl)oxy)phenyl)amino)-4-pyrimidinyl)carbamate;

2,6-dimethylphenyl 2,4-bis(methyloxy)phenyl(2-((4-(((2-(diethylamino)ethyl)(methyl)amino)carbonyl)phenyl)amino)-4-pyrimidinyl)carbamate;

2,6-dimethylphenyl 2-((3,4-bis(methyloxy)-5-((3-(4-methyl-1-piperazinyl)propyl)oxy)phenyl)amino)-4-pyrimidinyl(2,4-dimethylphenyl)carbamate;

2,4,6-trimethylphenyl 2,4-bis(methyloxy)phenyl(2-((4-(4-methyl-1-piperazinyl)phenyl)amino)-4-pyrimidinyl)carbamate;

2,6-dimethylphenyl 2,4-bis(methyloxy)phenyl(2-((3,5-difluoro-4-((2-(1-piperidinyl)ethyl)oxy)phenyl)amino)-4-pyrimidinyl)carbamate;

2,4,6-trimethylphenyl 2-((4-((2-(dimethylamino)ethyl)oxy)phenyl)amino)-4-pyrimidinyl(2-(2-(methyloxy)phenyl)ethyl)carbamate;

2,4,6-trimethylphenyl 2-((4-((2-(dimethylamino)ethyl)oxy)phenyl)amino)-4-pyrimidinyl(3-phenylpropyl)carbamate;

2,4,6-trimethylphenyl 2-((4-((2-(dimethylamino)ethyl)oxy)phenyl)amino)-4-pyrimidinyl(2-(4-morpholinyl)ethyl)carbamate;

2,4,6-trimethylphenyl 2-((4-((3-(1-piperidinyl)propyl)oxy)phenyl)amino)-4-pyrimidinyl((2-((trifluoromethyl)oxy)phenyl)methyl)carbamate;

2,4,6-trimethylphenyl 2-((3-(methyloxy)-4-((3-(4-methyl-1-piperazinyl)propyl)oxy)phenyl)amino)-4-pyrimidinyl((2-((trifluoromethyl)oxy)phenyl)methyl)carbamate;

2,4,6-trimethylphenyl 2-((3-(methyloxy)-4-((2-(4-methyl-1-piperazinyl)ethyl)oxy)phenyl)amino)-4-pyrimidinyl((2-((trifluoromethyl)oxy)phenyl)methyl)carbamate;

2,4,6-trimethylphenyl 2-((3,5-bis(methyloxy)-4-((3-(4-methyl-1-piperazinyl)propyl)oxy)phenyl)amino)-4-pyrimidinyl((2-((trifluoromethyl)oxy)phenyl)methyl)carbamate;

2,6-dimethylphenyl 2-((4-(4-amino-1-piperidinyl)phenyl)amino)-4-pyrimidinyl(2,4-bis(methyloxy)phenyl)carbamate;

2,6-dimethylphenyl 2-((3,4-bis(methyloxy)-5-((2-(4-methyl-1-piperazinyl)ethyl)oxy)phenyl)amino)-4-pyrimidinyl(2-(ethyloxy)phenyl)carbamate;

2,6-dimethylphenyl 2-((4-((2-(dimethylamino)ethyl)oxy)phenyl)amino)-4-pyrimidinyl(4-fluoro-2-((1-methylethyl)oxy)phenyl)carbamate;

2,6-dimethylphenyl 2-((3,4-bis(methyloxy)-5-((3-(4-methyl-1-piperazinyl)propyl)oxy)phenyl)amino)-4-pyrimidinyl(2-(ethyloxy)phenyl)carbamate;

2,6-dimethylphenyl 2-((3,5-bis(methyloxy)-4-((3-(4-methyl-1-piperazinyl)propyl)oxy)phenyl)amino)-4-pyrimidinyl(4-fluoro-2-((1-methylethyl)oxy)phenyl)carbamate;

2,6-dimethylphenyl 2-(ethyloxy)phenyl(2-((4-(4-methyl-1-piperazinyl)phenyl)amino)-4-pyrimidinyl)carbamate;

2,6-dimethylphenyl 4-fluoro-2-((1-methylethyl)oxy)phenyl(2-((4-(4-methyl-1-piperazinyl)phenyl)amino)-4-pyrimidinyl)carbamate;

2,4,6-trimethylphenyl (2,5-dichlorophenyl)methyl(2-((4-((3-(1-piperidinyl)propyl)oxy)phenyl)amino)-4-pyrimidinyl)carbamate;

2,4,6-trimethylphenyl (2,5-dichlorophenyl)methyl(2-((3-(methyloxy)-4-((3-(4-methyl-1-piperazinyl)propyl)oxy)phenyl)amino)-4-pyrimidinyl)carbamate;

2,4,6-trimethylphenyl (2,5-dichlorophenyl)methyl(2-((3-fluoro-4-((3-(1-piperidinyl)propyl)oxy)phenyl)amino)-4-pyrimidinyl)carbamate;

2,4,6-trimethylphenyl (2,5-dimethylphenyl)methyl(2-((4-((3-(1-piperidinyl)propyl)oxy)phenyl)amino)-4-pyrimidinyl)carbamate;

2,4,6-trimethylphenyl (2,5-dimethylphenyl)methyl(2-((3-(methyloxy)-4-((3-(4-methyl-1-piperazinyl)propyl)oxy)phenyl)amino)-4-pyrimidinyl)carbamate;

2,4,6-trimethylphenyl (2,5-dimethylphenyl)methyl(2-((3-fluoro-4-((3-(1-piperidinyl)propyl)oxy)phenyl)amino)-4-pyrimidinyl)carbamate;

2,6-dimethylphenyl 2-(ethyloxy)phenyl(2-((3-(methyloxy)-4-((2-(4-methyl-1-piperazinyl)ethyl)oxy)phenyl)amino)-4-pyrimidinyl)carbamate;

2,6-dimethylphenyl 2-((3-aminophenyl)amino)-4-pyrimidinyl(1,1'-biphenyl-3-yl)carbamate;

2,6-dimethylphenyl 2-((3-aminophenyl)amino)-4-pyrimidinyl(2-(ethyloxy)phenyl)carbamate;

2,4,6-trimethylphenyl (2,5-bis(methyloxy)phenyl)methyl(2-((4-(((2-(dimethylamino)ethyl)amino)carbonyl)phenyl)amino)-4-pyrimidinyl)carbamate;

2,6-dimethylphenyl 2-((3,5-bis(methyloxy)-4-((2-(4-methyl-1-piperazinyl)ethyl)oxy)phenyl)amino)-4-pyrimidinyl(4-fluoro-2-((1-methylethyl)oxy)phenyl)carbamate;

2,6-dimethylphenyl 2-((3,4-bis(methyloxy)-5-((3-(4-methyl-1-piperazinyl)propyl)oxy)phenyl)amino)-4-pyrimidinyl(4-fluoro-2-((1-methylethyl)oxy)phenyl)carbamate;

2,6-dimethylphenyl 4-fluoro-2-((1-methylethyl)oxy)phenyl (2-((3-(methyloxy)-4-((3-(4-methyl-1-piperazinyl)propyl)oxy)phenyl)amino)-4-pyrimidinyl)carbamate;

2,6-dimethylphenyl 4-fluoro-2-((1-methylethyl)oxy)phenyl (2-((3-(methyloxy)-4-((2-(4-methyl-1-piperazinyl)ethyl)oxy)phenyl)amino)-4-pyrimidinyl)carbamate;

2,6-dimethylphenyl 2-((4-(aminocarbonyl)phenyl)amino)-4-pyrimidinyl(1,1'-biphenyl-3-yl)carbamate;

2-chlorophenyl 2,4-bis(methyloxy)phenyl(2-((4-((3-(1-piperidinyl)propyl)oxy)phenyl)amino)-4-pyrimidinyl)carbamate;

2-chlorophenyl 2,4-bis(methyloxy)phenyl(2-((3-(methyloxy)-4-(4-methyl-1-piperazinyl)phenyl)amino)-4-pyrimidinyl)carbamate;

2,6-dimethylphenyl 2-ethyl-4-(methyloxy)phenyl(2-((4-((3-(1-piperidinyl)propyl)oxy)phenyl)amino)-4-pyrimidinyl)carbamate;

2,6-dimethylphenyl 2-(1,3-oxazol-5-yl)phenyl(2-((4-((3-(1-piperidinyl)propyl)oxy)phenyl)amino)-4-pyrimidinyl)carbamate;

2,6-difluorophenyl 2,4-bis(methyloxy)phenyl(2-((4-((3-(1-piperidinyl)propyl)oxy)phenyl)amino)-4-pyrimidinyl)carbamate;

2,4,6-trimethylphenyl 2-((4-(((2(dimethylamino)ethyl)amino)carbonyl)phenyl);amino)-4-pyrimidinyl(2-(methyloxy)phenyl)carbamate;

2,4,6-trimethylphenyl 2-((4-(((2-(diethylamino)ethyl)amino)carbonyl)phenyl)amino)-4-pyrimidinyl(2-(methyloxy)phenyl)carbamate;

2,4,6-trimethylphenyl 2-((2-(aminomethyl)phenyl)amino)-4-pyrimidinyl(2-(methyloxy)phenyl)carbamate;

2,4,6-trimethylphenyl (5-chloro-2-methylphenyl)methyl(2-((3-(methyloxy)-4-((3-(4-methyl-1-piperazinyl)propyl)oxy)phenyl)amino)-4-pyrimidinyl)carbamate;

2,4,6-trimethylphenyl (5-chloro-2-methylphenyl)methyl(2-((3-fluoro-4-((3-(1-piperidinyl)propyl)oxy)phenyl)amino)-4-pyrimidinyl)carbamate;

2,4,6-trimethylphenyl (2-chloro-5-(trifluoromethyl)phenyl)methyl(2-((3-(methyloxy)-4-((3-(4-methyl-1-piperazinyl)propyl)oxy)phenyl)amino)-4-pyrimidinyl)carbamate;

2,4,6-trimethylphenyl (2-chloro-5-(trifluoromethyl)phenyl)methyl(2-((3-fluoro-4-((3-(1-piperidinyl)propyl)oxy)phenyl)amino)-4-pyrimidinyl)carbamate;

2,6-dimethylphenyl (2,5-bis(methyloxy)phenyl)methyl(2-((4-(4-methyl-1-piperazinyl)phenyl)amino)-4-pyrimidinyl)carbamate;

2,6-dimethylphenyl (2,5-bis(methyloxy)phenyl)methyl(2-((3-fluoro-4-((3-(4-methyl-1-piperazinyl)propyl)oxy)phenyl)amino)-4-pyrimidinyl)carbamate;

2,6-dimethylphenyl (2,5-bis(methyloxy)phenyl)methyl(2-((3-fluoro-4-((3-(1-piperidinyl)propyl)oxy)phenyl)amino)-4-pyrimidinyl)carbamate;

2,6-dimethylphenyl (2,5-bis(methyloxy)phenyl)methyl(2-((3-fluoro-4-(4-methyl-1-piperazinyl)phenyl)amino)-4-pyrimidinyl)carbamate;

2,6-dimethylphenyl (2,5-bis(methyloxy)phenyl)methyl(2-((4-(4-(1-methylethyl)-1-piperazinyl)phenyl)amino)-4-pyrimidinyl)carbamate;

2,6-dimethylphenyl (2,5-bis(methyloxy)phenyl)methyl(2-((3-((difluoromethyl)oxy)-4-(4-methyl-1-piperazinyl)phenyl)amino)-4-pyrimidinyl)carbamate;

2,6-dimethylphenyl (2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

2,6-dimethylphenyl (2,5-bis(methyloxy)phenyl)methyl(2-((4-(2-(3,4-dimethyl-1-piperazinyl)ethyl)phenyl)amino)-4-pyrimidinyl)carbamate;

2,6-dimethylphenyl (2,5-bis(methyloxy)phenyl)methyl(2-((4-(3,4-dimethyl-1-piperazinyl)-3-fluorophenyl)amino)-4-pyrimidinyl)carbamate;

2,6-dimethylphenyl (2,5-bis(methyloxy)phenyl)methyl(2-((3-fluoro-4-(((1-methyl-3-piperidinyl)methyl)oxy)phenyl)amino)-4-pyrimidinyl)carbamate;

2,6-dimethylphenyl (2,5-bis(methyloxy)phenyl)methyl(2-((4-(((2-(diethylamino)ethyl)(methyl)amino)carbonyl)phenyl)amino)-4-pyrimidinyl)carbamate;

2,6-dimethylphenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

2,6-dimethylphenyl (2,5-bis(methyloxy)phenyl)methyl(2-((4-(4-(3-(dimethylamino)propyl)-1-piperazinyl)phenyl)amino)-4-pyrimidinyl)carbamate;

2,6-dimethylphenyl (2,5-bis(methyloxy)phenyl)methyl(2-((3-fluoro-4-((2-(4-methyl-1-piperazinyl)ethyl)oxy)phenyl)amino)-4-pyrimidinyl)carbamate;

2,6-dimethylphenyl (2,5-bis(methyloxy)phenyl)methyl(2-((3-(((2-(diethylamino) ethyl)(methyl)amino)carbonyl)phenyl)amino)-4-pyrimidinyl)carbamate;

2,6-dimethylphenyl (2,5-bis(methyloxy)phenyl)methyl(2-((4-(3,4-dimethyl-1-piperazinyl)phenyl)amino)-4-pyrimidinyl)carbamate;

2,6-dimethylphenyl (2,5-bis(methyloxy)phenyl)methyl(2-((4-((3R,5S)-3,4,5-trimethyl-1-piperazinyl)phenyl)amino)-4-pyrimidinyl)carbamate;

2,6-dimethylphenyl (2,5-bis(methyloxy)phenyl)methyl(2-((3-(4-methyl-1-piperazinyl)phenyl)amino)-4-pyrimidinyl)carbamate;

2,4,6-trimethylphenyl 2-((3-aminophenyl)amino)-4-pyrimidinyl(2-(methyloxy)phenyl)carbamate;

2,6-dimethylphenyl 2,4-bis(methyloxy)phenyl(2-((3-fluoro-4-((3-(4-methyl-1-piperazinyl)propyl)oxy)phenyl)amino)-4-pyrimidinyl)carbamate;

2,6-dimethylphenyl 2,4-bis(methyloxy)phenyl(2-((3-fluoro-4-(4-methyl-1-piperazinyl)phenyl)amino)-4-pyrimidinyl)carbamate;

2,6-dimethylphenyl 2,4-bis(methyloxy)phenyl(2-((3-((difluoromethyl)oxy)-4-(4-methyl-1-piperazinyl)phenyl)amino)-4-pyrimidinyl)carbamate;

2,6-dimethylphenyl 2,4-bis(methyloxy)phenyl(2-((3-chloro-4-(4-(1-methylethyl)-1-piperazinyl)phenyl)amino)-4-pyrimidinyl)carbamate;

2,6-dimethylphenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

2,6-dimethylphenyl 2,4-bis(methyloxy)phenyl(2-((4-(3,4-dimethyl-1-piperazinyl)-3-fluorophenyl)amino)-4-pyrimidinyl)carbamate;

2,6-dimethylphenyl 2,4-bis(methyloxy)phenyl(2-((3-fluoro-4-(((1-methyl-3-piperidinyl)methyl)oxy)phenyl)amino)-4-pyrimidinyl)carbamate;

2,6-dimethylphenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;
2,6-dimethylphenyl 2,4-bis(methyloxy)phenyl(2-((3-fluoro-4-((2-(4-methyl-1-piperazinyl)ethyl)oxy)phenyl)amino)-4-pyrimidinyl)carbamate;
2,6-dimethylphenyl 2,4-bis(methyloxy)phenyl(2-((3-(4-methyl-1-piperazinyl)phenyl)amino)-4-pyrimidinyl)carbamate;
2,6-dimethylphenyl 2,4-bis(methyloxy)phenyl(2-((3-fluoro-4-((3R,5S)-3,4,5-trimethyl-1-piperazinyl)phenyl)amino)-4-pyrimidinyl)carbamate;
2,6-dimethylphenyl 2-((3,5-bis(methyloxy)-4-((2-(4-methyl-1-piperazinyl)ethyl)oxy)phenyl)amino)-4-pyrimidinyl((2,5-bis(methyloxy)phenyl)methyl)carbamate;
2,6-dimethylphenyl (2,5-bis(methyloxy)phenyl)methyl(2-((4-(4-(2-(dimethylamino)ethyl)-1-piperazinyl)phenyl)amino)-4-pyrimidinyl)carbamate;
2,6-dimethylphenyl 2,4-bis(methyloxy)phenyl(2-((4-(2-(3,4-dimethyl-1-piperazinyl)ethyl)phenyl)amino)-4-pyrimidinyl)carbamate;
2,6-dimethylphenyl 2-((2-(aminomethyl)phenyl)amino)-4-pyrimidinyl(1,1'-biphenyl-3-yl)carbamate;
2,4,6-trimethylphenyl 2-((3-(acetylamino)phenyl)amino)-4-pyrimidinyl(2-(methyloxy)phenyl)carbamate;
4-chloro-2-(methyloxy)phenyl 2,4-bis(methyloxy)phenyl(2-((3-fluoro-4-((3-(4-methyl-1-piperazinyl)propyl)oxy)phenyl)amino)-4-pyrimidinyl)carbamate;
4-chloro-2-(methyloxy)phenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;
4-chloro-2-(methyloxy)phenyl 2,4-bis(methyloxy)phenyl(2-((3-fluoro-4-((3-(1-piperidinyl)propyl)oxy)phenyl)amino)-4-pyrimidinyl)carbamate;
2,6-dimethylphenyl 2,4-bis(methyloxy)phenyl(2-((4-(3,4-dimethyl-1-piperazinyl)phenyl)amino)-4-pyrimidinyl)carbamate;
2,6-dimethylphenyl 2,4-bis(methyloxy)phenyl(2-((4-(((6-(dimethylamino)hexyl)amino)carbonyl)phenyl)amino)-4-pyrimidinyl)carbamate;
2,6-dimethylphenyl 2,4-bis(methyloxy)phenyl(2-((4-(((4-(diethylamino)butyl)amino)carbonyl)phenyl)amino)-4-pyrimidinyl)carbamate;
2,6-dimethylphenyl 2,4-bis(methyloxy)phenyl(2-((3-(((6-(dimethylamino)hexyl)amino)carbonyl)phenyl)amino)-4-pyrimidinyl)carbamate;
2-methyl-6-(2-propenyl)phenyl 2,4-bis(methyloxy)phenyl(2-((3-fluoro-4-(((1-methyl-3-piperidinyl)methyl)oxy)phenyl)amino)-4-pyrimidinyl)carbamate;
2-methyl-6-(2-propenyl)phenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;
2-methyl-6-(2-propenyl)phenyl 2,4-bis(methyloxy)phenyl(2-((4-(((2-(diethylamino)ethyl)(methyl)amino)carbonyl)phenyl)amino)-4-pyrimidinyl)carbamate;
2-methyl-6-(2-propenyl)phenyl 2,4-bis(methyloxy)phenyl(2-((3-((3-(1-piperidinyl)propyl)oxy)phenyl)amino)-4-pyrimidinyl)carbamate;
2-methyl-6-(2-propenyl)phenyl 2,4-bis(methyloxy)phenyl(2-((3-fluoro-4-((3-(1-piperidinyl)propyl)oxy)phenyl)amino)-4-pyrimidinyl)carbamate;
2-methyl-6-(2-propenyl)phenyl 2,4-bis(methyloxy)phenyl(2-((3-fluoro-4-((3-(4-methyl-1-piperazinyl)propyl)oxy)phenyl)amino)-4-pyrimidinyl)carbamate;
2-methyl-6-(2-propenyl)phenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;
2,6-dimethylphenyl (2,5-bis(methyloxy)phenyl)methyl(2-((4-(((6-(dimethylamino)hexyl)amino)carbonyl)phenyl)amino)-4-pyrimidinyl)carbamate;
2,6-dimethylphenyl (2,5-bis(methyloxy)phenyl)methyl(2-((4-(((4-(diethylamino)butyl)amino)carbonyl)phenyl)amino)-4-pyrimidinyl)carbamate;
2,6-dimethylphenyl (2,5-bis(methyloxy)phenyl)methyl(2-((3-(((4-(diethylamino)butyl)amino)carbonyl)phenyl)amino)-4-pyrimidinyl)carbamate;
2,6-dimethylphenyl (2,5-bis(methyloxy)phenyl)methyl(2-((3-(((6-(dimethylamino)hexyl)amino)carbonyl)phenyl)amino)-4-pyrimidinyl)carbamate;
2,6-dimethylphenyl (2,5-bis(methyloxy)phenyl)methyl(2-((3-(((3-(diethylamino)propyl)amino)carbonyl)phenyl)amino)-4-pyrimidinyl)carbamate;
2,6-dimethylphenyl (2,5-bis(methyloxy)phenyl)methyl(2-((3-(methyloxy)-4-(((2S)-2-pyrrolidinylmethyl)oxy)phenyl)amino)-4-pyrimidinyl)carbamate;
2,6-bis(methyloxy)phenyl 2,4-bis(methyloxy)phenyl(2-((3-fluoro-4-((3-(4-methyl-1-piperazinyl)propyl)oxy)phenyl)amino)-4-pyrimidinyl)carbamate;
2,6-bis(methyloxy)phenyl 2,4-bis(methyloxy)phenyl(2-((3-fluoro-4-((3-(1-piperidinyl)propyl)oxy)phenyl)amino)-4-pyrimidinyl)carbamate;
2,6-bis(methyloxy)phenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;
2,6-bis(methyloxy)phenyl 2,4-bis(methyloxy)phenyl(2-((4-(3,4-dimethyl-1-piperazinyl)-3-fluorophenyl)amino)-4-pyrimidinyl)carbamate;
2,6-difluorophenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;
2,6-difluorophenyl 2,4-bis(methyloxy)phenyl(2-((3-fluoro-4-((3-(4-methyl-1-piperazinyl)propyl)oxy)phenyl)amino)-4-pyrimidinyl)carbamate;
2,6-difluorophenyl 2,4-bis(methyloxy)phenyl(2-((3-fluoro-4-((3-(1-piperidinyl)propyl)oxy)phenyl)amino)-4-pyrimidinyl)carbamate;
2,6-difluorophenyl 2,4-bis(methyloxy)phenyl(2-((3-((3-(1-piperidinyl)propyl)oxy)phenyl)amino)-4-pyrimidinyl)carbamate;
2,6-difluorophenyl 2,4-bis(methyloxy)phenyl(2-((4-(((2-(diethylamino)ethyl)(methyl)amino)carbonyl)phenyl)amino)-4-pyrimidinyl)carbamate;
2,6-difluorophenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;
2,6-difluorophenyl 2,4-bis(methyloxy)phenyl(2-((3-fluoro-4-(((1-methyl-3-piperidinyl)methyl)oxy)phenyl)amino)-4-pyrimidinyl)carbamate;
2,6-difluorophenyl 2,4-bis(methyloxy)phenyl(2-((4-(3,4-dimethyl-1-piperazinyl)-3-fluorophenyl)amino)-4-pyrimidinyl)carbamate;
4-chloro-2-(methyloxy)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;
4-chloro-2-(methyloxy)phenyl (2,5-bis(methyloxy)phenyl)methyl(2-((3-fluoro-4-((3-(4-methyl-1-piperazinyl)propyl)oxy)phenyl)amino)-4-pyrimidinyl)carbamate;
4-chloro-2-(methyloxy)phenyl (2,5-bis(methyloxy)phenyl)methyl(2-((3-fluoro-4-((3-(1-piperidinyl)propyl)oxy)phenyl)amino)-4-pyrimidinyl)carbamate;
4-chloro-2-(methyloxy)phenyl (2,5-bis(methyloxy)phenyl)methyl(2-((3-((3-(1-piperidinyl)propyl)oxy)phenyl)amino)-4-pyrimidinyl)carbamate;

4-chloro-2-(methyloxy)phenyl (2,5-bis(methyloxy)phenyl)methyl(2-(((4-(((2-(diethylamino)ethyl)(methyl)amino)carbonyl)phenyl)amino)-4-pyrimidinyl)carbamate;

4-chloro-2-(methyloxy)phenyl (2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

4-chloro-2-(methyloxy)phenyl (2,5-bis(methyloxy)phenyl)methyl(2-((3-fluoro-4-(((1-methyl-3-piperidinyl)methyl)oxy)phenyl)amino)-4-pyrimidinyl)carbamate;

4-chloro-2-(methyloxy)phenyl (2,5-bis(methyloxy)phenyl)methyl(2-((4-(3,4-dimethyl-1-piperazinyl)-3-fluorophenyl)amino)-4-pyrimidinyl)carbamate;

2,6-dimethylcyclohexyl 2,4-bis(methyloxy)phenyl(2-((3-fluoro-4-((3-(4-methyl-1-piperazinyl)propyl)oxy)phenyl)amino)-4-pyrimidinyl)carbamate;

2,6-dimethylphenyl 2,4-bis(methyloxy)phenyl(2-((3-(((4-(diethylamino)butyl)amino)carbonyl)phenyl)amino)-4-pyrimidinyl)carbamate;

2,6-dimethylphenyl 2,4-bis(methyloxy)phenyl(2-((3-(((3-(diethylamino)propyl)amino)carbonyl)phenyl)amino)-4-pyrimidinyl)carbamate;

2,6-dimethylphenyl 2-chlorophenyl(2-((3-fluoro-4-((3-(4-methyl-1-piperazinyl)propyl)oxy)phenyl)amino)-4-pyrimidinyl)carbamate;

2,6-dimethylphenyl 2-((3,4-bis(methyloxy)-5-((3-(4-methyl-1-piperazinyl)propyl)oxy)phenyl)amino)-4-pyrimidinyl(2-chlorophenyl)carbamate;

2,4,6-trimethylphenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

2,4,6-trimethylphenyl 2,4-bis(methyloxy)phenyl(2-((3-fluoro-4-((3-(4-methyl-1-piperazinyl)propyl)oxy)phenyl)amino)-4-pyrimidinyl)carbamate;

2,4,6-trimethylphenyl 2,4-bis(methyloxy)phenyl(2-((3-fluoro-4-((3-(1-piperidinyl)propyl)oxy)phenyl)amino)-4-pyrimidinyl)carbamate;

2,4,6-trimethylphenyl 2,4-bis(methyloxy)phenyl(2-((3-((3-(1-piperidinyl)propyl)oxy)phenyl)amino)-4-pyrimidinyl)carbamate;

2,4,6-trimethylphenyl 2,4-bis(methyloxy)phenyl(2-((4-(((2-(diethylamino)ethyl)(methyl)amino)carbonyl)phenyl)amino)-4-pyrimidinyl)carbamate;

2,4,6-trimethylphenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

2,4,6-trimethylphenyl 2,4-bis(methyloxy)phenyl(2-((3-fluoro-4-(((1-methyl-3-piperidinyl)methyl)oxy)phenyl)amino)-4-pyrimidinyl)carbamate;

2,4,6-trimethylphenyl 2,4-bis(methyloxy)phenyl(2-((4-(3,4-dimethyl-1-piperazinyl)-3-fluorophenyl)amino)-4-pyrimidinyl)carbamate;

2,4,6-trimethylphenyl (2,5-bis(methyloxy)phenyl)methyl(2-((4-(4-methyl-1-piperazinyl)phenyl)amino)-4-pyrimidinyl)carbamate;

2,4,6-trimethylphenyl (2,5-bis(methyloxy)phenyl)methyl(2-((3-fluoro-4-((3-(4-methyl-1-piperazinyl)propyl)oxy)phenyl)amino)-4-pyrimidinyl)carbamate;

2,4,6-trimethylphenyl (2,5-bis(methyloxy)phenyl)methyl(2-((3-fluoro-4-(4-methyl-1-piperazinyl)phenyl)amino)-4-pyrimidinyl)carbamate;

2,4,6-trimethylphenyl (2,5-bis(methyloxy)phenyl)methyl(2-((3-((difluoromethyl)oxy)-4-(4-methyl-1-piperazinyl)phenyl)amino)-4-pyrimidinyl)carbamate;

2,4,6-trimethylphenyl (2,5-bis(methyloxy)phenyl)methyl(2-((3-chloro-4-(4-(1-methylethyl)-1-piperazinyl)phenyl)amino)-4-pyrimidinyl)carbamate;

2,4,6-trimethylphenyl (2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

2,4,6-trimethylphenyl (2,5-bis(methyloxy)phenyl)methyl(2-((4-((3-(4-(1-methylethyl)-1-piperazinyl)propyl)oxy)-3-(methyloxy)phenyl)amino)-4-pyrimidinyl)carbamate;

2,4,6-trimethylphenyl (2,5-bis(methyloxy)phenyl)methyl(2-((4-(3,4-dimethyl-1-piperazinyl)-3-fluorophenyl)amino)-4-pyrimidinyl)carbamate;

2,4,6-trimethylphenyl (2,5-bis(methyloxy)phenyl)methyl(2-((3-fluoro-4-(((1-methyl-3-piperidinyl)methyl)oxy)phenyl)amino)-4-pyrimidinyl)carbamate;

2,4,6-trimethylphenyl (2,5-bis(methyloxy)phenyl)methyl(2-((4-(((2-(diethylamino)ethyl)(methyl)amino)carbonyl)phenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

2,4,6-trimethylphenyl 2-((3,5-bis(methyloxy)-4-((2-(4-methyl-1-piperazinyl)ethyl)oxy)phenyl)amino)-4-pyrimidinyl((2,5-bis(methyloxy)phenyl)methyl)carbamate;

2,4,6-trimethylphenyl (2,5-bis(methyloxy)phenyl)methyl(2-((3-fluoro-4-((2-(4-methyl-1-piperazinyl)ethyl)oxy)phenyl)amino)-4-pyrimidinyl)carbamate;

2,4,6-trimethylphenyl (2,5-bis(methyloxy)phenyl)methyl(2-((3-(4-methyl-1-piperazinyl)phenyl)amino)-4-pyrimidinyl)carbamate;

2,4,6-trimethylphenyl (2,5-bis(methyloxy)phenyl)methyl(2-((3-(((2-(diethylamino)ethyl)(methyl)amino)carbonyl)phenyl)amino)-4-pyrimidinyl)carbamate;

2,4,6-trimethylphenyl (2,5-bis(methyloxy)phenyl)methyl(2-((4-(3,4-dimethyl-1-piperazinyl)phenyl)amino)-4-pyrimidinyl)carbamate;

2,4,6-trimethylphenyl (2,5-bis(methyloxy)phenyl)methyl(2-((3-fluoro-4-((3R,5S)-3,4,5-trimethyl-1-piperazinyl)phenyl)amino)-4-pyrimidinyl)carbamate;

2-((methyloxy)methyl)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

2-((methyloxy)methyl)phenyl (2,5-bis(methyloxy)phenyl)methyl(2-((3-fluoro-4-((3-(4-methyl-1-piperazinyl)propyl)oxy)phenyl)amino)-4-pyrimidinyl)carbamate;

2-((methyloxy)methyl)phenyl (2,5-bis(methyloxy)phenyl)methyl(2-((3-fluoro-4-((3-(1-piperidinyl)propyl)oxy)phenyl)amino)-4-pyrimidinyl)carbamate;

2-((methyloxy)methyl)phenyl (2,5-bis(methyloxy)phenyl)methyl(2-((3-((3-(1-piperidinyl)propyl)oxy)phenyl)amino)-4-pyrimidinyl)carbamate;

2-((methyloxy)methyl)phenyl (2,5-bis(methyloxy)phenyl)methyl(2-((4-(((2-(diethylamino)ethyl)(methyl)amino)carbonyl)phenyl)amino)-4-pyrimidinyl)carbamate;

2-((methyloxy)methyl)phenyl (2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

2-((methyloxy)methyl)phenyl (2,5-bis(methyloxy)phenyl)methyl(2-((3-fluoro-4-(((1-methyl-3-piperidinyl)methyl)oxy)phenyl)amino)-4-pyrimidinyl)carbamate;

2-((methyloxy)methyl)phenyl (2,5-bis(methyloxy)phenyl)methyl(2-((4-(3,4-dimethyl-1-piperazinyl)-3-fluorophenyl)amino)-4-pyrimidinyl)carbamate;

2-((methyloxy)methyl)phenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

2-((methyloxy)methyl)phenyl 2,4-bis(methyloxy)phenyl(2-((3-fluoro-4-((3-(4-methyl-1-piperazinyl)propyl)oxy)phenyl)amino)-4-pyrimidinyl)carbamate;

2-((methyloxy)methyl)phenyl 2,4-bis(methyloxy)phenyl(2-((3-fluoro-4-((3-(1-piperidinyl)propyl)oxy)phenyl)amino)-4-pyrimidinyl)carbamate;

2-((methyloxy)methyl)phenyl 2,4-bis(methyloxy)phenyl(2-((3-(3-(1-piperidinyl)propyl)oxy)phenyl)amino)-4-pyrimidinyl)carbamate;

2-((methyloxy)methyl)phenyl 2,4-bis(methyloxy)phenyl(2-((4-(((2-(diethylamino)ethyl)(methyl)amino)carbonyl)phenyl)amino)-4-pyrimidinyl)carbamate;

2-((methyloxy)methyl)phenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

2-((methyloxy)methyl)phenyl 2,4-bis(methyloxy)phenyl(2-((3-fluoro-4-(((1-methyl-3-piperidinyl)methyl)oxy)phenyl)amino)-4-pyrimidinyl)carbamate;

2-((methyloxy)methyl)phenyl 2,4-bis(methyloxy)phenyl(2-((4-(3,4-dimethyl-1-piperazinyl)-3-fluorophenyl)amino)-4-pyrimidinyl)carbamate;

5-methyl-2-(methyloxy)phenyl 2,4-bis(methyloxy)phenyl(2-((4-(3,4-dimethyl-1-piperazinyl)-3-fluorophenyl)amino)-4-pyrimidinyl)carbamate;

5-methyl-2-(methyloxy)phenyl 2,4-bis(methyloxy)phenyl(2-((3-fluoro-4-(((1-methyl-3-piperidinyl)methyl)oxy)phenyl)amino)-4-pyrimidinyl)carbamate;

2,6-dimethylphenyl 2,4-bis(methyloxy)phenyl(2-((4-(((3-(diethylamino)propyl)amino)carbonyl)phenyl)amino)-4-pyrimidinyl)carbamate;

2,6-dimethylphenyl 2,4-bis(methyloxy)phenyl(2-((3-(((2-(diethylamino)ethyl)amino)carbonyl)phenyl)amino)-4-pyrimidinyl)carbamate;

2,6-dimethylphenyl (2,5-bis(methyloxy)phenyl)methyl(2-((4-(((2-(diethylamino)ethyl)amino)carbonyl)phenyl)amino)-4-pyrimidinyl)carbamate;

2,6-dimethylphenyl (2,5-bis(methyloxy)phenyl)methyl(2-((3-(((2-(diethylamino)ethyl)amino)carbonyl)phenyl)amino)-4-pyrimidinyl)carbamate;

2,6-dimethylphenyl 2,4-bis(methyloxy)phenyl(2-((4-(((2-(diethylamino)ethyl)amino)carbonyl)-3-fluorophenyl)amino)-4-pyrimidinyl)carbamate;

2,4,6-trimethylphenyl (3,5-bis(methyloxy)phenyl)methyl(2-((3-fluoro-4-((3-(4-methyl-1-piperazinyl)propyl)oxy)phenyl)amino)-4-pyrimidinyl)carbamate;

2,4,6-trimethylphenyl (3,5-bis(methyloxy)phenyl)methyl(2-((3-fluoro-4-((3-(1-piperidinyl)propyl)oxy)phenyl)amino)-4-pyrimidinyl)carbamate;

2,4,6-trimethylphenyl (3,5-bis(methyloxy)phenyl)methyl(2-((3-((3-(1-piperidinyl)propyl)oxy)phenyl)amino)-4-pyrimidinyl)carbamate;

2,4,6-trimethylphenyl (3,5-bis(methyloxy)phenyl)methyl(2-((4-(((2-(diethylamino)ethyl)(methyl)amino)carbonyl)phenyl)amino)-4-pyrimidinyl)carbamate;

2,4,6-trimethylphenyl (3,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

2,4,6-trimethylphenyl (3,5-bis(methyloxy)phenyl)methyl(2-((3-fluoro-4-(((1-methyl-3-piperidinyl)methyl)oxy)phenyl)amino)-4-pyrimidinyl)carbamate;

2,4,6-trimethylphenyl (3,5-bis(methyloxy)phenyl)methyl(2-((4-(3,4-dimethyl-1-piperazinyl)-3-fluorophenyl)amino)-4-pyrimidinyl)carbamate;

2,6-dimethylphenyl 2-chlorophenyl(2-((3-fluoro-4-((3-(1-piperidinyl)propyl)oxy)phenyl)amino)-4-pyrimidinyl)carbamate;

2,6-dimethylphenyl 2-chlorophenyl(2-((3-((3-(1-piperidinyl)propyl)oxy)phenyl)amino)-4-pyrimidinyl)carbamate;

2,6-dimethylphenyl 2-chlorophenyl(2-((4-(((2-(diethylamino)ethyl)(methyl)amino)carbonyl)phenyl)amino)-4-pyrimidinyl)carbamate;

2,6-dimethylphenyl 2-chlorophenyl(2-((3-fluoro-4-((2-(4-(1-methylethyl)-1-piperazinyl)ethyl)oxy)phenyl)amino)-4-pyrimidinyl)carbamate;

2,6-dimethylphenyl 2-chlorophenyl(2-((3-fluoro-4-(((1-methyl-3-piperidinyl)methyl)oxy)phenyl)amino)-4-pyrimidinyl)carbamate;

2,6-dimethylphenyl 2-chlorophenyl(2-((4-(3,4-dimethyl-1-piperazinyl)-3-fluorophenyl)amino)-4-pyrimidinyl)carbamate;

5-methyl-2-(methyloxy)phenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

5-methyl-2-(methyloxy)phenyl 2,4-bis(methyloxy)phenyl(2-((3-((3-(1-piperidinyl)propyl)oxy)phenyl)amino)-4-pyrimidinyl)carbamate;

2,6-dimethylphenyl cyclohexyl(2-((3-fluoro-4-((3-(1-piperidinyl)propyl)oxy)phenyl)amino)-4-pyrimidinyl)carbamate;

2-(methylsulfanyl)phenyl 2,4-bis(methyloxy)phenyl(2-((4-(3,4-dimethyl-1-piperazinyl)-3-fluorophenyl)amino)-4-pyrimidinyl)carbamate;

2-(methylsulfanyl)phenyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;

2,4,6-trimethylphenyl (2,5-dichlorophenyl)methyl(2-((4-(((4-(diethylamino)butyl)amino)carbonyl)phenyl)amino)-4-pyrimidinyl)carbamate;

2,4,6-trimethylphenyl (2,5-dichlorophenyl)methyl(2-((4-(((6-(dimethylamino)hexyl)amino)carbonyl)phenyl)amino)-4-pyrimidinyl)carbamate;

2,4,6-trimethylphenyl (2,5-dichlorophenyl)methyl(2-((3-(((4-(diethylamino)butyl)amino)carbonyl)phenyl)amino)-4-pyrimidinyl)carbamate;

2,4,6-trimethylphenyl (2,5-dichlorophenyl)methyl(2-((3-(((6-(dimethylamino)hexyl)amino)carbonyl)phenyl)amino)-4-pyrimidinyl)carbamate;

2,4,6-trimethylphenyl (2,5-dichlorophenyl)methyl(2-((3-(((2-(diethylamino)ethyl)amino)carbonyl)phenyl)amino)-4-pyrimidinyl)carbamate;

2,4,6-trimethylphenyl (2,5-dichlorophenyl)methyl(2-((3-(((3-(diethylamino)propyl)amino)carbonyl)phenyl)amino)-4-pyrimidinyl)carbamate;

2,4,6-trimethylphenyl (2,5-dichlorophenyl)methyl(2-((4-(((3-(diethylamino)propyl)amino)carbonyl)phenyl)amino)-4-pyrimidinyl)carbamate;

2,4,6-trimethylphenyl (2,5-dichlorophenyl)methyl(2-((4-(((2-(diethylamino)ethyl)amino)carbonyl)phenyl)amino)-4-pyrimidinyl)carbamate;

2,6-dimethylphenyl cyclohexyl(2-((3-fluoro-4-((2-(4-(1-methylethyl)-1-piperazinyl)ethyl)oxy)phenyl)amino)-4-pyrimidinyl)carbamate;

2,6-dimethylphenyl cyclohexyl(2-((3-fluoro-4-(((1-methyl-3-piperidinyl)methyl)oxy)phenyl)amino)-4-pyrimidinyl)carbamate;

2,6-dimethylphenyl cyclohexyl(2-((3-fluoro-4-((3-(4-methyl-1-piperazinyl)propyl)oxy)phenyl)amino)-4-pyrimidinyl)carbamate;

2,6-dimethylphenyl cyclohexyl(2-((4-(((2-(diethylamino)ethyl)(methyl)amino)carbonyl)phenyl)amino)-4-pyrimidinyl)carbamate;

2,6-dimethylphenyl (2,5-bis(methyloxy)phenyl)methyl(2-((4-(((6-(dimethylamino)hexyl)amino)carbonyl)-3-fluorophenyl)amino)-4-pyrimidinyl)carbamate;

2,6-dimethylcyclohexyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;
2,6-dimethylcyclohexyl 2,4-bis(methyloxy)phenyl(2-((3-fluoro-4-((3-(1-piperidinyl)propyl)oxy)phenyl)amino)-4-pyrimidinyl)carbamate;
2,6-dimethylcyclohexyl 2,4-bis(methyloxy)phenyl(2-((3-((3-(1-piperidinyl)propyl)oxy)phenyl)amino)-4-pyrimidinyl)carbamate;
2,6-dimethylcyclohexyl 2,4-bis(methyloxy)phenyl(2-((4-(((2-(diethylamino)ethyl)(methyl)amino)carbonyl)phenyl)amino)-4-pyrimidinyl)carbamate;
2,6-dimethylcyclohexyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;
2,6-dimethylcyclohexyl 2,4-bis(methyloxy)phenyl(2-((4-(3,4-dimethyl-1-piperazinyl)-3-fluorophenyl)amino)-4-pyrimidinyl)carbamate;
2-methyl-1-(1-methylethyl)propyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;
2-methyl-1-(1-methylethyl)propyl 2,4-bis(methyloxy)phenyl(2-((3-fluoro-4-((3-(4-methyl-1-piperazinyl)propyl)oxy)phenyl)amino)-4-pyrimidinyl)carbamate;
2-methyl-1-(1-methylethyl)propyl 2,4-bis(methyloxy)phenyl(2-((3-fluoro-4-((3-(1-piperidinyl)propyl)oxy)phenyl)amino)-4-pyrimidinyl)carbamate;
2-methyl-1-(1-methylethyl)propyl 2,4-bis(methyloxy)phenyl(2-((3-((3-(1-piperidinyl)propyl)oxy)phenyl)amino)-4-pyrimidinyl)carbamate;
2-methyl-1-(1-methylethyl)propyl 2,4-bis(methyloxy)phenyl(2-((4-(((2-(diethylamino)ethyl)(methyl)amino)carbonyl)phenyl)amino)-4-pyrimidinyl)carbamate;
2-methyl-1-(1-methylethyl)propyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;
2-methyl-1-(1-methylethyl)propyl 2,4-bis(methyloxy)phenyl(2-((3-fluoro-4-(((1-methyl-3-piperidinyl)methyl)oxy)phenyl)amino)-4-pyrimidinyl)carbamate;
2-methyl-1-(1-methylethyl)propyl 2,4-bis(methyloxy)phenyl(2-((4-(3,4-dimethyl-1-piperazinyl)-3-fluorophenyl)amino)-4-pyrimidinyl)carbamate;
2-methyl-1-(1-methylethyl)butyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;
2-methyl-1-(1-methylethyl)butyl 2,4-bis(methyloxy)phenyl(2-((3-fluoro-4-((3-(4-methyl-1-piperazinyl)propyl)oxy)phenyl)amino)-4-pyrimidinyl)carbamate;
2-methyl-1-(1-methylethyl)butyl 2,4-bis(methyloxy)phenyl(2-((3-fluoro-4-((3-(1-piperidinyl)propyl)oxy)phenyl)amino)-4-pyrimidinyl)carbamate;
2-methyl-1-(1-methylethyl)butyl 2,4-bis(methyloxy)phenyl(2-((3-((3-(1-piperidinyl)propyl)oxy)phenyl)amino)-4-pyrimidinyl)carbamate;
2-methyl-1-(1-methylethyl)butyl 2,4-bis(methyloxy)phenyl(2-((4-(((2-(diethylamino)ethyl)(methyl)amino)carbonyl)phenyl)amino)-4-pyrimidinyl)carbamate;
2-methyl-1-(1-methylethyl)butyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;
2-methyl-1-(1-methylethyl)butyl 2,4-bis(methyloxy)phenyl(2-((3-fluoro-4-(((1-methyl-3-piperidinyl)methyl)oxy)phenyl)amino)-4-pyrimidinyl)carbamate;
2-methyl-1-(1-methylethyl)butyl 2,4-bis(methyloxy)phenyl(2-((4-(3,4-dimethyl-1-piperazinyl)-3-fluorophenyl)amino)-4-pyrimidinyl)carbamate;
(1S)-1-phenylethyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;
(1S)-1-phenylethyl 2,4-bis(methyloxy)phenyl(2-((3-fluoro-4-((3-(4-methyl-1-piperazinyl)propyl)oxy)phenyl)amino)-4-pyrimidinyl)carbamate;
(1S)-1-phenylethyl 2,4-bis(methyloxy)phenyl(2-((3-fluoro-4-((3-(1-piperidinyl)propyl)oxy)phenyl)amino)-4-pyrimidinyl)carbamate;
(1S)-1-phenylethyl 2,4-bis(methyloxy)phenyl(2-((3-((3-(1-piperidinyl)propyl)oxy)phenyl)amino)-4-pyrimidinyl)carbamate;
(1S)-1-phenylethyl 2,4-bis(methyloxy)phenyl(2-((4-(((2-(diethylamino)ethyl)(methyl)amino)carbonyl)phenyl)amino)-4-pyrimidinyl)carbamate;
(1S)-1-phenylethyl 2,4-bis(methyloxy)phenyl(2-((3-fluoro-4-((2-(4-(1-methylethyl)-1-piperazinyl)ethyl)oxy)phenyl)amino)-4-pyrimidinyl)carbamate;
(1S)-1-phenylethyl 2,4-bis(methyloxy)phenyl(2-((3-fluoro-4-(((1-methyl-3-piperidinyl)methyl)oxy)phenyl)amino)-4-pyrimidinyl)carbamate;
(1S)-1-phenylethyl 2,4-bis(methyloxy)phenyl(2-((4-(3,4-dimethyl-1-piperazinyl)-3-fluorophenyl)amino)-4-pyrimidinyl)carbamate;
2,4,6-trimethylphenyl 2-((3,4-bis(methyloxy)-5-((3-(4-methyl-1-piperazinyl)propyl)oxy)phenyl)amino)-4-pyrimidinyl((2,3-bis(methyloxy)phenyl)methyl)carbamate;
2,4,6-trimethylphenyl (2,3-bis(methyloxy)phenyl)methyl(2-((3-fluoro-4-((3-(4-methyl-1-piperazinyl)propyl)oxy)phenyl)amino)-4-pyrimidinyl)carbamate;
2,4,6-trimethylphenyl (2,3-bis(methyloxy)phenyl)methyl(2-((3-fluoro-4-((3-(1-piperidinyl)propyl)oxy)phenyl)amino)-4-pyrimidinyl)carbamate;
2,4,6-trimethylphenyl (2,3-bis(methyloxy)phenyl)methyl(2-((3-fluoro-4-(((1-methyl-3-piperidinyl)methyl)oxy)phenyl)amino)-4-pyrimidinyl)carbamate;
2,4,6-trimethylphenyl (2,3-bis(methyloxy)phenyl)methyl(2-((4-(3,4-dimethyl-1-piperazinyl)-3-fluorophenyl)amino)-4-pyrimidinyl)carbamate;
2,4,6-trimethylphenyl (2,5-dichlorophenyl)methyl(2-((4-(4-methyl-1-piperazinyl)phenyl)amino)-4-pyrimidinyl)carbamate;
2,4,6-trimethylphenyl (2,5-dichlorophenyl)methyl(2-((3-fluoro-4-((3-(4-methyl-1-piperazinyl)propyl)oxy)phenyl)amino)-4-pyrimidinyl)carbamate;
2,4,6-trimethylphenyl (2,5-dichlorophenyl)methyl(2-((3-fluoro-4-(4-methyl-1-piperazinyl)phenyl)amino)-4-pyrimidinyl)carbamate;
2,4,6-trimethylphenyl (2,5-dichlorophenyl)methyl(2-((3-((difluoromethyl)oxy)-4-(4-methyl-1-piperazinyl)phenyl)amino)-4-pyrimidinyl)carbamate;
2,4,6-trimethylphenyl (2,5-dichlorophenyl)methyl(2-((3-fluoro-4-((2-(4-(1-methylethyl)-1-piperazinyl) ethyl) oxy) phenyl)amino)-4-pyrimidinyl)carbamate;
2,4,6-trimethylphenyl (2,5-dichlorophenyl)methyl(2-((4-((3-(4-(1-methylethyl)-1-piperazinyl)propyl)oxy)-3-(methyloxy)phenyl)amino)-4-pyrimidinyl)carbamate;
2,4,6-trimethylphenyl (2,5-dichlorophenyl)methyl(2-((4-((3-(4-(2-(dimethylamino)ethyl)-1-piperazinyl)propyl)oxy)-3-fluorophenyl)amino)-4-pyrimidinyl)carbamate;
2,4,6-trimethylphenyl (2,5-dichlorophenyl)methyl(2-((4-(3,4-dimethyl-1-piperazinyl)-3-fluorophenyl)amino)-4-pyrimidinyl)carbamate;
2,4,6-trimethylphenyl (2,5-dichlorophenyl)methyl(2-((3-fluoro-4-(((1-methyl-3-piperidinyl)methyl)oxy)phenyl)amino)-4-pyrimidinyl)carbamate;

2,4,6-trimethylphenyl (2,5-dichlorophenyl)methyl(2-((4-(((2-(diethylamino)ethyl)(methyl)amino)carbonyl)phenyl)amino)-4-pyrimidinyl)carbamate;

2,4,6-trimethylphenyl (2,5-dichlorophenyl)methyl(2-((3-fluoro-4-((2-(4-methyl-1-piperazinyl)ethyl)oxy)phenyl)amino)-4-pyrimidinyl)carbamate;

2,4,6-trimethylphenyl (2,5-dichlorophenyl)methyl(2-((4-(3,4-dimethyl-1-piperazinyl)phenyl)amino)-4-pyrimidinyl)carbamate;

methyl 2-((((2-((3,4-bis(methyloxy)-5-((3-(4-methyl-1-piperazinyl)propyl)oxy)phenyl)amino)-4-pyrimidinyl)((2,5-bis(methyloxy)phenyl)methyl)amino)carbonyl)oxy)benzoate;

methyl 2-(((((2,5-bis(methyloxy)phenyl)methyl)(2-((3-fluoro-4-((3-(4-methyl-1-piperazinyl)propyl)oxy)phenyl)amino)-4-pyrimidinyl)amino)carbonyl)oxy)benzoate;

methyl 2-(((((2,5-bis(methyloxy)phenyl)methyl)(2-((3-fluoro-4-((3-(1-piperidinyl)propyl)oxy)phenyl)amino)-4-pyrimidinyl)amino)carbonyl)oxy)benzoate;

methyl 2-(((((2,5-bis(methyloxy)phenyl)methyl)(2-((3-((3-(1-piperidinyl)propyl)oxy)phenyl)amino)-4-pyrimidinyl)amino)carbonyl)oxy)benzoate;

methyl 2-(((((2,5-bis(methyloxy)phenyl)methyl)(2-((4-(((2-(diethylamino)ethyl)(methyl)amino)carbonyl)phenyl)amino)-4-pyrimidinyl)amino)carbonyl)oxy)benzoate;

methyl 2-(((((2,5-bis(methyloxy)phenyl)methyl)(2-((3-fluoro-4-((2-(4-(1-methylethyl)-1-piperazinyl)ethyl)oxy)phenyl)amino)-4-pyrimidinyl)amino)carbonyl)oxy)benzoate;

methyl 2-(((((2,5-bis(methyloxy)phenyl)methyl)(2-((3-fluoro-4-(((1-methyl-3-piperidinyl)methyl)oxy)phenyl)amino)-4-pyrimidinyl)amino)carbonyl)oxy)benzoate;

methyl 2-(((((2,5-bis(methyloxy)phenyl)methyl)(2-((4-(3,4-dimethyl-1-piperazinyl)-3-fluorophenyl)amino)-4-pyrimidinyl)amino)carbonyl)oxy)benzoate;

methyl 2-((((2-((3,4-bis(methyloxy)-5-((3-(4-methyl-1-piperazinyl)propyl)oxy)phenyl)amino)-4-pyrimidinyl)(2,4-bis(methyloxy)phenyl)amino)carbonyl)oxy)benzoate;

methyl 2-((((2,4-bis(methyloxy)phenyl)(2-((3-fluoro-4-((3-(4-methyl-1-piperazinyl)propyl)oxy)phenyl)amino)-4-pyrimidinyl)amino)carbonyl)oxy)benzoate;

methyl 2-((((2,4-bis(methyloxy)phenyl)(2-((3-fluoro-4-((3-(1-piperidinyl)propyl)oxy)phenyl)amino)-4-pyrimidinyl)amino)carbonyl)oxy)benzoate;

methyl 2-((((2,4-bis(methyloxy)phenyl)(2-((3-((3-(1-piperidinyl)propyl)oxy)phenyl)amino)-4-pyrimidinyl)amino)carbonyl)oxy)benzoate;

methyl 2-((((2,4-bis(methyloxy)phenyl)(2-((4-(((2-(diethylamino)ethyl)(methyl)amino)carbonyl)phenyl)amino)-4-pyrimidinyl)amino)carbonyl)oxy)benzoate;

methyl 2-((((2,4-bis(methyloxy)phenyl)(2-((3-fluoro-4-((2-(4-(1-methylethyl)-1-piperazinyl)ethyl)oxy)phenyl)amino)-4-pyrimidinyl)amino)carbonyl)oxy)benzoate;

methyl 2-((((2,4-bis(methyloxy)phenyl)(2-((3-fluoro-4-(((1-methyl-3-piperidinyl)methyl)oxy)phenyl)amino)-4-pyrimidinyl)amino)carbonyl)oxy)benzoate;

methyl 2-((((2,4-bis(methyloxy)phenyl)(2-((4-(3,4-dimethyl-1-piperazinyl)-3-fluorophenyl)amino)-4-pyrimidinyl)amino)carbonyl)oxy)benzoate;

2,6-bis(methyloxy)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

2,6-bis(methyloxy)phenyl (2,5-bis(methyloxy)phenyl)methyl(2-((3-fluoro-4-((3-(1-piperidinyl)propyl)oxy)phenyl)amino)-4-pyrimidinyl)carbamate;

2,6-bis(methyloxy)phenyl (2,5-bis(methyloxy)phenyl)methyl(2-((3-((3-(1-piperidinyl)propyl)oxy)phenyl)amino)-4-pyrimidinyl)carbamate;

2,6-bis(methyloxy)phenyl (2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

2,6-difluorophenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

2,6-difluorophenyl (2,5-bis(methyloxy)phenyl)methyl(2-((3-fluoro-4-((3-(4-methyl-1-piperazinyl)propyl)oxy)phenyl)amino)-4-pyrimidinyl)carbamate;

2,6-difluorophenyl (2,5-bis(methyloxy)phenyl)methyl(2-((3-fluoro-4-((3-(1-piperidinyl)propyl)oxy)phenyl)amino)-4-pyrimidinyl)carbamate;

2,6-difluorophenyl (2,5-bis(methyloxy)phenyl)methyl(2-((3-((3-(1-piperidinyl)propyl)oxy)phenyl)amino)-4-pyrimidinyl)carbamate;

5-methyl-2-(methyloxy)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

5-methyl-2-(methyloxy)phenyl (2,5-bis(methyloxy)phenyl)methyl(2-((3-fluoro-4-((3-(4-methyl-1-piperazinyl)propyl)oxy)phenyl)amino)-4-pyrimidinyl)carbamate;

5-methyl-2-(methyloxy)phenyl (2,5-bis(methyloxy)phenyl)methyl(2-((3-fluoro-4-((3-(1-piperidinyl)propyl)oxy)phenyl)amino)-4-pyrimidinyl)carbamate;

5-methyl-2-(methyloxy)phenyl (2,5-bis(methyloxy)phenyl)methyl(2-((3-((3-(1-piperidinyl)propyl)oxy)phenyl)amino)-4-pyrimidinyl)carbamate;

5-methyl-2-(methyloxy)phenyl (2,5-bis(methyloxy)phenyl)methyl(2-((4-(((2-(diethylamino)ethyl)(methyl)amino)carbonyl)phenyl)amino)-4-pyrimidinyl)carbamate;

5-methyl-2-(methyloxy)phenyl (2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

5-methyl-2-(methyloxy)phenyl (2,5-bis(methyloxy)phenyl)methyl(2-((3-fluoro-4-(((1-methyl-3-piperidinyl)methyl)oxy)phenyl)amino)-4-pyrimidinyl)carbamate;

2,6-dimethylphenyl 2-((3,4-bis(methyloxy)-5-((3-(4-methyl-1-piperazinyl)propyl)oxy)phenyl)amino)-4-pyrimidinyl(2,5-bis(methyloxy)phenyl)carbamate;

2,6-dimethylphenyl 2,5-bis(methyloxy)phenyl(2-((3-fluoro-4-((3-(4-methyl-1-piperazinyl)propyl)oxy)phenyl)amino)-4-pyrimidinyl)carbamate;

2,6-dimethylphenyl 2,5-bis(methyloxy)phenyl(2-((3-fluoro-4-((3-(1-piperidinyl)propyl)oxy)phenyl)amino)-4-pyrimidinyl)carbamate;

2,6-dimethylphenyl 2,5-bis(methyloxy)phenyl(2-((3-((3-(1-piperidinyl)propyl)oxy)phenyl)amino)-4-pyrimidinyl)carbamate;

2,6-dimethylphenyl 2,5-bis(methyloxy)phenyl(2-((4-(((2-(diethylamino)ethyl)(methyl)amino)carbonyl)phenyl)amino)-4-pyrimidinyl)carbamate;

2,6-dimethylphenyl 2,5-bis(methyloxy)phenyl(2-((3-fluoro-4-((2-(4-(1-methylethyl)-1-piperazinyl)ethyl)oxy)phenyl)amino)-4-pyrimidinyl)carbamate;

2,6-dimethylphenyl 2,5-bis(methyloxy)phenyl(2-((3-fluoro-4-(((1-methyl-3-piperidinyl)methyl)oxy)phenyl)amino)-4-pyrimidinyl)carbamate;

2,6-dimethylphenyl 2,5-bis(methyloxy)phenyl(2-((4-(3,4-dimethyl-1-piperazinyl)-3-fluorophenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((3,5-bis(methyloxy)phenyl)methyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((5-chloro-2-fluorophenyl)methyl)carbamate;
2,4,6-trimethylphenyl (5-chloro-2-fluorophenyl)methyl(2-((3-fluoro-4-((3-(4-methyl-1-piperazinyl)propyl)oxy)phenyl)amino)-4-pyrimidinyl)carbamate;
2,4,6-trimethylphenyl (5-chloro-2-fluorophenyl)methyl(2-((3-((3-(1-piperidinyl)propyl)oxy)phenyl)amino)-4-pyrimidinyl)carbamate;
2,4,6-trimethylphenyl (2,5-bis(methyloxy)phenyl)methyl(2-((6-((3-(4-methyl-1-piperazinyl)propyl)oxy)-3-pyridinyl)amino)-4-pyrimidinyl)carbamate;
2,4,6-trimethylphenyl (2-chloro-5-(trifluoromethyl)phenyl)methyl(2-((6-((3-(4-methyl-1-piperazinyl)propyl)oxy)-3-pyridinyl)amino)-4-pyrimidinyl)carbamate;
2,4,6-trimethylphenyl (5-chloro-2-methylphenyl)methyl(2-((6-((3-(4-methyl-1-piperazinyl)propyl)oxy)-3-pyridinyl)amino)-4-pyrimidinyl)carbamate;
2,4,6-trimethylphenyl 2-((3,4-bis(methyloxy)-5-((3-(4-methyl-1-piperazinyl)propyl)oxy)phenyl)amino)-4-pyrimidinyl((3,5-dichlorophenyl)methyl)carbamate;
2,4,6-trimethylphenyl (3,5-dichlorophenyl)methyl(2-((3-fluoro-4-((3-(4-methyl-1-piperazinyl)propyl)oxy)phenyl)amino)-4-pyrimidinyl)carbamate;
2,4,6-trimethylphenyl (3,5-dichlorophenyl)methyl(2-((3-((3-(1-piperidinyl)propyl)oxy)phenyl)amino)-4-pyrimidinyl)carbamate;
2,4,6-trimethylphenyl (3,5-dichlorophenyl)methyl(2-((4-(((2-(diethylamino)ethyl)(methyl)amino)carbonyl)phenyl)amino)-4-pyrimidinyl)carbamate;
2,4,6-trimethylphenyl (3,5-dichlorophenyl)methyl(2-((3-fluoro-4-((2-(4-(1-methylethyl)-1-piperazinyl)ethyl)oxy)phenyl)amino)-4-pyrimidinyl)carbamate;
2,4,6-trimethylphenyl (3,5-dichlorophenyl)methyl(2-((3-fluoro-4-(((1-methyl-3-piperidinyl)methyl)oxy)phenyl)amino)-4-pyrimidinyl)carbamate;
2-methyl-6-(2-propenyl)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;
2-methyl-6-(2-propenyl)phenyl (2,5-bis(methyloxy)phenyl)methyl(2-((3-fluoro-4-((3-(4-methyl-1-piperazinyl)propyl)oxy)phenyl)amino)-4-pyrimidinyl)carbamate;
2-methyl-6-(2-propenyl)phenyl (2,5-bis(methyloxy)phenyl)methyl(2-((3-fluoro-4-((3-(1-piperidinyl)propyl)oxy)phenyl)amino)-4-pyrimidinyl)carbamate;
2-methyl-6-(2-propenyl)phenyl (2,5-bis(methyloxy)phenyl)methyl(2-((3-((3-(1-piperidinyl)propyl)oxy)phenyl)amino)-4-pyrimidinyl)carbamate;
2-methyl-6-(2-propenyl)phenyl (2,5-bis(methyloxy)phenyl)methyl(2-((4-(((2-(diethylamino)ethyl)(methyl)amino)carbonyl)phenyl)amino)-4-pyrimidinyl)carbamate;
2-methyl-6-(2-propenyl)phenyl (2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;
2-methyl-6-(2-propenyl)phenyl (2,5-bis(methyloxy)phenyl)methyl(2-((3-fluoro-4-(((1-methyl-3-piperidinyl)methyl)oxy)phenyl)amino)-4-pyrimidinyl)carbamate;
2-methyl-6-(2-propenyl)phenyl (2,5-bis(methyloxy)phenyl)methyl(2-((4-(3,4-dimethyl-1-piperazinyl)-3-fluorophenyl)amino)-4-pyrimidinyl)carbamate;
2,6-dimethylphenyl 2-((4-(((2-(diethylamino)ethyl)(methyl)amino)carbonyl)phenyl)amino)-4-pyrimidinyl(2-(methyloxy)-4-(2-((1-methylpropyl)amino)-2-oxoethyl)phenyl)carbamate;
2,6-dimethylphenyl 2-((3-fluoro-4-((3-(1-piperidinyl)propyl)oxy)phenyl)amino)-4-pyrimidinyl(2-(methyloxy)-4-(2-((1-methylpropyl)amino)-2-oxoethyl)phenyl)carbamate;
2,6-dimethylphenyl 2-((3-fluoro-4-((2-(4-(1-methylethyl)-1-piperazinyl)ethyl)oxy)phenyl)amino)-4-pyrimidinyl(2-(methyloxy)-4-(2-((1-methylpropyl)amino)-2-oxoethyl)phenyl)carbamate;
2,6-dimethylphenyl 4-(2-(diethylamino)-2-oxoethyl)-2-(methyloxy)phenyl(2-((3-fluoro-4-((3-(4-methyl-1-piperazinyl)propyl)oxy)phenyl)amino)-4-pyrimidinyl)carbamate;
2,6-dimethylphenyl 4-(2-(diethylamino)-2-oxoethyl)-2-(methyloxy)phenyl(2-((3-fluoro-4-((3-(1-piperidinyl)propyl)oxy)phenyl)amino)-4-pyrimidinyl)carbamate;
2,4,6-trimethylphenyl (3-chlorophenyl)methyl(2-((4-(((2-(diethylamino)ethyl)(methyl)amino)carbonyl)phenyl)amino)-4-pyrimidinyl)carbamate;
2,4,6-trimethylphenyl (3-chlorophenyl)methyl(2-((3-fluoro-4-((3-(4-methyl-1-piperazinyl)propyl)oxy)phenyl)amino)-4-pyrimidinyl)carbamate;
2,4,6-trimethylphenyl 2-((3,4-bis(methyloxy)-5-((3-(4-methyl-1-piperazinyl)propyl)oxy)phenyl)amino)-4-pyrimidinyl((3-chlorophenyl)methyl)carbamate;
2,4,6-trimethylphenyl (3-chlorophenyl)methyl(2-((3-fluoro-4-(((1-methyl-3-piperidinyl)methyl)oxy)phenyl)amino)-4-pyrimidinyl)carbamate;
2,4,6-trimethylphenyl (3-chlorophenyl)methyl(2-((3-fluoro-4-((2-(4-(1-methylethyl)-1-piperazinyl)ethyl)oxy)phenyl)amino)-4-pyrimidinyl)carbamate;
2-(methylsulfanyl)phenyl 2,4-bis(methyloxy)phenyl(2-((3-fluoro-4-(((1-methyl-3-piperidinyl)methyl)oxy)phenyl)amino)-4-pyrimidinyl)carbamate;
2-(methylsulfanyl)phenyl 2,4-bis(methyloxy)phenyl(2-((3-((3-(1-piperidinyl)propyl)oxy)phenyl)amino)-4-pyrimidinyl)carbamate;
2-(methylsulfanyl)phenyl 2,4-bis(methyloxy)phenyl(2-((4-(((2-(diethylamino)ethyl)(methyl)amino)carbonyl)phenyl)amino)-4-pyrimidinyl)carbamate;
2,4,6-trimethylphenyl (2-chloro-5-(trifluoromethyl)phenyl)methyl(2-((3-((difluoromethyl)oxy)-4-(4-methyl-1-piperazinyl)phenyl)amino)-4-pyrimidinyl)carbamate;
2,4,6-trimethylphenyl (2,5-dichlorophenyl)methyl(2-((3-(4-methyl-1-piperazinyl)phenyl)amino)-4-pyrimidinyl)carbamate;
2,4,6-trimethylphenyl (2-chloro-5-(trifluoromethyl)phenyl)methyl(2-((3-fluoro-4-(4-methyl-1-piperazinyl)phenyl)amino)-4-pyrimidinyl)carbamate;
2,4,6-trimethylphenyl (2,5-dichlorophenyl)methyl(2-((3-(((2-(diethylamino)ethyl)(methyl)amino)carbonyl)phenyl)amino)-4-pyrimidinyl)carbamate;
2,4,6-trimethylphenyl (2,5-dichlorophenyl)methyl(2-((3-fluoro-4-((3R,5S)-3,4,5-trimethyl-1-piperazinyl)phenyl)amino)-4-pyrimidinyl)carbamate;
2,4,6-trimethylphenyl (2-chloro-5-(trifluoromethyl)phenyl)methyl(2-((4-(4-methyl-1-piperazinyl)phenyl)amino)-4-pyrimidinyl)carbamate;
2,4,6-trimethylphenyl 2-((3,5-bis(methyloxy)-4-((2-(4-methyl-1-piperazinyl)ethyl)oxy)phenyl)amino)-4-pyrimidinyl((2,5-dichlorophenyl)methyl)carbamate;
2,4,6-trimethylphenyl (2-chloro-5-(trifluoromethyl)phenyl)methyl(2-((3-fluoro-4-((2-(4-(1-methylethyl)-1-piperazinyl)ethyl)oxy)phenyl)amino)-4-pyrimidinyl)carbamate;
2,4,6-trimethylphenyl 2-((3,4-bis(methyloxy)-5-((3-(4-methyl-1-piperazinyl)propyl)oxy)phenyl)amino)-4-pyrimidinyl((2,5-dichlorophenyl)methyl)carbamate;

2,4,6-trimethylphenyl 2-((3-chloro-4-(4-(1-methylethyl)-1-piperazinyl)phenyl)amino)-4-pyrimidinyl((2-chloro-5-(trifluoromethyl)phenyl)methyl)carbamate;

2,4,6-trimethylphenyl (2,3-bis(methyloxy)phenyl)methyl(2-((3-((3-(1-piperidinyl)propyl)oxy)phenyl)amino)-4-pyrimidinyl)carbamate;

2,6-dimethylphenyl 2-((3,4-bis(methyloxy)-5-((3-(4-methyl-1-piperazinyl)propyl)oxy)phenyl)amino)-4-pyrimidinyl(3-(3-((1-methylpropyl)amino)-3-oxopropyl)phenyl)carbamate;

2,6-dimethylphenyl 2-((3-fluoro-4-((3-(4-methyl-1-piperazinyl)propyl)oxy)phenyl)amino)-4-pyrimidinyl(3-(3-((1-methylpropyl)amino)-3-oxopropyl)phenyl)carbamate;

2,6-dimethylphenyl 2-((3-fluoro-4-((3-(1-piperidinyl)propyl)oxy)phenyl)amino)-4-pyrimidinyl(3-(3-((1-methylpropyl)amino)-3-oxopropyl)phenyl)carbamate;

2,6-dimethylphenyl 2-((4-(((2-(diethylamino)ethyl)(methyl)amino)carbonyl)phenyl)amino)-4-pyrimidinyl(3-(3-((1-methylpropyl)amino)-3-oxopropyl)phenyl)carbamate;

2,6-bis(methyloxy)phenyl (2,5-bis(methyloxy)phenyl)methyl(2-((3-fluoro-4-((3-(4-methyl-1-piperazinyl)propyl)oxy)phenyl)amino)-4-pyrimidinyl)carbamate;

2,6-difluorophenyl (2,5-bis(methyloxy)phenyl)methyl(2-((3-fluoro-4-(((1-methyl-3-piperidinyl)methyl)oxy)phenyl)amino)-4-pyrimidinyl)carbamate;

2,6-bis(methyloxy)phenyl (2,5-bis(methyloxy)phenyl)methyl(2-((3-fluoro-4-(((1-methyl-3-piperidinyl)methyl)oxy)phenyl)amino)-4-pyrimidinyl)carbamate;

2,6-difluorophenyl (2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

5-methyl-2-(methyloxy)phenyl 2-((3,4-bis(methyloxy)-5-((3-(4-methyl-1-piperazinyl)propyl)oxy)phenyl)amino)-4-pyrimidinyl(2,4-bis(methyloxy)phenyl)carbamate;

5-methyl-2-(methyloxy)phenyl 2,4-bis(methyloxy)phenyl(2-((3-fluoro-4-((3-(4-methyl-1-piperazinyl)propyl)oxy)phenyl)amino)-4-pyrimidinyl)carbamate;

5-methyl-2-(methyloxy)phenyl 2,4-bis(methyloxy)phenyl(2-((3-fluoro-4-((3-(1-piperidinyl)propyl)oxy)phenyl)amino)-4-pyrimidinyl)carbamate;

5-methyl-2-(methyloxy)phenyl 2,4-bis(methyloxy)phenyl(2-((4-(((2-(diethylamino)ethyl)(methyl)amino)carbonyl)phenyl)amino)-4-pyrimidinyl)carbamate;

2,6-bis(methyloxy)phenyl (2,5-bis(methyloxy)phenyl)methyl(2-((4-(((2-(diethylamino)ethyl)(methyl)amino)carbonyl)phenyl)amino)-4-pyrimidinyl)carbamate;

2,6-difluorophenyl (2,5-bis(methyloxy)phenyl)methyl(2-((4-(((2-(diethylamino)ethyl)(methyl)amino)carbonyl)phenyl)amino)-4-pyrimidinyl)carbamate;

2,6-difluorophenyl (2,5-bis(methyloxy)phenyl)methyl(2-((4-(3,4-dimethyl-1-piperazinyl)-3-fluorophenyl)amino)-4-pyrimidinyl)carbamate;

2,4,6-trimethylphenyl (2,5-dichlorophenyl)methyl(2-((6-((3-(4-methyl-1-piperazinyl)propyl)oxy)-3-pyridinyl)amino)-4-pyrimidinyl)carbamate;

2-methyl-1-(1-methylethyl)propyl 2-((3,4-bis(methyloxy)-5-((3-(4-methyl-1-piperazinyl)propyl)oxy)phenyl)amino)-4-pyrimidinyl((3-(methyloxy)phenyl)methyl)carbamate;

2-methyl-1-(1-methylethyl)propyl 2-((3-fluoro-4-((3-(4-methyl-1-piperazinyl)propyl)oxy)phenyl)amino)-4-pyrimidinyl((3-(methyloxy)phenyl)methyl)carbamate;

2-methyl-1-(1-methylethyl)propyl 2-((3-fluoro-4-((3-(1-piperidinyl)propyl)oxy)phenyl)amino)-4-pyrimidinyl((3-(methyloxy)phenyl)methyl)carbamate;

2-methyl-1-(1-methylethyl)propyl (3-(methyloxy)phenyl)methyl(2-((3-((3-(1-piperidinyl)propyl)oxy)phenyl)amino)-4-pyrimidinyl)carbamate;

2-methyl-1-(1-methylethyl)propyl 2-((4-(((2-(diethylamino)ethyl)(methyl)amino)carbonyl)phenyl)amino)-4-pyrimidinyl((3-(methyloxy)phenyl)methyl)carbamate;

2-methyl-1-(1-methylethyl)propyl 2-((3-fluoro-4-((2-(4-(1-methylethyl)-1-piperazinyl)ethyl)oxy)phenyl)amino)-4-pyrimidinyl((3-(methyloxy)phenyl)methyl)carbamate;

2-methyl-1-(1-methylethyl)propyl 2-((3-fluoro-4-(((1-methyl-3-piperidinyl)methyl)oxy)phenyl)amino)-4-pyrimidinyl((3-(methyloxy)phenyl)methyl)carbamate;

2-methyl-1-(1-methylethyl)butyl 2-((3,4-bis(methyloxy)-5-((3-(4-methyl-1-piperazinyl)propyl)oxy)phenyl)amino)-4-pyrimidinyl((3-(methyloxy)phenyl)methyl)carbamate;

2-methyl-1-(1-methylethyl)butyl 2-((3-fluoro-4-((3-(4-methyl-1-piperazinyl)propyl)oxy)phenyl)amino)-4-pyrimidinyl((3-(methyloxy)phenyl)methyl)carbamate;

2-methyl-1-(1-methylethyl)butyl 2-((3-fluoro-4-((3-(1-piperidinyl)propyl)oxy)phenyl)amino)-4-pyrimidinyl((3-(methyloxy)phenyl)methyl)carbamate;

2-methyl-1-(1-methylethyl)butyl (3-(methyloxy)phenyl)methyl(2-((3-((3-(1-piperidinyl)propyl)oxy)phenyl)amino)-4-pyrimidinyl)carbamate;

2-methyl-1-(1-methylethyl)butyl 2-((4-(((2-(diethylamino)ethyl)(methyl)amino)carbonyl)phenyl)amino)-4-pyrimidinyl((3-(methyloxy)phenyl)methyl)carbamate;

2-methyl-1-(1-methylethyl)butyl 2-((3-fluoro-4-((2-(4-(1-methylethyl)-1-piperazinyl)ethyl)oxy)phenyl)amino)-4-pyrimidinyl((3-(methyloxy)phenyl)methyl)carbamate;

2-methyl-1-(1-methylethyl)butyl 2-((3-fluoro-4-(((1-methyl-3-piperidinyl)methyl)oxy)phenyl)amino)-4-pyrimidinyl((3-(methyloxy)phenyl)methyl)carbamate;

2,6-dimethylcyclohexyl 2-((3,4-bis(methyloxy)-5-((3-(4-methyl-1-piperazinyl)propyl)oxy)phenyl)amino)-4-pyrimidinyl((3-(methyloxy)phenyl)methyl)carbamate;

2,4,6-trimethylphenyl (3,5-dichlorophenyl)methyl(2-((3-fluoro-4-((3-(1-piperidinyl)propyl)oxy)phenyl)amino)-4-pyrimidinyl)carbamate;

2,4,6-trimethylphenyl (3,5-dichlorophenyl)methyl(2-((4-(3,4-dimethyl-1-piperazinyl)-3-fluorophenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((3,5-dimethylphenyl)methyl)carbamate;

2,4,6-trimethylphenyl (3,5-dimethylphenyl)methyl(2-((3-fluoro-4-((3-(4-methyl-1-piperazinyl)propyl)oxy)phenyl)amino)-4-pyrimidinyl)carbamate;

2,4,6-trimethylphenyl (3,5-dimethylphenyl)methyl(2-((3-fluoro-4-((3-(1-piperidinyl)propyl)oxy)phenyl)amino)-4-pyrimidinyl)carbamate;

2,4,6-trimethylphenyl (3,5-dimethylphenyl)methyl(2-((3-((3-(1-piperidinyl)propyl)oxy)phenyl)amino)-4-pyrimidinyl)carbamate;

2,4,6-trimethylphenyl 2-((4-(((2-(diethylamino)ethyl)(methyl)amino)carbonyl)phenyl)amino)-4-pyrimidinyl((3,5-dimethylphenyl)methyl)carbamate;

2,4,6-trimethylphenyl (3,5-dimethylphenyl)methyl(2-((3-fluoro-4-((2-(4-(1-methylethyl)-1-piperazinyl)ethyl)oxy)phenyl)amino)-4-pyrimidinyl)carbamate;

2,4,6-trimethylphenyl (3,5-dimethylphenyl)methyl(2-((3-fluoro-4-(((1-methyl-3-piperidinyl)methyl)oxy)phenyl)amino)-4-pyrimidinyl)carbamate;

2,6-dimethylphenyl cyclohexyl(2-((3-((3-(1-piperidinyl)propyl)oxy)phenyl)amino)-4-pyrimidinyl)carbamate;

2,4,6-trimethylphenyl (3-chlorophenyl)methyl(2-((3-((3-(1-piperidinyl)propyl)oxy)phenyl)amino)-4-pyrimidinyl)carbamate;

2,6-dimethylphenyl 2-((3,4-bis(methyloxy)-5-((3-(4-methyl-1-piperazinyl)propyl)oxy)phenyl)amino)-4-pyrimidinyl(4-methyl-2-(methyloxy)phenyl)carbamate;

2,6-dimethylphenyl 2-((3-fluoro-4-((3-(4-methyl-1-piperazinyl)propyl)oxy)phenyl)amino)-4-pyrimidinyl(4-methyl-2-(methyloxy)phenyl)carbamate;

2,6-dimethylphenyl 2-((3-fluoro-4-((3-(1-piperidinyl)propyl)oxy)phenyl)amino)-4-pyrimidinyl(4-methyl-2-(methyloxy)phenyl)carbamate;

2,6-dimethylphenyl 4-methyl-2-(methyloxy)phenyl(2-((3-((3-(1-piperidinyl)propyl)oxy)phenyl)amino)-4-pyrimidinyl)carbamate;

2,6-dimethylphenyl 2-((4-(((2-(diethylamino)ethyl)(methyl)amino)carbonyl)phenyl)amino)-4-pyrimidinyl(4-methyl-2-(methyloxy)phenyl)carbamate;

2,6-dimethylphenyl 2-((3-fluoro-4-((2-(4-(1-methylethyl)-1-piperazinyl)ethyl)oxy)phenyl)amino)-4-pyrimidinyl(4-methyl-2-(methyloxy)phenyl)carbamate;

2,6-dimethylphenyl 2-((3-fluoro-4-(((1-methyl-3-piperidinyl)methyl)oxy)phenyl)amino)-4-pyrimidinyl(4-methyl-2-(methyloxy)phenyl)carbamate;

2,6-dimethylphenyl 2-((4-(3,4-dimethyl-1-piperazinyl)-3-fluorophenyl)amino)-4-pyrimidinyl(4-methyl-2-(methyloxy)phenyl)carbamate;

2,4,6-trimethylphenyl (5-chloro-2-fluorophenyl)methyl(2-((3-fluoro-4-((3-(1-piperidinyl)propyl)oxy)phenyl)amino)-4-pyrimidinyl)carbamate;

2,4,6-trimethylphenyl (5-chloro-2-fluorophenyl)methyl(2-((4-(((2-(diethylamino)ethyl)(methyl)amino)carbonyl)phenyl)amino)-4-pyrimidinyl)carbamate;

2,4,6-trimethylphenyl (5-chloro-2-fluorophenyl)methyl(2-((3-fluoro-4-((2-(4-(1-methylethyl)-1-piperazinyl)ethyl)oxy)phenyl)amino)-4-pyrimidinyl)carbamate;

2,4,6-trimethylphenyl (5-chloro-2-fluorophenyl)methyl(2-((3-fluoro-4-(((1-methyl-3-piperidinyl)methyl)oxy)phenyl)amino)-4-pyrimidinyl)carbamate;

2,4,6-trimethylphenyl (5-chloro-2-fluorophenyl)methyl(2-((4-(3,4-dimethyl-1-piperazinyl)-3-fluorophenyl)amino)-4-pyrimidinyl)carbamate;

2,6-dimethylphenyl 2-((4-(((2-(diethylamino)ethyl)(methyl)amino)carbonyl)phenyl)amino)-4-pyrimidinyl(4-(2-(diethylamino)-2-oxoethyl)-2-(methyloxy)phenyl)carbamate;

2,6-dimethylphenyl 4-(2-(diethylamino)-2-oxoethyl)-2-(methyloxy)phenyl(2-((4-(3,4-dimethyl-1-piperazinyl)-3-fluorophenyl)amino)-4-pyrimidinyl)carbamate;

2,6-dimethylphenyl 2-((3,4-bis(methyloxy)-5-((3-(4-methyl-1-piperazinyl)propyl)oxy)phenyl)amino)-4-pyrimidinyl(4-(2-(diethylamino)-2-oxoethyl)-2-(methyloxy)phenyl)carbamate;

2,6-dimethylphenyl 4-(2-(diethylamino)-2-oxoethyl)-2-(methyloxy)phenyl(2-((3-fluoro-4-(((1-methyl-3-piperidinyl)methyl)oxy)phenyl)amino)-4-pyrimidinyl)carbamate;

2,6-dimethylphenyl 4-(2-(diethylamino)-2-oxoethyl)-2-(methyloxy)phenyl(2-((3-fluoro-4-((2-(4-(1-methylethyl)-1-piperazinyl)ethyl)oxy)phenyl)amino)-4-pyrimidinyl)carbamate;

2,6-dimethylphenyl 4-(2-(diethylamino)-2-oxoethyl)-2-(methyloxy)phenyl(2-((3-((3-(1-piperidinyl)propyl)oxy)phenyl)amino)-4-pyrimidinyl)carbamate;

2,4,6-trimethylphenyl 2-((4-(((2-(diethylamino)ethyl)(methyl)amino)carbonyl)phenyl)amino)-4-pyrimidinyl(2-(4-(methyloxy)phenyl)ethyl)carbamate;

2,4,6-trimethylphenyl 2-((3-fluoro-4-((3-(4-methyl-1-piperazinyl)propyl)oxy)phenyl)amino)-4-pyrimidinyl(2-(4-(methyloxy)phenyl)ethyl)carbamate;

2,4,6-trimethylphenyl 2-((3-fluoro-4-((3-(1-piperidinyl)propyl)oxy)phenyl)amino)-4-pyrimidinyl(2-(4-(methyloxy)phenyl)ethyl)carbamate;

2,4,6-trimethylphenyl 2-((4-(3,4-dimethyl-1-piperazinyl)-3-fluorophenyl)amino)-4-pyrimidinyl(2-(4-(methyloxy)phenyl)ethyl)carbamate;

2,4,6-trimethylphenyl 2-((3,4-bis(methyloxy)-5-((3-(4-methyl-1-piperazinyl)propyl)oxy)phenyl)amino)-4-pyrimidinyl(2-(4-(methyloxy)phenyl)ethyl)carbamate;

2,4,6-trimethylphenyl 2-((3-fluoro-4-(((1-methyl-3-piperidinyl)methyl)oxy)phenyl)amino)-4-pyrimidinyl(2-(4-(methyloxy)phenyl)ethyl)carbamate;

2,4,6-trimethylphenyl 2-((3-fluoro-4-((2-(4-(1-methylethyl)-1-piperazinyl)ethyl)oxy)phenyl)amino)-4-pyrimidinyl(2-(4-(methyloxy)phenyl)ethyl)carbamate;

2,4,6-trimethylphenyl 2-(4-(methyloxy)phenyl)ethyl(2-((3-((3-(1-piperidinyl)propyl)oxy)phenyl)amino)-4-pyrimidinyl)carbamate;

2,4,6-trimethylphenyl 2-((4-(((2-(diethylamino)ethyl)(methyl)amino)carbonyl)phenyl)amino)-4-pyrimidinyl((3,5-difluorophenyl)methyl)carbamate;

2,4,6-trimethylphenyl (3,5-difluorophenyl)methyl(2-((3-fluoro-4-((3-(4-methyl-1-piperazinyl)propyl)oxy)phenyl)amino)-4-pyrimidinyl)carbamate;

2,4,6-trimethylphenyl (3,5-difluorophenyl)methyl(2-((3-fluoro-4-((3-(1-piperidinyl)propyl)oxy)phenyl)amino)-4-pyrimidinyl)carbamate;

2,4,6-trimethylphenyl (3,5-difluorophenyl)methyl(2-((4-(3,4-dimethyl-1-piperazinyl)-3-fluorophenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((3,5-difluorophenyl)methyl)carbamate;

2,4,6-trimethylphenyl (3,5-difluorophenyl)methyl(2-((3-fluoro-4-(((1-methyl-3-piperidinyl)methyl)oxy)phenyl)amino)-4-pyrimidinyl)carbamate;

2,4,6-trimethylphenyl (3,5-difluorophenyl)methyl(2-((3-fluoro-4-((2-(4-(1-methylethyl)-1-piperazinyl)ethyl)oxy)phenyl)amino)-4-pyrimidinyl)carbamate;

2,6-dimethylphenyl 2-((3,4-bis(methyloxy)-5-((3-(4-methyl-1-piperazinyl)propyl)oxy)phenyl)amino)-4-pyrimidinyl(3-(3-((2-(methyloxy)ethyl)amino)-3-oxopropyl)phenyl)carbamate;

2,6-dimethylphenyl 2-((3-fluoro-4-((3-(4-methyl-1-piperazinyl)propyl)oxy)phenyl)amino)-4-pyrimidinyl(3-(3-((2-(methyloxy)ethyl)amino)-3-oxopropyl)phenyl)carbamate;

2,6-dimethylphenyl 2-((3-fluoro-4-((3-(1-piperidinyl)propyl)oxy)phenyl)amino)-4-pyrimidinyl(3-(3-((2-(methyloxy)ethyl)amino)-3-oxopropyl)phenyl)carbamate;

2,6-dimethylphenyl 3-(3-((2-(methyloxy)ethyl)amino)-3-oxopropyl)phenyl(2-((3-((3-(1-piperidinyl)propyl)oxy)phenyl)amino)-4-pyrimidinyl)carbamate;

2,4,6-trimethylphenyl (2-chloro-5-(trifluoromethyl)phenyl)methyl(2-((4-((3-(4-(1-methylethyl)-1-piperazinyl)propyl)oxy)-3-(methyloxy)phenyl)amino)-4-pyrimidinyl)carbamate;

2,4,6-trimethylphenyl (2-chloro-5-(trifluoromethyl)phenyl)methyl(2-((3-fluoro-4-(((1-methyl-3-piperidinyl)methyl)oxy)phenyl)amino)-4-pyrimidinyl)carbamate;

2,4,6-trimethylphenyl (2-chloro-5-(trifluoromethyl)phenyl)methyl(2-((4-(((2-(diethylamino)ethyl)(methyl)amino)carbonyl)phenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((2-chloro-5-(trifluoromethyl)phenyl)methyl)carbamate;

2,4,6-trimethylphenyl 2-((3,5-bis(methyloxy)-4-((2-(4-methyl-1-piperazinyl)ethyl)oxy)phenyl)amino)-4-pyrimidinyl((2-chloro-5-(trifluoromethyl)phenyl)methyl)carbamate;

2,4,6-trimethylphenyl (2-chloro-5-(trifluoromethyl)phenyl)methyl(2-((3-fluoro-4-((2-(4-methyl-1-piperazinyl)ethyl)oxy)phenyl)amino)-4-pyrimidinyl)carbamate;

2,4,6-trimethylphenyl (2-chloro-5-(trifluoromethyl)phenyl)methyl(2-((3-(4-methyl-1-piperazinyl)phenyl)amino)-4-pyrimidinyl)carbamate;

2,4,6-trimethylphenyl (2-chloro-5-(trifluoromethyl)phenyl)methyl(2-((3-(((2-(diethylamino)ethyl)(methyl)amino)carbonyl)phenyl)amino)-4-pyrimidinyl)carbamate;

2,4,6-trimethylphenyl (2-chloro-5-(trifluoromethyl)phenyl)methyl(2-((4-(3,4-dimethyl-1-piperazinyl)phenyl)amino)-4-pyrimidinyl)carbamate;

2,4,6-trimethylphenyl (2-chloro-5-(trifluoromethyl)phenyl)methyl(2-((3-fluoro-4-((3R,5S)-3,4,5-trimethyl-1-piperazinyl)phenyl)amino)-4-pyrimidinyl)carbamate;

2,4,6-trimethylphenyl (5-chloro-2-methylphenyl)methyl(2-((4-(4-methyl-1-piperazinyl)phenyl)amino)-4-pyrimidinyl)carbamate;

2,4,6-trimethylphenyl (5-chloro-2-methylphenyl)methyl(2-((3-fluoro-4-((3-(4-methyl-1-piperazinyl)propyl)oxy)phenyl)amino)-4-pyrimidinyl)carbamate;

2,4,6-trimethylphenyl (5-chloro-2-methylphenyl)methyl(2-((3-fluoro-4-(4-methyl-1-piperazinyl)phenyl)amino)-4-pyrimidinyl)carbamate;

2,4,6-trimethylphenyl 2-((3-chloro-4-(4-(1-methylethyl)-1-piperazinyl)phenyl)amino)-4-pyrimidinyl((5-chloro-2-methylphenyl)methyl)carbamate;

2,4,6-trimethylphenyl (5-chloro-2-methylphenyl)methyl(2-((3-fluoro-4-((2-(4-(1-methylethyl)-1-piperazinyl)ethyl)oxy)phenyl)amino)-4-pyrimidinyl)carbamate;

2,4,6-trimethylphenyl (5-chloro-2-methylphenyl)methyl(2-((4-((3-(4-(1-methylethyl)-1-piperazinyl)propyl)oxy)-3-(methyloxy)phenyl)amino)-4-pyrimidinyl)carbamate;

2,4,6-trimethylphenyl (5-chloro-2-methylphenyl)methyl(2-((4-(2-(4-methyl-1-piperazinyl)ethyl)phenyl)amino)-4-pyrimidinyl)carbamate;

2,4,6-trimethylphenyl (5-chloro-2-methylphenyl)methyl(2-((3-fluoro-4-(((1-methyl-3-piperidinyl)methyl)oxy)phenyl)amino)-4-pyrimidinyl)carbamate;

2,4,6-trimethylphenyl (5-chloro-2-methylphenyl)methyl(2-((4-(((2-(diethylamino)ethyl)(methyl)amino)carbonyl)phenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((5-chloro-2-methylphenyl)methyl)carbamate;

2,4,6-trimethylphenyl 2-((3,5-bis(methyloxy)-4-((2-(4-methyl-1-piperazinyl)ethyl)oxy)phenyl)amino)-4-pyrimidinyl((5-chloro-2-methylphenyl)methyl)carbamate;

2,4,6-trimethylphenyl (5-chloro-2-methylphenyl)methyl(2-((3-(4-methyl-1-piperazinyl)phenyl)amino)-4-pyrimidinyl)carbamate;

2,4,6-trimethylphenyl (5-chloro-2-methylphenyl)methyl(2-((3-(((2-(diethylamino)ethyl)(methyl)amino)carbonyl)phenyl)amino)-4-pyrimidinyl)carbamate;

2,4,6-trimethylphenyl (5-chloro-2-methylphenyl)methyl(2-((4-(3,4-dimethyl-1-piperazinyl)phenyl)amino)-4-pyrimidinyl)carbamate;

2,4,6-trimethylphenyl (5-chloro-2-methylphenyl)methyl(2-((3-fluoro-4-((3R,5S)-3,4,5-trimethyl-1-piperazinyl)phenyl)amino)-4-pyrimidinyl)carbamate;

2,4,6-trimethylphenyl (5-chloro-2-methylphenyl)methyl(2-((3-((difluoromethyl)oxy)-4-(4-methyl-1-piperazinyl)phenyl)amino)-4-pyrimidinyl)carbamate;

2,4,6-trimethylphenyl (5-chloro-2-methylphenyl)methyl(2-((3-fluoro-4-((2-(4-methyl-1-piperazinyl)ethyl)oxy)phenyl)amino)-4-pyrimidinyl)carbamate;

2,6-dimethylphenyl 2-((3-fluoro-4-((3-(4-methyl-1-piperazinyl)propyl)oxy)phenyl)amino)-4-pyrimidinyl(3-(2-(3-methyl-1,2,4-oxadiazol-5-yl)ethyl)phenyl)carbamate;

2,6-dimethylphenyl 2-((3-fluoro-4-((3-(1-piperidinyl)propyl)oxy)phenyl)amino)-4-pyrimidinyl(3-(2-(3-methyl-1,2,4-oxadiazol-5-yl)ethyl)phenyl)carbamate;

2,6-dimethylphenyl 3-(2-(3-methyl-1,2,4-oxadiazol-5-yl)ethyl)phenyl(2-((3-((3-(1-piperidinyl)propyl)oxy)phenyl)amino)-4-pyrimidinyl)carbamate;

2,6-dimethylphenyl 2-((4-(((2-(diethylamino)ethyl)(methyl)amino)carbonyl)phenyl)amino)-4-pyrimidinyl(3-(2-(3-methyl-1,2,4-oxadiazol-5-yl)ethyl)phenyl)carbamate;

2,6-dimethylphenyl 2-((3-fluoro-4-((2-(4-(1-methylethyl)-1-piperazinyl)ethyl)oxy)phenyl)amino)-4-pyrimidinyl(3-(2-(3-methyl-1,2,4-oxadiazol-5-yl)ethyl)phenyl)carbamate;

2,6-dimethylphenyl 2-((3-fluoro-4-(((1-methyl-3-piperidinyl)methyl)oxy)phenyl)amino)-4-pyrimidinyl(3-(2-(3-methyl-1,2,4-oxadiazol-5-yl)ethyl)phenyl)carbamate;

2,6-dimethylphenyl 2-((4-(3,4-dimethyl-1-piperazinyl)-3-fluorophenyl)amino)-4-pyrimidinyl(3-(2-(3-methyl-1,2,4-oxadiazol-5-yl)ethyl)phenyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((2,5-difluorophenyl)methyl)carbamate;

2,4,6-trimethylphenyl (2,5-difluorophenyl)methyl(2-((3-fluoro-4-((3-(4-methyl-1-piperazinyl)propyl)oxy)phenyl)amino)-4-pyrimidinyl)carbamate;

2,4,6-trimethylphenyl (2,5-difluorophenyl)methyl(2-((3-fluoro-4-((3-(1-piperidinyl)propyl)oxy)phenyl)amino)-4-pyrimidinyl)carbamate;

2,4,6-trimethylphenyl (2,5-difluorophenyl)methyl(2-((3-((3-(1-piperidinyl)propyl)oxy)phenyl)amino)-4-pyrimidinyl)carbamate;

2,4,6-trimethylphenyl 2-((4-(((2-(diethylamino)ethyl)(methyl)amino)carbonyl)phenyl)amino)-4-pyrimidinyl((2,5-difluorophenyl)methyl)carbamate;

2,4,6-trimethylphenyl (2,5-difluorophenyl)methyl(2-((3-fluoro-4-((2-(4-(1-methylethyl)-1-piperazinyl)ethyl)oxy)phenyl)amino)-4-pyrimidinyl)carbamate;

2,4,6-trimethylphenyl (2,5-difluorophenyl)methyl(2-((3-fluoro-4-(((1-methyl-3-piperidinyl)methyl)oxy)phenyl)amino)-4-pyrimidinyl)carbamate;

2,4,6-trimethylphenyl (2,5-difluorophenyl)methyl(2-((4-(3,4-dimethyl-1-piperazinyl)-3-fluorophenyl)amino)-4-pyrimidinyl)carbamate;

2,4,6-trimethylphenyl (3,5-bis(trifluoromethyl)phenyl)methyl(2-((4-(((2-(diethylamino)ethyl)(methyl)amino)carbonyl)phenyl)amino)-4-pyrimidinyl)carbamate;

2,4,6-trimethylphenyl (3,5-bis(trifluoromethyl)phenyl)methyl(2-((3-fluoro-4-((3-(4-methyl-1-piperazinyl)propyl)oxy)phenyl)amino)-4-pyrimidinyl)carbamate;

2,4,6-trimethylphenyl (3,5-bis(trifluoromethyl)phenyl)methyl(2-((3-fluoro-4-((3-(1-piperidinyl)propyl)oxy)phenyl)amino)-4-pyrimidinyl)carbamate;

2,4,6-trimethylphenyl (3,5-bis(trifluoromethyl)phenyl)methyl(2-((4-(3,4-dimethyl-1-piperazinyl)-3-fluorophenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((3,5-bis(trifluoromethyl)phenyl)methyl)carbamate;

2,4,6-trimethylphenyl (3,5-bis(trifluoromethyl)phenyl)methyl(2-((3-fluoro-4-(((1-methyl-3-piperidinyl)methyl)oxy)phenyl)amino)-4-pyrimidinyl)carbamate;

2,4,6-trimethylphenyl (3,5-bis(trifluoromethyl)phenyl)methyl(2-((3-fluoro-4-((2-(4-(1-methylethyl)-1-piperazinyl)ethyl)oxy)phenyl)amino)-4-pyrimidinyl)carbamate;

2,4,6-trimethylphenyl (3,5-bis(trifluoromethyl)phenyl)methyl(2-((3-((3-(1-piperidinyl)propyl)oxy)phenyl)amino)-4-pyrimidinyl)carbamate;

2,4,6-trimethylphenyl (3-chlorophenyl)methyl(2-((4-(3,4-dimethyl-1-piperazinyl)-3-fluorophenyl)amino)-4-pyrimidinyl)carbamate;

2,4,6-trimethylphenyl (3,5-difluorophenyl)methyl(2-((3-((3-(1-piperidinyl)propyl)oxy)phenyl)amino)-4-pyrimidinyl)carbamate;

(1S)-1-phenylethyl 2-((3,4-bis(methyloxy)-5-((3-(4-methyl-1-piperazinyl)propyl)oxy)phenyl)amino)-4-pyrimidinyl((3-(methyloxy)phenyl)methyl)carbamate;

(1S)-1-phenylethyl 2-((3-fluoro-4-((3-(4-methyl-1-piperazinyl)propyl)oxy)phenyl)amino)-4-pyrimidinyl((3-(methyloxy)phenyl)methyl)carbamate;

(1S)-1-phenylethyl 2-((3-fluoro-4-((3-(1-piperidinyl)propyl)oxy)phenyl)amino)-4-pyrimidinyl((3-(methyloxy)phenyl)methyl)carbamate;

(1S)-1-phenylethyl (3-(methyloxy)phenyl)methyl(2-((3-((3-(1-piperidinyl)propyl)oxy)phenyl)amino)-4-pyrimidinyl)carbamate;

(1S)-1-phenylethyl 2-((4-(((2-(diethylamino)ethyl)(methyl)amino)carbonyl)phenyl)amino)-4-pyrimidinyl((3-(methyloxy)phenyl)methyl)carbamate;

(1S)-1-phenylethyl 2-((3-fluoro-4-((2-(4-(1-methylethyl)-1-piperazinyl)ethyl)oxy)phenyl)amino)-4-pyrimidinyl((3-(methyloxy)phenyl)methyl)carbamate;

(1S)-1-phenylethyl 2-((3-fluoro-4-(((1-methyl-3-piperidinyl)methyl)oxy)phenyl)amino)-4-pyrimidinyl((3-(methyloxy)phenyl)methyl)carbamate;

(1S)-1-phenylethyl 2-((4-(3,4-dimethyl-1-piperazinyl)-3-fluorophenyl)amino)-4-pyrimidinyl((3-(methyloxy)phenyl)methyl)carbamate;

2,6-dimethylcyclohexyl 2-((3-fluoro-4-((3-(4-methyl-1-piperazinyl)propyl)oxy)phenyl)amino)-4-pyrimidinyl((3-(methyloxy)phenyl)methyl)carbamate;

2,6-dimethylcyclohexyl 2-((3-fluoro-4-((3-(1-piperidinyl)propyl)oxy)phenyl)amino)-4-pyrimidinyl((3-(methyloxy)phenyl)methyl)carbamate;

2,6-dimethylcyclohexyl (3-(methyloxy)phenyl)methyl(2-((3-((3-(1-piperidinyl)propyl)oxy)phenyl)amino)-4-pyrimidinyl)carbamate;

2,6-dimethylcyclohexyl 2-((4-(((2-(diethylamino)ethyl)(methyl)amino)carbonyl)phenyl)amino)-4-pyrimidinyl((3-(methyloxy)phenyl)methyl)carbamate;

2,6-dimethylcyclohexyl 2-((3-fluoro-4-((2-(4-(1-methylethyl)-1-piperazinyl)ethyl)oxy)phenyl)amino)-4-pyrimidinyl((3-(methyloxy)phenyl)methyl)carbamate;

2,6-dimethylcyclohexyl 2-((3-fluoro-4-(((1-methyl-3-piperidinyl)methyl)oxy)phenyl)amino)-4-pyrimidinyl((3-(methyloxy)phenyl)methyl)carbamate;

2,6-dimethylcyclohexyl 2-((4-(3,4-dimethyl-1-piperazinyl)-3-fluorophenyl)amino)-4-pyrimidinyl((3-(methyloxy)phenyl)methyl)carbamate;

2-(methylsulfanyl)phenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

2-(methylsulfanyl)phenyl (2,5-bis(methyloxy)phenyl)methyl(2-((3-fluoro-4-((3-(4-methyl-1-piperazinyl)propyl)oxy)phenyl)amino)-4-pyrimidinyl)carbamate;

2-(methylsulfanyl)phenyl (2,5-bis(methyloxy)phenyl)methyl(2-((3-fluoro-4-((3-(1-piperidinyl)propyl)oxy)phenyl)amino)-4-pyrimidinyl)carbamate;

2-(methylsulfanyl)phenyl (2,5-bis(methyloxy)phenyl)methyl(2-((3-((3-(1-piperidinyl)propyl)oxy)phenyl)amino)-4-pyrimidinyl)carbamate;

2-(methylsulfanyl)phenyl (2,5-bis(methyloxy)phenyl)methyl(2-((4-(((2-(diethylamino)ethyl)(methyl)amino)carbonyl)phenyl)amino)-4-pyrimidinyl)carbamate;

2-(methylsulfanyl)phenyl (2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

2-(methylsulfanyl)phenyl (2,5-bis(methyloxy)phenyl)methyl(2-((3-fluoro-4-(((1-methyl-3-piperidinyl)methyl)oxy)phenyl)amino)-4-pyrimidinyl)carbamate;

2-(methylsulfanyl)phenyl (2,5-bis(methyloxy)phenyl)methyl(2-((4-(3,4-dimethyl-1-piperazinyl)-3-fluorophenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((2-phenyl-1,3-thiazol-4-yl)methyl)carbamate;

2,4,6-trimethylphenyl 2-((3-fluoro-4-((3-(4-methyl-1-piperazinyl)propyl)oxy)phenyl)amino)-4-pyrimidinyl((2-phenyl-1,3-thiazol-4-yl)methyl)carbamate;

2,4,6-trimethylphenyl 2-((3-fluoro-4-((3-(1-piperidinyl)propyl)oxy)phenyl)amino)-4-pyrimidinyl((2-phenyl-1,3-thiazol-4-yl)methyl)carbamate;

2,4,6-trimethylphenyl (2-phenyl-1,3-thiazol-4-yl)methyl(2-((3-((3-(1-piperidinyl)propyl)oxy)phenyl)amino)-4-pyrimidinyl)carbamate;

2,4,6-trimethylphenyl 2-((4-(((2-(diethylamino)ethyl)(methyl)amino)carbonyl)phenyl)amino)-4-pyrimidinyl((2-phenyl-1,3-thiazol-4-yl)methyl)carbamate;

2,4,6-trimethylphenyl 2-((3-fluoro-4-((2-(4-(1-methylethyl)-1-piperazinyl)ethyl)oxy)phenyl)amino)-4-pyrimidinyl((2-phenyl-1,3-thiazol-4-yl)methyl)carbamate;

2,4,6-trimethylphenyl 2-((3-fluoro-4-(((1-methyl-3-piperidinyl)methyl)oxy)phenyl)amino)-4-pyrimidinyl((2-phenyl-1,3-thiazol-4-yl)methyl)carbamate;

2,4,6-trimethylphenyl 2-((4-(3,4-dimethyl-1-piperazinyl)-3-fluorophenyl)amino)-4-pyrimidinyl((2-phenyl-1,3-thiazol-4-yl)methyl)carbamate;

(2,4,6-trimethylphenyl)methyl(2-((4-(2-(4-methyl-1-piperazinyl)ethyl)phenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((3-(2-((1-methylpropyl)amino)-2-oxoethyl)phenyl)methyl)carbamate;

2,4,6-trimethylphenyl 2-((3-fluoro-4-((3-(4-methyl-1-piperazinyl)propyl)oxy)phenyl)amino)-4-pyrimidinyl((3-(2-((1-methylpropyl)amino)-2-oxoethyl)phenyl)methyl)carbamate;

2,4,6-trimethylphenyl 2-((3-fluoro-4-((3-(1-piperidinyl)propyl)oxy)phenyl)amino)-4-pyrimidinyl((3-(2-((1-methylpropyl)amino)-2-oxoethyl)phenyl)methyl)carbamate;

2,4,6-trimethylphenyl (3-(2-((1-methylpropyl)amino)-2-oxoethyl)phenyl)methyl(2-((3-((3-(1-piperidinyl)propyl)oxy)phenyl)amino)-4-pyrimidinyl)carbamate;

2,4,6-trimethylphenyl (2-chloro-3,6-difluorophenyl)methyl(2-((4-(((2-(diethylamino)ethyl)(methyl)amino)carbonyl)phenyl)amino)-4-pyrimidinyl)carbamate;

2,4,6-trimethylphenyl (2-chloro-3,6-difluorophenyl)methyl(2-((3-fluoro-4-((3-(4-methyl-1-piperazinyl)propyl)oxy)phenyl)amino)-4-pyrimidinyl)carbamate;

2,4,6-trimethylphenyl (2-chloro-3,6-difluorophenyl)methyl(2-((3-fluoro-4-((3-(1-piperidinyl)propyl)oxy)phenyl)amino)-4-pyrimidinyl)carbamate;

2,4,6-trimethylphenyl (2-chloro-3,6-difluorophenyl)methyl(2-((4-(3,4-dimethyl-1-piperazinyl)-3-fluorophenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((2-chloro-3,6-difluorophenyl)methyl)carbamate;

2,4,6-trimethylphenyl (2-chloro-3,6-difluorophenyl)methyl(2-((3-fluoro-4-(((1-methyl-3-piperidinyl)methyl)oxy)phenyl)amino)-4-pyrimidinyl)carbamate;

2,4,6-trimethylphenyl (2-chloro-3,6-difluorophenyl)methyl(2-((3-fluoro-4-((2-(4-(1-methylethyl)-1-piperazinyl)ethyl)oxy)phenyl)amino)-4-pyrimidinyl)carbamate;

2,4,6-trimethylphenyl (2-chloro-3,6-difluorophenyl)methyl(2-((3-((3-(1-piperidinyl)propyl)oxy)phenyl)amino)-4-pyrimidinyl)carbamate;

2,6-dimethylphenyl 3-(3-((1-methylpropyl)amino)-3-oxopropyl)phenyl(2-((3-((3-(1-piperidinyl)propyl)oxy)phenyl)amino)-4-pyrimidinyl)carbamate;

2,6-dimethylphenyl 2-((3-fluoro-4-((2-(4-(1-methylethyl)-1-piperazinyl)ethyl)oxy)phenyl)amino)-4-pyrimidinyl(3-(3-((1-methylpropyl)amino)-3-oxopropyl)phenyl)carbamate;

2,6-dimethylphenyl 2-((3-fluoro-4-(((1-methyl-3-piperidinyl)methyl)oxy)phenyl)amino)-4-pyrimidinyl(3-(3-((1-methylpropyl)amino)-3-oxopropyl)phenyl)carbamate;

2,6-dimethylphenyl 2-((4-(3,4-dimethyl-1-piperazinyl)-3-fluorophenyl)amino)-4-pyrimidinyl(3-(3-((1-methylpropyl)amino)-3-oxopropyl)phenyl)carbamate;

2,6-dimethylphenyl 2-((4-(((2-(diethylamino)ethyl)(methyl)amino)carbonyl)phenyl)amino)-4-pyrimidinyl(3-(3-((2-(methyloxy)ethyl)amino)-3-oxopropyl)phenyl)carbamate;

2,6-dimethylphenyl 2-((3-fluoro-4-((2-(4-(1-methylethyl)-1-piperazinyl)ethyl)oxy)phenyl)amino)-4-pyrimidinyl(3-(3-((2-(methyloxy)ethyl)amino)-3-oxopropyl)phenyl)carbamate;

2,6-dimethylphenyl 2-((3-fluoro-4-(((1-methyl-3-piperidinyl)methyl)oxy)phenyl)amino)-4-pyrimidinyl(3-(3-((2-(methyloxy)ethyl)amino)-3-oxopropyl)phenyl)carbamate;

2,6-dimethylphenyl 2-((4-(3,4-dimethyl-1-piperazinyl)-3-fluorophenyl)amino)-4-pyrimidinyl(3-(3-((2-(methyloxy)ethyl)amino)-3-oxopropyl)phenyl)carbamate;

2,6-dimethylphenyl 2-((3,4-bis(methyloxy)-5-((3-(4-methyl-1-piperazinyl)propyl)oxy)phenyl)amino)-4-pyrimidinyl(3-(3-(diethylamino)-3-oxopropyl)phenyl)carbamate;

2,6-dimethylphenyl 3-(3-(diethylamino)-3-oxopropyl)phenyl(2-((3-fluoro-4-((3-(4-methyl-1-piperazinyl)propyl)oxy)phenyl)amino)-4-pyrimidinyl)carbamate;

2,6-dimethylphenyl 3-(3-(diethylamino)-3-oxopropyl)phenyl(2-((3-fluoro-4-((3-(1-piperidinyl)propyl)oxy)phenyl)amino)-4-pyrimidinyl)carbamate;

2,6-dimethylphenyl 3-(3-(diethylamino)-3-oxopropyl)phenyl(2-((3-((3-(1-piperidinyl)propyl)oxy)phenyl)amino)-4-pyrimidinyl)carbamate;

2,6-dimethylphenyl 2-((4-(((2-(diethylamino)ethyl)(methyl)amino)carbonyl)phenyl)amino)-4-pyrimidinyl(3-(3-(diethylamino)-3-oxopropyl)phenyl)carbamate;

2,6-dimethylphenyl 3-(3-(diethylamino)-3-oxopropyl)phenyl(2-((3-fluoro-4-((2-(4-(1-methylethyl)-1-piperazinyl)ethyl)oxy)phenyl)amino)-4-pyrimidinyl)carbamate;

2,6-dimethylphenyl 3-(3-(diethylamino)-3-oxopropyl)phenyl(2-((3-fluoro-4-(((1-methyl-3-piperidinyl)methyl)oxy)phenyl)amino)-4-pyrimidinyl)carbamate;

2,6-dimethylphenyl 3-(3-(diethylamino)-3-oxopropyl)phenyl(2-((4-(3,4-dimethyl-1-piperazinyl)-3-fluorophenyl)amino)-4-pyrimidinyl)carbamate;

2,6-dimethylphenyl 2-((3,4-bis(methyloxy)-5-((3-(4-methyl-1-piperazinyl)propyl)oxy)phenyl)amino)-4-pyrimidinyl(2-(methyloxy)-4-(((1-methylpropyl)amino)carbonyl)phenyl)carbamate;

2,6-dimethylphenyl 2-((3-fluoro-4-((3-(4-methyl-1-piperazinyl)propyl)oxy)phenyl)amino)-4-pyrimidinyl(2-(methyloxy)-4-(((1-methylpropyl)amino)carbonyl)phenyl)carbamate;

2,6-dimethylphenyl 2-((3-fluoro-4-((3-(1-piperidinyl)propyl)oxy)phenyl)amino)-4-pyrimidinyl(2-(methyloxy)-4-(((1-methylpropyl)amino)carbonyl)phenyl)carbamate;

2,6-dimethylphenyl 2-((3-fluoro-4-((2-(4-(1-methylethyl)-1-piperazinyl)ethyl)oxy)phenyl)amino)-4-pyrimidinyl(2-(methyloxy)-4-(((1-methylpropyl)amino)carbonyl)phenyl)carbamate;

2,4,6-trimethylphenyl 1,3-benzodioxol-5-ylmethyl(2-((3,4-bis(methyloxy)-5-((3-(4-methyl-1-piperazinyl)propyl)oxy)phenyl)amino)-4-pyrimidinyl)carbamate;

2,4,6-trimethylphenyl 1,3-benzodioxol-5-ylmethyl(2-((3-fluoro-4-((3-(4-methyl-1-piperazinyl)propyl)oxy)phenyl)amino)-4-pyrimidinyl)carbamate;

2,4,6-trimethylphenyl 1,3-benzodioxol-5-ylmethyl(2-((3-fluoro-4-((3-(1-piperidinyl)propyl)oxy)phenyl)amino)-4-pyrimidinyl)carbamate;

2,4,6-trimethylphenyl 1,3-benzodioxol-5-ylmethyl(2-((3-((3-(1-piperidinyl)propyl)oxy)phenyl)amino)-4-pyrimidinyl)carbamate;

2,4,6-trimethylphenyl 1,3-benzodioxol-5-ylmethyl(2-((4-(((2-(diethylamino)ethyl)(methyl)amino)carbonyl)phenyl)amino)-4-pyrimidinyl)carbamate;

2,4,6-trimethylphenyl 1,3-benzodioxol-5-ylmethyl(2-((3-fluoro-4-((2-(4-(1-methylethyl)-1-piperazinyl)ethyl)oxy)phenyl)amino)-4-pyrimidinyl)carbamate;

2,4,6-trimethylphenyl 1,3-benzodioxol-5-ylmethyl(2-((3-fluoro-4-(((1-methyl-3-piperidinyl)methyl)oxy)phenyl)amino)-4-pyrimidinyl)carbamate;

2,4,6-trimethylphenyl 1,3-benzodioxol-5-ylmethyl(2-((4-(3,4-dimethyl-1-piperazinyl)-3-fluorophenyl)amino)-4-pyrimidinyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((3,4-difluorophenyl)methyl)carbamate;

2,4,6-trimethylphenyl (3,4-difluorophenyl)methyl(2-((3-fluoro-4-((3-(4-methyl-1-piperazinyl)propyl)oxy)phenyl)amino)-4-pyrimidinyl)carbamate;

2,4,6-trimethylphenyl (3,4-difluorophenyl)methyl(2-((3-fluoro-4-((3-(1-piperidinyl)propyl)oxy)phenyl)amino)-4-pyrimidinyl)carbamate;

2,4,6-trimethylphenyl (3,4-difluorophenyl)methyl(2-((3-((3-(1-piperidinyl)propyl)oxy)phenyl)amino)-4-pyrimidinyl)carbamate;

2,4,6-trimethylphenyl 2-((4-(((2-(diethylamino)ethyl)(methyl)amino)carbonyl)phenyl)amino)-4-pyrimidinyl((3,4-difluorophenyl)methyl)carbamate;

2,4,6-trimethylphenyl (3,4-difluorophenyl)methyl(2-((3-fluoro-4-((2-(4-(1-methylethyl)-1-piperazinyl)ethyl)oxy)phenyl)amino)-4-pyrimidinyl)carbamate;

2,4,6-trimethylphenyl (3,4-difluorophenyl)methyl(2-((3-fluoro-4-(((1-methyl-3-piperidinyl)methyl)oxy)phenyl)amino)-4-pyrimidinyl)carbamate;

2,4,6-trimethylphenyl (3,4-difluorophenyl)methyl(2-((4-(3,4-dimethyl-1-piperazinyl)-3-fluorophenyl)amino)-4-pyrimidinyl)carbamate;

2,4,6-trimethylphenyl (6-fluoro-4H-1,3-benzodioxin-8-yl)methyl(2-((3-fluoro-4-((3-(4-methyl-1-piperazinyl)propyl)oxy)phenyl)amino)-4-pyrimidinyl)carbamate;

2,4,6-trimethylphenyl (6-fluoro-4H-1,3-benzodioxin-8-yl)methyl(2-((3-fluoro-4-((3-(1-piperidinyl)propyl)oxy)phenyl)amino)-4-pyrimidinyl)carbamate;

2,4,6-trimethylphenyl 2-((4-(((2-(diethylamino)ethyl)(methyl)amino)carbonyl)phenyl)amino)-4-pyrimidinyl((6-fluoro-4H-1,3-benzodioxin-8-yl)methyl)carbamate;

2,4,6-trimethylphenyl (6-fluoro-4H-1,3-benzodioxin-8-yl)methyl(2-((3-fluoro-4-((2-(4-(1-methylethyl)-1-piperazinyl)ethyl)oxy)phenyl)amino)-4-pyrimidinyl)carbamate;

2,4,6-trimethylphenyl 2-((3-fluoro-4-((3-(4-methyl-1-piperazinyl)propyl)oxy)phenyl)amino)-4-pyrimidinyl((3-(1H-pyrazol-1-ylmethyl)phenyl)methyl)carbamate;

2,4,6-trimethylphenyl 2-((3-fluoro-4-((3-(1-piperidinyl)propyl)oxy)phenyl)amino)-4-pyrimidinyl((3-(1H-pyrazol-1-ylmethyl)phenyl)methyl)carbamate;

2,4,6-trimethylphenyl 2-((3-((3-(1-piperidinyl)propyl)oxy)phenyl)amino)-4-pyrimidinyl((3-(1H-pyrazol-1-ylmethyl)phenyl)methyl)carbamate;

2,4,6-trimethylphenyl 2-((4-(((2-(diethylamino)ethyl)(methyl)amino)carbonyl)phenyl)amino)-4-pyrimidinyl((3-(1H-pyrazol-1-ylmethyl)phenyl)methyl)carbamate;

2,4,6-trimethylphenyl 2-((3-fluoro-4-((2-(4-(1-methylethyl)-1-piperazinyl)ethyl)oxy)phenyl)amino)-4-pyrimidinyl((3-(1H-pyrazol-1-ylmethyl)phenyl)methyl)carbamate;

2,4,6-trimethylphenyl 2-((3-fluoro-4-(((1-methyl-3-piperidinyl)methyl)oxy)phenyl)amino)-4-pyrimidinyl((3-(1H-pyrazol-1-ylmethyl)phenyl)methyl)carbamate;

2,4,6-trimethylphenyl 2-((4-(3,4-dimethyl-1-piperazinyl)-3-fluorophenyl)amino)-4-pyrimidinyl((3-(1H-pyrazol-1-ylmethyl)phenyl)methyl)carbamate;

2,4,6-trimethylphenyl 4-(3-(diethylamino)-2-methyl-3-oxopropyl)-2-(methyloxy)phenyl(2-((3-fluoro-4-((3-(4-methyl-1-piperazinyl)propyl)oxy)phenyl)amino)-4-pyrimidinyl)carbamate;

2,4,6-trimethylphenyl 4-(3-(diethylamino)-2-methyl-3-oxopropyl)-2-(methyloxy)phenyl(2-((3-fluoro-4-((3-(1-piperidinyl)propyl)oxy)phenyl)amino)-4-pyrimidinyl)carbamate;

2,4,6-trimethylphenyl 4-(3-(diethylamino)-2-methyl-3-oxopropyl)-2-(methyloxy)phenyl(2-((3-((3-(1-piperidinyl)propyl)oxy)phenyl)amino)-4-pyrimidinyl)carbamate;

2,4,6-trimethylphenyl 2-((4-(((2-(diethylamino)ethyl)(methyl)amino)carbonyl)phenyl)amino)-4-pyrimidinyl(4-(3-(diethylamino)-2-methyl-3-oxopropyl)-2-(methyloxy)phenyl)carbamate;

2,4,6-trimethylphenyl 4-(3-(diethylamino)-2-methyl-3-oxopropyl)-2-(methyloxy)phenyl(2-((3-fluoro-4-((2-(4-(1-methylethyl)-1-piperazinyl)ethyl)oxy)phenyl)amino)-4-pyrimidinyl)carbamate;

2,4,6-trimethylphenyl 4-(3-(diethylamino)-2-methyl-3-oxopropyl)-2-(methyloxy)phenyl(2-((3-fluoro-4-(((1-methyl-3-piperidinyl)methyl)oxy)phenyl)amino)-4-pyrimidinyl)carbamate;

2,4,6-trimethylphenyl 4-(3-(diethylamino)-2-methyl-3-oxopropyl)-2-(methyloxy)phenyl(2-((4-(3,4-dimethyl-1-piperazinyl)-3-fluorophenyl)amino)-4-pyrimidinyl)carbamate;

2,6-dimethylphenyl 2-((3-fluoro-4-((3-(4-methyl-1-piperazinyl)propyl)oxy)phenyl)amino)-4-pyrimidinyl(2-(methyloxy)-4-(3-((1-methylpropyl)amino)-3-oxopropyl)phenyl)carbamate;

2,6-dimethylphenyl 2-((3-fluoro-4-((3-(1-piperidinyl)propyl)oxy)phenyl)amino)-4-pyrimidinyl(2-(methyloxy)-4-(3-((1-methylpropyl)amino)-3-oxopropyl)phenyl)carbamate;

2,6-dimethylphenyl 2-(methyloxy)-4-(3-((1-methylpropyl)amino)-3-oxopropyl)phenyl(2-((3-((3-(1-piperidinyl)propyl)oxy)phenyl)amino)-4-pyrimidinyl)carbamate;

2,6-dimethylphenyl 2-((4-(((2-(diethylamino)ethyl)(methyl)amino)carbonyl)phenyl)amino)-4-pyrimidinyl(2-(methyloxy)-4-(3-((1-methylpropyl)amino)-3-oxopropyl)phenyl)carbamate;

2,6-dimethylphenyl 2-((3-fluoro-4-((2-(4-(1-methylethyl)-1-piperazinyl)ethyl)oxy)phenyl)amino)-4-pyrimidinyl(2-(methyloxy)-4-(3-((1-methylpropyl)amino)-3-oxopropyl)phenyl)carbamate;

2,6-dimethylphenyl 2-((3-fluoro-4-(((1-methyl-3-piperidinyl)methyl)oxy)phenyl)amino)-4-pyrimidinyl(2-(methyloxy)-4-(3-((1-methylpropyl)amino)-3-oxopropyl)phenyl)carbamate;

2,6-dimethylphenyl 2-((3,4-bis(methyloxy)-5-((3-(4-methyl-1-piperazinyl)propyl)oxy)phenyl)amino)-4-pyrimidinyl(2-(methyloxy)-4-(1H-pyrazol-1-yl)phenyl)carbamate;

2,6-dimethylphenyl 2-((3-fluoro-4-((3-(4-methyl-1-piperazinyl)propyl)oxy)phenyl)amino)-4-pyrimidinyl(2-(methyloxy)-4-(1H-pyrazol-1-yl)phenyl)carbamate;

2,6-dimethylphenyl 2-((3-fluoro-4-((3-(1-piperidinyl)propyl)oxy)phenyl)amino)-4-pyrimidinyl(2-(methyloxy)-4-(1H-pyrazol-1-yl)phenyl)carbamate;

2,6-dimethylphenyl 2-(methyloxy)-4-(1H-pyrazol-1-yl)phenyl(2-((3-((3-(1-piperidinyl)propyl)oxy)phenyl)amino)-4-pyrimidinyl)carbamate;

2,6-dimethylphenyl 2-((4-(((2-(diethylamino)ethyl)(methyl)amino)carbonyl)phenyl)amino)-4-pyrimidinyl(2-(methyloxy)-4-(1H-pyrazol-1-yl)phenyl)carbamate;

2,6-dimethylphenyl 2-((3-fluoro-4-(((1-methyl-3-piperidinyl)methyl)oxy)phenyl)amino)-4-pyrimidinyl(2-(methyloxy)-4-(1H-pyrazol-1-yl)phenyl)carbamate;

2,6-dimethylphenyl 2-((4-(3,4-dimethyl-1-piperazinyl)-3-fluorophenyl)amino)-4-pyrimidinyl(2-(methyloxy)-4-(1H-pyrazol-1-yl)phenyl)carbamate;

4-fluoro-2,6-dimethylphenyl 2-((3,4-bis(methyloxy)-5-((3-(4-methyl-1-piperazinyl)propyl)oxy)phenyl)amino)-4-pyrimidinyl((2,5-bis(methyloxy)phenyl)methyl)carbamate;

4-fluoro-2,6-dimethylphenyl (2,5-bis(methyloxy)phenyl)methyl(2-((3-fluoro-4-((3-(4-methyl-1-piperazinyl)propyl)oxy)phenyl)amino)-4-pyrimidinyl)carbamate;

4-fluoro-2,6-dimethylphenyl (2,5-bis(methyloxy)phenyl)methyl(2-((3-fluoro-4-((3-(1-piperidinyl)propyl)oxy)phenyl)amino)-4-pyrimidinyl)carbamate;

4-fluoro-2,6-dimethylphenyl (2,5-bis(methyloxy)phenyl)methyl(2-((3-((3-(1-piperidinyl)propyl)oxy)phenyl)amino)-4-pyrimidinyl)carbamate;

4-fluoro-2,6-dimethylphenyl (2,5-bis(methyloxy)phenyl)methyl(2-((4-(((2-(diethylamino)ethyl)(methyl)amino)carbonyl)phenyl)amino)-4-pyrimidinyl)carbamate;

4-fluoro-2,6-dimethylphenyl (2,5-bis(methyloxy)phenyl)methyl(2-((3-fluoro-4-((2-(4-(1-methylethyl)-1-piperazinyl)ethyl)oxy)phenyl)amino)-4-pyrimidinyl)carbamate;

4-fluoro-2,6-dimethylphenyl (2,5-bis(methyloxy)phenyl)methyl(2-((3-fluoro-4-(((1-methyl-3-piperidinyl)methyl)oxy)phenyl)amino)-4-pyrimidinyl)carbamate;

4-fluoro-2,6-dimethylphenyl (2,5-bis(methyloxy)phenyl)methyl(2-((4-(3,4-dimethyl-1-piperazinyl)-3-fluorophenyl)amino)-4-pyrimidinyl)carbamate;

2,6-dimethylphenyl 2-((3,5-bis(methyloxy)-4-((3-(4-methyl-1-piperazinyl)propyl)oxy)phenyl)amino)-4-pyrimidinyl(4-((E)-2-(3-methyl-1,2,4-oxadiazol-5-yl)ethenyl)-2-(methyloxy)phenyl)carbamate;

2,6-dimethylphenyl 2-((3-fluoro-4-((3-(4-methyl-1-piperazinyl)propyl)oxy)phenyl)amino)-4-pyrimidinyl(4-((E)-2-(3-methyl-1,2,4-oxadiazol-5-yl)ethenyl)-2-(methyloxy)phenyl)carbamate;

2,6-dimethylphenyl 2-((3-fluoro-4-((3-(1-piperidinyl)propyl)oxy)phenyl)amino)-4-pyrimidinyl(4-((E)-2-(3-methyl-1,2,4-oxadiazol-5-yl)ethenyl)-2-(methyloxy)phenyl)carbamate;

2,6-dimethylphenyl 2-((3-fluoro-4-((2-(4-(1-methylethyl)-1-piperazinyl)ethyl)oxy)phenyl)amino)-4-pyrimidinyl(4-((E)-2-(3-methyl-1,2,4-oxadiazol-5-yl)ethenyl)-2-(methyloxy)phenyl)carbamate;

2,4,6-trimethylphenyl 2-((4-(((2-(diethylamino)ethyl)(methyl)amino)carbonyl)phenyl)amino)-4-pyrimidinyl(2,3-dihydro-1H-inden-1-yl)carbamate;

2,4,6-trimethylphenyl 2,3-dihydro-1H-inden-1-yl(2-((3-fluoro-4-((3-(4-methyl-1-piperazinyl)propyl)oxy)phenyl)amino)-4-pyrimidinyl)carbamate;

2,4,6-trimethylphenyl 2,3-dihydro-1H-inden-1-yl(2-((3-fluoro-4-((3-(1-piperidinyl)propyl)oxy)phenyl)amino)-4-pyrimidinyl)carbamate;

2,4,6-trimethylphenyl 2,3-dihydro-1H-inden-1-yl(2-((4-(3,4-dimethyl-1-piperazinyl)-3-fluorophenyl)amino)-4-pyrimidinyl)carbamate;

2,4,6-trimethylphenyl 2,3-dihydro-1H-inden-1-yl(2-((3-fluoro-4-(((1-methyl-3-piperidinyl)methyl)oxy)phenyl)amino)-4-pyrimidinyl)carbamate;

2,4,6-trimethylphenyl 2,3-dihydro-1H-inden-1-yl(2-((3-fluoro-4-((2-(4-(1-methylethyl)-1-piperazinyl)ethyl)oxy)phenyl)amino)-4-pyrimidinyl)carbamate;

2,4,6-trimethylphenyl 2,3-dihydro-1H-inden-1-yl(2-((3-((3-(1-piperidinyl)propyl)oxy)phenyl)amino)-4-pyrimidinyl)carbamate;

2,4,6-trimethylphenyl 2-((4-(((2-(diethylamino)ethyl)(methyl)amino)carbonyl)phenyl)amino)-4-pyrimidinyl((4-(1H-1,2,4-triazol-1-ylmethyl)phenyl)methyl)carbamate;

2,4,6-trimethylphenyl 2-((3-fluoro-4-((3-(1-piperidinyl)propyl)oxy)phenyl)amino)-4-pyrimidinyl((4-(1H-1,2,4-triazol-1-ylmethyl)phenyl)methyl)carbamate;

2,4,6-trimethylphenyl 2-((3,4-bis(methyloxy)-5-((3-(4-methyl-1-piperazinyl)propyl)oxy)phenyl)amino)-4-pyrimidinyl((4-(1H-1,2,4-triazol-1-ylmethyl)phenyl)methyl)carbamate;

2,4,6-trimethylphenyl 2-((3-fluoro-4-(((1-methyl-3-piperidinyl)methyl)oxy)phenyl)amino)-4-pyrimidinyl((4-(1H-1,2,4-triazol-1-ylmethyl)phenyl)methyl)carbamate;

2,4,6-trimethylphenyl 2-((3-fluoro-4-((2-(4-(1-methylethyl)-1-iperazinyl)ethyl)oxy)phenyl)amino)-4-pyrimidinyl((4-(1H-1,2,4-triazol-1-lmethyl)phenyl)methyl)carbamate;

2,4,6-trimethylphenyl 2-((4-(((2-(diethylamino)ethyl)(methyl)amino)carbonyl)phenyl)amino)-4-yrimidinyl(2,3-dihydro-1,4-benzodioxin-6-ylmethyl)carbamate;

2,4,6-trimethylphenyl 2,3-dihydro-1,4-benzodioxin-6-ylmethyl(2-((3-fluoro-4-((3-4-methyl-1-piperazinyl)propyl)oxy)phenyl)amino)-4-pyrimidinyl)carbamate;

2,4,6-trimethylphenyl 2,3-dihydro-1,4-benzodioxin-6-ylmethyl(2-((3-fluoro-4-((3-1-piperidinyl)propyl)oxy)phenyl)amino)-4-pyrimidinyl)carbamate;

2,4,6-trimethylphenyl 2-((3,4-bis(methyloxy)-5-((3-(4-methyl-1-iperazinyl)propyl)oxy)phenyl)amino)-4-pyrimidinyl(2,3-dihydro-1,4-enzodioxin-6-ylmethyl)carbamate;

2,4,6-trimethylphenyl 2,3-dihydro-1,4-benzodioxin-6-ylmethyl(2-((3-fluoro-4-(((1-ethyl-3-piperidinyl)methyl)oxy)phenyl)amino)-4-pyrimidinyl)carbamate;

2,4,6-trimethylphenyl 2,3-dihydro-1,4-benzodioxin-6-ylmethyl(2-((3-fluoro-4-((2-4-(1-methylethyl)-1-piperazinyl)ethyl)oxy)phenyl)amino)-4-yrimidinyl)carbamate;

2,4,6-trimethylphenyl 2-((3,5-bis(methyloxy)-4-((2-(4-methyl-1-iperazinyl)ethyl)oxy)phenyl)amino)-4-pyrimidinyl((5-chloro-2-luorophenyl)methyl)carbamate;

2,4,6-trimethylphenyl (5-chloro-2-fluorophenyl)methyl(2-((3-fluoro-4-(4-methyl-1-iperazinyl)phenyl)amino)-4-pyrimidinyl)carbamate;

2,4,6-trimethylphenyl (5-chloro-2-fluorophenyl)methyl(2-((3-fluoro-4-((2-(4-ethyl-1-piperazinyl)ethyl)oxy)phenyl)amino)-4-pyrimidinyl)carbamate;

2,4,6-trimethylphenyl (5-chloro-2-fluorophenyl)methyl(2-((3-(difluoromethyl)oxy)-4-(4-methyl-1-piperazinyl)phenyl)amino)-4-yrimidinyl)carbamate;

2,4,6-trimethylphenyl (5-chloro-2-fluorophenyl)methyl(2-((3-chloro-4-(4-(1-ethylethyl)-1-piperazinyl)phenyl)amino)-4-pyrimidinyl)carbamate;

2,4,6-trimethylphenyl (5-chloro-2-fluorophenyl)methyl(2-((3-(4-methyl-1-iperazinyl)phenyl)amino)-4-pyrimidinyl carbamate;

2,4,6-trimethylphenyl (5-chloro-2-fluorophenyl)methyl(2-((3-(((2-diethylamino)ethyl)(methyl)amino)carbonyl)phenyl)amino)-4-yrimidinyl)carbamate;

2,4,6-trimethylphenyl (5-chloro-2-fluorophenyl)methyl(2-((4-((3-(4-(1-ethylethyl)-1-piperazinyl)propyl)oxy)-3-(methyloxy)phenyl)amino)-4-yrimidinyl)carbamate;

2,4,6-trimethylphenyl (5-chloro-2-fluorophenyl)methyl(2-((4-(3,4-dimethyl-1-iperazinyl)phenyl)amino)-4-pyrimidinyl)carbamate;

2,4,6-trimethylphenyl (5-chloro-2-fluorophenyl)methyl(2-((3-fluoro-4-((3R,5S)-,4,5-trimethyl-1-piperazinyl)phenyl)amino)-4-pyrimidinyl)carbamate;

2,4,6-trimethylphenyl (5-chloro-2-fluorophenyl)methyl(2-((4-(2-(4-methyl-1-iperazinyl)ethyl)amino)-4-pyrimidinyl)carbamate;

2,4,6-trimethylphenyl 2-((3-fluoro-4-((3-(4-methyl-1-iperazinyl)propyl)oxy)phenyl)amino)-4-pyrimidinyl((3-(5-methyl-1,2,4-xadiazol-3-yl)phenyl)methyl)carbamate;

2,4,6-trimethylphenyl 2-((4-(3,4-dimethyl-1-piperazinyl)-3-fluorophenyl)amino)-4-yrimidinyl((3-(5-methyl-1,2,4-oxadiazol-3-yl)phenyl)methyl)carbamate;

2,4,6-trimethylphenyl 2-((3,4-bis(methyloxy)-5-((3-(4-methyl-1-iperazinyl)propyl)oxy)phenyl)amino)-4-pyrimidinyl((4-(5-methyl-1,2,4-xadiazol-3-yl)phenyl)methyl)carbamate;

2,4,6-trimethylphenyl 2-((3-fluoro-4-((3-(4-methyl-1-iperazinyl)propyl)oxy)phenyl)amino)-4-pyrimidinyl((4-(5-methyl-1,2,4-xadiazol-3-yl)phenyl)methyl)carbamate;

2,4,6-trimethylphenyl 2-((3-fluoro-4-((3-(1-piperidinyl)propyl)oxy)phenyl)amino)-pyrimidinyl((4-(5-methyl-1,2,4-oxadiazol-3-yl)phenyl)methyl)carbamate;

2,4,6-trimethylphenyl (4-(5-methyl-1,2,4-oxadiazol-3-yl)phenyl)methyl(2-((3-((3-1-iperidinyl)propyl)oxy)phenyl)amino)-4-pyrimidinyl)carbamate;

2,6-trimethylphenyl 2-((4-(((2-(diethylamino)ethyl)(methyl)amino)carbonyl)phenyl)amino)-4-yrimidinyl((4-(5-methyl-1,2,4-oxadiazol-3-yl)phenyl)methyl)carbamate;

2,4,6-trimethylphenyl 2-((3-fluoro-4-((2-(4-(1-methylethyl)-1-iperazinyl)ethyl)oxy)phenyl)amino)-4-pyrimidinyl((4-(5-methyl-1,2,4-xadiazol-3-yl)phenyl)methyl)carbamate;

2,4,6-trimethylphenyl 2-((3-fluoro-4-(((1-methyl-3-iperidinyl)methyl)oxy)phenyl)amino)-4-pyrimidinyl((4-(5-methyl-1,2,4-xadiazol-3-yl)phenyl)methyl)carbamate;

2,4,6-trimethylphenyl 2-((4-(3,4-dimethyl-1-piperazinyl)-3-fluorophenyl)amino)-4-yrimidinyl((4-(5-methyl-1,2,4-oxadiazol-3-yl)phenyl)methyl)carbamate;

2,4,6-trimethylphenyl 2-((3,4-bis(methyloxy)-5-((3-(4-methyl-1-iperazinyl)propyl)oxy)phenyl)amino)-4-pyrimidinyl((6-fluoro-4H-1,3-enzodioxin-8-yl)methyl)carbamate;

1,1-dimethylethyl 2-(4-((5-(((2,6-dimethylphenyl)oxy)methyl)-2-((4-(1-iperazinyl)phenyl)amino)-4-pyrimidinyl)amino)phenyl)ethylcarbamate;

1,1-dimethylethyl 2-(4-((5-(((2,6-dimethylphenyl)oxy)methyl)-2-((3-(methyloxy)-4-1-piperazinyl)phenyl)amino)-4-pyrimidinyl)amino)phenyl)ethylcarbamate;

2-((4-(4-methyl-1-piperazinyl)phenyl)amino)-6-((1S)-1-henylethyl)pyrimido[5',4':5,6]pyrimido[1,2-a]benzimidazol-5-(6H)-one;

5-iodo-4-((2-(methyloxy)phenyl)oxy)-N-(4-(4-methyl-1-piperazinyl)phenyl)-2-yrimidinamine;

5-(((2,6-dimethylphenyl)amino)methyl)-4-((2-(methyloxy)phenyl)oxy)-N-(3,4,5-ris(methyloxy)phenyl)-2-pyrimidinamine;

N-(2,6-dimethylphenyl)-2,4-bis(phenylamino)-5-pyrimidinecarboxamide(2,6-dimethylphenyl)-2-((3-fluoro-4-((3-(4-methyl-1-iperazinyl)propyl)oxy)phenyl)amino)-4-(phenylamino)-5-yrimidinecarboxamide;

5-((E)-2-(2-chlorophenyl)ethenyl)-4-((2-(methyloxy)phenyl)oxy)-N-(4-(4-methyl-1-iperazinyl)phenyl)-2-pyrimidinamine;

methyl (2E)-3-(4-((2-(methyloxy)phenyl)oxy)-2-((4-(4-methyl-1-iperazinyl)phenyl)amino)-5-pyrimidinyl)-2-propenoate;

5-((Z)-2-(2-chlorophenyl)-1-fluoroethenyl)-4-((2-(methyloxy)phenyl)oxy)-N-(4-(4-ethyl-1-piperazinyl)phenyl)-2-pyrimidinamine;

N-(2,6-dimethylphenyl)-2-((4-(4-methyl-1-piperazinyl)phenyl)amino)-4-phenylamino)-5-pyrimidinecarboxamide;

N-(2,6-dimethylphenyl)-2-((3-fluoro-4-((3-(1-iperidinyl)propyl)oxy)phenyl)amino)-4-(phenylamino)-5-yrimidinecarboxamide;

N-(2,6-dimethylphenyl)-2-((3-fluoro-4-(4-methyl-1-piperazinyl)phenyl)amino)-4-phenylamino)-5-pyrimidinecarboxamide;

N-(2,6-dimethylphenyl)-2-((4-(4-(1-methylethyl)-1-piperazinyl)phenyl)amino)-4-phenylamino)-5-pyrimidinecarboxamide;

2-((4-(4-(2-(dimethylamino)ethyl)-1-piperazinyl)phenyl)amino)-N-(2,6-imethylphenyl)-4-(phenylamino)-5-pyrimidinecarboxamide;

2-((4-(4-(3-(dimethylamino)propyl)-1-piperazinyl)phenyl)amino)-N-(2,6-imethylphenyl)-4-(phenylamino)-5-pyrimidinecarboxamide;

2-((4-(((2-(dimethylamino)ethyl)amino)carbonyl)phenyl)amino)-N-(2,6-imethylphenyl)-4-(phenylamino)-5-pyrimidinecarboxamide;

N-(2,6-dimethylphenyl)-2-((4-(4-methyl-1-piperazinyl)phenyl)amino)-4-((3-(1,1,2,2-tetrafluoroethyl)oxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((3-((1,1,2,2-tetrafluoroethyl)oxy)phenyl)oxy)-5-pyrimidinecarboxamide;

N-(2,6-dimethylphenyl)-2-((3-fluoro-4-(4-methyl-1-piperazinyl)phenyl)amino)-4-((3-((1,1,2,2-tetrafluoroethyl)oxy)phenyl)oxy)-5-pyrimidinecarboxamide;

N-(2,6-dimethylphenyl)-2-((4-(4-(1-methylethyl)-1-piperazinyl)phenyl)amino)-4-((3-((1,1,2,2-tetrafluoroethyl)oxy)phenyl)oxy)-5-pyrimidinecarboxamide;

2-((4-(diethylamino)butyl)amino)-N-(2,6-dimethylphenyl)-4-((2-(ethyloxy)phenyl)oxy)-5-pyrimidinecarboxamide;

N-(2,6-dimethylphenyl)-4-((2-(ethyloxy)phenyl)oxy)-2-((2-(4-(phenylmethyl)-1-piperazinyl)ethyl)amino)-5-pyrimidinecarboxamide;

N-(2,6-dimethylphenyl)-2-((4-(4-methyl-1-piperazinyl)phenyl)amino)-4-(1-naphthalenyloxy)-5-pyrimidinecarboxamide;

N-(2,6-dimethylphenyl)-2-((4-(4-(1-methylethyl)-1-piperazinyl)phenyl)amino)-4-((2-(methyloxy)-4-(3-(((1R)-1-methylpropyl)amino)-3-oxopropyl)phenyl)oxy)-5-pyrimidinecarboxamide;

N-(2,6-dimethylphenyl)-4-((2-(methyloxy)-4-((1E)-3-oxo-3-((phenylmethyl)amino)-1-propenyl)phenyl)oxy)-2-(phenylamino)-5-pyrimidinecarboxamide;

N-(2,6-dimethylphenyl)-2-((3-fluoro-4-(4-methyl-1-piperazinyl)phenyl)amino)-4-((2-(methyloxy)-4-(3-(((1R)-1-methylpropyl)amino)-3-oxopropyl)phenyl)oxy)-5-pyrimidinecarboxamide;

N-(2,6-dimethylphenyl)-4-((2-(methyloxy)-4-(3-(((1S)-1-methylpropyl)amino)-3-oxopropyl)phenyl)oxy)-2-((4-(4-methyl-1-piperazinyl)phenyl)amino)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(3-(((1S)-1-methylpropyl)amino)-3-oxopropyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-(3-(((1S)-1-methylpropyl)amino)-3-oxopropyl)phenyl)oxy)-5-pyrimidinecarboxamide;

N-(2,6-dimethylphenyl)-2-((3-fluoro-4-(4-methyl-1-piperazinyl)phenyl)amino)-4-((2-(methyloxy)-4-(3-(((1S)-1-methylpropyl)amino)-3-oxopropyl)phenyl)oxy)-5-pyrimidinecarboxamide;

N-(2,6-dimethylphenyl)-2-((4-(4-(1-methylethyl)-1-piperazinyl)phenyl)amino)-4-((2-(methyloxy)-4-(3-(((1S)-1-methylpropyl)amino)-3-oxopropyl)phenyl)oxy)-5-pyrimidinecarboxamide;

4-((3-(acetylamino)phenyl)oxy)-N-(2,6-dimethylphenyl)-2-((4-(4-(1-methylethyl)-1-piperazinyl)phenyl)amino)-5-pyrimidinecarboxamide;

2-((4-(diethylamino)butyl)amino)-N-(2,6-dimethylphenyl)-4-((2-(methyloxy)-4-propylphenyl)oxy)-5-pyrimidinecarboxamide;

N-(2,6-dimethylphenyl)-4-((2-(ethyloxy)phenyl)oxy)-2-((3-fluoro-4-((3-(1H-imidazol-1-yl)propyl)oxy)phenyl)amino)-5-pyrimidinecarboxamide;

4-((3-((aminocarbonyl)amino)phenyl)oxy)-N-(2,6-dimethylphenyl)-2-((4-(4-methyl-1-piperazinyl)phenyl)amino)-5-pyrimidinecarboxamide;

4-((3-((aminocarbonyl)amino)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-((butyloxy)methyl)-2-(methyloxy)phenyl)oxy)-N-(2,6-dimethylphenyl)-2-((3-fluoro-4-((3-(1H-imidazol-1-yl)propyl)oxy)phenyl)amino)-5-pyrimidinecarboxamide;

4-((4-((butyloxy)methyl)-2-(methyloxy)phenyl)oxy)-N-(2,6-dimethylphenyl)-2-((4-(4-methyl-1-piperazinyl)phenyl)amino)-5-pyrimidinecarboxamide;

4-((4-((butyloxy)methyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-((butyloxy)methyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-((butyloxy)methyl)-2-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((4-((butyloxy)methyl)-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((4-((butyloxy)methyl)-2-(methyloxy)phenyl)oxy)-2-((4-(4-(3-(dimethylamino)propyl)-1-piperazinyl)phenyl)amino)-N-(2,6-dimethylphenyl)-5-pyrimidinecarboxamide;

4-((4-((butyloxy)methyl)-2-(methyloxy)phenyl)oxy)-N-(2,6-dimethylphenyl)-2-((3-fluoro-4-((3-(4-(2-(methyloxy)ethyl)-1-piperazinyl)propyl)oxy)phenyl)amino)-5-pyrimidinecarboxamide;

N-(2,6-dimethylphenyl)-2-((3-fluoro-4-((3-(4-methyl-1-piperazinyl)propyl)oxy)phenyl)amino)-4-((3-(4-morpholinyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((3-(4-morpholinyl)phenyl)oxy)-5-pyrimidinecarboxamide;

2-((4-(4-(3-(dimethylamino)propyl)-1-piperazinyl)phenyl)amino)-N-(2,6-dimethylphenyl)-4-((3-(4-morpholinyl)phenyl)oxy)-5-pyrimidinecarboxamide;

4-((3-(acetylamino)phenyl)oxy)-N-(2,6-dimethylphenyl)-2-((3-fluoro-4-((3-(1-piperidinyl)propyl)oxy)phenyl)amino)-5-pyrimidinecarboxamide;

4-((3-(acetylamino)phenyl)oxy)-N-(2,6-dimethylphenyl)-2-((3-fluoro-4-(4-methyl-1-piperazinyl)phenyl)amino)-5-pyrimidinecarboxamide;

4-((3-(acetylamino)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

2-((3,5-bis(methyloxy)-4-((3-(4-methyl-1-piperazinyl)propyl)oxy)phenyl)amino)-4-((4-(3-(diethylamino)-3-oxopropyl)-2-(methyloxy)phenyl)oxy)-N-(2,6-dimethylphenyl)-5-pyrimidinecarboxamide;

4-((4-(3-(diethylamino)-3-oxopropyl)-2-(methyloxy)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

2-((4-(diethylamino)butyl)amino)-4-((4-(3-(diethylamino)-3-oxopropyl)-2-(methyloxy)phenyl)oxy)-N-(2,6-dimethylphenyl)-5-pyrimidinecarboxamide;

N-(2,6-dichlorophenyl)-4-((4-(3-(diethylamino)-3-oxopropyl)-2-(methyloxy)phenyl)oxy)-2-((3-fluoro-4-((3-(4-methyl-1-piperazinyl)propyl)oxy)phenyl)amino)-5-pyrimidinecarboxamide;

N-(2,6-dichlorophenyl)-4-((4-(3-(diethylamino)-3-oxopropyl)-2-(methyloxy)phenyl)oxy)-2-((3-fluoro-4-((3-(1-piperidinyl)propyl)oxy)phenyl)amino)-5-pyrimidinecarboxamide;

2-((3-chloro-4-(4-(1-methylethyl)-1-piperazinyl)phenyl)amino)-4-((4-(3-(diethylamino)-3-oxopropyl)-2-(methyloxy)phenyl)oxy)-N-(2,6-dimethylphenyl)-5-pyrimidinecarboxamide;

4-((2-chloro-4-(2-(diethylamino)-2-oxoethyl)phenyl)oxy)-N-(2,6-dimethylphenyl)-2-((4-(4-methyl-1-piperazinyl)phenyl)amino)-5-pyrimidinecarboxamide;

4-((2-chloro-4-(2-(diethylamino)-2-oxoethyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-(2-(diethylamino)-2-oxoethyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-(2-(diethylamino)-2-oxoethyl)phenyl)oxy)-N-(2,6-dimethylphenyl)-2-((3-fluoro-4-(4-methyl-1-piperazinyl)phenyl)amino)-5-pyrimidinecarboxamide;

4-((2-chloro-4-(2-(diethylamino)-2-oxoethyl)phenyl)oxy)-N-(2,6-dimethylphenyl)-2-((4-(4-(1-methylethyl)-1-piperazinyl)phenyl)amino)-5-pyrimidinecarboxamide;

4-((2-chloro-4-(2-(diethylamino)-2-oxoethyl)phenyl)oxy)-2-((4-(4-(3-(dimethylamino)propyl)-1-piperazinyl)phenyl)amino)-N-(2,6-dimethylphenyl)-5-pyrimidinecarboxamide;

2-((4-(((2-(dimethylamino)ethyl)amino)carbonyl)phenyl)amino)-4-((2,2-dimethyl-2,3-dihydro-1-benzofuran-7-yl)oxy)-N-(2,6-dimethylphenyl)-5-pyrimidinecarboxamide;

2-((3,5-bis(methyloxy)-4-((3-(4-methyl-1-piperazinyl)propyl)oxy)phenyl)amino)-4-((2,2-dimethyl-2,3-dihydro-1-benzofuran-7-yl)oxy)-N-(2,6-dimethylphenyl)-5-pyrimidinecarboxamide;

4-((2,2-dimethyl-2,3-dihydro-1-benzofuran-7-yl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

N-(2,6-dimethylphenyl)-2-((3-fluoro-4-(4-methyl-1-piperazinyl)phenyl)amino)-4-((2-(methyloxy)-5-(3-oxo-3-((phenylmethyl)amino)propyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-5-(3-oxo-3-((phenylmethyl)amino)propyl)phenyl)oxy)-5-pyrimidinecarboxamide;

N-(2,6-dimethylphenyl)-2-((3-fluoro-4-(4-methyl-1-piperazinyl)phenyl)amino)-4-((2-(methyloxy)-5-((1E)-3-oxo-3-((phenylmethyl)amino)-1-propenyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-5-((1E)-3-oxo-3-((phenylmethyl)amino)-1-propenyl)phenyl)oxy)-5-pyrimidinecarboxamide;

N-(2,6-dimethylphenyl)-4-((2-(methyloxy)-5-((1E)-3-oxo-3-((phenylmethyl)amino)-1-propenyl)phenyl)oxy)-2-((4-(4-methyl-1-piperazinyl)phenyl)amino)-5-pyrimidinecarboxamide;

N-(2,6-dimethylphenyl)-4-((3-(2-(3-methyl-1,2,4-oxadiazol-5-yl)ethyl)phenyl)oxy)-2-((4-(4-methyl-1-piperazinyl)phenyl)amino)-5-pyrimidinecarboxamide;

N-(2,6-dimethylphenyl)-2-((3-fluoro-4-((3-(4-methyl-1-piperazinyl)propyl)oxy)phenyl)amino)-4-((3-(2-(3-methyl-1,2,4-oxadiazol-5-yl)ethyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((3-(2-(3-methyl-1,2,4-oxadiazol-5-yl)ethyl)phenyl)oxy)-5-pyrimidinecarboxamide;

N-(2,6-dimethylphenyl)-2-((3-fluoro-4-(4-methyl-1-piperazinyl)phenyl)amino)-4-((3-(2-(3-methyl-1,2,4-oxadiazol-5-yl)ethyl)phenyl)oxy)-5-pyrimidinecarboxamide;

N-(2,6-dimethylphenyl)-2-((4-(4-(1-methylethyl)-1-piperazinyl)phenyl)amino)-4-((3-(2-(3-methyl-1,2,4-oxadiazol-5-yl)ethyl)phenyl)oxy)-5-pyrimidinecarboxamide;

2-((4-(4-(3-(dimethylamino)propyl)-1-piperazinyl)phenyl)amino)-N-(2,6-dimethylphenyl)-4-((3-(2-(3-methyl-1,2,4-oxadiazol-5-yl)ethyl)phenyl)oxy)-5-pyrimidinecarboxamide;

N-(2,6-dimethylphenyl)-2-((4-(4-methyl-1-piperazinyl)phenyl)amino)-4-((3-((trifluoromethyl)oxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((3-((trifluoromethyl)oxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((3-((trifluoromethyl)oxy)phenyl)oxy)-5-pyrimidinecarboxamide;

N-(2,6-dimethylphenyl)-2-((3-fluoro-4-(4-methyl-1-piperazinyl)phenyl)amino)-4-((3-((trifluoromethyl)oxy)phenyl)oxy)-5-pyrimidinecarboxamide;

N-(2,6-dimethylphenyl)-2-((4-(4-(1-methylethyl)-1-piperazinyl)phenyl)amino)-4-((3-((trifluoromethyl)oxy)phenyl)oxy)-5-pyrimidinecarboxamide;

2-((4-(4-(3-(dimethylamino)propyl)-1-piperazinyl)phenyl)amino)-N-(2,6-dimethylphenyl)-4-((3-((trifluoromethyl)oxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((4-((trifluoromethyl)oxy)phenyl)oxy)-5-pyrimidinecarboxamide;

N-(2,6-dimethylphenyl)-2-((4-(4-methyl-1-piperazinyl)phenyl)amino)-4-((3-(2-phenyl-4-pyrimidinyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((3-(2-phenyl-4-pyrimidinyl)phenyl)oxy)-5-pyrimidinecarboxamide;

N-(2,6-dimethylphenyl)-2-((4-(4-(1-methylethyl)-1-piperazinyl)phenyl)amino)-4-((3-(2-phenyl-4-pyrimidinyl)phenyl)oxy)-5-pyrimidinecarboxamide;

2-((4-(((2-(diethylamino)ethyl)(methyl)amino)carbonyl)phenyl)amino)-N-(2,6-dimethylphenyl)-4-((2-(methyloxy)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((2-(methyloxy)phenyl)oxy)-5-pyrimidinecarboxamide;

N-(2,6-dimethylphenyl)-2-((4-(3,4-dimethyl-1-piperazinyl)-3-fluorophenyl)amino)-4-((2-(methyloxy)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)-4-(4-morpholinylcarbonyl)phenyl)oxy)-5-pyrimidinecarboxamide;

N-(2,6-dimethylphenyl)-2-((4-(3,4-dimethyl-1-piperazinyl)-3-fluorophenyl)amino)-4-((2-(methyloxy)-4-(4-morpholinylcarbonyl)phenyl)oxy)-5-pyrimidinecarboxamide;

N-(2,6-dimethylphenyl)-4-((2-(methyloxy)phenyl)oxy)-2-((3-((3-(1-piperidinyl)propyl)oxy)phenyl)amino)-5-pyrimidinecarboxamide;

4-((2-chloro-4-((diethylamino)carbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

4-((2-chloro-4-((diethylamino)carbonyl)phenyl)oxy)-N-(2,6-dimethylphenyl)-2-((3-((3-(1-piperidinyl)propyl)oxy)phenyl)amino)-5-pyrimidinecarboxamide;

2-((3,4-bis(methyloxy)-5-((3-(4-methyl-1-piperazinyl)propyl)oxy)phenyl)amino)-4-((2-chloro-4-((diethylamino)carbonyl)phenyl)oxy)-N-(2,6-dimethylphenyl)-5-pyrimidinecarboxamide;

4-((4-((2-(diethylamino)-2-oxoethyl)oxy)-2-(methyloxy)phenyl)oxy)-2-((4-(4-(3-(dimethylamino)propyl)-1-piperazinyl)phenyl)amino)-N-(2,6-dimethylphenyl)-5-pyrimidinecarboxamide;

4-((4-((2-(diethylamino)-2-oxoethyl)oxy)-2-(methyloxy)phenyl)oxy)-2-((4-(4-(2-(dimethylamino)ethyl)-1-piperazinyl)phenyl)amino)-N-(2,6-dimethylphenyl)-5-pyrimidinecarboxamide;

4-((4-(3-(diethylamino)-3-oxopropyl)-2-(methyloxy)phenyl)oxy)-N-(2,6-dimethylphenyl)-2-((3-((3-(1-piperidinyl)propyl)oxy)phenyl)amino)-5-pyrimidinecarboxamide;

4-((4-(3-(diethylamino)-3-oxopropyl)-2-(methyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

2-((3,4-bis(methyloxy)-5-((3-(4-methyl-1-piperazinyl)propyl)oxy)phenyl)amino)-4-((4-(3-(diethylamino)-3-oxopropyl)-2-(methyloxy)phenyl)oxy)-N-(2,6-dimethylphenyl)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((4-(1H-imidazol-2-yl)phenyl)oxy)-5-pyrimidinecarboxamide;

N-(2,6-dimethylphenyl)-2-((4-(3,4-dimethyl-1-piperazinyl)-3-fluorophenyl)amino)-4-((4-(1H-imidazol-1-yl)phenyl)oxy)-5-pyrimidinecarboxamide;

N-(2,6-dimethylphenyl)-2-((3-((3-(1-piperidinyl)propyl)oxy)phenyl)amino)-4-((4-(1H-pyrrol-1-yl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((4-(1H-pyrrol-1-yl)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((4-(1H-pyrrol-1-yl)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((4-(1H-pyrrol-1-yl)phenyl)oxy)-5-pyrimidinecarboxamide;

N-(2,6-dichlorophenyl)-4-((2,2-dimethyl-2,3-dihydro-1-benzofuran-7-yl)oxy)-2-((3-fluoro-4-((3-(1-piperidinyl)propyl)oxy)phenyl)amino)-5-pyrimidinecarboxamide;

N-(2,6-dichlorophenyl)-4-((2,2-dimethyl-2,3-dihydro-1-benzofuran-7-yl)oxy)-2-((3-fluoro-4-((3-(4-methyl-1-piperazinyl)propyl)oxy)phenyl)amino)-5-pyrimidinecarboxamide;

4-((4-(3-(diethylamino)-3-oxopropyl)-2-(methyloxy)phenyl)oxy)-N-(2,6-dimethylphenyl)-2-((4-(3,4-dimethyl-1-piperazinyl)-3-fluorophenyl)amino)-5-pyrimidinecarboxamide;

2-((4-(((2-(diethylamino)ethyl)(methyl)amino)carbonyl)phenyl)amino)-4-((4-(3-(diethylamino)-3-oxopropyl)-2-(methyloxy)phenyl)oxy)-N-(2,6-dimethylphenyl)-5-pyrimidinecarboxamide;

4-((2-chloro-4-((diethylamino)carbonyl)phenyl)oxy)-N-(2,6-dichlorophenyl)-2-((3-fluoro-4-((3-(1-piperidinyl)propyl)oxy)phenyl)amino)-5-pyrimidinecarboxamide;

2-((4-(diethylamino)butyl)amino)-N-(2,6-dimethylphenyl)-4-((2-(methyloxy)-4-(3-oxo-3-(1-pyrrolidinyl)propyl)phenyl)oxy)-5-pyrimidinecarboxamide;

N-(2,6-dimethylphenyl)-2-((4-(4-(1-methylethyl)-1-piperazinyl)phenyl)amino)-4-((2-(methyloxy)-4-(3-oxo-3-(1-pyrrolidinyl)propyl)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((3-(2-methyl-1,3-thiazol-4-yl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((3-(2-methyl-1,3-thiazol-4-yl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((3-(2-methyl-1,3-thiazol-4-yl)phenyl)oxy)-5-pyrimidinecarboxamide;

N-(2,6-dimethylphenyl)-4-((3-(2-methyl-1,3-thiazol-4-yl)phenyl)oxy)-2-((3-((3-(1-piperidinyl)propyl)oxy)phenyl)amino)-5-pyrimidinecarboxamide;

2-((4-(((2-(diethylamino)ethyl)(methyl)amino)carbonyl)phenyl)amino)-N-(2,6-dimethylphenyl)-4-((3-(2-methyl-1,3-thiazol-4-yl)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((3-(2-methyl-1,3-thiazol-4-yl)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((3-(2-methyl-1,3-thiazol-4-yl)phenyl)oxy)-5-pyrimidinecarboxamide;

N-(2,6-dimethylphenyl)-2-((4-(3,4-dimethyl-1-piperazinyl)-3-fluorophenyl)amino)-4-((3-(2-methyl-1,3-thiazol-4-yl)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((3-(2-phenyl-1,3-thiazol-4-yl)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((3-(2-phenyl-1,3-thiazol-4-yl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((4-(1H-imidazol-1-yl)phenyl)oxy)-5-pyrimidinecarboxamide;

N-(2,6-dimethylphenyl)-4-((4-(1H-imidazol-1-yl)phenyl)oxy)-2-((3-((3-(1-piperidinyl)propyl)oxy)phenyl)amino)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((4-(1H-imidazol-1-yl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((4-(1H-imidazol-1-yl)phenyl)oxy)-5-pyrimidinecarboxamide;

N-(2,6-dimethylphenyl)-4-((4-(3-(4-(1-methylethyl)-1-piperazinyl)-3-oxopropyl)-2-(methyloxy)phenyl)oxy)-2-((3-((3-(1-piperidinyl)propyl)oxy)phenyl)amino)-5-pyrimidinecarboxamide;

N-(2,6-dimethylphenyl)-2-((3-fluoro-4-((3-(1-piperidinyl)propyl)oxy)phenyl)amino)-4-((4-(3-(4-(1-methylethyl)-1-piperazinyl)-3-oxopropyl)-2-(methyloxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((4-(3-(4-(1-methylethyl)-1-piperazinyl)-3-oxopropyl)-2-(methyloxy)phenyl)oxy)-5-pyrimidinecarboxamide;

2-((4-(diethylamino)butyl)amino)-4-((2,2-dimethyl-2,3-dihydro-1-benzofuran-7-yl)oxy)-N-(2,6-dimethylphenyl)-5-pyrimidinecarboxamide;

N-(2,6-dimethylphenyl)-4-((2-(methyloxy)-5-(3-oxo-3-((phenylmethyl)amino)propyl)phenyl)oxy)-2-((4-(4-methyl-1-piperazinyl)phenyl)amino)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-5-(3-oxo-3-((phenylmethyl)amino)propyl)phenyl)oxy)-5-pyrimidinecarboxamide;

N-(2,6-dimethylphenyl)-2-((4-(4-(1-methylethyl)-1-piperazinyl)phenyl)amino)-4-((2-(methyloxy)-5-(3-oxo-3-((phenylmethyl)amino)propyl)phenyl)oxy)-5-pyrimidinecarboxamide;

N-(2,6-dimethylphenyl)-4-((2-(methyloxy)-5-(3-oxo-3-((phenylmethyl)amino)propyl)phenyl)oxy)-2-(phenylamino)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(3-oxo-3-(1-pyrrolidinyl)propyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-(3-oxo-3-(1-pyrrolidinyl)propyl)phenyl)oxy)-5-pyrimidinecarboxamide;

N-(2,6-dimethylphenyl)-2-((3-fluoro-4-(4-methyl-1-piperazinyl)phenyl)amino)-4-((2-(methyloxy)-4-(3-oxo-3-(1-pyrrolidinyl)propyl)phenyl)oxy)-5-pyrimidinecarboxamide;

N-(2,6-dimethylphenyl)-4-((2-(methyloxy)-4-(3-oxo-3-(1-pyrrolidinyl)propyl)phenyl)oxy)-2-(phenylamino)-5-pyrimidinecarboxamide;

N-(2,6-dimethylphenyl)-2-((2-hydroxypropyl)amino)-4-((2-(methyloxy)-4-(3-oxo-3-(1-pyrrolidinyl)propyl)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)-4-(3-(4-morpholinyl)-3-oxopropyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(3-(4-morpholinyl)-3-oxopropyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-(3-(4-morpholinyl)-3-oxopropyl)phenyl)oxy)-5-pyrimidinecarboxamide;

N-(2,6-dimethylphenyl)-4-((2-(methyloxy)-4-(3-(4-morpholinyl)-3-oxopropyl)phenyl)oxy)-2-((3-((3-(1-piperidinyl)propyl)oxy)phenyl)amino)-5-pyrimidinecarboxamide;

2-((4-(((2-(diethylamino)ethyl)(methyl)amino)carbonyl)phenyl)amino)-N-(2,6-dimethylphenyl)-4-((2-(methyloxy)-4-(3-(4-morpholinyl)-3-oxopropyl)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)-4-(3-(4-morpholinyl)-3-oxopropyl)phenyl)oxy)-5-pyrimidinecarboxamide;

4-(1,1'-biphenyl-3-yloxy)-2-((3,4-bis(methyloxy)-5-((3-(4-methyl-1-piperazinyl)propyl)oxy)phenyl)amino)-N-(2,6-dimethylphenyl)-5-pyrimidinecarboxamide;

4-(1,1'-biphenyl-3-yloxy)-N-(2,6-dimethylphenyl)-2-((3-fluoro-4-((3-(4-methyl-1-piperazinyl)propyl)oxy)phenyl)amino)-5-pyrimidinecarboxamide;

4-(1,1'-biphenyl-3-yloxy)-N-(2,6-dimethylphenyl)-2-((3-fluoro-4-((3-(1-piperidinyl)propyl)oxy)phenyl)amino)-5-pyrimidinecarboxamide;

4-(1,1'-biphenyl-3-yloxy)-N-(2,6-dimethylphenyl)-2-((3-((3-(1-piperidinyl)propyl)oxy)phenyl)amino)-5-pyrimidinecarboxamide;

4-(1,1'-biphenyl-3-yloxy)-2-((4-(((2-(diethylamino)ethyl)(methyl)amino)carbonyl)phenyl)amino)-N-(2,6-dimethylphenyl)-5-pyrimidinecarboxamide;

4-(1,1'-biphenyl-3-yloxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(4-morpholinylcarbonyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-(4-morpholinylcarbonyl)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)-4-(4-morpholinylcarbonyl)phenyl)oxy)-5-pyrimidinecarboxamide;

4-((4-((2-(diethylamino)ethyl)oxy)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-((2-(diethylamino)ethyl)oxy)-2-(methyloxy)phenyl)oxy)-N-(2,6-dimethylphenyl)-2-((4-(4-(1-methylethyl)-1-piperazinyl)phenyl)amino)-5-pyrimidinecarboxamide;

4-((4-((2-(diethylamino)ethyl)oxy)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-((2-(diethylamino)ethyl)oxy)-2-(methyloxy)phenyl)oxy)-2-((4-(4-(2-(dimethylamino)ethyl)-1-piperazinyl)phenyl)amino)-N-(2,6-dimethylphenyl)-5-pyrimidinecarboxamide;

4-((4-((2-(diethylamino)ethyl)oxy)-2-(methyloxy)phenyl)oxy)-2-((4-(4-(3-(dimethylamino)propyl)-1-piperazinyl)phenyl)amino)-N-(2,6-dimethylphenyl)-5-pyrimidinecarboxamide;

4-((4-((2-(diethylamino)-2-oxoethyl)oxy)-2-(methyloxy)phenyl)oxy)-N-(2,6-dimethylphenyl)-2-((4-(4-methyl-1-piperazinyl)phenyl)amino)-5-pyrimidinecarboxamide;

4-((4-((2-(diethylamino)-2-oxoethyl)oxy)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-((2-(diethylamino)-2-oxoethyl)oxy)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-((2-(diethylamino)-2-oxoethyl)oxy)-2-(methyloxy)phenyl)oxy)-N-(2,6-dimethylphenyl)-2-((3-fluoro-4-(4-methyl-1-piperazinyl)phenyl)amino)-5-pyrimidinecarboxamide;

4-((4-((2-(diethylamino)-2-oxoethyl)oxy)-2-(methyloxy)phenyl)oxy)-N-(2,6-dimethylphenyl)-2-((4-(4-(1-methylethyl)-1-piperazinyl)phenyl)amino)-5-pyrimidinecarboxamide;

2-((3,4-bis(methyloxy)-5-((3-(4-methyl-1-piperazinyl)propyl)oxy)phenyl)amino)-4-((2-chloro-4-(1-pyrrolidinylcarbonyl)phenyl)oxy)-N-(2,6-dimethylphenyl)-5-pyrimidinecarboxamide;

4-((2-chloro-4-(1-pyrrolidinylcarbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-(1-pyrrolidinylcarbonyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-(1-pyrrolidinylcarbonyl)phenyl)oxy)-N-(2,6-dimethylphenyl)-2-((3-((3-(1-piperidinyl)propyl)oxy)phenyl)amino)-5-pyrimidinecarboxamide;

4-((2-chloro-4-(1-pyrrolidinylcarbonyl)phenyl)oxy)-2-((4-(((2-(diethylamino)ethyl)(methyl)amino)carbonyl)phenyl)amino)-N-(2,6-dimethylphenyl)-5-pyrimidinecarboxamide;

4-((2-chloro-4-(1-pyrrolidinylcarbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

4-((2-chloro-4-(1-pyrrolidinylcarbonyl)phenyl)oxy)-N-(2,6-dimethylphenyl)-2-((4-(3,4-dimethyl-1-piperazinyl)-3-fluorophenyl)amino)-5-pyrimidinecarboxamide;

4-((2-chloro-4-((diethylamino)carbonyl)phenyl)oxy)-N-(2,6-dichlorophenyl)-2-((3-fluoro-4-((3-(4-methyl-1-piperazinyl)propyl)oxy)phenyl)amino)-5-pyrimidinecarboxamide;

N-(2,6-dichlorophenyl)-4-((2-(ethyloxy)phenyl)oxy)-2-((3-fluoro-4-((3-(4-methyl-1-piperazinyl)propyl)oxy)phenyl)amino)-5-pyrimidinecarboxamide;

N-(2,6-dichlorophenyl)-4-((2-(ethyloxy)phenyl)oxy)-2-((3-fluoro-4-((3-(1-piperidinyl)propyl)oxy)phenyl)amino)-5-pyrimidinecarboxamide;

N-(2,6-dichlorophenyl)-2-((3-fluoro-4-((3-(4-methyl-1-piperazinyl)propyl)oxy)phenyl)amino)-4-((2-(methyloxy)-4-propylphenyl)oxy)-5-pyrimidinecarboxamide;

N-(2,6-dichlorophenyl)-2-((3-fluoro-4-((3-(1-piperidinyl)propyl)oxy)phenyl)amino)-4-((2-(methyloxy)-4-propylphenyl)oxy)-5-pyrimidinecarboxamide;

N-(2,6-dichlorophenyl)-4-((4-((diethylamino)carbonyl)-2-(methyloxy)phenyl)oxy)-2-((3-fluoro-4-((3-(4-methyl-1-piperazinyl)propyl)oxy)phenyl)amino)-5-pyrimidinecarboxamide;

N-(2,6-dichlorophenyl)-4-((4-((diethylamino)carbonyl)-2-(methyloxy)phenyl)oxy)-2-((3-fluoro-4-((3-(1-piperidinyl)propyl)oxy)phenyl)amino)-5-pyrimidinecarboxamide;

N-(2,6-dimethylphenyl)-2-((4-(4-methyl-1-piperazinyl)phenyl)amino)-4-((3-(1H-pyrazol-3-yl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((3-(lH-pyrazol-3-yl)phenyl)oxy)-5-pyrimidinecarboxamide;

N-(2,6-dimethylphenyl)-2-((3-fluoro-4-(4-methyl-1-piperazinyl)phenyl)amino)-4-((3-(1H-pyrazol-3-yl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((3-(1H-pyrazol-3-yl)phenyl)oxy)-5-pyrimidinecarboxamide;

N-(2,6-dimethylphenyl)-2-((4-(4-(1-methylethyl)-1-piperazinyl)phenyl)amino)-4-((3-(1H-pyrazol-3-yl)phenyl)oxy)-5-pyrimidinecarboxamide;

2-((4-(4-(2-(dimethylamino)ethyl)-1-piperazinyl)phenyl)amino)-N-(2,6-dimethylphenyl)-4-((3-(1H-pyrazol-3-yl)phenyl)oxy)-5-pyrimidinecarboxamide;

2-((4-(4-(3-(dimethylamino)propyl)-1-piperazinyl)phenyl)amino)-N-(2,6-dimethylphenyl)-4-((3-(1H-pyrazol-3-yl)phenyl)oxy)-5-pyrimidinecarboxamide;

2-((4-(diethylamino)butyl)amino)-N-(2,6-dimethylphenyl)-4-((1H-pyrazol-3-yl)phenyl)oxy)-5-pyrimidinecarboxamide;

N-(2,6-dimethylphenyl)-2-((4-(3,4-dimethyl-1-piperazinyl)-3-fluorophenyl)amino)-4-((3-(1H-pyrazol-3-yl)phenyl)oxy)-5-pyrimidinecarboxamide;

N-(2,6-dimethylphenyl)-4-((2-(ethyloxy)phenyl)oxy)-6-((4-(4-methyl-1-piperazinyl)phenyl)amino)-3-pyridinecarboxamide;

4-((2-chloro-4-((diethylamino)carbonyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

4-((2-chloro-4-((diethylamino)carbonyl)phenyl)oxy)-N-(2,6-dimethylphenyl)-2-((4-(3,4-dimethyl-1-piperazinyl)-3-fluorophenyl)amino)-5-pyrimidinecarboxamide;

2-((3,5-bis(methyloxy)-4-((3-(4-methyl-1-piperazinyl)propyl)oxy)phenyl)amino)-4-((2-chloro-4-((diethylamino)carbonyl)phenyl)oxy)-N-(2,6-dimethylphenyl)-5-pyrimidinecarboxamide;

4-((2-chloro-4-((diethylamino)carbonyl)phenyl)oxy)-N-(2,6-dimethylphenyl)-2-((3-(methyloxy)-4-((2-(4-methyl-1-piperazinyl)ethyl)oxy)phenyl)amino)-5-pyrimidinecarboxamide;

4-((2-chloro-4-((diethylamino)carbonyl)phenyl)oxy)-N-(2,6-dimethylphenyl)-2-((3-(methyloxy)-4-(4-methyl-1-piperazinyl)phenyl)amino)-5-pyrimidinecarboxamide;

4-((2-chloro-4-((diethylamino)carbonyl)phenyl)oxy)-2-((3-((difluoromethyl)oxy)-4-(4-methyl-1-piperazinyl)phenyl)amino)-N-(2,6-dimethylphenyl)-5-pyrimidinecarboxamide;

4-((2-chloro-4-((diethylamino)carbonyl)phenyl)oxy)-2-((3-chloro-4-(4-(1-methylethyl)-1-piperazinyl)phenyl)amino)-N-(2,6-dimethylphenyl)-5-pyrimidinecarboxamide;

N-(2,6-dimethylphenyl)-2-((4-(3,4-dimethyl-1-piperazinyl)-3-fluorophenyl)amino)-4-((2-(methyloxy)-4-(1-pyrrolidinylcarbonyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-(1-pyrrolidinylcarbonyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(1-pyrrolidinylcarbonyl)phenyl)oxy)-5-pyrimidinecarboxamide;

4-((3-(acetylamino)phenyl)oxy)-2-((4-(diethylamino)butyl)amino)-N-(2,6-dimethylphenyl)-5-pyrimidinecarboxamide;

4-((3-(acetylamino)phenyl)oxy)-N-(2,6-dimethylphenyl)-2-((4-(4-methyl-1-piperazinyl)phenyl)amino)-5-pyrimidinecarboxamide;

4-((2-chloro-4-(1-pyrrolidinylcarbonyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-((1-methylethyl)oxy)phenyl)oxy)-5-pyrimidinecarboxamide;

N-(2,6-dimethylphenyl)-4-((2-((1-methylethyl)oxy)phenyl)oxy)-2-((3-((3-(1-piperidinyl)propyl)oxy)phenyl)amino)-5-pyrimidinecarboxamide;

2-((4-(((2-(diethylamino)ethyl)(methyl)amino)carbonyl)phenyl)amino)-N-(2,6-dimethylphenyl)-4-((2-((1-methylethyl)oxy)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-((1-methylethyl)oxy)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((2-((1-methylethyl)oxy)phenyl)oxy)-5-pyrimidinecarboxamide;

N-(2,6-dimethylphenyl)-2-((4-(3,4-dimethyl-1-piperazinyl)-3-fluorophenyl)amino)-4-((2-((1-methylethyl)oxy)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)-4-(3-(((1R)-1-methylpropyl)amino)-3-oxopropyl)phenyl)oxy)-5-pyrimidinecarboxamide;

2-((4-(((2-(diethylamino)ethyl)(methyl)amino)carbonyl)phenyl)amino)-N-(2,6-dimethylphenyl)-4-((2-(methyloxy)-4-(3-(((1R)-1-methylpropyl)amino)-3-oxopropyl)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)-4-(3-(((1R)-1-methylpropyl)amino)-3-oxopropyl)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((2-(methyloxy)-4-(3-(((1R)-1-methylpropyl)amino)-3-oxopropyl)phenyl)oxy)-5-pyrimidinecarboxamide;

N-(2,6-dimethylphenyl)-2-((4-(3,4-dimethyl-1-piperazinyl)-3-fluorophenyl)amino)-4-((2-(methyloxy)-4-(3-(((1R)-1-methylpropyl)amino)-3-oxopropyl)phenyl)oxy)-5-pyrimidinecarboxamide;

4-((4-(4-(diethylamino)-4-oxobutyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-(4-(diethylamino)-4-oxobutyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-((diethylamino)carbonyl)phenyl)oxy)-2-((3-fluoro-4-((3-(4-methyl-1-piperazinyl)propyl)oxy)phenyl)amino)-N-(2-pyridinylmethyl)-5-pyrimidinecarboxamide;

4-((2-chloro-4-((diethylamino)carbonyl)phenyl)oxy)-2-((3-fluoro-4-((3-(1-piperidinyl)propyl)oxy)phenyl)amino)-N-(2-pyridinylmethyl)-5-pyrimidinecarboxamide;

2-((3-chloro-4-(4-(1-methylethyl)-1-piperazinyl)phenyl)amino)-4-((2,2-dimethyl-2,3-dihydro-1-benzofuran-7-yl)oxy)-N-(2,6-dimethylphenyl)-5-pyrimidinecarboxamide;

2-((4-(((2-(diethylamino)ethyl)(methyl)amino)carbonyl)phenyl)amino)-4-((2,2-dimethyl-2,3-dihydro-1-benzofuran-7-yl)oxy)-N-(2,6-dimethylphenyl)-5-pyrimidinecarboxamide;

4-((2,2-dimethyl-2,3-dihydro-1-benzofuran-7-yl)oxy)-N-(2,6-dimethylphenyl)-2-((4-(3,4-dimethyl-1-piperazinyl)-3-fluorophenyl)amino)-5-pyrimidinecarboxamide;

2-((3,4-bis(methyloxy)-5-((3-(4-methyl-1-piperazinyl)propyl)oxy)phenyl)amino)-4-((2,2-dimethyl-2,3-dihydro-1-benzofuran-7-yl)oxy)-N-(2,6-dimethylphenyl)-5-pyrimidinecarboxamide;

4-((2,2-dimethyl-2,3-dihydro-1-benzofuran-7-yl)oxy)-N-(2,6-dimethylphenyl)-2-((3-fluoro-4-(((1-methyl-3-piperidinyl)methyl)oxy)phenyl)amino)-5-pyrimidinecarboxamide;

4-((2-chloro-4-((diethylamino)carbonyl)phenyl)oxy)-2-((3-fluoro-4-((3-(4-methyl-1-piperazinyl)propyl)oxy)phenyl)amino)-N-((1S)-1-phenylethyl)-5-pyrimidinecarboxamide;

4-((2-chloro-4-((diethylamino)carbonyl)phenyl)oxy)-2-((3-fluoro-4-((3-(1-piperidinyl)propyl)oxy)phenyl)amino)-N-((1S)-1-phenylethyl)-5-pyrimidinecarboxamide;

4-((2-chloro-4-((diethylamino)carbonyl)phenyl)oxy)-2-((3-fluoro-4-((3-(4-methyl-1-piperazinyl)propyl)oxy)phenyl)amino)-N-(4-fluorophenyl)-5-pyrimidinecarboxamide;

4-((2-chloro-4-((diethylamino)carbonyl)phenyl)oxy)-N-(4-fluorophenyl)-2-((3-fluoro-4-((3-(1-piperidinyl)propyl)oxy)phenyl)amino)-5-pyrimidinecarboxamide;

4-((2-chloro-4-((diethylamino)carbonyl)phenyl)oxy)-2-((3-fluoro-4-((3-(4-methyl-1-piperazinyl)propyl)oxy)phenyl)amino)-N-(2-fluorophenyl)-5-pyrimidinecarboxamide;

4-((2-chloro-4-((diethylamino)carbonyl)phenyl)oxy)-N-(2-fluorophenyl)-2-((3-fluoro-4-((3-(1-piperidinyl)propyl)oxy)phenyl)amino)-5-pyrimidinecarboxamide;

4-((2-chloro-4-((diethylamino)carbonyl)phenyl)oxy)-2-((3-fluoro-4-((3-(4-methyl-1-piperazinyl)propyl)oxy)phenyl)amino)-N-(2,6-trimethylphenyl)-5-pyrimidinecarboxamide;

4-((2-chloro-4-((diethylamino)carbonyl)phenyl)oxy)-2-((3-fluoro-4-((3-(1-piperidinyl)propyl)oxy)phenyl)amino)-N-(2,6-trimethylphenyl)-5-pyrimidinecarboxamide;

4-((2-chloro-4-((diethylamino)carbonyl)phenyl)oxy)-2-((3-fluoro-4-((3-(4-methyl-1-piperazinyl)propyl)oxy)phenyl)amino)-N-(2,6-trifluorophenyl)-5-pyrimidinecarboxamide;

4-((2-chloro-4-((diethylamino)carbonyl)phenyl)oxy)-2-((3-fluoro-4-((3-(1-piperidinyl)propyl)oxy)phenyl)amino)-N-(2,6-trifluorophenyl)-5-pyrimidinecarboxamide;

4-((4-(2-(diethylamino)-2-oxoethyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-(2-(diethylamino)-2-oxoethyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

2-((4-(((2-(diethylamino)ethyl)(methyl)amino)carbonyl)phenyl)amino)-4-((4-(2-(diethylamino)-2-oxoethyl)-2-(methyloxy)phenyl)oxy)-N-(2,6-dimethylphenyl)-5-pyrimidinecarboxamide;

4-((4-(2-(diethylamino)-2-oxoethyl)-2-(methyloxy)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

4-((4-(2-(diethylamino)-2-oxoethyl)-2-(methyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

4-((4-(2-(diethylamino)-2-oxoethyl)-2-(methyloxy)phenyl)oxy)-N-(2,6-dimethylphenyl)-2-((4-(3,4-dimethyl-1-piperazinyl)-3-fluorophenyl)amino)-5-pyrimidinecarboxamide;

2-((3,4-bis(methyloxy)-5-((3-(4-methyl-1-piperazinyl)propyl)oxy)phenyl)amino)-4-((4-(2-(diethylamino)-2-oxoethyl)-2-(methyloxy)phenyl)oxy)-N-(2,6-dimethylphenyl)-5-pyrimidinecarboxamide;

N-(2,6-dimethylphenyl)-4-((2-(methyloxy)-4-(3-oxo-3-(1-pyrrolidinyl)propyl)phenyl)oxy)-2-((4-(4-methyl-1-piperazinyl)phenyl)amino)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((4-(2-(3-methyl-1,2,4-oxadiazol-5-yl)ethyl)-2-(methyloxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((4-(2-(3-methyl-1,2,4-oxadiazol-5-yl)ethyl)-2-(methyloxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((4-(2-(3-methyl-1,2,4-oxadiazol-5-yl)ethyl)-2-(methyloxy)phenyl)oxy)-5-pyrimidinecarboxamide;

2-((4-(((2-(diethylamino)ethyl)(methyl)amino)carbonyl)phenyl)amino)-N-(2,6-dimethylphenyl)-4-((4-(2-(3-methyl-1,2,4-oxadiazol-5-yl)ethyl)-2-(methyloxy)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((4-(2-(3-methyl-1,2,4-oxadiazol-5-yl)ethyl)-2-(methyloxy)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((4-(2-(3-methyl-1,2,4-oxadiazol-5-yl)ethyl)-2-(methyloxy)phenyl)oxy)-5-pyrimidinecarboxamide;

N-(2,6-dimethylphenyl)-2-((4-(3,4-dimethyl-1-piperazinyl)-3-fluorophenyl)amino)-4-((4-(2-(3-methyl-1,2,4-oxadiazol-5-yl)ethyl)-2-(methyloxy)phenyl)oxy)-5-pyrimidinecarboxamide;

4-((2-chloro-4-(2-(diethylamino)ethyl)phenyl)oxy)-N-(2,6-dimethylphenyl)-2-((3-fluoro-4-(4-methyl-1-piperazinyl)phenyl)amino)-5-pyrimidinecarboxamide;

4-((2-chloro-4-(2-(diethylamino)ethyl)phenyl)oxy)-N-(2,6-dimethylphenyl)-2-((4-(4-(1-methylethyl)-1-piperazinyl)phenyl)amino)-5-pyrimidinecarboxamide;

4-((2-chloro-4-(2-(diethylamino)ethyl)phenyl)oxy)-2-((4-(4-(3-(dimethylamino)propyl)-1-piperazinyl)phenyl)amino)-N-(2,6-dimethylphenyl)-5-pyrimidinecarboxamide;

2-((4-(((2-(dimethylamino)ethyl)amino)carbonyl)phenyl)amino)-N-(2,6-dimethylphenyl)-4-((2-(methyloxy)-4-propylphenyl)oxy)-5-pyrimidinecarboxamide;

2-((3-(((2-(dimethylamino)ethyl)amino)carbonyl)phenyl)amino)-N-(2,6-dimethylphenyl)-4-((2-(methyloxy)-4-propylphenyl)oxy)-5-pyrimidinecarboxamide;

2-((4-(((2-(dimethylamino)ethyl)amino)carbonyl)phenyl)amino)-N-(2,6-dimethylphenyl)-4-((2-(ethyloxy)phenyl)oxy)-5-pyrimidinecarboxamide;

2-((3-(((2-(dimethylamino)ethyl)amino)carbonyl)phenyl)amino)-N-(2,6-dimethylphenyl)-4-((2-(ethyloxy)phenyl)oxy)-5-pyrimidinecarboxamide;

4-((2-chloro-4-(2-oxo-2-(1-pyrrolidinyl)ethyl)phenyl)oxy)-2-((4-(((2-(diethylamino)ethyl)(methyl)amino)carbonyl)phenyl)amino)-N-(2,6-dimethylphenyl)-5-pyrimidinecarboxamide;

4-((2-chloro-4-(2-oxo-2-(1-pyrrolidinyl)ethyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-(2-oxo-2-(1-pyrrolidinyl)ethyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

2-((4-(((2-(diethylamino)ethyl)(methyl)amino)carbonyl)phenyl)amino)-N-(2,6-dimethylphenyl)-4-((2-(methyloxy)-4-(1-pyrrolidinylcarbonyl)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)-4-(1-pyrrolidinylcarbonyl)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)-4-(1-pyrrolidinylcarbonyl)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)-4-((2-oxo-2-(1-pyrrolidinyl)ethyl)oxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-((2-oxo-2-(1-pyrrolidinyl)ethyl)oxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-((2-oxo-2-(1-pyrrolidinyl)ethyl)oxy)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)-4-((2-oxo-2-(1-pyrrolidinyl)ethyl)oxy)phenyl)oxy)-5-pyrimidinecarboxamide;

N-(2,6-dimethylphenyl)- 2-((3-fluoro-4-(((1-methyl-3-piperidinyl)methyl)oxy)phenyl)amino)-4-((2-(methyloxy)-4-((2-oxo-2-(1-pyrrolidinyl)ethyl)oxy)phenyl)oxy)-5-pyrimidinecarboxamide;

N-(2,6-dimethylphenyl)-2-((4-(3,4-dimethyl-1-piperazinyl)-3-fluorophenyl)amino)-4-((2-(methyloxy)-4-((2-oxo-2-(1-pyrrolidinyl)ethyl)oxy)phenyl)oxy)-5-pyrimidinecarboxamide;

4-((2-chloro-4-((diethylamino)carbonyl)phenyl)oxy)-2-((4-(((2-(diethylamino)ethyl)(methyl)amino)carbonyl)phenyl)amino)-N-(2,6-dimethylphenyl)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((4-(((1-methylethyl)amino)carbonyl)-2-(methyloxy)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((4-(((1-methylethyl)amino)carbonyl)-2-(methyloxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((4-(((1-methylethyl)amino)carbonyl)-2-(methyloxy)phenyl)oxy)-5-pyrimidinecarboxamide;

N-(2,6-dimethylphenyl)-4-((4-(((1-methylethyl)amino)carbonyl)-2-(methyloxy)phenyl)oxy)-2-((3-((3-(1-piperidinyl)propyl)oxy)phenyl)amino)-5-pyrimidinecarboxamide;

2-((4-(((2-(diethylamino)ethyl)(methyl)amino)carbonyl)phenyl)amino)-N-(2,6-dimethylphenyl)-4-((4-(((1-methylethyl)amino)carbonyl)-2-(methyloxy)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((4-(((1-methylethyl)amino)carbonyl)-2-(methyloxy)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((4-(((1-methylethyl)amino)carbonyl)-2-(methyloxy)phenyl)oxy)-5-pyrimidinecarboxamide;

N-(2,6-dimethylphenyl)-2-((4-(3,4-dimethyl-1-piperazinyl)-3-fluorophenyl)amino)-4-((4-(((1-methylethyl)amino)carbonyl)-2-(methyloxy)phenyl)oxy)-5-pyrimidinecarboxamide;

2-((3,4-bis(methyloxy)-5-((3-(4-methyl-1-piperazinyl)propyl)oxy)phenyl)amino)-4-((4-((cyclopentylamino)carbonyl)-2-(methyloxy)phenyl)oxy)-N-(2,6-dimethylphenyl)-5-pyrimidinecarboxamide;

4-((4-((cyclopentylamino)carbonyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-((cyclopentylamino)carbonyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

4-((4-((cyclopentylamino)carbonyl)-2-(methyloxy)phenyl)oxy)-N-(2,6-dimethylphenyl)-2-((3-((3-(1-piperidinyl)propyl)oxy)phenyl)amino)-5-pyrimidinecarboxamide;

4-((4-((cyclopentylamino)carbonyl)-2-(methyloxy)phenyl)oxy)-2-((4-(((2-(diethylamino)ethyl)(methyl)amino)carbonyl)phenyl)amino)-N-(2,6-dimethylphenyl)-5-pyrimidinecarboxamide;

4-((4-((cyclopentylamino)carbonyl)-2-(methyloxy)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

4-((4-((cyclopentylamino)carbonyl)-2-(methyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

4-((4-((cyclopentylamino)carbonyl)-2-(methyloxy)phenyl)oxy)-N-(2,6-dimethylphenyl)-2-((4-(3,4-dimethyl-1-piperazinyl)-3-fluorophenyl)amino)-5-pyrimidinecarboxamide;

4-((4-(2-(diethylamino)-2-oxoethyl)-2-(methyloxy)phenyl)oxy)-N-(2,6-dimethylphenyl)-2-((3-((3-(1-piperidinyl)propyl)oxy)phenyl)amino)-5-pyrimidinecarboxamide;

4-((2-chloro-4-((4-(1-methylethyl)-1-piperazinyl)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-((4-(1-methylethyl)-1-piperazinyl)carbonyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-((4-(1-methylethyl)-1-piperazinyl)carbonyl)phenyl)oxy)-N-(2,6-dimethylphenyl)-2-((3-((3-(1-piperidinyl)propyl)oxy)phenyl)amino)-5-pyrimidinecarboxamide;

4-((2-chloro-4-((4-(1-methylethyl)-1-piperazinyl)carbonyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

4-((2-chloro-4-((4-(1-methylethyl)-1-piperazinyl)carbonyl)phenyl)oxy)-N-(2,6-dimethylphenyl)-2-((4-(3,4-dimethyl-1-piperazinyl)-3-fluorophenyl)amino)-5-pyrimidinecarboxamide;

2-((3,4-bis(methyloxy)-5-((3-(4-methyl-1-piperazinyl)propyl)oxy)phenyl)amino)-4-((2-chloro-4-(((2-(methyloxy)ethyl)amino)carbonyl)phenyl)oxy)-N-(2,6-dimethylphenyl)-5-pyrimidinecarboxamide;

2-((4-(((2-(diethylamino)ethyl)(methyl)amino)carbonyl)phenyl)amino)-N-(2,6-dimethylphenyl)-4-((4-(3-(4-(1-methylethyl)-1-piperazinyl)-3-oxopropyl)-2-(methyloxy)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((4-(3-(4-(1-methylethyl)-1-piperazinyl)-3-oxopropyl)-2-(methyloxy)phenyl)oxy)-5-pyrimidinecarboxamide;

N-(2,6-dimethylphenyl)-2-((4-(3,4-dimethyl-1-piperazinyl)-3-fluorophenyl)amino)-4-((4-(3-(4-(1-methylethyl)-1-piperazinyl)-3-oxopropyl)-2-(methyloxy)phenyl)oxy)-5-pyrimidinecarboxamide;

2-((3,4-bis(methyloxy)-5-((3-(4-methyl-1-piperazinyl)propyl)oxy)phenyl)amino)-4-((2-chloro-4-((cyclopentylamino)carbonyl)phenyl)oxy)-N-(2,6-dimethylphenyl)-5-pyrimidinecarboxamide;

4-((2-chloro-4-((cyclopentylamino)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-((cyclopentylamino)carbonyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-((cyclopentylamino)carbonyl)phenyl)oxy)-2-((4-(((2-(diethylamino)ethyl)(methyl)amino)carbonyl)phenyl)amino)-N-(2,6-dimethylphenyl)-5-pyrimidinecarboxamide;

4-((2-chloro-4-((cyclopentylamino)carbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

4-((2-chloro-4-((cyclopentylamino)carbonyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

4-((2-chloro-4-(4-morpholinylcarbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-(4-morpholinylcarbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

4-((2-chloro-4-(4-morpholinylcarbonyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

4-((2-chloro-4-(((1-methylethyl)amino)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-(((1-methylethyl)amino)carbonyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-(((1-methylethyl)amino)carbonyl)phenyl)oxy)-2-((4-(((2-(diethylamino)ethyl)(methyl)amino)carbonyl)phenyl)amino)-N-(2,6-dimethylphenyl)-5-pyrimidinecarboxamide;

2-((3,4-bis(methyloxy)-5-((3-(4-methyl-1-piperazinyl)propyl)oxy)phenyl)amino)-4-((2-chloro-4-(((1-methylethyl)amino)carbonyl)phenyl)oxy)-N-(2,6-dimethylphenyl)-5-pyrimidinecarboxamide;

N-(2,6-dimethylphenyl)-4-((2-ethylimidazo[1,2-a]pyridin-8-yl)oxy)-2-((3-fluoro-4-((3-(4-methyl-1-piperazinyl)propyl)oxy)phenyl)amino)-5-pyrimidinecarboxamide;

2-((4-(((2-(diethylamino)ethyl)(methyl)amino)carbonyl)phenyl)amino)-4-((3-(3-(diethylamino)-3-oxopropyl)phenyl)oxy)-N-(2,6-dimethylphenyl)-5-pyrimidinecarboxamide;

2-((3,4-bis(methyloxy)-5-((3-(4-methyl-1-piperazinyl)propyl)oxy)phenyl)amino)-4-((3-(3-(diethylamino)-3-oxopropyl)phenyl)oxy)-N-(2,6-dimethylphenyl)-5-pyrimidinecarboxamide;

4-((3-(3-(diethylamino)-3-oxopropyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

4-((3-(3-(diethylamino)-3-oxopropyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

4-((3-(3-(diethylamino)-3-oxopropyl)phenyl)oxy)-N-(2,6-dimethylphenyl)-2-((3-((3-(1-piperidinyl)propyl)oxy)phenyl)amino)-5-pyrimidinecarboxamide;

4-((2-chloro-4-(4-morpholinylcarbonyl)phenyl)oxy)-N-(2,6-dimethylphenyl)-2-((4-(3,4-dimethyl-1-piperazinyl)-3-fluorophenyl)amino)-5-pyrimidinecarboxamide;

4-((2-chloro-4-((diethylamino)carbonyl)phenyl)oxy)-N-(2,6-dichloro-4-fluorophenyl)-2-((3-fluoro-4-((3-(4-methyl-1-piperazinyl)propyl)oxy)phenyl)amino)-5-pyrimidinecarboxamide;

4-((2-chloro-4-((diethylamino)carbonyl)phenyl)oxy)-N-(2,6-dichloro-4-fluorophenyl)-2-((3-fluoro-4-((3-(1-piperidinyl)propyl)oxy)phenyl)amino)-5-pyrimidinecarboxamide;

4-((2-chloro-4-((diethylamino)carbonyl)phenyl)oxy)-N-(4-fluoro-2,6-dimethylphenyl)-2-((3-fluoro-4-((3-(4-methyl-1-piperazinyl)propyl)oxy)phenyl)amino)-5-pyrimidinecarboxamide;

4-((2-chloro-4-((diethylamino)carbonyl)phenyl)oxy)-N-(4-fluoro-2,6-dimethylphenyl)-2-((3-fluoro-4-((3-(1-piperidinyl)propyl)oxy)phenyl)amino)-5-pyrimidinecarboxamide;

4-((2-chloro-4-((diethylamino)carbonyl)phenyl)oxy)-2-((3-fluoro-4-((3-(4-methyl-1-piperazinyl)propyl)oxy)phenyl)amino)-N-((5-methyl-3-isoxazolyl)methyl)-5-pyrimidinecarboxamide;

4-((2-chloro-4-((diethylamino)carbonyl)phenyl)oxy)-2-((3-fluoro-4-((3-(1-piperidinyl)propyl)oxy)phenyl)amino)-N-((5-methyl-3-isoxazolyl)methyl)-5-pyrimidinecarboxamide;

4-((2-chloro-4-(((2-(methyloxy)ethyl)amino)carbonyl)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((2-chloro-4-(((2-(methyloxy)ethyl)amino)carbonyl)phenyl)oxy)-N-(2,6-dimethylphenyl)-2-((3-fluoro-4-((3-(1-piperidinyl)propyl)oxy)phenyl)amino)-5-pyrimidinecarboxamide;

2-((3,4-bis(methyloxy)-5-((3-(4-methyl-1-piperazinyl)propyl)oxy)phenyl)amino)-4-((4-((diethylamino)carbonyl)-2-(methyloxy)phenyl)oxy)-N-(2,6-dimethylphenyl)-5-pyrimidinecarboxamide;

4-((4-((diethylamino)carbonyl)-2-(methyloxy)phenyl)oxy)-N-(2,6-dimethylphenyl)-2-((3-((3-(1-piperidinyl)propyl)oxy)phenyl)amino)-5-pyrimidinecarboxamide;

4-((4-((diethylamino)carbonyl)-2-(methyloxy)phenyl)oxy)-2-((4-(((2-(diethylamino)ethyl)(methyl)amino)carbonyl)phenyl)amino)-N-(2,6-dimethylphenyl)-5-pyrimidinecarboxamide;

4-((4-((diethylamino)carbonyl)-2-(methyloxy)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

4-((4-((diethylamino)carbonyl)-2-(methyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

4-((4-((diethylamino)carbonyl)-2-(methyloxy)phenyl)oxy)-N-(2,6-dimethylphenyl)-2-((4-(3,4-dimethyl-1-piperazinyl)-3-fluorophenyl)amino)-5-pyrimidinecarboxamide;

4-((4-(3-(cyclopentylamino)-3-oxopropyl)-2-(methyloxy)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

N-(2,6-dimethylphenyl)-2-((3-fluoro-4-(((1-methyl-3-piperidinyl)methyl)oxy)phenyl)amino)-4-((4-(3-((1-methylethyl)amino)-3-oxopropyl)-2-(methyloxy)phenyl)oxy)-5-pyrimidinecarboxamide;

N-(2,6-dimethylphenyl)-2-((4-(3,4-dimethyl-1-piperazinyl)-3-fluorophenyl)amino)-4-((2-(methyloxy)-4-(3-((2-(methyloxy)ethyl)amino)-3-oxopropyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(3-((2-(methyloxy)ethyl)amino)-3-oxopropyl)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((4-(3-((1-methylethyl)amino)-3-oxopropyl)-2-(methyloxy)phenyl)oxy)-5-pyrimidinecarboxamide;

4-((4-(3-(cyclopentylamino)-3-oxopropyl)-2-(methyloxy)phenyl)oxy)-N-(2,6-dimethylphenyl)-2-((3-fluoro-4-((3-(1-piperidinyl)propyl)oxy)phenyl)amino)-5-pyrimidinecarboxamide;

2-((3,4-bis(methyloxy)-5-((3-(4-methyl-1-piperazinyl)propyl)oxy)phenyl)amino)-4-((4-(3-(cyclopentylamino)-3-oxopropyl)-2-(methyloxy)phenyl)oxy)-N-(2,6-dimethylphenyl)-5-pyrimidinecarboxamide;

4-((4-(3-(cyclopentylamino)-3-oxopropyl)-2-(methyloxy)phenyl)oxy)-N-(2,6-dimethylphenyl)-2-((3-fluoro-4-((3-(4-methyl-1-piperazinyl)propyl)oxy)phenyl)amino)-5-pyrimidinecarboxamide;

4-((4-(3-(cyclopentylamino)-3-oxopropyl)-2-(methyloxy)phenyl)oxy)-N-(2,6-dimethylphenyl)-2-((4-(3,4-dimethyl-1-piperazinyl)-3-fluorophenyl)amino)-5-pyrimidinecarboxamide;

N-(2,6-dimethylphenyl)-2-((4-(3,4-dimethyl-1-piperazinyl)-3-fluorophenyl)amino)-4-((4-(3-((1-methylethyl)amino)-3-oxopropyl)-2-(methyloxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((4-(3-((1-methylethyl)amino)-3-oxopropyl)-2-(methyloxy)phenyl)oxy)-5-pyrimidinecarboxamide;

N-(2,6-dimethylphenyl)-4-((2-(methyloxy)-4-((2-oxo-2-(1-pyrrolidinyl)ethyl)oxy)phenyl)oxy)-2-((3-((3-(1-piperidinyl)propyl)oxy)phenyl)amino)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-((2-(4-morpholinyl)-2-oxoethyl)oxy)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-((2-(4-morpholinyl)-2-oxoethyl)oxy)phenyl)oxy)-5-pyrimidinecarboxamide;

N-(2,6-dimethylphenyl)-4-((2-(methyloxy)-4-((2-(4-morpholinyl)-2-oxoethyl)oxy)phenyl)oxy)-2-((3-((3-(1-piperidinyl)propyl)oxy)phenyl)amino)-5-pyrimidinecarboxamide;

2-((4-(((2-(diethylamino)ethyl)(methyl)amino)carbonyl)phenyl)amino)-N-(2,6-dimethylphenyl)-4-((2-(methyloxy)-4-((2-(4-morpholinyl)-2-oxoethyl)oxy)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((2-(methyloxy)-4-(1-pyrrolidinylcarbonyl)phenyl)oxy)-5-pyrimidinecarboxamide;

4-((2-chloro-4-(2-oxo-2-(1-pyrrolidinyl)ethyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-(2-oxo-2-(1-pyrrolidinyl)ethyl)phenyl)oxy)-N-(2,6-dimethylphenyl)-2-((4-(3,4-dimethyl-1-piperazinyl)-3-fluorophenyl)amino)-5-pyrimidinecarboxamide;

2-((3,4-bis(methyloxy)-5-((3-(4-methyl-1-piperazinyl)propyl)oxy)phenyl)amino)-4-((2-chloro-4-(2-oxo-2-(1-pyrrolidinyl)ethyl)phenyl)oxy)-N-(2,6-dimethylphenyl)-5-pyrimidinecarboxamide;

4-((2-chloro-4-(2-oxo-2-(1-pyrrolidinyl)ethyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

4-((2-chloro-4-(2-(4-morpholinyl)-2-oxoethyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

4-((2-chloro-4-(2-(4-morpholinyl)-2-oxoethyl)phenyl)oxy)-2-((4-(((2-(diethylamino)ethyl)(methyl)amino)carbonyl)phenyl)amino)-N-(2,6-dimethylphenyl)-5-pyrimidinecarboxamide;

2-((3,4-bis(methyloxy)-5-((3-(4-methyl-1-piperazinyl)propyl)oxy)phenyl)amino)-4-((2-chloro-4-(2-(4-morpholinyl)-2-oxoethyl)phenyl)oxy)-N-(2,6-dimethylphenyl)-5-pyrimidinecarboxamide;

4-((2-chloro-4-(2-(4-morpholinyl)-2-oxoethyl)phenyl)oxy)-N-(2,6-dimethylphenyl)-2-((3-fluoro-4-(((1-methyl-3-piperidinyl)methyl)oxy)phenyl)amino)-5-pyrimidinecarboxamide;

4-((2-chloro-4-(2-(4-morpholinyl)-2-oxoethyl)phenyl)oxy)-N-(2,6-dimethylphenyl)-2-((3-((3-(1-piperidinyl)propyl)oxy)phenyl)amino)-5-pyrimidinecarboxamide;

4-((2-chloro-4-(2-(4-morpholinyl)-2-oxoethyl)phenyl)oxy)-N-(2,6-dimethylphenyl)-2-((3-fluoro-4-((3-(1-piperidinyl)propyl)oxy)phenyl)amino)-5-pyrimidinecarboxamide;

4-((2-chloro-4-(((2-(methyloxy)ethyl)amino)carbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

4-((2-chloro-4-(((2-(methyloxy)ethyl)amino)carbonyl)phenyl)oxy)-N-(2,6-dimethylphenyl)-2-((4-(3,4-dimethyl-1-piperazinyl)-3-fluorophenyl)amino)-5-pyrimidinecarboxamide;

4-((2-chloro-4-((4-(1-methylethyl)-1-piperazinyl)carbonyl)phenyl)oxy)-N-(2,6-dimethylphenyl)-2-((3-fluoro-4-((2-(4-(1-methylethyl)-1-piperazinyl)ethyl)oxy)phenyl)amino)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)-4-(2-(4-morpholinyl)-2-oxoethyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-(2-(4-morpholinyl)-2-oxoethyl)phenyl)oxy)-5-pyrimidinecarboxamide;

N-(2,6-dimethylphenyl)-4-((2-(methyloxy)-4-(2-(4-morpholinyl)-2-oxoethyl)phenyl)oxy)-2-((3-((3-(1-piperidinyl)propyl)oxy)phenyl)amino)-5-pyrimidinecarboxamide;

2-((3,4-bis(methyloxy)-5-((3-(4-methyl-1-piperazinyl)propyl)oxy)phenyl)amino)-4-((2-(methyloxy)-4-(3-(((1R)-1-methylpropyl)amino)-3-oxopropyl)phenyl)oxy)-N-(2,4,6-trimethylphenyl)-5-pyrimidinecarboxamide;

2-((3-fluoro-4-((3-(4-methyl-1-piperazinyl)propyl)oxy)phenyl)amino)-4-((2-(methyloxy)-4-(3-(((1R)-1-methylpropyl)amino)-3-oxopropyl)phenyl)oxy)-N-(2,4,6-trimethylphenyl)-5-pyrimidinecarboxamide;

2-((3-fluoro-4-((3-(1-piperidinyl)propyl)oxy)phenyl)amino)-4-((2-(methyloxy)-4-(3-(((1R)-1-methylpropyl)amino)-3-oxopropyl)phenyl)oxy)-N-(2,4,6-trimethylphenyl)-5-pyrimidinecarboxamide;

4-((2-(methyloxy)-4-(3-(((1R)-1-methylpropyl)amino)-3-oxopropyl)phenyl)oxy)-2-((3-((3-(1-piperidinyl)propyl)oxy)phenyl)amino)-N-(2,4,6-trimethylphenyl)-5-pyrimidinecarboxamide;

2-((4-(((2-(diethylamino)ethyl)(methyl)amino)carbonyl)phenyl)amino)-4-((2-(methyloxy)-4-(3-(((1R)-1-methylpropyl)amino)-3-oxopropyl)phenyl)oxy)-N-(2,4,6-trimethylphenyl)-5-pyrimidinecarboxamide;

2-((4-(4-(1-methylethyl)-1-piperazinyl)phenyl)amino)-4-((2-(methyloxy)-4-(3-(((1R)-1-methylpropyl)amino)-3-oxopropyl)phenyl)oxy)-N-(2,4,6-trimethylphenyl)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-(2-(4-morpholinyl)-2-oxoethyl)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)-4-((2-(4-morpholinyl)-2-oxoethyl)oxy)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)-4-((2-(4-morpholinyl)-2-oxoethyl)oxy)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((2-(methyloxy)-4-((2-(4-morpholinyl)-2-oxoethyl)oxy)phenyl)oxy)-5-pyrimidinecarboxamide;

N-(2,6-dimethylphenyl)-2-((4-(3,4-dimethyl-1-piperazinyl)-3-fluorophenyl)amino)-4-((2-(methyloxy)-4-((2-(4-morpholinyl)-2-oxoethyl)oxy)phenyl)oxy)-5-pyrimidinecarboxamide;

2-((4-(((2-(diethylamino)ethyl)(methyl)amino)carbonyl)phenyl)amino)-N-(2,6-dimethylphenyl)-4-((2-(methyloxy)-4-((2-oxo-2-(1-pyrrolidinyl)ethyl)oxy)phenyl)oxy)-5-pyrimidinecarboxamide;

4-((4-(3-(diethylamino)-3-oxopropyl)-2-(methyloxy)phenyl)oxy)-2-((3-(((2-(dimethylamino)ethyl)amino)carbonyl)phenyl)amino)-N-(2,6-dimethylphenyl)-5-pyrimidinecarboxamide;

2-((4-(((2-(diethylamino)ethyl)(methyl)amino)carbonyl)phenyl)amino)-N-(2,6-dimethylphenyl)-4-((2-(methyloxy)-4-(2-(4-morpholinyl)-2-oxoethyl)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)-4-(2-(4-morpholinyl)-2-oxoethyl)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((2-(methyloxy)-4-(2-(4-morpholinyl)-2-oxoethyl)phenyl)oxy)-5-pyrimidinecarboxamide;

N-(2,6-dimethylphenyl)-2-((4-(3,4-dimethyl-1-piperazinyl)-3-fluorophenyl)amino)-4-((2-(methyloxy)-4-(2-(4-morpholinyl)-2-oxoethyl)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)-4-(2-((2-(methyloxy)ethyl)amino)-2-oxoethyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(2-((2-(methyloxy)ethyl)amino)-2-oxoethyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-(2-((2-(methyloxy)ethyl)amino)-2-oxoethyl)phenyl)oxy)-5-pyrimidinecarboxamide;

N-(2,6-dimethylphenyl)-4-((2-(methyloxy)-4-(2-((2-(methyloxy)ethyl)amino)-2-oxoethyl)phenyl)oxy)-2-((3-((3-(1-piperidinyl)propyl)oxy)phenyl)amino)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)-4-(2-((2-(methyloxy)ethyl)amino)-2-oxoethyl)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((2-(methyloxy)-4-(2-((2-(methyloxy)ethyl)amino)-2-oxoethyl)phenyl)oxy)-5-pyrimidinecarboxamide;

N-(2,6-dimethylphenyl)-2-((4-(3,4-dimethyl-1-piperazinyl)-3-fluorophenyl)amino)-4-((2-(methyloxy)-4-(2-((2-(methyloxy)ethyl)amino)-2-oxoethyl)phenyl)oxy)-5-pyrimidinecarboxamide;

N-(2,6-dimethylphenyl)-2-((3-fluoro-4-((3-(4-methyl-1-piperazinyl)propyl)oxy)phenyl)amino)-4-((2-oxo-1,2,3,4-tetrahydro-7-quinolinyl)oxy)-5-pyrimidinecarboxamide;

N-(2,6-dimethylphenyl)-2-((4-(3,4-dimethyl-1-piperazinyl)-3-fluorophenyl)amino)-4-((2-oxo-1,2,3,4-tetrahydro-7-quinolinyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-oxo-1,2,3,4-tetrahydro-7-quinolinyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((2-oxo-1,2,3,4-tetrahydro-7-quinolinyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-oxo-1,2,3,4-tetrahydro-7-quinolinyl)oxy)-5-pyrimidinecarboxamide;

N-(2,6-dimethylphenyl)-2-((4-(3,4-dimethyl-1-piperazinyl)-3-fluorophenyl)amino)-4-((4-((4-(1-methylethyl)-1-piperazinyl)carbonyl)-2-(methyloxy)phenyl)oxy)-5-pyrimidinecarboxamide;

2-((4-(((2-(diethylamino)ethyl)(methyl)amino)carbonyl)phenyl)amino)-N-(2,6-dimethylphenyl)-4-((4-((4-(1-methylethyl)-1-piperazinyl)carbonyl)-2-(methyloxy)phenyl)oxy)-5-pyrimidinecarboxamide;

2-((3,4-bis(methyloxy)-5-((3-(4-methyl-1-piperazinyl)propyl)oxy)phenyl)amino)-N-(2,6-dimethylphenyl)-4-((2-(methyloxy)-4-(((2-(methyloxy)ethyl)amino)carbonyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((2-(methyloxy)-4-(((2-(methyloxy)ethyl)amino)carbonyl)phenyl)oxy)-5-pyrimidinecarboxamide;

N-(2,6-dimethylphenyl)-2-((3-fluoro-4-((3-(1-piperidinyl)propyl)oxy)phenyl)amino)-4-((4-((4-(1-methylethyl)-1-piperazinyl)carbonyl)-2-(methyloxy)phenyl)oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((4-((4-(1-methylethyl)-1-piperazinyl)carbonyl)-2-(methyloxy)phenyl)oxy)-5-pyrimidinecarboxamide;

4-((3-(3-(diethylamino)-3-oxopropyl)phenyl)oxy)-N-(2,6-dimethylphenyl)-2-((4-(3,4-dimethyl-1-piperazinyl)-3-fluorophenyl)amino)-5-pyrimidinecarboxamide;

4-((4-(3-(diethylamino)-3-oxopropyl)-2-(methyloxy)phenyl)oxy)-2-((4-(((2-(dimethylamino)ethyl)amino)carbonyl)phenyl)amino)-N-(2,6-dimethylphenyl)-5-pyrimidinecarboxamide;

N-(2,6-dimethylphenyl)-2-((3-fluoro-4-((3-(4-methyl-1-piperazinyl)propyl)oxy)phenyl)amino)-4-((4-(3-(((1-methylethyl)amino)-3-oxopropyl)-2-(methyloxy)phenyl)
oxy)-5-pyrimidinecarboxamide;

2-((4-(((2-(diethylamino)ethyl)(methyl)amino)carbonyl)
phenyl)amino)-N-(2,6-dimethylphenyl)-4-((4-(3-((1-methylethyl)amino)-3-oxopropyl)-2-(methyloxy)phenyl)
oxy)-5-pyrimidinecarboxamide;

4-((4-(3-(cyclopentylamino)-3-oxopropyl)-2-(methyloxy)
phenyl)oxy)-2-((4-(((2-(diethylamino)ethyl)(methyl)
amino)carbonyl)phenyl)amino)-N-(2,6-dimethylphenyl)-
5-pyrimidinecarboxamide;

2-((4-(((2-(diethylamino)ethyl)(methyl)amino)carbonyl)
phenyl)amino)-N-(2,6-dimethylphenyl)-4-((2-(methyloxy)-4-(3-((2-(methyloxy)ethyl)amino)-3-oxopropyl)
phenyl)oxy)-5-pyrimidinecarboxamide;

2-((4-(((2-(diethylamino)ethyl)(methyl)amino)carbonyl)
phenyl)amino)-N-(2,6-dimethylphenyl)-4-((2-oxo-1,2,3,
4-tetrahydro-7-quinolinyl)oxy)-5-pyrimidinecarboxamide;

2-((3,4-bis(methyloxy)-5-((3-(4-methyl-1-piperazinyl)propyl)oxy)phenyl)amino)-4-((4-((diethylamino)carbonyl)-
2-(ethyloxy)phenyl)oxy)-N-(2,6-dimethylphenyl)-5-pyrimidinecarboxamide;

4-((4-((diethylamino)carbonyl)-2-(ethyloxy)phenyl)oxy)-
N-(2,6-dimethylphenyl)-2-((3-fluoro-4-((3-(1-piperidinyl)propyl)oxy)phenyl)amino)-5-pyrimidinecarboxamide;

4-((4-((diethylamino)carbonyl)-2-(ethyloxy)phenyl)oxy)-2-
((4-(((2-(diethylamino)ethyl)(methyl)amino)carbonyl)
phenyl)amino)-N-(2,6-dimethylphenyl)-5-pyrimidinecarboxamide;

4-((4-((diethylamino)carbonyl)-2-(ethyloxy)phenyl)oxy)-
N-(2,6-dimethylphenyl)-2-((3-fluoro-4-(((1-methyl-3-piperidinyl)methyl)oxy)phenyl)amino)-5-pyrimidinecarboxamide;

4-((4-((diethylamino)carbonyl)-2-(ethyloxy)phenyl)oxy)-
N-(2,6-dimethylphenyl)-2-((4-(3,4-dimethyl-1-piperazinyl)-3-fluorophenyl)amino)-5-pyrimidinecarboxamide;

N-(2,6-dimethylphenyl)-2-((3-fluoro-4-((3-(4-methyl-1-piperazinyl)propyl)oxy)phenyl)amino)-4-((2-(methyloxy)-4-(((2-(methyloxy)ethyl)amino)carbonyl)phenyl)
oxy)-5-pyrimidinecarboxamide;

N-(2,6-dimethylphenyl)-4-((2-(methyloxy)-4-(((2-(methyloxy)ethyl)amino)carbonyl)phenyl)oxy)-2-((3-((3-(1-piperidinyl)propyl)oxy)phenyl)amino)-5-pyrimidinecarboxamide;

2-((4-(((2-(diethylamino)ethyl)(methyl)amino)carbonyl)
phenyl)amino)-N-(2,6-dimethylphenyl)-4-((2-(methyloxy)-4-(((2-(methyloxy)ethyl)amino)carbonyl)phenyl)
oxy)-5-pyrimidinecarboxamide;

N-(2,6-dimethylphenyl)-2-((3-fluoro-4-((2-(4-(1-methylethyl)-1-piperazinyl)ethyl)oxy)phenyl)amino)-4-((2-(methyloxy)-4-(((2-(methyloxy)ethyl)amino)carbonyl)phenyl)oxy)-5-pyrimidinecarboxamide;

N-(2,6-dimethylphenyl)-2-((3-fluoro-4-(((1-methyl-3-piperidinyl)methyl)oxy)phenyl)amino)-4-((2-(methyloxy)-
4-(((2-(methyloxy)ethyl)amino)carbonyl)phenyl)oxy)-5-
pyrimidinecarboxamide;

2-((3-fluoro-4-((3-(4-methyl-1-piperazinyl)propyl)oxy)phenyl)amino)-4-((2-(methyloxy)-4-(3-(((1R)-1-methylpropyl)amino)-3-oxopropyl)phenyl)oxy)-N-(2,4,6-trifluorophenyl)-5-pyrimidinecarboxamide;

2-((3-fluoro-4-((3-(1-piperidinyl)propyl)oxy)phenyl)
amino)-4-((2-(methyloxy)-4-(3-(((1R)-1-methylpropyl)
amino)-3-oxopropyl)phenyl)oxy)-N-(2,4,6-trifluorophenyl)-5-pyrimidinecarboxamide;

4-((2-(methyloxy)-4-(3-(((1R)-1-methylpropyl)amino)-3-
oxopropyl)phenyl)oxy)-2-((3-((3-(1-piperidinyl)propyl)
oxy)phenyl)amino)-N-(2,4,6-trifluorophenyl)-5-pyrimidinecarboxamide;

2-((4-(((2-(diethylamino)ethyl)(methyl)amino)carbonyl)
phenyl)amino)-4-((2-(methyloxy)-4-(3-(((1R)-1-methylpropyl)amino)-3-oxopropyl)phenyl)oxy)-N-(2,4,6-trifluorophenyl)-5-pyrimidinecarboxamide;

2-((3-fluoro-4-((2-(4-(1-methylethyl)-1-piperazinyl)ethyl)
oxy)phenyl)amino)-4-((2-(methyloxy)-4-(3-(((1R)-1-methylpropyl)amino)-3-oxopropyl)phenyl)oxy)-N-(2,4,6-
trifluorophenyl)-5-pyrimidinecarboxamide;

2-((3-fluoro-4-(((1-methyl-3-piperidinyl)methyl)oxy)phenyl)amino)-4-((2-(methyloxy)-4-(3-(((1R)-1-methylpropyl)amino)-3-oxopropyl)phenyl)oxy)-N-(2,4,6-trifluorophenyl)-5-pyrimidinecarboxamide; and 2-((4-(3,4-dimethyl-1-piperazinyl)-3-fluorophenyl)amino)-
4-((2-(methyloxy)-4-(3-(((1R)-1-methylpropyl)amino)-3-
oxopropyl)phenyl)oxy)-N-(2,4,6-trifluorophenyl)-5-pyrimidinecarboxamide.

xxx

Human Mixed Lymphocyte Reaction (huMLR):

The purpose of this assay is to test the potency of T cell activation inhibitors in an in vitro model of allogeneic T cell stimulation. Human peripheral blood lymphocytes (hPBL; $2\times10^5$/well) are incubated with mitomycin C-treated B lymphoblastoid cells (JY cell line; $1\times10^5$/well) as allogeneic stimulators in the presence or absence of dilutions of potential inhibitor compound in 96-well round-bottom tissue culture plates. These cultures are incubated at 37° C. in 5% $CO_2$ for 6 days total. The proliferative response of the hPBL is measured by $^3$H-thymidine incorporation overnight between days 5 and 6 after initiation of culture. Cells are harvested onto glass fiber filters and $^3$H-thymidine incorporation into DNA is analyzed by liquid scintillation counter.

Jurkat Proliferation/Survival Assay:

The purpose of this assay is to test the general anti-proliferative/cytotoxic effect of compounds on the Jurkat human T cell line. Jurkat cells ($1\times10^5$/well) are plated in 96-well flat-bottom tissue culture plates with or without compound dilutions and cultured for 72 h at 37° C. in 5% $CO_2$. Viable cell number is determined during the last 4 h of culture by adding 10 µL/well WST-1 dye. WST-1 dye conversion relies on active mitochondrial electron transport for reduction of the tetrazolium dye. The dye conversion is read by OD at 450-600 mn.

Anti-CD3/CD28-induced T Cell IL-2 Secretion and Proliferation Assay:

The purpose of this assay is to test the potency of T cell receptor (TCR; CD3) and CD28 signaling pathway inhibitors in human T cells. T cells are purified from human peripheral blood lymphocytes (hPBL) and pre-incubated with or without compound prior to stimulation with a combination of an anti-CD3 and an anti-CD28 antibody in 96-well tissue culture plates ($1\times10^5$T cells/well). Cells are cultured for ~20 h at 37° C. in 5% $CO_2$, then secreted IL-2 in the supernatants is quantified by cytokine ELISA (Pierce/Endogen). The cells remaining in the wells are then pulsed with $^3$H-thymidine overnight to assess the T cell proliferative response. Cells are harvested onto glass fiber filters and $^3$H-thymidine incorporation into DNA is analyzed by liquid scintillation counter. For comparison purposes, phorbol myristic acid (PMA) and calcium ionophore can be used in combination to induce IL-2 secretion from purified T cells. Potential inhibitor compounds can be tested for inhibition of this response as described above for anti-CD3 and -CD28 antibodies.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

For the treatment of Lck-mediated diseases and other diseases listed above, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients and the like as described herein. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multidose pharmaceutical composition, such as powders, liquids and the like, in which an effective amount of the compound is administered by administering a portion of the composition.

The dosage regimen for treating Lck-mediated diseases and other diseases listed above with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

What is claimed is:

1. A compound of formula

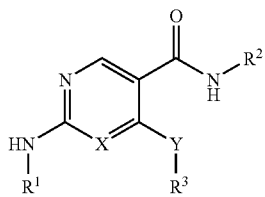

I or a pharmaceutically-acceptable salt thereof, wherein

X is N;

Y is NH, O or S;

$R^1$ is selected from —$R^{11}$, —$R^{11}$—$R^{12}$, —$R^{11}$—$R^{14}$, —$R^{12}$—$R^{14}$, —$R^{11}$—$R^{12}$—$R^{14}$, —$R^{11}$—$R^{13}$—$R^{14}$, —$R^{12}$—$R^{13}$—$R^{14}$, —$R^{11}$—$R^{13}$—$R^{12}$—$R^{14}$ and —$R^{11}$—$R^{12}$—$R^{13}$—$R^{14}$, any of which is substituted by 0, 1, 2, 3 or 4 substituents independently selected from $R^c$;

$R^2$ is selected from —$R^{21}$, —$R^{21}$—$R^{22}$, —$R^{21}$—$R^{24}$, —$R^{22}$—$R^{24}$, —$R^{21}$—$R^{22}$—$R^{24}$, —$R^{21}$—$R^{23}$—$R^{24}$, —$R^{22}$—$R^{23}$—$R^{24}$, —$R^{21}$—$R^{23}$—$R^{22}$—$R^{24}$ and —$R^{21}$—$R^{22}$—$R^{23}$—$R^{24}$, any of which is substituted by 0, 1, 2, 3 or 4 substituents independently selected from $R^c$;

$R^3$ is selected from —$R^{31}$, —$R^{31}$—$R^{32}$, —$R^{31}$—$R^{34}$, —$R^{31}$—$R^{32}$—$R^{34}$, —$R^{31}$—$R^{33}$—$R^{34}$, —$R^{32}$—$R^{33}$—$R^{34}$, —$R^{31}$—$R^{33}$—$R^{32}$—$R^{34}$ and —$R^{31}$—$R^{32}$—$R^{33}$—$R^{34}$, any of which is substituted by 0, 1, 2, 3 or 4 substituents independently selected from $R^c$;

$R^{11}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{12}$ is independently at each instance $C_{1-8}$alkyl;

$R^{13}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

$R^{14}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{21}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{22}$ is independently at each instance $C_{1-8}$alkyl;

$R^{23}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

$R^{24}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{31}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

$R^{32}$ is independently at each instance $C_{1-8}$alkyl;

$R^{33}$ is independently at each instance —C(=O)—, —C(=O)O—, —C(=O)NR$^a$—, —C(=NR$^a$)NR$^a$—, —O—, —OC(=O)—, —OC(=O)NR$^a$—, —OC(=O)N(R$^a$)S(=O)$_2$—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)—, —S(=O)$_2$N(R$^a$)C(=O)O—, —S(=O)$_2$N(R$^a$)C(=O)NR$^a$—, —N(R$^a$)—, —N(R$^a$)C(=O)—, —N(R$^a$)C(=O)O—, —N(R$^a$)C(=O)N(R$^a$)—, —N(R$^a$)C (=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

R$^{34}$ is independently at each instance a saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

R$^a$ is independently at each instance H or R$^b$;

R$^b$ is independently at each instance C$_{1-8}$alkyl, phenyl or benzyl; and

R$^c$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$.

2. A compound according to claim 1 wherein Y is O.

3. A compound according to claim 1 wherein R$^{11}$ is phenyl substituted by 0, 1, 2, 3 or 4 substituents independently selected from R$^c$.

4. A compound according to claim 1 wherein R$^{21}$ is phenyl substituted by 0, 1, 2, 3 or 4 substituents independently selected from R$^c$.

5. A compound according to claim 1 wherein R$^{31}$ is phenyl substituted by 0, 1, 2, 3 or 4 substituents independently selected from R$^c$.

6. A compound according to claim 1 wherein R$^{13}$ is independently at each instance —C(=O)NR$^a$—, —O—, —OC$_{2-6}$lkylNR$^a$—, —OC$_{2-6}$alkylO—, —S—, —S(=O)$_2$NR$^a$—, —N(R$^a$)—, —N(R$^a$)C(=O)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—; and R$^{14}$ is independently at each instance a saturated or unsaturated 5-, 6- or 7-membered monocyclic ring containing 0, 1, 2, 3 or 4 atoms selected from N, O and S.

7. A compound according to claim 1 wherein R$^{33}$ is independently at each instance —C(=O)—, —C(=O)NR$^a$—, —O—, —OC$_{2-6}$alkylNR$^a$—, —OC$_{2-6}$alkylO—, —S—, —S(=O)$_2$NR$^a$—, —N(R$^a$)—, —N(R$^a$)C(=O)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—; and R$^{34}$ is independently at each instance a saturated or unsaturated 5-, 6- or 7-membered monocyclic ring or 6-, 7-, 8-, 9-, 10-containing 0, 1, 2, 3 or 4 atoms selected from N, O and S.

8. A compound according to claim 1, of Formula I

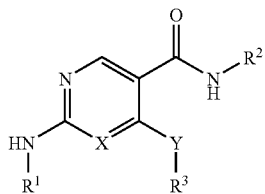

I or a pharmaceutically-acceptable salt thereof, wherein

X is N;

Y is O;

R$^1$ is selected from —R$^{11}$, —R$^{11}$—R$^{12}$, —R$^{11}$—R$^{14}$, —R$^{12}$—R$^{14}$, —R$^{11}$—R$^{12}$—R$^{14}$, —R$^{11}$—R$^{13}$—R$^{14}$, —R$^{12}$—R$^{13}$—R$^{14}$, —R$^{11}$—R$^{13}$—R$^{12}$—R$^{14}$ and —R$^{11}$—R$^{12}$—R$^{13}$—R$^{14}$, any of which is substituted by 0, 1, 2, 3 or 4 substituents independently selected from R$^c$;

R$^2$ is selected from —R$^{21}$ substituted by 0, 1, 2, 3 or 4 substituents independently selected from R$^c$;

R$^3$ is selected from —R$^{31}$, —R$^{31}$—R$^{32}$, —R$^{31}$—R$^{34}$, —R$^{31}$—R$^{32}$—R$^{34}$, —R$^{31}$—R$^{33}$—R$^{34}$, —R$^{32}$—R$^{33}$—R$^{34}$, —R$^{31}$—R$^{33}$—R$^{32}$—R$^{34}$ and —R$^{31}$—R$^{32}$—R$^{33}$—R$^{34}$, any of which is substituted by 0, 1, 2, 3 or 4 substituents independently selected from R$^c$;

R$^{11}$ is independently at each instance a saturated or unsaturated 5-, 6- or 7-membered monocyclic ring containing 0, 1, 2, 3 or 4 atoms selected from N, O and S;

R$^{12}$ is independently at each instance C$_{1-8}$alkyl;

R$^{13}$ is independently at each instance —C(=O)—, —C(=O)NR$^a$—, —C(=NR$^a$)NR$^a$—, —O—, —OC$_{2-6}$alkylNR$^a$—, —OC$_{2-6}$alkylO—, —S—, —S(=O)—, —S(=O)$_2$—, —S(=O)$_2$NR$^a$—, —N(R$^a$)—, —N(R$^a$)C(=O)—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

R$^{14}$ is independently at each instance a saturated or unsaturated 5-, 6- or 7-membered monocyclic ring containing 0, 1, 2, 3 or 4 atoms selected from N, O and S, so long as the combination of O and S atoms is not greater than 2, wherein the carbon atoms of the ring are substituted by 0, 1 or 2 oxo groups;

R$^{21}$ is phenyl;

R$^{31}$ is independently at each instance a saturated or unsaturated 5-, 6- or 7-membered monocyclic ring containing 0, 1, 2, 3 or 4 atoms selected from N, O and S;

R$^{32}$ is independently at each instance C$_{1-8}$alkyl;

R$^{33}$ is independently at each instance —C(=O)—, —C(=O)NR$^a$—, —C(=NR$^a$)NR$^a$—, —O—, —OC$_{2-6}$alkylNR$^a$—, —OC$_{2-6}$alkylO—, —S—, —S(=O)—, —S(=O)$_2$—, —S(=O)$_2$NR$^a$—, —S(=O)$_2$N(R$^a$)C(=O)O—, —S(=O)$_2$N(R$^a$)C(=O)NR$^a$—, —N(R$^a$), —N(R$^a$)C(=O)—, —N(R$^a$)C(=O)N(R$^a$)—, —N(R$^a$)C(=NR$^a$)N(R$^a$)—, —N(R$^a$)S(=O)$_2$—, —N(R$^a$)S(=O)$_2$N(R$^a$)—, —NR$^a$C$_{2-6}$alkylN(R$^a$)— or —NR$^a$C$_{2-6}$alkylO—;

R$^{34}$ is independently at each instance a saturated or unsaturated 5-, 6- or 7-membered monocyclic ring containing 0, 1, 2, 3 or 4 atoms selected from N, O and S;

R$^a$ is independently at each instance H or R$^b$;

R$^b$ is independently at each instance C$_{1-8}$alkyl, phenyl or benzyl; and

R$^c$ is independently at each instance C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$.

9. A compound according to claim 8, wherein $R^{11}$ is phenyl substituted by 0, 1, 2, 3 or 4 substituents independently selected from $R^c$; and $R^{31}$ is phenyl substituted by 0, 1, 2, 3 or 4 substituents independently selected from $R^c$.

10. A method for making a compound according to claim 1, comprising the steps of:

chloronating a compound having the structure

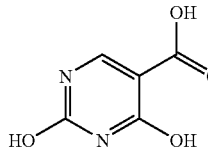 to give 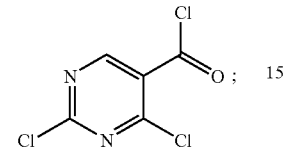;

reacting the chloronated compound with $R^2NH_2$ to give

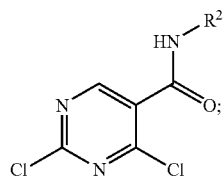

reacting the formed amide with $R^3OH$ to give

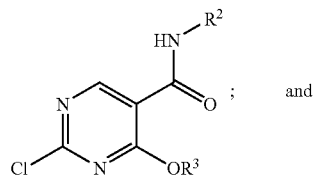; and reacting the formed ether with $R^1NH_2$ to give

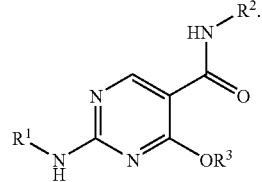

11. A pharmaceutical composition comprising a compound according to claim 1 and a pharmaceutically acceptable carrier.

12. A method of treatment of arthritis, rheumatoid arthritis, psoriatic arthritis, or osteoarthritis in a mammal comprising administering a therapeutically-effective amount of a compound according to claim 1.

* * * * *